US006395490B1

(12) United States Patent
Gonsalves et al.

(10) Patent No.: US 6,395,490 B1
(45) **Date of Patent: *May 28, 2002**

(54) DETECTION OF RUPESTRIS STEM PITTING ASSOCIATED VIRUS

(75) Inventors: Dennis Gonsalves; Baozhong Meng, both of Geneva, NY (US)

(73) Assignee: Cornell Research Foundation, Inc., Ithaca, NY (US)

( * ) Notice: Subject to any disclaimer, the term of this patent is extended or adjusted under 35 U.S.C. 154(b) by 0 days.

This patent is subject to a terminal disclaimer.

(21) Appl. No.: 09/574,141

(22) Filed: May 18, 2000

Related U.S. Application Data

(60) Provisional application No. 60/047,147, filed on May 20, 1997, and provisional application No. 60/069,902, filed on Dec. 17, 1997.

(51) Int. Cl.[7] .......................... C12Q 1/68; C12P 19/34; C07H 21/04

(52) U.S. Cl. .......................... 435/6; 435/91.2; 536/24.3

(58) Field of Search .................... 435/6, 91.2; 536/24.3

(56) References Cited

U.S. PATENT DOCUMENTS

| | | | | |
|---|---|---|---|---|
| 4,358,535 A | | 11/1982 | Falkow et al. | 435/5 |
| 4,480,040 A | | 10/1984 | Owens et al. | 436/504 |
| 5,043,272 A | | 8/1991 | Hartley | 435/91 |
| 5,104,792 A | | 4/1992 | Silver et al. | 435/6 |
| 5,106,727 A | | 4/1992 | Hartley et al. | 435/6 |
| 5,196,305 A | | 3/1993 | Findlay et al. | 435/6 |
| 5,288,611 A | | 2/1994 | Kohne | 435/6 |
| 5,322,770 A | | 6/1994 | Gelfand | 435/6 |
| 5,328,825 A | | 7/1994 | Warren, III et al. | 435/6 |
| 5,503,999 A | | 4/1996 | Jilka et al. | 435/172.3 |
| 6,093,544 A | * | 7/2000 | Gonsalves et al. | 435/6 |

FOREIGN PATENT DOCUMENTS

| | | | |
|---|---|---|---|
| EP | 0 571 911 A2 | 12/1993 | C12Q/1/68 |
| WO | WO 96/21034 | 7/1996 | C12N/15/86 |
| WO | WO 97/37037 | 10/1997 | C12Q/1/42 |

OTHER PUBLICATIONS

Minafra et al., "Detection of an unusual RNA in grapevines indexing positive for rupestris stem pitting," 12th Meeting of the International Council for the Study of Viruses and Virus–Like Diseases of the Grapevine (ICVG) Extended Abstracts 43, (Sep. 28–Oct. 2, 1997).

Stobbs et al., "Survey for rupestris stem–pitting and corky bark diseases of grapevine in the Niagara peninsula, Ontario," *Canadian Plant Disease Survey* 75:19–21, (1995).

Meng et al., "Necleotide sequence and genomic organization of grapevine Rupestris stem pitting–associated virus and its detection by RT–PCR," *Phytopathology* 87:S65–S66, 1997.

Zhang et al., "Nucleotide Sequence and RT–PCR Detection of a Virus Associated with Grapevine Rupestris Stem–Pitting Disease," *Phytopatology* 88:1231–1237, 1998.

Azzam et al., "Detection of dsRNA in Grapevines Showing Symptoms of rupestris Stem Pitting Disease and the Variabilities Encountered," *Plant Disease* 75:960–964 (1991).

Azzam et al., "Detection of dsRNA from Cleistothecia and Conidia of the Grape Powdery Mildew Pathogen, *Uncinula necator*," *Plant Disease* 75(9):964–967 (1991).

Beachy et al., "Coat Protein–Mediated Resistance Against Virus Infection," *Annu. Rev. Phytopathol.* 28:451–474 (1990).

Credi, "Characterization of Grapevine Rugose Wood Disease Sources from Italy,"*Plant Diseases* 81(11):1288–1292 (1997).

Krastanova et al., "Transformation of Grapevine Rootstocks with the Coat Protein Gene of Grapevine Fanleaf Nepovirus," *Plant Cell Reports* 14:550–554 (1995).

Le Gall et al., "Agrobacterium–Mediated Genetic Transformation of Grapevine Somatic Embryos and Regeneration of Transgenic Plants Expressing the Coat Protein of Grapevine Chrome Mosaic Nepovirus (GCMV)," *Plant Science* 102:161–170 (1994).

Meng et al., "Nucleotide Sequence and Genomic Organization of Grapevine Rupestris Stem Pitting Associated Virus and Its Detection by RT–PCR," *Phytopathology* 87:S65–66 (1997).

Meng et al., Rupestris Stem Pitting of Grapevines: Nucleotide Sequence, RT–PCR Detection, and Viral Origin of Associated DsRNA, 12th ICVG Meeting pp. 35–36 (1997).

Meng et al., "Nucleotide Sequence and Genome Structure of Grapevine Rupestris Stem Pitting Associated Virus–1 Reveal Similarities to Stem Pitting Virus," *Journal of General Virology*, 79:2059–2069 (1998).

Monette et al., "The Use of In Vitro Cultures in the Investigation of Grapevine Virus–like Diseases," *Canad. J. Plant Pathol.* 12(3):337 (1990).

Monette et al., "Double–Stranded RNA from Rupestris Stem Pitting–Affected Grapevines," *Vitis* 28:137–144 (1989).

Salati et al., "Dectection of Grapevine Viruses Associated with Leafroll, Corky Bark, and Rupestris Stem Pitting Using $F(ab')_2$–ELISA and dsRNA Techniques," *Am. J. Enol. Vitic* 45(3):372 (1994).

Schell et al., "Transformation of 'Nova' Tangelo With the coat Protein Gene of Citrus Tristeza Closteroviurs," *Phytopathology* 84:1076 (1994).

Wetzel et al., "A Highly Sensitive Immunocapture Polymerase Chain Reaction Method for Plum Pox Potyvirus Detection," *Journal of Virological Methods* 39:27–37 (1992).

* cited by examiner

*Primary Examiner*—W. Gary Jones
*Assistant Examiner*—Joyce Tung
(74) *Attorney, Agent, or Firm*—Clark & Elbing LLP

(57) ABSTRACT

The present invention relates to an isolated protein or polypeptide corresponding to a protein or polypeptide of a Rupestris stem pitting associated virus. The encoding DNA molecule, either alone in isolated form, in an expression system, a host cell, or a transgenic grape plant, is also disclosed. Other aspects of the present invention relate to a method of imparting Rupestris stem pitting associated virus resistance to grape plants by transforming them with the DNA molecule of the present invention, and a method of detecting the presence of a Rupestris stem pitting associated virus, such as RSPaV-1, in a sample.

40 Claims, 16 Drawing Sheets

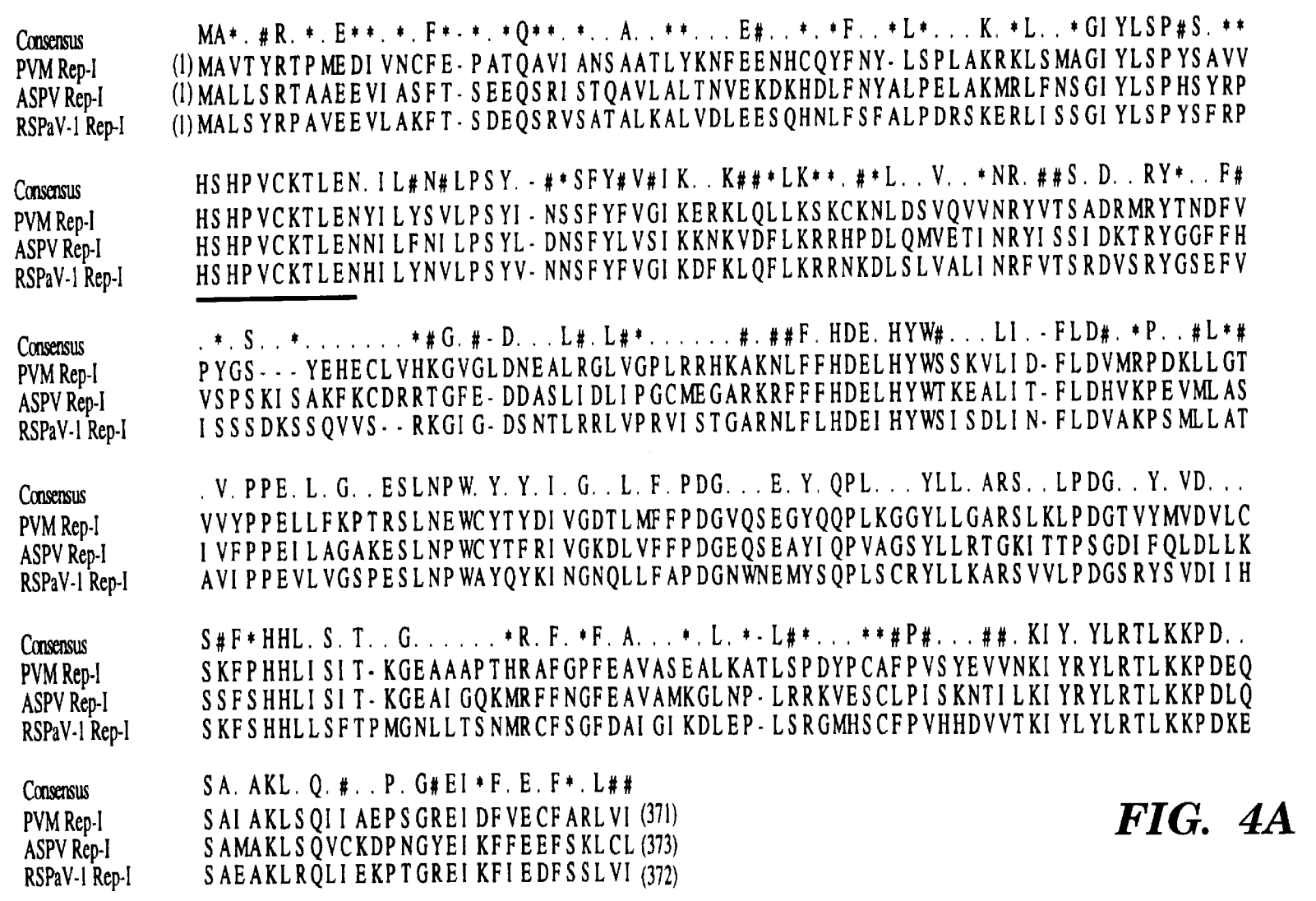

```
Consensus           MA*.#R.*.E**.*.F*-*.*Q**.*..A..**...E#..*.*F..*L*...K.*L..*GIYLSP#S.**
PVM Rep-I        (1)MAVTYRTPMEDIVNCFE-PATQAVIANSAATLYKNFEENHCQYFNY-LSPLAKRKLSMAGIYLSPYSAVV
ASPV Rep-I       (1)MALLSRTAAEEVIASFT-SEEQSRISTQAVLALTNVEKDKHDLFNYALPELAKMRLFNSGIYLSPHSYRP
RSPaV-1 Rep-I    (1)MALSYRPAVEEVLAKFT-SDEQSRVSATALKALVDLEESQHNLFSFALPDRSKERLISSGIYLSPYSFRP

Consensus           HSHPVCKTLEN.IL#N#LPSY.-#*SFY#V#IK..K##*LK**.#*L..V..*NR.##S.D..RY*..F#
PVM Rep-I           HSHPVCKTLENYILYSVLPSYI-NSSFYFVGIKERKLQLLKSKCKNLDSVQVVNRYVTSADRMRYTNDFV
ASPV Rep-I          HSHPVCKTLENNILFNILPSYL-DNSFYLVSIKKNKVDFLKRRHPDLQMVETINRYISSIDKTRYGGFFH
RSPaV-1 Rep-I       HSHPVCKTLENHILYNVLPSYV-NNSFYFVGIKDFKLQFLKRRNKDLSLVALINRFVTSRDVSRYGSEFV

Consensus           .*.S..*.......*#G.#-D...L#.L#*......#.##F.HDE.HYW#...LI.-FLD#.*P..#L*#
PVM Rep-I           PYGS---YEHECLVHKGVGLDNEALRGLVGPLRRHKAKNLFFHDELHYWSSKVLID-FLDVMRPDKLLGT
ASPV Rep-I          VSPSKISAKFKCDRRTGFE-DDASLIDLIPGCMEGARKRFFFHDELHYWTKEALIT-FLDHVKPEVMLAS
RSPaV-1 Rep-I       ISSSDKSSQVVS--RKGIG-DSNTLRRLVPRVISTGARNLFLHDEIHYWSISDLIN-FLDVAKPSMLLAT

Consensus           .V.PPE.L.G..ESLNPW.Y.Y.I.G..L.F.PDG...E.Y.QPL...YLL.ARS..LPDG..Y.VD...
PVM Rep-I           VVYPPELLFKPTRSLNEWCYTYDIVGDTLMFFPDGVQSEGYQQPLKGGYLLGARSLKLPDGTVYMVDVLC
ASPV Rep-I          IVFPPEILAGAKESLNPWCYTFRIVGKDLVFFPDGEQSEAYIQPVAGSYLLRTGKITTPSGDIFQLDLLK
RSPaV-1 Rep-I       AVIPPEVLVGSPESLNPWAYQYKINGNQLLFAPDGNWNEMYSQPLSCRYLLKARSVVLPDGSRYSVDIIH

Consensus           S#F*HHL.S.T..G......*R.F.*F.A...*.L.*-L#*...**#P#...##.KIY.YLRTLKKPD..
PVM Rep-I           SKFPHHLISIT-KGEAAAPTHRAFGPFEAVASEALKATLSPDYPCAFPVSYEVVNKIYRYLRTLKKPDEQ
ASPV Rep-I          SSFSHHLISIT-KGEAIGQKMRFFNGFEAVAMKGLNP-LRRKVESCLPISKNTILKIYRYLRTLKKPDLQ
RSPaV-1 Rep-I       SKFSHHLLSFTPMGNLLTSNMRCFSGFDAIGIKDLEP-LSRGMHSCFPVHHDVVTKIYLYLRTLKKPDKE

Consensus           SA.AKL.Q.#..P.G#EI*F.E.F*.L##
PVM Rep-I           SAIAKLSQIIAEPSGREIDFVECFARLVI (371)
ASPV Rep-I          SAMAKLSQVCKDPNGYEIKFFEEFSKLCL (373)
RSPaV-1 Rep-I       SAEAKLRQLIEKPTGREIKFIEDFSSLVI (372)
```

*FIG. 4A*

```
Consensus               .*GTFG.GKS.L.-K.*.#.*.GK..*FVSPRR#LA.**#.**.#......#K#G.**......V.T*E.
PVM Rep-II        (1163)IVGTFGSGKSTLF-KNLLKYGAGKSLDFVSPRRALAEDFKRTVGMNERGGRAKAGQE----NWRVTTLET
ASPV Rep-II       (1372)ILGTFGCGKSSLF-KKFIEKSPGKAITFVSPRRSLAESINHDLGLARVGGK-KTGKSKDLKNVRVKTFEL
RSPaV-1 Rep-II    (1354)VLGTFGAGKSFLY-KSFMKRSEGKFVTFVSPRRALANSIKNDLEMDDSCKVAKAGRSKKEGWD-VVTFEV
                           A

Consensus               F#..#..#*.G*.V#.DE.QL*PPGY*DL..*....#..*.#*GDP*QS.YD#.#DR.*###..***.*.
PVM Rep-II              FLARVEFLTEGQVVILDEMQLYPPGYFDLVVSMLKVDVRLFLVGDPAQSDYDSEKDRLVLGAMEENMSVV
ASPV Rep-II             FILHLDSIKEGHTVVIDEIQLFPPGYIDLIILGLKPNVNIIIAGDPCQSDYDCSSDRHIFAGSESDIMRI
RSPaV-1 Rep-II          FLRKVAGLKAGHCVIFDEVQLFPPGYIDLCLLIIRSDAFISLAGDPCQSTYDSQKDRAILGAEQSDILRL

Consensus               L.*..Y.#**.S.RF.N*.F..RLPC...K...T.....*...#....*##...*.....VLVSSF*EK*
PVM Rep-II              LGAREYNYKVRSHRFLNCNFIGRLPCEINKDDCTIDEPHIMRMHL--ENLLDVAEEYKSVVLVSSFDEKM
ASPV Rep-II             LSGRSYKFNILSQRFRNPVFYGRLPCNLNKTRLTLDEEEYTLWDSIQEFSMMGRKDCPV-VLVSSFEEKK
RSPaV-1 Rep-II          LEGKTYRYNIESRRFVNPMFESRLPCHFKKGSMTAAFADYAIFHNMHDFLLARSKGPLDAVLVSSFEEKK

Consensus               *V....*.*...#T#GESTGL*F..G.I*##..S..T.*RRW.TAL*RF**##..#N..G........**
PVM Rep-II              VVCAHLPEA-KVLTFGESTGLTFMHGTIYISAVSERTNERRWITALRRFRFNLCFVNCSGMDYQQLAGRY
ASPV Rep-II             IVAAHLGLKMKCITYGESTGLNFQKGAILVTYESALTSDRRWWTALSRFSHDIHFINGMGVTWDNAITHF
RSPaV-1 Rep-II          IVQSYFGMKQLTLTFGESTGLNFKNGGILISHDSFHTDDRRWLTALSRFSHNLDLVNITGLRVESFLSHF

Consensus               .G***..F#*.......*.**LPG.*.#.#**...#G#.EGVRE#KL.GDPWLK.M.*L*Q..*.E.*#.
PVM Rep-II              KGRVRSKFLCKTAIPDDLNSMLPGQALFKSEYPRLIGKDEGVREEKLAGDPWLKTMINLYQAPEVEIAEE
ASPV Rep-II             VGKPLHKFFTKRACNDDIIDLLPGRPELIEGFQSQVGADEGVREAKLVGDPWLKTKIFLGQNPDFEIEIA
RSPaV-1 Rep-II          AGKPLYHFLTAKSGENVIRDLLPGEPNFFSGFNVSIGKNEGVREEKLCGDPWLKVMLFLGQDEDCEVEEM

Consensus               ......E#WF*TH*P...LE#.RA.WV.K...#E#RE#R.G...*.QF.*.H....G.-#L.NA.ER#E.
PVM Rep-II              PEVVMQEEWFRTHLPRDELESVRAQWVHKILAKEYREVRMGDMVSEQFTHDHTKQLGAKQLTNAAERFET
ASPV Rep-II             DEVEAAEDWFKTHIPIMSLEAVRAQWVHKLISREDREFRIGDITTEQFTDDHSKNRGQ-ELTNAAERYEA
RSPaV-1 Rep-II          ESECSNEEWFKTHIPLSNLESTRARWVGKMALKEYREVRCGYEMTQQFFDEHRGGTGE-QLSNACERFES
```

FIG. 4B

```
Consensus          IYPRH**.D..TFLMAV.KRL.FS.P..E.**L**A**#GK*LL*.FL...PL#.*H#..*..EA*-..F
PVM Rep-II         IYPRHRASDTVTFLMAVKKRLSFSNPGKEKGNLFHAASYGKALLSEFLKRVPLKPNHNVRFMEEAL-WNF
ASPV Rep-II        IYPRHKGTDTATFLMAVKKRLSFSSPAAEHAKLRRAKPFGKFLLDTFLKRVPLNSSHDEKMMQEAV-HAF
RSPaV-1 Rep-II     IYPRHKGNDSITFLMAVRKRLKFSKPQVEAAKLRRAKPYGKFLLDSFLSKIPLKASHNSIMFHEAV-QEF

Consensus          E.KK.SKS#ATIENH.GRSC#DW..D#A*IF*KSQ.CTKFDNR-.R#AKA*Q***CFQH#VL.RFAPYMR
PVM Rep-II         EEKKLSKSAATIENHSGRSCRDWPTDVAQIFSKSQLCTKFDNR-FRVAKAAQSIVCFQHAVLCRFAPYMR
ASPV Rep-II        EEKKLSKSMATIENHSGRSCEDWPVDKALIFMKSQLCTKFDNR-FRSAKAGQTLACFQHSVLCRFAPYMR
RSPaV-1 Rep-II     EAKKASKSAATIENHAGRSCRDWLLDVALIFMKSQHCTKFDNR-LRVAKAGQTLACFQHAVLVRFAPYMR

Consensus          YIE.K....L..N.YIHSGK###*#L..WV.*..-F.*#CTESDYEAFDASQD*FI*AFEL..MK*L*LP.
PVM Rep-II         YIEMKVHEVLPKNYYIHSGKGLEELDAWVKKGK-FDRICTESDYEAFDASQDEFIMAFELELMKYLRLPS
ASPV Rep-II        YIESKVTEVLPKNLYIHSGKNIDDLAAWVTTSK-FNGVCTESDYEAFDASQDHFILAFELEVMKFLGLPS
RSPaV-1 Rep-II     YIEKKLMQALKPNFYIHSGKGLDELNEWVRTRG-FTGICTESDYEAFDASQDHFILAFELQIMKFLGLPE

Consensus          DLI.DY.FIK.*LGSKLG*F.IMRF*GEASTFLFNT*ANMLFTF*RY.*.G.E.I.FAGDDMCA*#RL..
PVM Rep-II         DLIEDYKFIKTSLGSKLGNFAIMRFSGEASTFLFNTLANMLFTFMRYNIRGDEFICFAGDDMCASRRLQP
ASPV Rep-II        DLIADYTFIKTHLGSKLGSFAIMRFTGEASTFLFNTMANMLFTFLRYDLNGREAICFAGDDMCANSRLKV
RSPaV-1 Rep-II     DLILDYEFIKIHLGSKLGSFSIMRFTGEASTFLFNTMANMLFTFLRYELTGSESIAFAGDDMCANRRLRL
                                                                             B

Consensus          ......FL..I.LKAKVQF#..-----PTFCGW.L...G#*KKP#L..ER.#IA*E#.NL*NCIDNYAIE
PVM Rep-II         TKKFAHFLDKLKLKAKVQFVQFVN--KPTFCGWHLCPDGIYKKPQLVLERMCIAKEMNNLSNCIDNYAIE
ASPV Rep-II        TNRFSNFLDKIKLKAKVQFTAT-----PTFCGWGLCEHGVFKKPDLVLERLQIARETRNLENCIDNYAIE
RSPaV-1 Rep-II     KTEHEGFLNMICLKAKVQFVSN-----PTFCGWCLFKEGIFKKPQLIWERICIAREMGNLENCIDNYAIE

Consensus          V*#AY.#GE.#...#*##EV.A*YNCVR*.V###H
PVM Rep-II         VAYAYKLGEKAVNRMDEEEVAAFYNCVRIIVRNKH
ASPV Rep-II        VSCAYKMGENLNLYLTPQEVDAHYNCVRFIVQHNH
RSPaV-1 Rep-II     VSYAYRLGELAIEMMTEEEVEAHYNCVRFLVRNKH
```

FIG. 4C

```
Consensus      M...#..L..*.F......L-..P.V.H.VPG*GK##LI###...#.*#.A.T#GV*#.#*#.G.*I*..
PVM 25K        MDVIVDLLYKYKFERLSNKL-VCPIVVHCVPGAGKSSLIRELLELDSRFCAYTAGVEDQPRLSGNWIRKW
ASPV 25K       METVLSLLNEFGFERTVEPL-SDPIVVHAVPGSGKTTLIKQALIRNNNIEAVTFGVPEKANIHGTYIKKA
RSPaV-1 24.4K  MNNLVKALSAFEFVGVFSVL-KFPVVIHSVPGSGKSSLIRELISEDENFIAFTAGVPDSPNLTGRYIKPY

Majority       #.G....G#..*LDEY**.-....**..LF*DP*Q-N.#....A*F*.#...RFG..T#..L...G..#.
PVM 25K        S-GQQPEGKFVVLDEYTLL-TEVPPVFALFGDPIQSNTSAVQRADFVCSVSRRFGSATCGLLRELGWNVR
ASPV 25K       RQGQRGRGNYSILDEYLSG-EYSTGFNCLFSDPYQ-NHGDCLRAHFIGRCSHRFGRQTVQILRDLGYNIA
RSPaV-1 24.4K  SPGCAVPGKVNILDEYLSV-QDFSGFDVLFSDPYQ-NISIPKEAHFIKSKTCRFGVNTCKYLSSFGFKVS

Majority       --S...D.V.#...*#*#..*G*.**..*#..*#...H..E.*.**#**G.TF.#VT...#.......#.
PVM 25K        --SEKADLVQVSDIYTKD-PLGKVVFSEEEVGCLLRSHGVEALSLQEITGQTFEVVTFVTSENSPVINRA
ASPV 25K       --SSKEDIVEKKNIFQLIEPEGVIICLEKGVEDFLKWHSVEYKFPCQVRGATFDIVTFIHEKPLEELVGP
RSPaV-1 24.4K  --SDGLDKVIVGSPFTLDV-EGVLICFGKEAVDLAVAHNSEFKLPCEVRGSTFNVVTLLKSRDPTPEDRH

Majority       ..-#.*.TRHR.**-....
PVM 25K        AA-YQCMTRHRRLC-TSVS
ASPV 25K       DL-FVALTRHRSKL-VLVSN
RSPaV-1 24.4K  WF-YIAATRHREKL-IIMQ
```

FIG. 5A

```
Consensus      MP*.*-----P....K...*..*G....#V*..L..S.LP..GD**H..PHGG.Y#DGTK#*.Y**P..*
PVM 12K        MP-----LTPPPDFTKVYLSAALGVSLALVVWLLIRSTLPVVGDRDHNLPHGGWYRDGTKSVFYNSP--G
ASPV 12K       MPFAQ-----PPDYSKSVFPIAVGIAVAVVLFTLTRSTLPQVGDNIHNLPHGGNYQDGTKRISYCGPRDS
RSPaV-1 12.8K  MPFQQ-----PANWAKTITPLTVGLGIGLVLHFLRKSNLPYSGDNIHQFPHGGRYRDGTKSITYCGPKQS Majority       ***S.....*..........*.L*..*.*#..*..**..*##.*.*....*......
PVM 12K        RLNSIEARKAPLLGQPWAIVVLLVL---LIWASHKLGRPNCR-ACA--GS----HT
ASPV 12K       FPSSSLIS-SGTPMIIGIIIFLIFAIYVSEKWSRSGSRRCSCCVPGAPACTATVHE
RSPaV-1 12.8K  FPSSGIFGQSENFVPLMLVIGLIAFIHVLSVWN-SGLGRNCNCHPNPCSCRQQ
```

*FIG. 5B*

```
Consensus      M....*..L....#V.*...L....#....*...C.*..TGES.....C..***..#.**.##..##.*G
PVM 7K         MIVYVLVGLSAFCIV---LYL---ISQGQS---DCVVLITGESVRVQGCRIDGEFGS----VLSKLKPFG
ASPV 8K        MFPRSGLGLAVAAAVVAYLVLLLAQQLYMSNSSQCTIVITGESVSVVGCVYSEAFIELVKGLKPYYHPLG
RSPaV-1 8.4K   MYCLFGI-LVLVGIVIAIQILAHVDSSSG-NHQGCFIRATGESILIENCGPSEALASTVKEVLGGLKALG

Majority       .............
PVM 7K         CGSFRS
ASPV 8K
RSPaV-1 8.4K   VSRAVEEIDYHC
```

*FIG. 5C*

```
Consensus           *..TLR#.C..YA*.*WN..L.*..PPA*W#.*#F.....#A*FD*F.*V....#**P..G..R.PT.*E
PVM CP       (188)  DAETLRRVCRLYAPVTWNHMLTHNAPPAEWAAMGFQYEDRFAPFDCFDYVENTAAVQPLEGLIRRPTPRE
ASPV CP      (301)  EGCTLRQYCAFYAKHVWNLMLQTQSPPANWVGKEFKFETRYAAFDFFFGVESTASLEPADGLIRLPTQAE
RSPaV-1 CP  (142)  EVTTLRRFCMYYAKIVWNIHLETGIPPANWAKKGFNENEKFAAFDFFLGVTDESALEPKGGIKRAPTKAE

Majority            .VA*..*.*.*..R.#..**..##*.*E..GG..G.....*.......
PVM CP              KVAHNTHKDIAL-RGANRNQVFSSLNAEVTGGMNGPELTRDYVKSNRK
ASPV CP             RVANATSKEIQMYRIRSMEGTQAVNFGEVTGGKIGP---KPVLSI-RK
RSPaV-1 CP         MVANIASFEVQVLRQAMAEGKRSSNLGEISGGTAGALINNPFSNVTHE
```

*FIG. 5D*

```
Consensus      ...G.T.A..AA.TC..C..CA.TTC.....T.CA.TA.TT...C..TTT...AA.G.TG.....A.CCT...
ASPV 3'UTR     TTAGTTAATTAATTCTCCTGCA-TTCAAT--TTCAGTACTTATGCTTTTTAGTAAAGTTGATCCCAACCTAAC
RSPaV-1 3'UTR  --GGATGACGAAGTCAGCGACAATTCCGCAGTCCAATAATTCCCCGATTT--CAAGGCTGGGTTAAGCCTGTT

Consensus      CG..GG....C..T.......GT.T.....TT.CATGCT..A.C.TATTT...........TGT.........
ASPV 3'UTR     CG--GGGCGGCTATGT-----GTGTGTTTCTTTCATGCTTTAGCTTATTTT----------TGT---------
RSPaV-1 3'UTR  CGCTGGAATACCGTACTAATAGTATTCCCTTTCCATGCTAAATCCTATTTAATATATAAGGTGTGGAAAGTAA

Consensus      .......TTT............TAG.TTT...TC
ASPV 3'UTR     -------TTTAAC---------TAGATTT---TC
RSPaV-1 3'UTR  AAGAAGATTTGGTGTGTTTTTATAGTTTTCATTC
```

*FIG. 6A*

```
Consensus      .........................................................................
PVM 3' UTR     .........................................................................
RSPaV-1 3'UTR  GGATGACGAAGTCAGCGACAATTCCGCAGTCCAATAATTCCCCGATTTCAAGGCTGGGTTAAGCCTGTTCGCT

Consensus      ............................CCAT..TAAATCCTATTTAATATATAA.GTGTG..A....AAA.A
PVM 3' UTR     ............................CCAT--TAAATCCTATTTAATATATAACGTGTGCTACTATAAATA
RSPaV-1 3'UTR  GGAATACCGTACTAATAGTATTCCCTTTCCATGCTAAATCCTATTTAATATATAAGGTGTGGAAAGTAAAAGA

Consensus      A.A.TTGGT.T.T...TAT..TTTT.....
PVM 3' UTR     AAACTTGGTTTTTAACTAT--TTTTAGCCA
RSPaV-1 3'UTR  AGATTTGGTGTGTTTTTATAGTTTTCATTC
```

*FIG. 6B*

AMINO ACID IDENTITIES BETWEEN RSPaV-1, RSP14-4, AND RSP158

| | RSPaV-1/RSP47-4 | RSPaV-1/RSP158 |
|---|---|---|
| Nucleotide | 79 % | 87.6 % |
| ORF1 (partial) | 94.1 % | 99.3 % |
| ORF2 | 88.2 % | 95 % |
| ORF3 | 88.9 % | 99.1 % |
| ORF4 | 86.2 % | 88.8 % |
| ORF5 (partial) | 92.9 % | 95.1 % |

```
Consensus          .C.GG..T.AA.G.TGG.CA.TGTGT.ATTTT.GA.GAGGT.CAGTTGTTTCC.CC.GGA.A.ATCGAT.T..G.T..CTT.T.A.ACG.AG.GA.GCTT

140/94-19T7+R1     GCAGGATTGAAGGCTGGCCACTGTGTGATTTTTGATGAGGTCCAGTTGTTTCCTCCTGGATACATCGATCTATGCTTGCTTATTATACGTAGTGATGCTT
140/94-24T7+R1     TCTGGTTTGAAAGCTGGTCATTGTGTGATTTTTGATGAGGTTCAGTTGTTTCCCCCTGGATACATCGATCTGTGTTTACTTGTCATACGAAGTGATGCTT
140/94-2T3+F1RC    GCAGGTCTAAAAGCTGGTCACTGTGTAATTTTCGATGAGGTCCAGTTGTTTCCCCCTGGATACATCGATCTATGTTTGCTTATTATACGTAGTGATGCTT
140/94-42T3RC      GCAGGTNTAAAAGTTGGTCACTGTGTAATTTTGGANGAGGTCCAGTTGTTTCCCCCNGGAAACATCGATNTANGTTNGCTTATNANACGTAGNGANGCTT
140/94-64T7+R1RC   GCAGGATTGAAGGCTGGCCACTGTGTGATTTTCGATGAGGTCCAGTTGTTTCCTCCTGGATACATCGATCTATGCTTGCTTATTATACGTAGTGATGCTT
140/94-6T3+F       GCAGGATTGAAGGCTGGCCACTGTGTGATTTTTGATGAGGTCCAGTTGTTTCCTCCTGGATACATCGATCTATGCTTGCTTATTATACGTAGTGATGCTT
140/94-72T7+R1     TCTGGTTTGAAGGCTGGTCATTGTGTGATTTTCGATGAGGTTCAGTTGTTTCCCCCTGGATATATCGATCTATGTTTACTTGTCATACGCAGTGATGCTT
RSPaV-1            GCAGGATTGAAGGCTGGCCACTGTGTGATTTTTGATGAGGTCCAGTTGTTTCCTCCTGGATACATCGATCTATGCTTGCTTATTATACGTAGTGATGCTT

Consensus          T.ATTT.ACT.GC.GGTGA.CCATG.C..AGCACATATGA.TC.CA.AA.GATCG.GC.ATTTTGGG.GCTGAGCAGAGTGACATACT.A.A.T.CTTGA

140/94-19T7+R1     TCATTTCACTTGCCGGTGATCCATGTCAAAGCACATATGATTCGCAAAAGGATCGGGCAATTTTGGGCGCTGAGCAGAGTGACATACTTAGAATGCTTGA
140/94-24T7+R1     TCATTTCACTTGCTGGTGATCCATGCCAGAGCACATATGATTCACAGAAGGATCGAGCAATTTTGGGAGCTGAGCAGAGTGACATACTCAGACTGCTTGA
140/94-2T3+F1RC    TCATTTCACTTGCTGGTGACCCATGTCAGAGCACATATGACTCACAAAAAGATCGGGCGATTTTGGGCGCTGAGCAGAGTGACATACTCAAAATACTTGA
140/94-42T3RC      TCATTTNACTNGCTGGTGACCCATGTCNGAGCACATATGANTCACAAAAAGATCGGGCGATTTTGGGCGCTGAGCAGAGTGACATACTCAAAATACTTGA
140/94-64T7+R1RC   TCATTTCACTTGCCGGTGATCCATGTCAAAGCACATATGATTCGCAAAAGGATCGGGCAATTTTGGGCGCTGAGCAGAGTGACATACTTAGACTGCTTGA
140/94-6T3+F       TCATTTCACTTGCCGGTGATCCATGTCAAAGCACATATGATTCGCAAAAGGATCGGGCAATTTTGGGCGCTGAGCAGAGTGACATACTTAGAATGCTTGA
140/94-72T7+R1     TTATTTCACTTGCCGGTGATCCATGCCAGAGCACATATGATTCACAAAAGGATCGGGCAATTTTGGGAGCTGAGCAGAGTGACATACTCAGATTGCTTGA
RSPaV-1            TCATTTCACTTGCTGGTGATCCATGTCAAAGCACATATGACTCGCAAAAGGATCGGGCAATTTTGGGCGCTGAGCAGAGTGACATACTTAGACTGCTTGA

Consensus          .GG.AA.AC.TATAGGTA.AACAT.GAAAGCAG..G.TTTGTGAA.CCAATGTT.GAAT...GACT.CCATGTCA.TTCAAAAA.GGG..C.ATGACTGC

140/94-19T7+R1     GGGCAAAACGTATAGGTATAACATAGAAAGCAGGAGGTTTGTGAACCCAATGTTCGAATCAAGACTGCCATGTCACTTCAAAAA-GGGTTCGATGACTGC
140/94-24T7+R1     AGGAAAGACATATAGGTACAACATAGAAAGCAGACGTTTTGTGAACCCAATGTTTGAATCTAGACTACCATGTCACTTCAAAAA-GGGTTCAATGACTGC
140/94-2T3+F1RC    AGGCAAGACGTATAGGTACAACATAGAAAGCAGAAGATTTGTGAACCCAATGTTTGAATCTCGACTGCCATGTCACTTCAAAAA-GGGTACAATGACTGC
140/94-42T3RC      AGGCAAGACGTATAGGTACAACATAGAAAGCAGAAGATTTGTGAACCCAATGTTTGAATCTCGACTGCCATGTCACTTCAAAAA-GGGTACAATGACTGC
140/94-64T7+R1RC   GGGCAAGACGTATAGGTATAACATTGAAAGCAGGAGGTTTGTGAATCCAATGTTCGAATCAAGACTGCCATGTCAATTCAAAAA-GGGCTCAATGACTGC
140/94-6T3+F       GGGCAAAACGTATAGGTATAACATAGAAAGCAGGAGGTTTGTGAACCCAATGTTCGAATCAAGACTGCCATGTCACTTCAAAAA-GGGTTCGATGACTGC
140/94-72T7+R1     AGGAAAGACGTATAGGTACAACATAGAAAGCAGACGTTTTGTGAACCCAATGTTTGAATTTAGACTACCATGTCACTTCAAAAAAGGGTTCAATGACTGC
RSPaV-1            GGGCAAAACGTATAGGTATAACATAGAAAGCAGGAGGTTTGTGAACCCAATGTTCGAATCAAGACTGCCATGTCACTTCAAAAA-GGGCTCGATGACTGC

Consensus          .GC.TT.GCTGATTATGC.AT.TT..................................................................

140/94-19T7+R1     CGCTTTCGCTGATTATGCAATCTTCCATAATATGCATGACTTTCTCCTGGCGAGGTCAAAAGGTCCTTTGGATGCCGTTTTGGTTTCCAGTTTTGAGGAG
140/94-24T7+R1     AGCCTTTGCTGATTATGCAATCTTCCACAATATGCATGACTTCCTCCTGGCGAGGTCAAAAGGCCCCTTGGATGCTGTTCTAGTTTCCAGTTTTGAGGAG
140/94-2T3+F1RC    TGCCTTTGCTGATTATGCCATTTTCCACAATATGCATGATTTCCTCCTGGCAAGGTCAAAAGGTCCTTTGGATGCCATTCTGGTTTCTAGTTTTGAGGAG
140/94-42T3RC      TGCCTTTGCTGATTATGCCATTTTCCACAATATGCATGATTTCCTCCTGGCAAGGTCAAAAGGTCCTTTGGATGCCATTCTGGTTTCAAGTTTTGAGGAG
140/94-64T7+R1RC   CGCTTTCGCTGATTATGCAATCTTCCATAATATGCATGACTTTCTCCTGGCGAGGTCAAAAGGTCCTTTGGATGCCGTTTTGGTTTCCAGTTTTGAGGAG
140/94-6T3+F       CGCTTTCGCTGATTATGCAATCTTCCATAATATGCATGACTTTCTCCTGGCGAGGTCAAAAGGTCCTTTGGATGCCGTTTTGGTTTCCAGTTTTGAGGAG
140/94-72T7+R1     TGCCTTTGCTGATTATGCAATCTT
RSPaV-1            CGCTTTCGCTGATTATGCAATCTTCCATAATATGCATGACTTTCTCCTGGCGAGGTCAAAAGGTCCCTTGGATGCCGTTTTGGTTTCCAGTTTTGAGGAG
```

FIG. 9

DETECTION OF RUPESTRIS STEM PITTING ASSOCIATED VIRUS

This application claims the benefit of U.S. Provisional Patent Applications Serial No. 60/047,147, filed May 20, 1997, and No, 60/069,902, filed Dec. 17, 1997.

This work was supported by the U.S. Department of Agriculture Clonal Repository-Geneva, Grant Nos. 58-2349-9-01 and 58-2349-9 and U.S. Department of Agriculture Cooperative Agreement Grant Nos. 58-1908-4-023, 58-3615-5-036, and 58-3615-7-060. The U.S. Government may have certain rights in the invention.

FIELD OF THE INVENTION

The present invention relates to Rupestris stem pitting associated virus ("RSPaV") proteins, DNA molecules encoding these proteins, and diagnostic and other uses thereof.

BACKGROUND OF THE INVENTION

The world's most widely grown fruit crop, the grape (Vitis sp.), is cultivated on all continents except Antarctica. However, major grape production centers are in European countries (including Italy, Spain, and France), which constitute about 70% of the world grape production (Mullins et al., *Biology of the Grapevine*, Cambridge, U.K.:University Press (1992)). The United States, with 300,000 hectares of grapevines, is the eighth largest grape grower in the world. Although grapes have many uses, a major portion of grape production (~80%) is used for wine production. Unlike cereal crops, most of the world's vineyards ate planted with traditional grapevine cultivars, which have been perpetuated for centuries by vegetative propagation. Several important grapevine virus and virus-like diseases, such as grapevine leafroll, corky bark, and Rupestris stem pitting ("RSP"), are transmitted and spread through the use of infected vegetatively propagated materials. Thus, propagation of certified, virus-free materials is one of the most important disease control measures. Traditional breeding for disease resistance is difficult due to the highly heterozygous nature and outcrossing behavior of grapevines, and due to polygenic patterns of inheritance. Moreover, introduction of a new cultivar may be prohibited by custom or law. Recent biotechnology developments have made possible the introduction of special traits, such as disease resistance, into an established cultivar without altering its horticultural characteristics.

Many plant pathogens, such as fungi, bacteria, phytoplasmas, viruses, and nematodes can infect grapes, and the resultant diseases can cause substantial losses in production (Pearson et al., *Compendium of Grape Diseases*, American Phytopathological Society Press (1988)). Among these, viral diseases constitute a major hindrance to profitable growing of grapevines. About 34 viruses have been isolated and characterized from grapevines. The major virus diseases are grouped into: (1) the grapevine degeneration caused by the fanleaf nepovirus, other European nepoviruses, and American nepoviruses, (2) the leafroll complex, and (3) the rugose wood complex (Martelli, ed., *Graft Transmissible Diseases of Grapevines, Handbook for Detection and Diagnosis*, FAO, UN, Rome, Italy (1993)).

Rugose wood (RW) complex is a term to describe a group of graft-transmissible diseases which are important and widespread on grapevines grown world-wide. Symptoms of RW are characterized by pitting, grooving, or distortion to the woody cylinder of the grapevine scion, rootstock, or both. Based on symptoms developed on different indicator plants after graft inoculation, RW complex can be divided into four components: Kober 5BB stem grooving (KSG), LN 33 stem grooving (LNSG), grapevine corky bark (GCB), and Rupestris stem pitting (RSP) (Martelli, "Rugose Wood Complex," in *Graft-Transmissible Diseases of Grapevines, Handbook for Detection and Diagnosis*, pp. 45–54, Martelli, ed., Food and Agriculture Organization of the United Nations, Rome, Italy (1993)). Because RW can cause severe decline and death to grapevines (Savino et al., "Rugose Wood Complex of Grapevine: Can Grafting to Vitis Indicators Discriminate Between Diseases?", in *Proceedings of the* 9$^{th}$ *Meetings of the International Council for the Study of Viruses and Virus Diseases of the Grapevine*, Anavim, Israel (1989); Credi and Babini, "Effect of Virus and Virus-like Infections on the Growth of Grapevine Rootstocks," *Adv. Hort. Sci.,* 10:95–98 (1996)), it has been included in healthy grapevine detection schemes used in major grapevine growing countries including Italy, France, and the United States.

RSP was discovered in California in the late 1970s (Prudencio, "M. Sc. Thesis: Comparative Effects of Corky Bark and Rupestris Stem Pitting Diseases on Selected Germplasm Lines of Grapes," University of California, Davis, Calif., 36 pages (1985); Goheen, "Rupestris Stem Pitting," in *Compendium of Grape Diseases*. p. 53, Pearson and Goheen, eds., American Phytopathological Society Press, St. Paul, Minn., USA (1988) ("Goheen")). The disease was defined by Goheen as follows: after graft inoculation with a chip bud from an infected grapevine, the woody cylinder of the indicator plant *Vitis rupestris* Scheele St. George ("St. George") develops a narrow strip of small pits extending from the inoculum bud to the root zone. Grafted St. George plants were checked for wood symptoms 2 to 3 years after inoculation. In contrast to GCB, which elicits pitting and grooving on St. George and LN 33, RSP does not produce symptoms on the latter (Goheen, "Rupestris Stem Pitting," in *Compendium of Grape Diseases*, p. 53, Pearson and Goheen, eds., American Phytopathological Society Press, St. Paul, Minn. , USA (1988)).

RSP is probably the most common component of the RW complex on grapevines. Surveys in California revealed a high disease incidence in many grapevine cultivars imported from Western Europe and Australia (Goheen, "Rupestris Stem Pitting," in *Compendium of Grape Diseases*, p. 53, Pearson and Goheen, eds., American Phytopathological Society Press, St. Paul, Minn. , USA (1988)). An examination of indexing records in California compiled over 23 years revealed RSP infection in 30.5% of 6482 grapevine selections introduced from around the world (Golino and Butler, "A Preliminary Analysis of Grapevine Indexing Records at Davis, Calif.," in *Proceedings of the* 10th Meeting of the ICVG, pp. 369–72, Rumbos et al., eds., Volos, Greece (1990)). Indexing in New York State showed that 66% of 257 grapevines tested on St. George developed typical small pits below the inoculum bud or around the woody cylinder (Azzam and Gonsalves, Abstract: "Survey of Grapevine Stem-Pitting in New York and Isolation of dsRNA from a Grapevine Selection Infected with Stem Pitting," *Phytopatholoy* 78:1568 (1988)). Furthermore, several reports have indicated that RSP is the most frequently detected component of the RW complex in Italy (Borgo and Bonotto, "Rugose Wood Complex of Grapevine in Northeastern Italy: Occurrence of Rupestris Stem Pitting and Kober Stem Grooving," in *Extended Abstracts of the* 11*th Meeting of the International Council for the Study of Viruses and Virus Diseases of the Grapevine* (*ICVG*), pp. 61–62, Gugerli, ed., Montreux, Switzerland (1993); Credi, "Differential Indexing Trials on Grapevine Rugose Wood Syndrome," *Extended Abstracts of the* 11*th Meeting of the International Council for the Study of Viruses and Virus Diseases of the Grapevine* (*ICVG*), p. 63, Gugerh, P., ed., Montreux, Switzerland (1993)).

The effect of RSP on growth, yield, and grapevine quality is not well understood and, thus, subject to debate. The reason for this ambiguity is the absence of a rapid and sensitive diagnostic tool. RSP is the most difficult grapevine disease to diagnose. Serological or molecular methods are not available for diagnosing RSP. Biological indexing on St. George, as described above, has remained the only approach to diagnose RSP. Biological indexing is labor intensive, time consuming (i.e., often requiring up to about three years to obtain results), and, by its very nature, subjective. Moreover, symptoms on St. George can be variable and not exactly as those defined by Goheen. In particular, Credi, "Characterization of Grapevine Rugose Wood Sources from Italy," *Plant Disease,* 82:1288–92 (1997), recently showed that some RSP infected grapevines induced pitting that is restricted to below the inoculum bud, while others induced pitting around the woody cylinder of inoculated St. George. Thus, the present method of identifying the presence of RSP is not entirely adequate.

The etiology of RSP is unknown. Efforts to isolate virus particles from RSP-infected grapevines and to mechanically transfer the causal virus(es) to herbaceous host plants failed (Azzam and Gonsalves, "Detection of in Grapevines Showing Symptoms of Rupestris Stem Pitting Disease and the Variabilities Encountered," *Plant Disease,* 75:96–964 (1991)). However, a major dsRNA species of ca. 8.3 kb, accompanied by a smaller dsRNA of ca. 7.6 kb, was consistently isolated from one Pinot Gris and four Pinot Noir clones that had been indexed positive for RSP (Walter and Cameron, "Double-Stranded RNA Isolated from Grapevines Affected by Rupestris Stem Pitting Disease," *Am. J. of Enology and Viticulture,* 42:175–79 (1991)). In addition, a third dsRNA of ca. 5.5 kb was observed in three clones. Likewise, an apparently similar dsRNA species of ca. 8.0 and 6.7 kbp was isolated from dormant canes of RSP-infected grapevines collected from California, Canada, and New York (Azzam and Gonsalves, "Detection of dsRNA in Grapevines Showing Symptoms of Rupestris Stem Pitting Disease and the Variabilities Encountered," *Plant Disease,* 75:960–64 (1991)). Six of eight Californian and three of five Canadian samples contained these two dsRNA species. However, results of New York samples were not consistent. Among eight RSP infected grapevine selections tested, only one showed these two dsRNAs. Using explants growing in tissue culture as source materials, dsRNA of ca. 359 bp was isolated from 21 of 31 grapevine cultivars, all of which were previously indexed on St. George and considered to be infected with RSP (Monette et al., "Double-Stranded RNA from Rupestris Stem Pitting-Affected Grapevines," *Vitis,* 28:137–44 (1989)).

In view of the serious risk RSP poses to vineyards and the absence of an effective treatment of it, the need to prevent this affliction continues to exist. Moreover, the absence of a rapid and accurate diagnostic assay prevents proper identification of RSP. The present invention is directed to overcoming these deficiencies in the art.

SUMMARY OF THE INVENTION

The present invention relates to an isolated protein or polypeptide corresponding to a protein or polypeptide of a RSP virus. The encoding RNA molecule or DNA molecule, in either isolated form or incorporated in an expression system, a host cell, or a transgenic Vitis scion or rootstock cultivar, are also disclosed.

Another aspect of the present invention relates to a method of imparting RSP virus resistance to Vitis scion or rootstock cultivars by transforming them with a DNA molecule encoding the protein or polypeptide corresponding to a protein or polypeptide of a RSP virus.

The present invention also relates to an antibody or binding portion thereof or probe which recognizes proteins or polypeptides of the present invention.

Still another aspect of the present invention relates to diagnostic tests which involve methods for detecting the presence of a RSP virus in a sample. The methods include the use of an antibody or binding portion of the present invention (i.e., in an immunoassay), or a nucleic acid probe obtained from a DNA molecule of the present invention (i.e., in a nucleic acid hybridization assay or gene amplification detection procedure). The antibody or binding portion thereof, or nucleic acid probe, is introduced into contact with the sample, whereby the presence of Rupestris stem pitting virus in the sample is detected using an assay system.

The characterization of an RSP virus is particularly desirable because it will allow for the determination of whether the virus is associated to the specific (restricted) or nonspecific (nonrestricted) pitting symptoms of RSP, or to both. Also, RSP virus resistant transgenic variants of the current commercial grape cultivars and rootstocks allows for more complete control of the virus while retaining the varietal characteristics of specifics cultivars. Furthermore, these variants permit control over RSP virus transmitted by infected scions or rootstocks. Moreover, the diagnostic tests offer significant improvement over conventional diagnostic means currently employed, namely, rapid results and greater accuracy.

BRIEF DESCRIPTION OF THE DRAWINGS

FIG. 4A is a comparative sequence listing of amino acid sequences of region I (aa 1–372) of RSPaV-1 ORF1 (SEQ ID NO:58) with the corresponding sequences of carlavirus PVM (SEQ ID NO:56) and ASPV (SEQ ID NO:57). The methyltransferase motif is underlined. Capital letters indicate consensus residues (SEQ ID NO:55). FIG. 4B is a comparative sequence listing of amino acid sequences of region II (aa 1354 to end) of RSPaV-1 ORF1 (SEQ ID NO:62) with the corresponding regions of ASPV (SEQ ID NO:61) and PVM carlavirus (SEQ ID NO:60). In FIG. 4B, the NTP binding motif is underlined at (A) and at the GDD containing sequence is underlined at (B). In FIGS. 4A and 4B, capital letters indicate consensus residues (SEQ ID NO:59), the symbol * indicates identical amino acid residues between RSPaB-1 and ASPV, and the symbol# indicates identical amino acid residues between RSPaV-1 and PMV. FIG. 4C is a comparative sequence listing of amino acid sequences of region II of RSPaV-1 ORF1 (SEQ ID NO:66), with the corresponding regions of ASPV (SEQ ID NO:65) and and PVM carlavirus (SEQ ID NO:64). In FIG. 4C the top line indicates consensus residues (SEQ ID NO:63).

FIGS. 5A–D are comparative sequence listings of amino acid sequences for ORF2, ORF3, ORF4, and a C-terminal part of ORF5 (CP) of RSPaV-1, respectively, with ASPV and PVM carlavirus. FIG. 5A is a comparative sequence listing of amino acid sequences for ORF2 of RSPaV-1 (SEQ ID NO:70), with the corresponding regions of ASPV (SEQ ID NO:69) and PVM carlavirus (SEQ ID NO:68). The top line shows the consensus sequence for ORF2 (SEQ ID NO:67). The NTP binding motif located near the C-terminus of ORF2 is underlined. FIG. 5B is a comparative sequence listing of amino acid sequences for ORF3 of RSPaV-1 (SEQ ID NO:74) with the corresponding regions of PVM (SEQ ID NO:72) and ASPV (SEQ ID NO:73). The top line shows the consensus sequence for ORF3 (SEQ ID NO:71). FIG. 5C is a comparative sequence listing of amino acid sequences for ORF4 of RSPaV-1 (SEQ ID NO: 78) with the corresponding regions of PVM (SEQ ID NO:76) and ASPV (SEQ ID NO:77). The top line shows the consensus sequence for ORF4 (SEQ ID NO:75). FIG. 5D is a comparative sequence listing of amino acid sequences for a C-terminal part of ORF5 of RSPaV-1 (SEQ ID NO:82) with the corresponding regions of PVM (SEQ ID NO: 80) and ASPV (SEQ ID NO:81). The top line shows the consensus sequence for ORF4 (SEQ ID NO:79). The conserved motif (RR/QX——XFDF), located in the central region of the coat proteins and proposed to be involved in the formation of a salt bridge structure, is underlined. In each of the figures, capital letters indicate consensus residues. The symbol * indicates identical amino acid residues between RSPaV-1 and ASPV, and the symbol # indicates identical amino acid residues between RSPaV-1 and PMV. In FIG. 5D, numbers which appear in parentheses and precede the sequences indicate the start points of the c-terminal portions of CPs being compared.

FIG. 6A is a comparative sequence listing of DNA nucleotide sequences for the 3' untranslated region (UTR) of RSPaV-1 (SEQ ID NO:85) and ASPV (SEQ ID NO:84). The top line depicts the consensus sequence for the 3' UTR(SEQ ID NO:83). FIG. 6B is a comparative sequence listing of DNA nucleotide sequences for the 3' untranslated region (UTR) of RSPaV-1 (SEQ ID NO:88) and PVM (SEQ ID NO:87). Clustal method of MegAlign (DNASTAR) was used to generate sequence alignments. The 21 identical consecutive nucleotides between RSPaV-1 and PVM are indicated as shadowed letters (SEQ ID NO:86).

FIG. 9 is a comparative alignment of nucleotide sequences of seven other clones (SEQ ID NO:90–96) with the comparable region of RSPaV-1 (SEQ ID NO:97). Shaded areas indicate identical nucleotide sequences, whereas white boxes represent different nucleotide sequences. The top line depicts the consensus sequence (SEQ ID NO:89) for the nucleotide sequences.

DETAILED DESCRIPTION OF THE INVENTION

Figure 1:
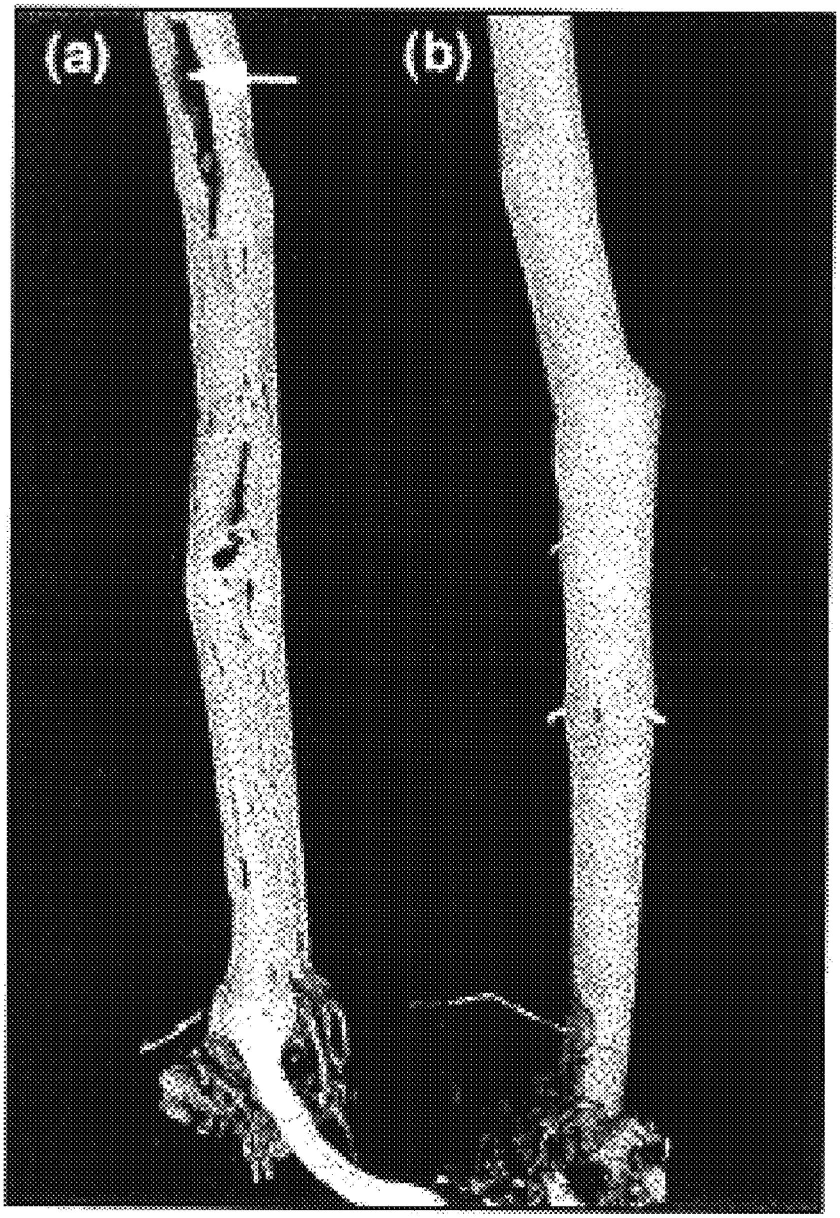
FIG. 1 is a photograph of St. George indicators which comparatively display the symptoms of RSP. The St. George indicator (a) has been graft-inoculated with infected bud wood from a grapevine accession, resulting in the indicator displaying pitting below the inoculum bud, as indicated by an arrow. This RSP symptom was defined by Goheen, "Rupestris Stem Pitting," in *Compendium of Grape Diseases*, p. 53, Pearson and Goheen, eds., American Phytopathological Society Press, St. Paul, Minn., USA (1988), which is hereby incorporated by reference. The St. George indicator (b) was not graft-inoculated and represents a normal appearance.

The present invention relates to isolated DNA molecules encoding for the proteins or polypeptides of a Rupestris stem pitting associated virus. Since the nucleotide sequence was derived from cDNA clones of the dsRNA that was associated with RSP, the viral agent has been designated as Rupestris stem pitting associated virus ("RSPaV"). RSP is likely caused by one or a number of viral strains. The genome of each RSPaV has a plurality of open reading frames, each containing DNA molecules in accordance with the present invention. The complete genome of one strain has been sequenced and the strain is designated RSPaV-1.

Substantial portions of the genomes of two other RSPaV strains have also been sequenced. These strains are designated by their clone names, RSP47-4 and RSP158.

The DNA molecule which constitutes the complete RSPaV-1 genome comprises the nucleotide sequence corresponding to SEQ. ID. No. 1 as follows:

```
CGATAAACAT AACAACAGAA TCTGCATTGC AGTAATATTC CTTGAATATA ATTGCAACGC     60
AATGGCCCTC TCTTATAGGC CTGCTGTTGA AGAGGTGCTC GCAAAATTCA CCTCTGATGA    120
ACAATCCAGG GTTTCTGCTA CAGCTCTCAA GGCATTAGTA GACTTAGAGG AAAGTCAGCA    180
CAATTTGTTC TCTTTCGCAT TGCCTGATAG AAGCAAAGAA AGGCTGATAT CTTCTGGCAT    240
TTACTTAAGT CCTTACAGTT TCAGACCCCA CTCACATCCA GTTTGTAAAA CTTTAGAAAA    300
TCACATTTTG TACAATGTTT TACCTAGTTA TGTTAATAAT TCATTTTACT TTGTAGGAAT    360
CAAGGATTTT AAGCTGCAGT TCTTGAAAAG GAGGAATAAG GATCTCAGCT TGGTAGCACT    420
CATAAATAGG TTTGTGACAA GTCGTGATGT TAGTAGGTAT GGGTCTGAGT TCGTTATAAG    480
TTCTAGTGAC AAATCAAGTC AGGTTGTCAG TAGAAAGGGC ATTGGTGATT CTAACACACT    540
CCGGAGATTG GTCCCACGTG TAATTTCCAC AGGTGCCAGG AATCTTTTTC TGCATGATGA    600
GATTCACTAC TGGTCAATTA GTGATCTGAT CAATTTTTTG GACGTTGCCA AGCCAAGCAT    660
GCTCTTGGCA ACTGCAGTAA TCCCTCCAGA AGTGCTGGTT GGCTCTCCAG AGAGTCTTAA    720
CCCTTGGGCC TACCAGTATA AAATCAATGG CAACCAACTG CTCTTCGCAC CAGATGGCAA    780
CTGGAATGAG ATGTACTCAC AACCTTTGTC ATGCAGATAC CTGCTCAAGG CCAGATCTGT    840
AGTTCTGCCC GATGGCTCAC GCTACTCGGT TGACATCATT CACTCAAAAT TTAGTCACCA    900
CTTGCTTAGT TTCACCCCTA TGGGTAATCT TTTGACTTCA AACATGCGAT GTTTTTCTGG    960
CTTCGATGCA ATAGGCATAA AAGATCTTGA ACCTCTAAGC CGCGGCATGC ACAGTTGCTT   1020
CCCAGTACAT CATGATGTTG TAACTAAGAT ATATCTTTAT TTGAGAACTC TCAAGAAGCC   1080
AGATAAGGAG TCTGCCGAGG CAAAGCTTCG ACAACTCATA GAAAAACCCA CAGGGAGGGA   1140
GATAAAGTTT ATCGAGGATT TTTCCTCACT AGTAATAAAT TGTGGGAGGA GTGGCTCTTT   1200
GCTTATGCCC AACATTTCTA AGTTGGTCAT ATCATTCTTT TGCCGGATGA TGCCAAATGC   1260
ACTCGCCAGG CTCTCTTCTA GCTTTCGAGA GTGTTCGCTA GATTCATTTG TGTACTCACT   1320
TGAGCCCTTT AATTTTTCCG TTAATTTAGT GGATATAACT CCTGATTTCT TTGAGCATTT   1380
ATTTCTCTTC TCCTGCCTAA ATGAGTTGAT CGAGGAGGAC GTTGAAGAGG TCATGGACAA   1440
TTCTTGGTTT GGACTTGGGG ACTTACAATT CAATCGCCAG AGGGCCCCGT TCTTTCTTGG   1500
GTCTTCATAT TGGCTCAACT CCAAATTTTC AGTTGAGCAC AAGTTTTCAG GCACCATCAA   1560
TTCTCAAATC ATGCAAGTTA TTTTATCTTT GATCCCATTT TCTGATGATC CCACTTTTAG   1620
GCCATCTTCT ACAGAGGTTA ACCTTGCACT ATCAGAGGTT AAGGCTGCGC TAGAAGCTAC   1680
TGGGCAGTCA AAATTGTTCA GGTTTTTGGT GGACGACTGT GCTATGCGTG AGGTTAGAAG   1740
TTCCTATAAG GTGGGCCTTT TTAAGCACAT AAAAGCCCTC ACTCATTGCT TTAATTCTTG   1800
TGGCCTCCAA TGGTTCCTCC TTAGGCAAAG GTCCAACCTC AAATTTCTGA AGGACAGGGC   1860
ATCGTCCTTT GCTGATCTTG ATTGTGAGGT TATCAAAGTT TATCAGCTTG TAACATCACA   1920
GGCAATACTT CCTGAGGCTC TGCTTAGCTT GACCAAAGTC TTTGTCAGGG ATTCTGACTC   1980
AAAGGGTGTT TCCATTCCCA GATTGGTCTC GAGAAATGAG CTAGAGGAAC TAGCTCACCC   2040
AGCTAATTCA GCCCTTGAGG AGCCTCAATC AGTTGATTGT AATGCAGGCA GGGTTCAAGC   2100
AAGCGTTTCA AGTTCCCAGC AGCTTGCCGA CACCCACTCT CTTGGTAGCG TTAAGTCATC   2160
AATTGAGACA GCTAACAAGG CTTTTAACTT GGAGGAGCTA AGGATCATGA TTAGAGTCTT   2220
GCCGGAGGAT TTTAACTGGG TGGCGAAGAA CATTGGTTTT AAAGACAGGC TGAGAGGCAG   2280
```

-continued

```
GGGTGCATCA TTCTTCTCAA AACCAGGAAT TTCATGTCAT AGTTACAATG GTGGGAGCCA  2340
CACAAGCTTA GGGTGGCCAA AGTTCATGGA TCAGATTCTA AGCTCCACTG GTGGACGTAA  2400
TTACTACAAT TCATGCCTGG CTCAGATCTA TGAGGAAAAT TCAAAATTGG CTCTTCATAA  2460
GGATGATGAG AGTTGCTATG AAATTGGGCA CAAAGTTTTG ACTGTTAATT TAATCGGCTC  2520
AGCAACTTTC ACTATTAGTA AGTCGCGAAA TTTGGTTGGG GGTAATCATT GCAGCCTGAC  2580
AATTGGGCCA AATGAGTTTT TCGAAATGCC TAGGGGCATG CAATGCAATT ACTTCCATGG  2640
GGTTTCCAAT TGTACGCCAG GGCGGGTATC GCTGACCTTT AGGCGCCAAA AGTTGGAAGA  2700
TGATGATTTG ATCTTCATAA ATCCACAGGT GCCCATTGAG CTCAATCATG AAAAGCTTGA  2760
CCGAAGTATG TGGCAGATGG GCCTTCATGG AATTAAGAAA TCTATTTCTA TGAATGGCAC  2820
GAGTTTTACC TCAGACCTAT GCTCTTGTTT CTCTTGCCAC AACTTTCATA AATTCAAGGA  2880
TCTCATCAAT AACTTGAGAT TGGCCCTAGG AGCACAAGGG CTAGGTCAGT GTGACAGGGT  2940
TGTGTTTGCA ACAACAGGTC CTGGTCTATC TAAGGTTTTA GAAATGCCTC GGAGCAAAAA  3000
GCAATCAATT TTGGTTCTTG AAGGTGCCCT ATCCATAGAA ACAGATTATG GTCCAAAAGT  3060
CCTGGGGTCT TTTGAAGTTT TCAAAGGGGA CTTTCACATT AAGAAGATGG AGGAAGGTTC  3120
AATTTTTGTA ATAACGTACA AGGCCCCAAT TAGATCCACT GGCAGGTTGA GGGTTCACAG  3180
TTCAGAATGC TCATTTTCCG GATCCAAAGA GGTATTGCTA GGCTGCCAGA TTGAGGCATG  3240
TGCTGATTAT GATATTGATG ATTTTAACAC TTTCTCTGTG CCTGGTGATG GCAATTGCTT  3300
TTGGCATTCT GTTGGTTTTT TACTTAGCAC TGATGGACTT GCCCTAAAGG CCGGTATTCG  3360
ATCTTTCGTG GAGAGTGAGC GCTTGGTAAG TCCAGATCTT TCAGCCCCAG CAATTTCTAA  3420
ACAATTGGAA GAGAATGCTT ATGCCGAGAA TGAGATGATC GCATTATTCT GCATTCGGCA  3480
CCACGTAAGG CCTATAGTGA TCACACCAGA ATATGAAGTT AGTTGGAAAT TCGGGGAAGG  3540
TGAGTGGCCC CTATGTGGAA TTCTTTGCCT TAAATCAAAT CACTTCCAAC CATGCGCCCC  3600
ACTGAATGGT TGCATGATCA CAGCCATTGC TTCAGCACTT GGAAGGCGTG AAGTTGATGT  3660
GTTAAATTAT CTGTGTAGAC CCAGCACTAA TCATATTTTT GAGGAGCTTT GTCAGGGAGG  3720
GGGCCTTAAC ATGATGTATT TAGCTGAAGC TTTTGAGGCC TTTGACATTT GCGCTAAATG  3780
TGATATAAAT GGAGAGATTG AAGTGATTAA TCCGTGTGGT AAAATTTCTG CATTGTTTGA  3840
CATAACTAAT GAGCACATAA GGCATGTTGA GAAAATAGGT AATGGCCCTC AGAGCATAAA  3900
AGTGGATGAA TTGCGGAAGG TCAAGCGATC CGCCCTCGAT TTCCTTTCAA TGAATGGGTC  3960
TAAAATAACC TACTTCCCAA GCTTTGAGCG GGCTGAAAAG TTGCAAGGAT GTTTGCTAGG  4020
GGGCCTAACT GGCGTTATAA GTGATGAGAA GTTCAGTGAT GCAAAACCTT GGCTTTCTGG  4080
TATATCTACT ACTGATATTA AGCCAAGGGA ATTGACTGTC GTGCTTGGTA CATTTGGGGC  4140
TGGGAAGAGT TTCTTGTACA AGAGTTTCAT GAAAAGGTCT GAGGGTAAAT TCGTAACCTT  4200
TGTTTCTCCC AGACGTGCTT TAGCAAATTC AATCAAAAAT GATCTTGAAA TGGATGATAG  4260
CTGCAAAGTT GCTAAAGCAG GTAGGTCAAA GAAGGAAGGG TGGGATGTAG TAACTTTTGA  4320
GGTTTTCCTT AGAAAAGTTG CAGGATTGAA GGCTGGCCAC TGTGTGATTT TTGATGAGGT  4380
CCAGTTGTTT CCTCCTGGAT ACATCGATCT ATGCTTGCTT ATTATACGTA GTGATGCTTT  4440
CATTTCACTT GCTGGTGATC CATGTCAAAG CACATATGAC TCGCAAAAGG ATCGGGCAAT  4500
TTTGGGCGCT GAGCAGAGTG ACATACTTAG ACTGCTTGAG GGCAAAACGT ATAGGTATAA  4560
CATAGAAAGC AGGAGGTTTG TGAACCCAAT GTTCGAATCA AGACTGCCAT GTCACTTCAA  4620
AAAGGGCTCG ATGACTGCCG CTTTCGCTGA TTATGCAATC TTCCATAATA TGCATGACTT  4680
```

-continued

```
TCTCCTGGCG AGGTCAAAAG GTCCCTTGGA TGCCGTTTTG GTTTCCAGTT TTGAGGAGAA  4740
AAAGATAGTC CAGTCCTACT TTGGAATGAA ACAGCTCACA CTCACATTTG GTGAATCAAC  4800
TGGGTTGAAT TTCAAAAATG GGGGAATTCT CATATCACAT GATTCCTTTC ACACAGATGA  4860
TCGGCGGTGG CTTACTGCTT TATCTCGCTT CAGCCACAAT TTGGATTTGG TGAACATCAC  4920
AGGTCTGAGG GTGGAAAGTT TTCTCTCGCA CTTTGCTGGC AAACCCCTCT ACCATTTTTT  4980
AACAGCCAAA AGTGGGGAGA ATGTCATACG AGATTTGCTC CCAGGTGAGC CTAACTTCTT  5040
CAGTGGCTTT AACGTTAGCA TTGGAAAGAA TGAAGGTGTT AGGGAGGAGA AGTTATGTGG  5100
TGACCCATGG TTAAAAGTTA TGCTTTTCCT GGGTCAAGAT GAGGATTGTG AAGTTGAAGA  5160
GATGGAGTCA GAATGCTCAA ATGAAGAATG GTTTAAAACC CACATCCCCT TGAGTAATCT  5220
GGAGTCAACC AGGGCCAGGT GGGTGGGTAA AATGGCCTTG AAAGAGTATC GGGAGGTGCG  5280
TTGTGGTTAT GAAATGACTC AACAATTCTT TGATGAGCAT AGGGGTGGAA CTGGTGAGCA  5340
ACTGAGCAAT GCATGTGAGA GGTTTGAAAG CATTTACCCA AGGCATAAAG GAAATGATTC  5400
AATAACCTTC CTCATGGCTG TCCGAAAGCG TCTCAAATTT TCGAAGCCCC AGGTTGAAGC  5460
TGCCAAACTG AGGCGGGCCA AACGATATGG GAAATTCTTA TTAGATTCTT TCCTATCCAA  5520
AATCCCATTG AAAGCCAGTC ATAATTCCAT CATGTTTCAT GAAGCGGTAC AGGAGTTTGA  5580
GGCGAAGAAG GCTAGTAAGA GTGCAGCAAC TATAGAGAAT CATGCAGGTA GGTCATGCAG  5640
GGATTGGTTA TTAGATGTTG CTCTGATTTT TATGAAGTCA CAACACTGTA CTAAATTTGA  5700
CAACAGGCTT AGAGTAGCTA AAGCTGGGCA AACCCTTGCT TGCTTCCAAC ATGCTGTTCT  5760
GGTTCGCTTT GCACCCTATA TGAGATACAT TGAGAAAAAG CTAATGCAAG CTCTGAAGCC  5820
TAACTTCTAC ATCCATTCAG GGAAAGGTCT GACGAGCTGA ACGAGTGGGT CAGAACTAGA  5880
GGATTCACTG GAATTTGCAC AGAATCAGAC TACGAAGCCT TTGATGCTTC CCAAGACCAC  5940
TTCATCCTAG CATTCGAATT GCAGATAATG AAATTTTTGG GGTTACCTGA AGATTTAATT  6000
TTGGACTATG AATTCATAAA AATTCATTTG GGATCAAAGC TCGGATCATT CTCTATAATG  6060
AGGTTTACTG GGGAGGCCAG CACATTTCTG TTTAACACTA TGGCTAACAT GTTGTTCACC  6120
TTTCTGAGGT ACGAACTAAC AGGCTCTGAG TCAATAGCAT TTGCAGGTGA TGACATGTGT  6180
GCTAATCGAA GGTTGCGGCT TAAAACAGAG CATGAGGGTT TTCTGAACAT GATTTGCCTT  6240
AAGGCCAAGG TTCAGTTTGT TTCCAATCCC ACATTCTGCG GATGGTGTTT ATTTAAGGAA  6300
GGGATCTTCA AGAAGCCTCA ATTAATCTGG GAGCGGATAT GCATTGCTAG GGAGATGGGC  6360
AACCTGGAGA ATTGTATTGA CAATTATGCG ATAGAGGTCT CCTATGCATA CCGACTGGGA  6420
GAGCTAGCCA TTGAAATGAT GACCGAGGAA GAAGTGGAGG CCCATTATAA TTGTGTTAGA  6480
TTCTTGGTCA GGAACAAGCA TAAGATGAGA TGCTCAATTT CAGGCCTATT TGAAGCTATT  6540
GATTAGGCCT TAAGTATTTG GCATTATTTG AGTATTATGA ATAATTTAGT TAAAGCATTG  6600
TCAGCATTTG AGTTTGTAGG TGTTTTCAGT GTGCTTAAAT TTCCAGTAGT CATTCATAGT  6660
GTGCCTGGTA GTGGTAAAAG TAGTTTAATA AGGGAGCTAA TTTCCGAGGA TGAGAATTTC  6720
ATAGCTTTCA CAGCAGGTGT TCCAGACAGC CCTAATCTCA CAGGAAGGTA CATTAAGCCT  6780
TATTCTCCAG GGTGTGCAGT GCCAGGGAAA GTTAATATAC TTGATGAGTA CTTGTCCGTC  6840
CAAGATTTTT CAGGTTTTGA TGTGCTGTTC TCGGACCCAT ACCAAAACAT CAGCATTCCT  6900
AAAGAGGCAC ATTTCATCAA GTCAAAAACT TGTAGGTTTG GCGTGAATAC TTGCAAATAT  6960
CTTTCCTCCT TCGGTTTTAA GGTTAGCAGT GACGGTTTGG ACAAAGTCAT TGTGGGGTCG  7020
CCTTTTACAC TAGATGTTGA AGGGGTGCTA ATATGCTTTG GTAAGGAGGC AGTGGATCTC  7080
```

-continued

```
GCTGTTGCGC ACAACTCTGA ATTCAAATTA CCTTGTGAAG TTAGAGGTTC AACTTTTAAC  7140
GTCGTAACTC TTTTGAAATC AAGAGATCCA ACCCCAGAGG ATAGGCACTG GTTTTACATT  7200
GCTGCTACAA GACACAGGGA GAAATTGATA ATCATGCAGT AAGATGCCTT TTCAGCAGCC  7260
TGCGAATTGG GCAAAAACCA TAACTCCATT GACAGTTGGC TTGGGCATTG GGCTTGTGCT  7320
GCATTTTCTG AGGAAGTCAA ATCTACCTTA TTCAGGGGAC AACATCCATC AATTCCCTCA  7380
CGGTGGGCGT TACAGGGACG GTACAAAAAG TATAACTTAC TGTGGTCCAA AGCAATCCTT  7440
CCCCAGCTCT GGGATATTCG GCCAATCTGA GAATTTTGTG CCCTTAATGC TTGTCATAGG  7500
TCTAATCGCA TTCATACATG TATTGTCTGT TTGGAATTCT GGTCTTGGTA GGAATTGTAA  7560
TTGCCATCCA AATCCTTGCT CATGTAGACA GCAGTAGTGG CAACCACCAA GGTTGCTTCA  7620
TTAGGGCCAC TGGAGAGTCA ATTTTGATTG AAAACTGCGG CCCAAGTGAG GCCCTTGCAT  7680
CCACTGTGAA GGAGGTGCTG GGAGGTTTGA AGGCTTTAGG GGTTAGCCGT GCTGTTGAAG  7740
AAATTGATTA TCATTGTTAA ATTGGCTGAA TGGCAAGTCA AATTGGGAAA CTCCCCGGTG  7800
AATCAAATGA GGCTTTTGAA GCCCGGCTAA AATCGCTGGA GTTAGCTAGA GCTCAAAAGC  7860
AGCCGGAAGG TTCTAATGCA CCACCTACTC TCAGTGGCAT TCTTGCCAAA CGCAAGAGGA  7920
TTATAGAGAA TGCACTTTCA AAGACGGTGG ACATGAGGGA GGTTTTGAAA CACGAAACGG  7980
TGGTGATTTC CCCAAATGTC ATGGATGAAG GTGCAATAGA CGAGCTGATT CGTGCATTTG  8040
GTGAATCTGG CATAGCTGAA AGCGTGCAAT TTGATGTGGC CATAGATATA GCACGTCACT  8100
GCTCTGATGT TGGTAGCTCC CAGAGGTCAA CCCTGATTGG CAAGAGTCCA TTTTGTGACC  8160
TAAACAGATC AGAAATAGCT GGGATTATAA GGGAGGTGAC CACATTACGT AGATTTTGCA  8220
TGTACTATGC AAAAATCGTG TGGAACATCC ATCTGGAGAC GGGGATACCA CCAGCTAACT  8280
GGGCCAAGAA AGGATTTAAT GAGAATGAAA AGTTTGCAGC CTTTGATTTT TTCTTGGGAG  8340
TCACAGATGA GAGTGCGCTT GAACCAAAGG GTGGAATTAA AAGAGCTCCA ACGAAAGCTG  8400
AGATGGTTGC TAATATCGCC TCTTTTGAGG TTCAAGTGCT CAGACAAGCT ATGGCTGAAG  8460
GCAAGCGGAG TTCCAACCTT GGAGAGATTA GTGGTGGAAC GGCTGGTGCA CTCATCAACA  8520
ACCCCTTTTC AAATGTTACA CATGAATGAG GATGACGAAG TCAGCGACAA TTCCGCAGTC  8580
CAATAATTCC CCGATTTCAA GGCTGGGTTA AGCCTGTTCG CTGGAATACC GTACTAATAG  8640
TATTCCCTTT CCATGCTAAA TCCTATTTAA TATATAAGGT GTGGAAAGTA AAAGAAGATT  8700
TGGTGTGTTT TTATAGTTTT CATTCAAAAA AAAAAAAAAA AAA                   8743
```

The DNA molecule of SEQ. ID. No. 1 contains at least five open reading frames (e.g., ORF1–ORF5), each of which encodes a particular protein or polypeptide of RSPaV-1, and a 3' untranscribed region downstream of ORF5.

Another DNA molecule of the present invention (RSPaV-1 ORF1) includes nucleotides 62–6547 of SEQ. ID. No. 1. The DNA molecule of RSPaV-1 ORF1 encodes for a RSPaV-1 replicase and comprises a nucleotide sequence corresponding to SEQ. ID. No. 2 as follows:

```
ATGGCCCTCT CTTATAGGCC TGCTGTTGAA GAGGTGCTCG CAAAATTCAC CTCTGATGAA   60
CAATCCAGGG TTTCTGCTAC AGCTCTCAAG GCATTAGTAG ACTTAGAGGA AAGTCAGCAC  120
AATTTGTTCT CTTTCGCATT GCCTGATAGA AGCAAAGAAA GGCTGATATC TTCTGGCATT  180
TACTTAAGTC CTTACAGTTT CAGACCCCAC TCACATCCAG TTTGTAAAAC TTTAGAAAAT  240
CACATTTTGT ACAATGTTTT ACCTAGTTAT GTTAATAATT CATTTTACTT TGTAGGAATC  300
AAGGATTTTA AGCTGCAGTT CTTGAAAAGG AGGAATAAGG ATCTCAGCTT GGTAGCACTC  360
```

-continued

```
ATAAATAGGT TTGTGACAAG TCGTGATGTT AGTAGGTATG GGTCTGAGTT CGTTATAAGT   420
TCTAGTGACA AATCAAGTCA GGTTGTCAGT AGAAAGGGCA TTGGTGATTC TAACACACTC   480
CGGAGATTGG TCCCACGTGT AATTTCCACA GGTGCCAGGA ATCTTTTTCT GCATGATGAG   540
ATTCACTACT GGTCAATTAG TGATCTGATC AATTTTTTGG ACGTTGCCAA GCCAAGCATG   600
CTCTTGGCAA CTGCAGTAAT CCCTCCAGAA GTGCTGGTTG GCTCTCCAGA GAGTCTTAAC   660
CCTTGGGCCT ACCAGTATAA AATCAATGGC AACCAACTGC TCTTCGCACC AGATGGCAAC   720
TGGAATGAGA TGTACTCACA ACCTTTGTCA TGCAGATACC TGCTCAAGGC CAGATCTGTA   780
GTTCTGCCCG ATGGCTCACG CTACTCGGTT GACATCATTC ACTCAAAATT TAGTCACCAC   840
TTGCTTAGTT TCACCCCTAT GGGTAATCTT TTGACTTCAA ACATGCGATG TTTTTCTGGC   900
TTCGATGCAA TAGGCATAAA AGATCTTGAA CCTCTAAGCC GCGGCATGCA CAGTTGCTTC   960
CCAGTACATC ATGATGTTGT AACTAAGATA TATCTTTATT TGAGAACTCT CAAGAAGCCA  1020
GATAAGGAGT CTGCCGAGGC AAAGCTTCGA CAACTCATAG AAAAACCCAC AGGGAGGGAG  1080
ATAAAGTTTA TCGAGGATTT TTCCTCACTA GTAATAAATT GTGGGAGGAG TGGCTCTTTG  1140
CTTATGCCCA ACATTTCTAA GTTGGTCATA TCATTCTTTT GCCGGATGAT GCCAAATGCA  1200
CTCGCCAGGC TCTCTTCTAG CTTTCGAGAG TGTTCGCTAG ATTCATTTGT GTACTCACTT  1260
GAGCCCTTTA ATTTTTCCGT TAATTTAGTG GATATAACTC CTGATTTCTT TGAGCATTTA  1320
TTTCTCTTCT CCTGCCTAAA TGAGTTGATC GAGGAGGACG TTGAAGAGGT CATGGACAAT  1380
TCTTGGTTTG GACTTGGGGA CTTACAATTC AATCGCCAGA GGGCCCCGTT CTTTCTTGGG  1440
TCTTCATATT GGCTCAACTC CAAATTTTCA GTTGAGCACA AGTTTTCAGG CACCATCAAT  1500
TCTCAAATCA TGCAAGTTAT TTTATCTTTG ATCCCATTTT CTGATGATCC CACTTTTAGG  1560
CCATCTTCTA CAGAGGTTAA CCTTGCACTA TCAGAGGTTA AGGCTGCGCT AGAAGCTACT  1620
GGGCAGTCAA AATTGTTCAG GTTTTTGGTG GACGACTGTG CTATGCGTGA GGTTAGAAGT  1680
TCCTATAAGG TGGGCCTTTT TAAGCACATA AAAGCCCTCA CTCATTGCTT TAATTCTTGT  1740
GGCCTCCAAT GGTTCCTCCT TAGGCAAAGG TCCAACCTCA AATTTCTGAA GGACAGGGCA  1800
TCGTCCTTTG CTGATCTTGA TTGTGAGGTT ATCAAAGTTT ATCAGCTTGT AACATCACAG  1860
GCAATACTTC CTGAGGCTCT GCTTAGCTTG ACCAAAGTCT TTGTCAGGGA TTCTGACTCA  1920
AAGGGTGTTT CCATTCCCAG ATTGGTCTCG AGAAATGAGC TAGAGGAACT AGCTCACCCA  1980
GCTAATTCAG CCCTTGAGGA GCCTCAATCA GTTGATTGTA ATGCAGGCAG GGTTCAAGCA  2040
AGCGTTTCAA GTTCCCAGCA GCTTGCCGAC ACCCACTCTC TTGGTAGCGT TAAGTCATCA  2100
ATTGAGACAG CTAACAAGGC TTTTAACTTG GAGGAGCTAA GGATCATGAT TAGAGTCTTG  2160
CCGGAGGATT TTAACTGGGT GGCGAAGAAC ATTGGTTTTA AAGACAGGCT GAGAGGCAGG  2220
GGTGCATCAT TCTTCTCAAA ACCAGGAATT TCATGTCATA GTTACAATGG TGGGAGCCAC  2280
ACAAGCTTAG GGTGGCCAAA GTTCATGGAT CAGATTCTAA GCTCCACTGG TGGACGTAAT  2340
TACTACAATT CATGCCTGGC TCAGATCTAT GAGGAAAATT CAAAATTGGC TCTTCATAAG  2400
GATGATGAGA GTTGCTATGA AATTGGGCAC AAAGTTTTGA CTGTTAATTT AATCGGCTCA  2460
GCAACTTTCA CTATTAGTAA GTCGCGAAAT TTGGTTGGGG GTAATCATTG CAGCCTGACA  2520
ATTGGGCCAA ATGAGTTTTT CGAAATGCCT AGGGGCATGC AATGCAATTA CTTCCATGGG  2580
GTTTCCAATT GTACGCCAGG GCGGGTATCG CTGACCTTTA GGCGCCAAAA GTTGGAAGAT  2640
GATGATTTGA TCTTCATAAA TCCACAGGTG CCCATTGAGC TCAATCATGA AAAGCTTGAC  2700
CGAAGTATGT GGCAGATGGG CCTTCATGGA ATTAAGAAAT CTATTTCTAT GAATGGCACG  2760
```

-continued

```
AGTTTTACCT CAGACCTATG CTCTTGTTTC TCTTGCCACA ACTTTCATAA ATTCAAGGAT  2820
CTCATCAATA ACTTGAGATT GGCCCTAGGA GCACAAGGGC TAGGTCAGTG TGACAGGGTT  2880
GTGTTTGCAA CAACAGGTCC TGGTCTATCT AAGGTTTTAG AAATGCCTCG GAGCAAAAAG  2940
CAATCAATTT TGGTTCTTGA AGGTGCCCTA TCCATAGAAA CAGATTATGG TCCAAAAGTC  3000
CTGGGGTCTT TTGAAGTTTT CAAAGGGGAC TTTCACATTA AGAAGATGGA GGAAGGTTCA  3060
ATTTTTGTAA TAACGTACAA GGCCCCAATT AGATCCACTG GCAGGTTGAG GGTTCACAGT  3120
TCAGAATGCT CATTTTCCGG ATCCAAAGAG GTATTGCTAG GCTGCCAGAT TGAGGCATGT  3180
GCTGATTATG ATATTGATGA TTTTAACACT TTCTCTGTGC CTGGTGATGG CAATTGCTTT  3240
TGGCATTCTG TTGGTTTTTT ACTTAGCACT GATGGACTTG CCCTAAAGGC CGGTATTCGA  3300
TCTTTCGTGG AGAGTGAGCG CTTGGTAAGT CCAGATCTTT CAGCCCCAGC AATTTCTAAA  3360
CAATTGGAAG AGAATGCTTA TGCCGAGAAT GAGATGATCG CATTATTCTG CATTCGGCAC  3420
CACGTAAGGC CTATAGTGAT CACACCAGAA TATGAAGTTA GTTGGAAATT CGGGGAAGGT  3480
GAGTGGCCCC TATGTGCAAT TCTTTGCCTT AAATCAAATC ACTTCCAACC ATGCGCCCCA  3540
CTGAATGGTT GCATGATCAC AGCCATTGCT TCAGCACTTG GAAGGCGTGA AGTTGATGTG  3600
TTAAATTATC TGTGTAGACC CAGCACTAAT CATATTTTTG AGGAGCTTTG TCAGGGAGGG  3660
GGCCTTAACA TGATGTATTT AGCTGAAGCT TTTGAGGCCT TTGACATTTG CGCTAAATGT  3720
GATATAAATG GAGAGATTGA AGTGATTAAT CCGTGTGGTA AAATTTCTGC ATTGTTTGAC  3780
ATAACTAATG AGCACATAAG GCATGTTGAG AAAATAGGTA ATGGCCCTCA GAGCATAAAA  3840
GTGGATGAAT TGCGGAAGGT CAAGCGATCC GCCCTCGATT TCCTTTCAAT GAATGGGTCT  3900
AAAATAACCT ACTTCCCAAG CTTTGAGCGG GCTGAAAAGT TGCAAGGATG TTTGCTAGGG  3960
GGCCTAACTG GCGTTATAAG TGATGAGAAG TTCAGTGATG CAAAACCTTG GCTTTCTGGT  4020
ATATCTACTA CTGATATTAA GCCAAGGGAA TTGACTGTCG TGCTTGGTAC ATTTGGGGCT  4080
GGGAAGAGTT TCTTGTACAA GAGTTTCATG AAAAGGTCTG AGGGTAAATT CGTAACCTTT  4140
GTTTCTCCCA GACGTGCTTT AGCAAATTCA ATCAAAAATG ATCTTGAAAT GGATGATAGC  4200
TGCAAAGTTG CTAAAGCAGG TAGGTCAAAG AAGGAAGGGT GGGATGTAGT AACTTTTGAG  4260
GTTTTCCTTA GAAAAGTTGC AGGATTGAAG GCTGGCCACT GTGTGATTTT TGATGAGGTC  4320
CAGTTGTTTC CTCCTGGATA CATCGATCTA TGCTTGCTTA TTATACGTAG TGATGCTTTC  4380
ATTTCACTTG CTGGTGATCC ATGTCAAAGC ACATATGACT CGCAAAAGGA TCGGGCAATT  4440
TTGGGCGCTG AGCAGAGTGA CATACTTAGA CTGCTTGAGG GCAAAACGTA TAGGTATAAC  4500
ATAGAAAGCA GGAGGTTTGT GAACCCAATG TTCGAATCAA GACTGCCATG TCACTTCAAA  4560
AAGGGCTCGA TGACTGCCGC TTTCGCTGAT TATGCAATCT TCCATAATAT GCATGACTTT  4620
CTCCTGGCGA GGTCAAAAGG TCCCTTGGAT GCCGTTTTGG TTTCCAGTTT TGAGGAGAAA  4680
AAGATAGTdC AGTCCTACTT TGGAATGAAA CAGCTCACAC TCACATTTGG TGAATCAACT  4740
GGGTTGAATT TCAAAAATGG GGGAATTCTC ATATCACATG ATTCCTTTCA CACAGATGAT  4800
CGGCGGTGGC TTACTGCTTT ATCTCGCTTC AGCCACAATT TGGATTTGGT GAACATCACA  4860
GGTCTGAGGG TGGAAAGTTT TCTCTCGCAC TTTGCTGGCA AACCCCTCTA CCATTTTTTA  4920
ACAGCCAAAA GTGGGGAGAA TGTCATACGA GATTTGCTCC CAGGTGAGCC TAACTTCTTC  4980
AGTGGCTTTA ACGTTAGCAT TGGAAAGAAT GAAGGTGTTA GGGAGGAGAA GTTATGTGGT  5040
GACCCATGGT TAAAAGTTAT GCTTTTCCTG GGTCAAGATG AGGATTGTGA AGTTGAAGAG  5100
ATGGAGTCAG AATGCTCAAA TGAAGAATGG TTTAAAACCC ACATCCCCTT GAGTAATCTG  5160
```

-continued

```
GAGTCAACCA GGGCCAGGTG GGTGGGTAAA ATGGCCTTGA AAGAGTATCG GGAGGTGCGT  5220

TGTGGTTATG AAATGACTCA ACAATTCTTT GATGAGCATA GGGGTGGAAC TGGTGAGCAA  5280

CTGAGCAATG CATGTGAGAG GTTTGAAAGC ATTTACCCAA GGCATAAAGG AAATGATTCA  5340

ATAACCTTCC TCATGGCTGT CCGAAAGCGT CTCAAATTTT CGAAGCCCCA GGTTGAAGCT  5400

GCCAAACTGA GGCGGGCCAA ACCATATGGG AAATTCTTAT TAGATTCTTT CCTATCCAAA  5460

ATCCCATTGA AAGCCAGTCA TAATTCCATC ATGTTTCATG AAGCGGTACA GGAGTTTGAG  5520

GCGAAGAAGG CTAGTAAGAG TGCAGCAACT ATAGAGAATC ATGCAGGTAG GTCATGCAGG  5580

GATTGGTTAT TAGATGTTGC TCTGATTTTT ATGAAGTCAC AACACTGTAC TAAATTTGAC  5640

AACAGGCTTA GAGTAGCTAA AGCTGGGCAA ACCCTTGCTT GCTTCCAACA TGCTGTTCTG  5700

GTTCGCTTTG CACCCTATAT GAGATACATT GAGAAAAAGC TAATGCAAGC TCTGAAGCCT  5760

AACTTCTACA TCCATTCAGG GAAAGGTCTG ACGAGCTGAA CGAGTGGGTC AGAACTAGAG  5820

GATTCACTGG AATTTGCACA GAATCAGACT ACGAAGCCTT TGATGCTTCC CAAGACCACT  5880

TCATCCTAGC ATTCGAATTG CAGATAATGA AATTTTTGGG GTTACCTGAA GATTTAATTT  5940

TGGACTATGA ATTCATAAAA ATTCATTTGG GATCAAAGCT CGGATCATTC TCTATAATGA  6000

GGTTTACTGG GGAGGCCAGC ACATTTCTGT TTAACACTAT GGCTAACATG TTGTTCACCT  6060

TTCTGAGGTA CGAACTAACA GGCTCTGAGT CAATAGCATT TGCAGGTGAT GACATGTGTG  6120

CTAATCGAAG GTTGCGGCTT AAAACAGAGC ATGAGGGTTT TCTGAACATG ATTTGCCTTA  6180

AGGCCAAGGT TCAGTTTGTT TCCAATCCCA CATTCTGCGG ATGGTGTTTA TTTAAGGAAG  6240

GGATCTTCAA GAAGCCTCAA TTAATCTGGG AGCGGATATG CATTGCTAGG GAGATGGGCA  6300

ACCTGGAGAA TTGTATTGAC AATTATGCGA TAGAGGTCTC CTATGCATAC CGACTGGGAG  6360

AGCTAGCCAT TGAAATGATG ACCGAGGAAG AAGTGGAGGC CCATTATAAT TGTGTTAGAT  6420

TCTTGGTCAG GAACAAGCAT AAGATGAGAT GCTCAATTTC AGGCCTATTT GAAGCTATTG  6480

ATTAG                                                              6485
```

The RSPaV-1 replicase has a deduced amino acid sequence corresponding to SEQ. ID. No. 3 as follows:

```
Met Ala Leu Ser Tyr Arg Pro Ala Val Glu Glu Val Leu Ala Lys Phe
1               5                   10                  15

Thr Ser Asp Glu Gln Ser Arg Val Ser Ala Thr Ala Leu Lys Ala Leu
            20                  25                  30

Val Asp Leu Glu Glu Ser Gln His Asn Leu Phe Ser Phe Ala Leu Pro
        35                  40                  45

Asp Arg Ser Lys Glu Arg Leu Ile Ser Ser Gly Ile Tyr Leu Ser Pro
    50                  55                  60

Tyr Ser Phe Arg Pro His Ser His Pro Val Cys Lys Thr Leu Glu Asn
65                  70                  75                  80

His Ile Leu Tyr Asn Val Leu Pro Ser Tyr Val Asn Asn Ser Phe Tyr
                85                  90                  95

Phe Val Gly Ile Lys Asp Phe Lys Leu Gln Phe Leu Lys Arg Arg Asn
            100                 105                 110

Lys Asp Leu Ser Leu Val Ala Leu Ile Asn Arg Phe Val Thr Ser Arg
        115                 120                 125

Asp Val Ser Arg Tyr Gly Ser Glu Phe Val Ile Ser Ser Ser Asp Lys
    130                 135                 140
```

-continued

```
Ser Ser Gln Val Val Ser Arg Lys Gly Ile Gly Asp Ser Asn Thr Leu
145                 150                 155                 160

Arg Arg Leu Val Pro Arg Val Ile Ser Thr Gly Ala Arg Asn Leu Phe
                165                 170                 175

Leu His Asp Glu Ile His Tyr Trp Ser Ile Ser Asp Leu Ile Asn Phe
            180                 185                 190

Leu Asp Val Ala Lys Pro Ser Met Leu Leu Ala Thr Ala Val Ile Pro
        195                 200                 205

Pro Glu Val Leu Val Gly Ser Pro Glu Ser Leu Asn Pro Trp Ala Tyr
    210                 215                 220

Gln Tyr Lys Ile Asn Gly Asn Gln Leu Leu Phe Ala Pro Asp Gly Asn
225                 230                 235                 240

Trp Asn Glu Met Tyr Ser Gln Pro Leu Ser Cys Arg Tyr Leu Leu Lys
                245                 250                 255

Ala Arg Ser Val Val Leu Pro Asp Gly Ser Arg Tyr Ser Val Asp Ile
            260                 265                 270

Ile His Ser Lys Phe Ser His His Leu Leu Ser Phe Thr Pro Met Gly
       275                 280                 285

Asn Leu Leu Thr Ser Asn Met Arg Cys Phe Ser Gly Phe Asp Ala Ile
    290                 295                 300

Gly Ile Lys Asp Leu Glu Pro Leu Ser Arg Gly Met His Ser Cys Phe
305                 310                 315                 320

Pro Val His His Asp Val Val Thr Lys Ile Tyr Leu Tyr Leu Arg Thr
                325                 330                 335

Leu Lys Lys Pro Asp Lys Glu Ser Ala Glu Ala Lys Leu Arg Gln Leu
            340                 345                 350

Ile Glu Lys Pro Thr Gly Arg Glu Ile Lys Phe Ile Glu Asp Phe Ser
        355                 360                 365

Ser Leu Val Ile Asn Cys Gly Arg Ser Gly Ser Leu Leu Met Pro Asn
    370                 375                 380

Ile Ser Lys Leu Val Ile Ser Phe Phe Cys Arg Met Met Pro Asn Ala
385                 390                 395                 400

Leu Ala Arg Leu Ser Ser Ser Phe Arg Glu Cys Ser Leu Asp Ser Phe
                405                 410                 415

Val Tyr Ser Leu Glu Pro Phe Asn Phe Ser Val Asn Leu Val Asp Ile
            420                 425                 430

Thr Pro Asp Phe Phe Glu His Leu Phe Leu Phe Ser Cys Leu Asn Glu
        435                 440                 445

Leu Ile Glu Glu Asp Val Glu Glu Val Met Asp Asn Ser Trp Phe Gly
    450                 455                 460

Leu Gly Asp Leu Gln Phe Asn Arg Gln Arg Ala Pro Phe Phe Leu Gly
465                 470                 475                 480

Ser Ser Tyr Trp Leu Asn Ser Lys Phe Ser Val Glu His Lys Phe Ser
                485                 490                 495

Gly Thr Ile Asn Ser Gln Ile Met Gln Val Ile Leu Ser Leu Ile Pro
            500                 505                 510

Phe Ser Asp Asp Pro Thr Phe Arg Pro Ser Ser Thr Glu Val Asn Leu
        515                 520                 525

Ala Leu Ser Glu Val Lys Ala Ala Leu Glu Ala Thr Gly Gln Ser Lys
    530                 535                 540

Leu Phe Arg Phe Leu Val Asp Asp Cys Ala Met Arg Glu Val Arg Ser
545                 550                 555                 560

Ser Tyr Lys Val Gly Leu Phe Lys His Ile Lys Ala Leu Thr His Cys
```

-continued

```
                565                 570                 575

Phe Asn Ser Cys Gly Leu Gln Trp Phe Leu Leu Arg Gln Arg Ser Asn
            580                 585                 590

Leu Lys Phe Leu Lys Asp Arg Ala Ser Ser Phe Ala Asp Leu Asp Cys
        595                 600                 605

Glu Val Ile Lys Val Tyr Gln Leu Val Thr Ser Gln Ala Ile Leu Pro
    610                 615                 620

Glu Ala Leu Leu Ser Leu Thr Lys Val Phe Val Arg Asp Ser Asp Ser
625                 630                 635                 640

Lys Gly Val Ser Ile Pro Arg Leu Val Ser Arg Asn Glu Leu Glu Glu
                645                 650                 655

Leu Ala His Pro Ala Asn Ser Ala Leu Glu Glu Pro Gln Ser Val Asp
            660                 665                 670

Cys Asn Ala Gly Arg Val Gln Ala Ser Val Ser Ser Ser Gln Gln Leu
        675                 680                 685

Ala Asp Thr His Ser Leu Gly Ser Val Lys Ser Ser Ile Glu Thr Ala
    690                 695                 700

Asn Lys Ala Phe Asn Leu Glu Glu Leu Arg Ile Met Ile Arg Val Leu
705                 710                 715                 720

Pro Glu Asp Phe Asn Trp Val Ala Lys Asn Ile Gly Phe Lys Asp Arg
                725                 730                 735

Leu Arg Gly Arg Gly Ala Ser Phe Phe Ser Lys Pro Gly Ile Ser Cys
            740                 745                 750

His Ser Tyr Asn Gly Gly Ser His Thr Ser Leu Gly Trp Pro Lys Phe
        755                 760                 765

Met Asp Gln Ile Leu Ser Ser Thr Gly Gly Arg Asn Tyr Tyr Asn Ser
    770                 775                 780

Cys Leu Ala Gln Ile Tyr Glu Glu Asn Ser Lys Leu Ala Leu His Lys
785                 790                 795                 800

Asp Asp Glu Ser Cys Tyr Glu Ile Gly His Lys Val Leu Thr Val Asn
                805                 810                 815

Leu Ile Gly Ser Ala Thr Phe Thr Ile Ser Lys Ser Arg Asn Leu Val
            820                 825                 830

Gly Gly Asn His Cys Ser Leu Thr Ile Gly Pro Asn Glu Phe Phe Glu
        835                 840                 845

Met Pro Arg Gly Met Gln Cys Asn Tyr Phe His Gly Val Ser Asn Cys
    850                 855                 860

Thr Pro Gly Arg Val Ser Leu Thr Phe Arg Arg Gln Lys Leu Glu Asp
865                 870                 875                 880

Asp Asp Leu Ile Phe Ile Asn Pro Gln Val Pro Ile Glu Leu Asn His
                885                 890                 895

Glu Lys Leu Asp Arg Ser Met Trp Gln Met Gly Leu His Gly Ile Lys
            900                 905                 910

Lys Ser Ile Ser Met Asn Gly Thr Ser Phe Thr Ser Asp Leu Cys Ser
        915                 920                 925

Cys Phe Ser Cys His Asn Phe His Lys Phe Lys Asp Leu Ile Asn Asn
    930                 935                 940

Leu Arg Leu Ala Leu Gly Ala Gln Gly Leu Gly Gln Cys Asp Arg Val
945                 950                 955                 960

Val Phe Ala Thr Thr Gly Pro Gly Leu Ser Lys Val Leu Glu Met Pro
                965                 970                 975

Arg Ser Lys Lys Gln Ser Ile Leu Val Leu Glu Gly Ala Leu Ser Ile
            980                 985                 990
```

-continued

```
Glu Thr Asp Tyr Gly Pro Lys Val Leu Gly Ser Phe Glu Val Phe Lys
        995                 1000                1005

Gly Asp Phe His Ile Lys Lys Met Glu Glu Gly Ser Ile Phe Val Ile
    1010                1015                1020

Thr Tyr Lys Ala Pro Ile Arg Ser Thr Gly Arg Leu Arg Val His Ser
1025                1030                1035                1040

Ser Glu Cys Ser Phe Ser Gly Ser Lys Glu Val Leu Leu Gly Cys Gln
                1045                1050                1055

Ile Glu Ala Cys Ala Asp Tyr Asp Ile Asp Asp Phe Asn Thr Phe Ser
            1060                1065                1070

Val Pro Gly Asp Gly Asn Cys Phe Trp His Ser Val Gly Phe Leu Leu
        1075                1080                1085

Ser Thr Asp Gly Leu Ala Leu Lys Ala Gly Ile Arg Ser Phe Val Glu
    1090                1095                1100

Ser Glu Arg Leu Val Ser Pro Asp Leu Ser Ala Pro Ala Ile Ser Lys
1105                1110                1115                1120

Gln Leu Glu Glu Asn Ala Tyr Ala Glu Asn Glu Met Ile Ala Leu Phe
                1125                1130                1135

Cys Ile Arg His His Val Arg Pro Ile Val Ile Thr Pro Glu Tyr Glu
            1140                1145                1150

Val Ser Trp Lys Phe Gly Glu Gly Glu Trp Pro Leu Cys Gly Ile Leu
        1155                1160                1165

Cys Leu Lys Ser Asn His Phe Gln Pro Cys Ala Pro Leu Asn Gly Cys
    1170                1175                1180

Met Ile Thr Ala Ile Ala Ser Ala Leu Gly Arg Arg Glu Val Asp Val
1185                1190                1195                1200

Leu Asn Tyr Leu Cys Arg Pro Ser Thr Asn His Ile Phe Glu Glu Leu
                1205                1210                1215

Cys Gln Gly Gly Gly Leu Asn Met Met Tyr Leu Ala Glu Ala Phe Glu
            1220                1225                1230

Ala Phe Asp Ile Cys Ala Lys Cys Asp Ile Asn Gly Glu Ile Glu Val
        1235                1240                1245

Ile Asn Pro Cys Gly Lys Ile Ser Ala Leu Phe Asp Ile Thr Asn Glu
    1250                1255                1260

His Ile Arg His Val Glu Lys Ile Gly Asn Gly Pro Gln Ser Ile Lys
1265                1270                1275                1280

Val Asp Glu Leu Arg Lys Val Lys Arg Ser Ala Leu Asp Phe Leu Ser
                1285                1290                1295

Met Asn Gly Ser Lys Ile Thr Tyr Phe Pro Ser Phe Glu Arg Ala Glu
            1300                1305                1310

Lys Leu Gln Gly Cys Leu Leu Gly Gly Leu Thr Gly Val Ile Ser Asp
        1315                1320                1325

Glu Lys Phe Ser Asp Ala Lys Pro Trp Leu Ser Gly Ile Ser Thr Thr
    1330                1335                1340

Asp Ile Lys Pro Arg Glu Leu Thr Val Val Leu Gly Thr Phe Gly Ala
1345                1350                1355                1360

Gly Lys Ser Phe Leu Tyr Lys Ser Phe Met Lys Arg Ser Glu Gly Lys
                1365                1370                1375

Phe Val Thr Phe Val Ser Pro Arg Arg Ala Leu Ala Asn Ser Ile Lys
            1380                1385                1390

Asn Asp Leu Glu Met Asp Asp Ser Cys Lys Val Ala Lys Ala Gly Arg
        1395                1400                1405

Ser Lys Lys Glu Gly Trp Asp Val Val Thr Phe Glu Val Phe Leu Arg
    1410                1415                1420
```

-continued

```
Lys Val Ala Gly Leu Lys Ala Gly His Cys Val Ile Phe Asp Glu Val
1425                1430                1435                1440

Gln Leu Phe Pro Pro Gly Tyr Ile Asp Leu Cys Leu Leu Ile Ile Arg
                1445                1450                1455

Ser Asp Ala Phe Ile Ser Leu Ala Gly Asp Pro Cys Gln Ser Thr Tyr
            1460                1465                1470

Asp Ser Gln Lys Asp Arg Ala Ile Leu Gly Ala Glu Gln Ser Asp Ile
        1475                1480                1485

Leu Arg Leu Leu Glu Gly Lys Thr Tyr Arg Tyr Asn Ile Glu Ser Arg
    1490                1495                1500

Arg Phe Val Asn Pro Met Phe Glu Ser Arg Leu Pro Cys His Phe Lys
1505                1510                1515                1520

Lys Gly Ser Met Thr Ala Ala Phe Ala Asp Tyr Ala Ile Phe His Asn
                1525                1530                1535

Met His Asp Phe Leu Leu Ala Arg Ser Lys Gly Pro Leu Asp Ala Val
            1540                1545                1550

Leu Val Ser Ser Phe Glu Glu Lys Lys Ile Val Gln Ser Tyr Phe Gly
        1555                1560                1565

Met Lys Gln Leu Thr Leu Thr Phe Gly Glu Ser Thr Gly Leu Asn Phe
    1570                1575                1580

Lys Asn Gly Gly Ile Leu Ile Ser His Asp Ser Phe His Thr Asp Asp
1585                1590                1595                1600

Arg Arg Trp Leu Thr Ala Leu Ser Arg Phe Ser His Asn Leu Asp Leu
                1605                1610                1615

Val Asn Ile Thr Gly Leu Arg Val Glu Ser Phe Leu Ser His Phe Ala
            1620                1625                1630

Gly Lys Pro Leu Tyr His Phe Leu Thr Ala Lys Ser Gly Glu Asn Val
        1635                1640                1645

Ile Arg Asp Leu Leu Pro Gly Glu Pro Asn Phe Phe Ser Gly Phe Asn
    1650                1655                1660

Val Ser Ile Gly Lys Asn Glu Gly Val Arg Glu Glu Lys Leu Cys Gly
1665                1670                1675                1680

Asp Pro Trp Leu Lys Val Met Leu Phe Leu Gly Gln Asp Glu Asp Cys
                1685                1690                1695

Glu Val Glu Glu Met Glu Ser Glu Cys Ser Asn Glu Glu Trp Phe Lys
            1700                1705                1710

Thr His Ile Pro Leu Ser Asn Leu Glu Ser Thr Arg Ala Arg Trp Val
        1715                1720                1725

Gly Lys Met Ala Leu Lys Glu Tyr Arg Glu Val Arg Cys Gly Tyr Glu
    1730                1735                1740

Met Thr Gln Gln Phe Phe Asp Glu His Arg Gly Gly Thr Gly Glu Gln
1745                1750                1755                1760

Leu Ser Asn Ala Cys Glu Arg Phe Glu Ser Ile Tyr Pro Arg His Lys
                1765                1770                1775

Gly Asn Asp Ser Ile Thr Phe Leu Met Ala Val Arg Lys Arg Leu Lys
            1780                1785                1790

Phe Ser Lys Pro Gln Val Glu Ala Ala Lys Leu Arg Arg Ala Lys Pro
        1795                1800                1805

Tyr Gly Lys Phe Leu Leu Asp Ser Phe Leu Ser Lys Ile Pro Leu Lys
    1810                1815                1820

Ala Ser His Asn Ser Ile Met Phe His Glu Ala Val Gln Glu Phe Glu
1825                1830                1835                1840

Ala Lys Lys Ala Ser Lys Ser Ala Ala Thr Ile Glu Asn His Ala Gly
```

-continued

```
                1845                1850                1855

Arg Ser Cys Arg Asp Trp Leu Leu Asp Val Ala Leu Ile Phe Met Lys
            1860                1865                1870

Ser Gln His Cys Thr Lys Phe Asp Asn Arg Leu Arg Val Ala Lys Ala
        1875                1880                1885

Gly Gln Thr Leu Ala Cys Phe Gln His Ala Val Leu Val Arg Phe Ala
    1890                1895                1900

Pro Tyr Met Arg Tyr Ile Glu Lys Lys Leu Met Gln Ala Leu Lys Pro
1905                1910                1915                1920

Asn Phe Tyr Ile His Ser Gly Lys Gly Leu Asp Glu Leu Asn Glu Trp
                1925                1930                1935

Val Arg Thr Arg Gly Phe Thr Gly Ile Cys Thr Glu Ser Asp Tyr Glu
            1940                1945                1950

Ala Phe Asp Ala Ser Gln Asp His Phe Ile Leu Ala Phe Glu Leu Gln
        1955                1960                1965

Ile Met Lys Phe Leu Gly Leu Pro Glu Asp Leu Ile Leu Asp Tyr Glu
    1970                1975                1980

Phe Ile Lys Ile His Leu Gly Ser Lys Leu Gly Ser Phe Ser Ile Met
1985                1990                1995                2000

Arg Phe Thr Gly Glu Ala Ser Thr Phe Leu Phe Asn Thr Met Ala Asn
                2005                2010                2015

Met Leu Phe Thr Phe Leu Arg Tyr Glu Leu Thr Gly Ser Glu Ser Ile
            2020                2025                2030

Ala Phe Ala Gly Asp Asp Met Cys Ala Asn Arg Arg Leu Arg Leu Lys
        2035                2040                2045

Thr Glu His Glu Gly Phe Leu Asn Met Ile Cys Leu Lys Ala Lys Val
    2050                2055                2060

Gln Phe Val Ser Asn Pro Thr Phe Cys Gly Trp Cys Leu Phe Lys Glu
2065                2070                2075                2080

Gly Ile Phe Lys Lys Pro Gln Leu Ile Trp Glu Arg Ile Cys Ile Ala
                2085                2090                2095

Arg Glu Met Gly Asn Leu Glu Asn Cys Ile Asp Asn Tyr Ala Ile Glu
            2100                2105                2110

Val Ser Tyr Ala Tyr Arg Leu Gly Glu Leu Ala Ile Glu Met Met Thr
        2115                2120                2125

Glu Glu Glu Val Glu Ala His Tyr Asn Cys Val Arg Phe Leu Val Arg
    2130                2135                2140

Asn Lys His Lys Met Arg Cys Ser Ile Ser Gly Leu Phe Glu Ala Ile
2145                2150                2155                2160

Asp
```

The replicase of SEQ. ID. No. 3 has a molecular weight of about 240 to 246 kDa, preferably about 244 kDa.

Another DNA molecule of the present invention (RSPaV-1 ORF2) includes nucleotides 6578–7243 of SEQ. ID. No. 1. The DNA molecule of RSPaV-1 ORF2 encodes for a first protein or polypeptide of an RSPaV-1 triple gene block and comprises a nucleotide sequence corresponding to SEQ. ID. No. 4 as follows:

```
ATGAATAATT TAGTTAAAGC ATTGTCAGCA TTTGAGTTTG TAGGTGTTTT CAGTGTGCTT    60

AAATTTCCAG TAGTCATTCA TAGTGTGCCT GGTAGTGGTA AAAGTAGTTT AATAAGGGAG   120

CTAATTTCCG AGGATGAGAA TTTCATAGCT TTCACAGCAG GTGTTCCAGA CAGCCCTAAT   180

CTCACAGGAA GGTACATTAA GCCTTATTCT CCAGGGTGTG CAGTGCCAGG GAAAGTTAAT   240

ATACTTGATG AGTACTTGTC CGTCCAAGAT TTTTCAGGTT TTGATGTGCT GTTCTCGGAC   300
```

-continued

```
CCATACCAAA ACATCAGCAT TCCTAAAGAG GCACATTTCA TCAAGTCAAA AACTTGTAGG  360

TTTGGCGTGA ATACTTGCAA ATATCTTTCC TCCTTCGGTT TTAAGGTTAG CAGTGACGGT  420

TTGGACAAAG TCATTGTGGG GTCGCCTTTT ACACTAGATG TTGAAGGGGT GCTAATATGC  480

TTTGGTAAGG AGGCAGTGGA TCTCGCTGTT GCGCACAACT CTGAATTCAA ATTACCTTGT  540

GAAGTTAGAG GTTCAACTTT TAACGTCGTA ACTCTTTTGA AATCAAGAGA TCCAACCCCA  600

GAGGATAGGC ACTGGTTTTA CATTGCTGCT ACAAGACACA GGGAGAAATT GATAATCATG  660

CAG                                                                663
```

The first protein or polypeptide of the RSPaV-1 triple gene block has a deduced amino acid sequence corresponding to SEQ. ID. No. 5 as follows:

```
Met Asn Asn Leu Val Lys Ala Leu Ser Ala Phe Glu Phe Val Gly Val
1               5                   10                  15

Phe Ser Val Leu Lys Phe Pro Val Val Ile His Ser Val Pro Gly Ser
            20                  25                  30

Gly Lys Ser Ser Leu Ile Arg Glu Leu Ile Ser Glu Asp Glu Asn Phe
        35                  40                  45

Ile Ala Phe Thr Ala Gly Val Pro Asp Ser Pro Asn Leu Thr Gly Arg
    50                  55                  60

Tyr Ile Lys Pro Tyr Ser Pro Gly Cys Ala Val Pro Gly Lys Val Asn
65                  70                  75                  80

Ile Leu Asp Glu Tyr Leu Ser Val Gln Asp Phe Ser Gly Phe Asp Val
                85                  90                  95

Leu Phe Ser Asp Pro Tyr Gln Asn Ile Ser Ile Pro Lys Glu Ala His
            100                 105                 110

Phe Ile Lys Ser Lys Thr Cys Arg Phe Gly Val Asn Thr Cys Lys Tyr
        115                 120                 125

Leu Ser Ser Phe Gly Phe Lys Val Ser Ser Asp Gly Leu Asp Lys Val
    130                 135                 140

Ile Val Gly Ser Pro Phe Thr Leu Asp Val Glu Gly Val Leu Ile Cys
145                 150                 155                 160

Phe Gly Lys Glu Ala Val Asp Leu Ala Val Ala His Asn Ser Glu Phe
                165                 170                 175

Lys Leu Pro Cys Glu Val Arg Gly Ser Thr Phe Asn Val Val Thr Leu
            180                 185                 190

Leu Lys Ser Arg Asp Pro Thr Pro Glu Asp Arg His Trp Phe Tyr Ile
        195                 200                 205

Ala Ala Thr Arg His Arg Glu Lys Leu Ile Ile Met Gln
    210                 215                 220
```

The first protein or polypeptide of the RSPaV-1 triple gene block has a molecular weight of about 20 to 26 kDa, preferably 24.4 kDa Another DNA molecule of the present invention (RSPaV-1 ORF3) includes nucleotides 7245–7598 of SEQ. ID. No. 1. The DNA molecule of RSPaV-1 ORF3 encodes for a second protein or polypeptide of the triple gene block and comprises a nucleotide sequence corresponding to SEQ. ID. No. 6 as follows:

```
ATGCCTTTTC AGCAGCCTGC GAATTGGGCA AAAACCATAA CTCCATTGAC AGTTGGCTTG   60

GGCATTGGGC TTGTGCTGCA TTTTCTGAGG AAGTCAAATC TACCTTATTC AGGGGACAAC  120

ATCCATCAAT TCCCTCACGG TGGGCGTTAC AGGGACGGTA CAAAAAGTAT AACTTACTGT  180
```

-continued

```
GGTCCAAAGC AATCCTTCCC CAGCTCTGGG ATATTCGGCC AATCTGAGAA TTTTGTGCCC  240

TTAATGCTTG TCATAGGTCT AATCGCATTC ATACATGTAT TGTCTGTTTG GAATTCTGGT  300

CTTGGTAGGA ATTGTAATTG CCATCCAAAT CCTTGCTCAT GTAGACAGCA G           351
```

The second protein or polypeptide of the RSPaV-1 triple gene block has a deduced amino acid sequence corresponding to SEQ. ID. No. 7 as follows:

```
Met Pro Phe Gln Gln Pro Ala Asn Trp Ala Lys Thr Ile Thr Pro Leu
1               5                   10                  15

Thr Val Gly Leu Gly Ile Gly Leu Val Leu His Phe Leu Arg Lys Ser
            20                  25                  30

Asn Leu Pro Tyr Ser Gly Asp Asn Ile His Gln Phe Pro His Gly Gly
        35                  40                  45

Arg Tyr Arg Asp Gly Thr Lys Ser Ile Thr Tyr Cys Gly Pro Lys Gln
    50                  55                  60

Ser Phe Pro Ser Ser Gly Ile Phe Gly Gln Ser Glu Asn Phe Val Pro
65                  70                  75                  80

Leu Met Leu Val Ile Gly Leu Ile Ala Phe Ile His Val Leu Ser Val
                85                  90                  95

Trp Asn Ser Gly Leu Gly Arg Asn Cys Asn Cys His Pro Asn Pro Cys
            100                 105                 110

Ser Cys Arg Gln Gln
        115
```

The second protein or polypeptide of the RSPaV-1 triple gene block has a molecular weight of about 10 to 15 kDa, preferably 12.8 kDa.

Yet another DNA molecule of the present invention (RSPaV-1 ORF4) includes nucleotides 7519–7761 of SEQ. ID. No. 1. The DNA molecule of RSPaV-1 ORF4 encodes for a third protein or polypeptide of the RSPaV-1 triple gene block and comprises a nucleotide sequence corresponding to SEQ. ID. No. 8 as follows:

```
ATGTATTGTC TGTTTGGAAT TCTGGTCTTG GTAGGAATTG TAATTGCCAT CCAAATCCTT   60

GCTCATGTAG ACAGCAGTAG TGGCAACCAC CAAGGTTGCT TCATTAGGGC CACTGGAGAG  120

TCAATTTTGA TTGAAAACTG CGGCCCAAGT GAGGCCCTTG CATCCACTGT GAAGGAGGTG  180

CTGGGAGGTT TGAAGGCTTT AGGGGTTAGC CGTGCTGTTG AAGAAATTGA TTATCATTGT  240
```

The third protein or polypeptide of the RSPaV-1 triple gene block has a deduced amino acid sequence corresponding to SEQ. ID. No. 9 as follows:

```
Met Tyr Cys Leu Phe Gly Ile Leu Val Leu Val Gly Ile Val Ile Ala
1               5                   10                  15

Ile Gln Ile Leu Ala His Val Asp Ser Ser Ser Gly Asn His Gln Gly
            20                  25                  30

Cys Phe Ile Arg Ala Thr Gly Glu Ser Ile Leu Ile Glu Asn Cys Gly
        35                  40                  45

Pro Ser Glu Ala Leu Ala Ser Thr Val Lys Glu Val Leu Gly Gly Leu
```

-continued

```
 50                  55                  60

Lys Ala Leu Gly Val Ser Arg Ala Val Glu Glu Ile Asp Tyr His Cys
65                  70                  75                  80
```

The third protein or polypeptide of the RSPaV-1 triple gene block has a molecular weight of about 5 to 10 kDa, preferably 8.4 kDa.

Still another DNA molecule of the present invention (RSPaV-1 ORF5) includes nucleotides 7771–8550 of SEQ. ID. No. 1. The DNA molecule of RSPaV-1 ORF5 encodes for a RSPaV-1 coat protein and comprises a nucleotide sequence corresponding to SEQ. ID. No. 10 as follows:

```
ATGGCAAGTC AAATTGGGAA ACTCCCCGGT GAATCAAATG AGGCTTTTGA AGCCCGGCTA   60

AAATCGCTGG AGTTAGCTAG AGCTCAAAAG CAGCCGGAAG GTTCTAATGC ACCACCTACT  120

CTCAGTGGCA TTCTTGCCAA ACGCAAGAGG ATTATAGAGA ATGCACTTTC AAAGACGGTG  180

GACATGAGGG AGGTTTTGAA ACACGAAACG GTGGTGATTT CCCCAAATGT CATGGATGAA  240

GGTGCAATAG ACGAGCTGAT TCGTGCATTT GGTGAATCTG GCATAGCTGA AAGCGTGCAA  300

TTTGATGTGG CCATAGATAT AGCACGTCAC TGCTCTGATG TTGGTAGCTC CCAGAGTTCA  360

ACCCTGATTG GCAAGAGTCC ATTTTGTGAC CTAAACAGAT CAGAAATAGC TGGGATTATA  420

AGGGAGGTGA CCACATTACG TAGATTTTGC ATGTACTATG CAAAAATCGT GTGGAACATC  480

CATCTGGAGA CGGGGATACC ACCAGCTAAC TGGGCCAAGA AAGGATTTAA TGAGAATGAA  540

AAGTTTGCAG CCTTTGATTT TTTCTTGGGA GTCACAGATG AGAGTGCGCT TGAACCAAAG  600

GGTGGAATTA AAAGAGCTCC AACGAAAGCT GAGATGGTTG CTAATATCGC CTCTTTTGAG  660

GTTCAAGTGC TCAGACAAGC TATGGCTGAA GGCAAGCGGA GTTCCAACCT TGGAGAGATT  720

AGTGGTGGAA CGGCTGGTGC ACTCATCAAC AACCCCTTTT CAAATGTTAC ACATGAA     777
```

The RSPaV-1 coat protein has a deduced amino acid sequence corresponding to SEQ. ID. No. 11 as follows:

```
Met Ala Ser Gln Ile Gly Lys Leu Pro Gly Glu Ser Asn Glu Ala Phe
1               5                   10                  15

Glu Ala Arg Leu Lys Ser Leu Glu Leu Ala Arg Ala Gln Lys Gln Pro
            20                  25                  30

Glu Gly Ser Asn Ala Pro Pro Thr Leu Ser Gly Ile Leu Ala Lys Arg
        35                  40                  45

Lys Arg Ile Ile Glu Asn Ala Leu Ser Lys Thr Val Asp Met Arg Glu
    50                  55                  60

Val Leu Lys His Glu Thr Val Val Ile Ser Pro Asn Val Met Asp Glu
65                  70                  75                  80

Gly Ala Ile Asp Glu Leu Ile Arg Ala Phe Gly Glu Ser Gly Ile Ala
                85                  90                  95

Glu Ser Val Gln Phe Asp Val Ala Ile Asp Ile Ala Arg His Cys Ser
            100                 105                 110

Asp Val Gly Ser Ser Gln Ser Ser Thr Leu Ile Gly Lys Ser Pro Phe
        115                 120                 125

Cys Asp Leu Asn Arg Ser Glu Ile Ala Gly Ile Ile Arg Glu Val Thr
    130                 135                 140

Thr Leu Arg Arg Phe Cys Met Tyr Tyr Ala Lys Ile Val Trp Asn Ile
```

-continued

```
145                 150                 155                 160

His Leu Glu Thr Gly Ile Pro Pro Ala Asn Trp Ala Lys Lys Gly Phe
                165                 170                 175

Asn Glu Asn Glu Lys Phe Ala Ala Phe Asp Phe Phe Leu Gly Val Thr
            180                 185                 190

Asp Glu Ser Ala Leu Glu Pro Lys Gly Gly Ile Lys Arg Ala Pro Thr
        195                 200                 205

Lys Ala Glu Met Val Ala Asn Ile Ala Ser Phe Glu Val Gln Val Leu
    210                 215                 220

Arg Gln Ala Met Ala Glu Gly Lys Arg Ser Ser Asn Leu Gly Glu Ile
225                 230                 235                 240

Ser Gly Gly Thr Ala Gly Ala Leu Ile Asn Asn Pro Phe Ser Asn Val
                245                 250                 255

Thr His Glu
```

The RSPaV-1 coat protein has a molecular weight of about 25 to 30 kDa, preferably 28 kDa.

The DNA molecule which constitutes the substantial portion of the RSPaV strain RSP47-4 genome comprises the nucleotide sequence corresponding to SEQ. ID. No. 12 as follows:

```
GGCTGGGCAA ACTTTGGCCT GCTTTCAACA CGCCGTCTTG GTTCGCTTTG CACCCTACAT    60

GCGATACATT GAAAAGAAGC TTGTGCAGGC ATTGAAACCA AATTTCTACA TTCATTCTGG   120

CAAAGGTCTT GATGAGCTAA GTGAATGGGT TAGAGCCAGA GGTTTCACAG GTGTGTGTAC   180

TGAGTCAGAC TATGAAGCTT TTGATGCATC CCAAGATCAT TTCATCCTGG CATTTGAACT   240

GCAAATCATG AGATTTTTAG GACTGCCAGA AGATCTGATT TTAGATTATG AGTTCATCAA   300

AATTCATCTT GGGTCAAAGC TTGGCTCTTT TGCAATTATG AGATTCACAG GTGAGGCAAG   360

CACCTTCCTA TTCAATACTA TGGCCAACAT GCTATTCACT TTCCTGAGGT ATGAGTTGAC   420

AGGTTCTGAA TCAATTGCAT TTGCTGGAGA TGATATGTGT GCTAATCGCA GGTTAAGACT   480

CAAGACTGAG CACGCCGGCT TTCTAAACAT GATCTGTCTC AAAGCTAAGG TGCAGTTTGT   540

CACAAATCCC ACCTTCTGTG GATGGTGTTT GTTTAAAGAG GGAATCTTTA AAAAACCCCA   600

GCTCATTTGG GAAAGGATCT GCATTGCTAG GGAAATGGGT AACTTGGACA ATTGCATTGA   660

CAATTACGCA ATTGAGGTGT CTTATGCTTA CAGACTTGGG GAATTGTCCA TAGGCGTGAT   720

GACTGAGGAG GAAGTTGAAG CACATTCTAA CTGCGTGCGT TTCCTGGTTC GCAATAAGCA   780

CAAGATGAGG TGCTCAATTT CTGGTTTGTT TGAAGTAATT GTTTAGGCCT TAAGTGTTTG   840

GCATGGTGTG AGTATTATGA ATAACTTAGT CAAAGCTTTG TCTGCTTTTG AATTTGTTGG   900

TGTGTTTTGT GTACTTAAAT TTCCAGTTGT TGTTCACAGT GTTCCAGGTA GCGGTAAAAG   960

TAGCCTAATA AGGGAGCTCA TTTCTGAAGA CGAGGCTTTT GTGGCCTTTA CAGCAGGTGT  1020

GCCAGACAGT CCAAATCTGA CAGGGAGGTA CATCAAGCCC TACGCTCCAG GGTGTGCAGT  1080

GCAAGGGAAA ATAAACATAC TTGATGAGTA CTTGTCTGTC TCTGATACTT CTGGCTTTGA  1140

TGTGCTGTTC TCAGACCCTT ACCAGAATGT CAGCATTCCA AGGGAGGCAC ACTTCATAAA  1200

AACCAAAACC TGTAGGTTTG GTACCAACAC CTGCAAGTAC CTTCAATCTT TTGGCTTTAA  1260

TGTTTGTAGT GATGGGGTGG ATAAAGTTGT TGTAGGGTCG CCATTTGAAC TGGAGGTTGA  1320

GGGGGTTCTC ATTTGCTTTG GAAAGGAGGC TGTAGATCTA GCAGTTGCAC ACAATTCTGA  1380
```

-continued

```
CTTCAAGTTG CCCTGCGAGG TGCGGGGTTC AACATTTGAC GTTGTAACGT TATTGAAGTC  1440
CAGGGATCCA ACTTCAGAAG ATAAGCATTG GTTCTACGTT GCAGCCACAA GGCATCGAAG  1500
TAAACTGATA ATAATGCAGT AAAATGCCTT TTCAGCAACC TGCCAACTGG GCTAAGACCA  1560
TAACTCCATT AACTATTGGT TTGGGCATTG GGTTGGTTCT GCACTTCTTA AGGAAATCAA  1620
ATCTGCCATA TTCAGGAGAC AATATTCACC AGTTCCCACA CGGAGGGCAT TACAGGGACG  1680
GCACGAAGAG TATAACCTAT TGTGGCCCTA GGCAGTCATT CCCAAGCTCA GGAATATTCG  1740
GTCAGTCTGA AAATTTCGTA CCTCTAATAT TGGTCGTGAC TCTGGTCGCT TTTATACATG  1800
CGTTATCTCT TTGGAATTCT GGTCCTAGTA GGAGTTGCAA TTGCCATCCA AATCCTTGCA  1860
CATGTAGACA GCAGTAGTGG CAACCATCAA GGCTGTTTCA TAAGAGCCAC CGGGGAGTCA  1920
ATAGTAATTG AGAATTGTGG GCCGAGCGAG GCCCTAGCTG CTACAGTCAA AGAGGTGTTG  1980
GGCGGTCTAA AGGCTTTAGG GGTTAGCCAA AAGGTTGATG AAATTAATTA CAGTTGTTGA  2040
GACAGTTGAA TGGCAAGTCA AGTTGGAAAA TTGCCTGGCG AATCAAATGA AGCATATGAG  2100
GCTAGACTCA AGGCTTTAGA GTTAGCAAGG GCCCAAAAAG CTCCAGAAGT CTCCAACCAA  2160
CCTCCCACAC TTGGAGGCAT TCTAGCCAAA AGGAAAAGAG TGATTGAGAA TGCACTCTCA  2220
AAGACAGTGG ATATGCGTGA AGTCTTAAGG CATGAATCTG TTGTACTCTC CCCGAATGTA  2280
ATGGACGAGG GAGCAATAGA CGAGCTGATT CGTGCCTTTG GGGAGTCGGG CATAGCTGAA  2340
AATGTGCAGT TTGATGTTGC AATAGACATT GCTCGCCACT GTTCTGATGT GGGGAGCTCT  2400
CAGAGGTCAA CCCTTATTGG TAAAAGCCCC TTCTGTGAGT TAAATAGGTC TGAAATTGCC  2460
GGAATAATAA GGGAGGTGAC CACGCTGCGC AGATTTTGCA TGTACTACGC AAAGATTGTG  2520
TGGAACATCC ATTTGGAGAC GGGAATACCA CCAGCTAATT GGGCCAAGAA AGGATTTAAT  2580
GAGAATGAAA AGTTTGCAGC CTTTGACTTC TTCCTTGGAG TCACAGATGA AAGCGCGCTT  2640
GAGCCTAAGG GTGGAGTCAA GAGAGCTCCA ACAAAAGCAG                        2680
```

The RSP47-4 strain contains five open reading frames (i.e., ORF1–5). ORF1 and ORF5 are only partially sequenced. RSP47-4 is 79% identical in nucleotide sequence to the corresponding region of RSPaV-1. The amino acid sequence identities between the corresponding ORFs of RSP47-4 and RSPaV-1 are: 94.1% for ORF1, 88.2% for ORF2, 88.9% for ORF3, 86.2% for ORF4, and 92.9% for ORF5. The nucleotide sequences of the five potential ORFs of RSP47-4 are given below.

Another DNA molecule of the present invention (RSP47-4 incomplete ORF1) includes nucleotides 1–768 of SEQ. ID. No. 12. This DNA molecule is believed to code for a polypeptide portion of a RSP47-4 replicase and comprises a nucleotide sequence corresponding to SEQ. ID. No. 13 as follows:

```
ATGCGATACA TTGAAAAGAA GCTTGTGCAG GCATTGAAAC CAAATTTCTA CATTCATTCT   60
GGCAAAGGTC TTGATGAGCT AAGTGAATGG GTTAGAGCCA GAGGTTTCAC AGGTGTGTGT  120
ACTGAGTCAG ACTATGAAGC TTTTGATGCA TCCCAAGATC ATTTCATCCT GGCATTTGAA  180
CTGCAAATCA TGAGATTTTT AGGACTGCCA GAAGATCTGA TTTTAGATTA TGAGTTCATC  240
AAAATTCATC TTGGGTCAAA GCTTGGCTCT TTTGCAATTA TGAGATTCAC AGGTGAGGCA  300
AGCACCTTCC TATTCAATAC TATGGCCAAC ATGCTATTCA CTTTCCTGAG GTATGAGTTG  360
ACAGGTTCTG AATCAATTGC ATTTGCTGGA GATGATATGT GTGCTAATCG CAGGTTAAGA  420
CTCAAGACTG AGCACGCCGG CTTTCTAAAC ATGATCTGTC TCAAAGCTAA GGTGCAGTTT  480
GTCACAAATC CCACCTTCTG TGGATGGTGT TTGTTTAAAG AGGGAATCTT TAAAAAACCC  540
CAGCTCATTT GGGAAAGGAT CTGCATTGCT AGGGAAATGG GTAACTTGGA CAATTGCATT  600
```

-continued

```
GACAATTACG CAATTGAGGT GTCTTATGCT TACAGACTTG GGGAATTGTC CATAGGCGTG  660

ATGACTGAGG AGGAAGTTGA AGCACATTCT AACTGCGTGC GTTTCCTGGT TCGCAATAAG  720

CACAAGATGA GGTGCTCAAT TTCTGGTTTG TTTGAAGTAA TTGTTTA                767
```

The polypeptide has a deduced amino acid sequence corresponding to SEQ. ID. No. 14 as follows:

```
Met Arg Tyr Ile Glu Lys Lys Leu Val Gln Ala Leu Lys Pro Asn Phe
1               5                   10                  15
Tyr Ile His Ser Gly Lys Gly Leu Asp Glu Leu Ser Glu Trp Val Arg
            20                  25                  30
Ala Arg Gly Phe Thr Gly Val Cys Thr Glu Ser Asp Tyr Glu Ala Phe
        35                  40                  45
Asp Ala Ser Gln Asp His Phe Ile Leu Ala Phe Glu Leu Gln Ile Met
    50                  55                  60
Arg Phe Leu Gly Leu Pro Glu Asp Leu Ile Leu Asp Tyr Glu Phe Ile
65                  70                  75                  80
Lys Ile His Leu Gly Ser Lys Leu Gly Ser Phe Ala Ile Met Arg Phe
                85                  90                  95
Thr Gly Glu Ala Ser Thr Phe Leu Phe Asn Thr Met Ala Asn Met Leu
            100                 105                 110
Phe Thr Phe Leu Arg Tyr Glu Leu Thr Gly Ser Glu Ser Ile Ala Phe
        115                 120                 125
Ala Gly Asp Asp Met Cys Ala Asn Arg Arg Leu Arg Leu Lys Thr Glu
    130                 135                 140
His Ala Gly Phe Leu Asn Met Ile Cys Leu Lys Ala Lys Val Gln Phe
145                 150                 155                 160
Val Thr Asn Pro Thr Phe Cys Gly Trp Cys Leu Phe Lys Glu Gly Ile
                165                 170                 175
Phe Lys Lys Pro Gln Leu Ile Trp Glu Arg Ile Cys Ile Ala Arg Glu
            180                 185                 190
Met Gly Asn Leu Asp Asn Cys Ile Asp Asn Tyr Ala Ile Glu Val Ser
        195                 200                 205
Tyr Ala Tyr Arg Leu Gly Glu Leu Ser Ile Gly Val Met Thr Glu Glu
    210                 215                 220
Glu Val Glu Ala His Ser Asn Cys Val Arg Phe Leu Val Arg Asn Lys
225                 230                 235                 240
His Lys Met Arg Cys Ser Ile Ser Gly Leu Phe Glu Val Ile Val
                245                 250                 255
```

Another DNA molecule of the present invention (RSP47-4 ORF2) includes nucleotides 857–1522 of SEQ. ID. No. 12. This DNA molecule codes for a first protein or polypeptide of an RSP47-4 triple gene block and comprises a nucleotide sequence corresponding to SEQ. ID. No. 15 as follows:

```
ATGAATAACT TAGTCAAAGC TTTGTCTGCT TTTGAATTTG TTGGTGTGTT TTGTGTACTT   60

AAATTTCCAG TTGTTGTTCA CAGTGTTCCA GGTAGCGGTA AAAGTAGCCT AATAAGGGAG  120

CTCATTTCTG AAGACGAGGC TTTTGTGGCC TTTACAGCAG GTGTGCCAGA CAGTCCAAAT  180

CTGACAGGGA GGTACATCAA GCCCTACGCT CCAGGGTGTG CAGTGCAAGG GAAAATAAAC  240

ATACTTGATG AGTACTTGTC TGTCTCTGAT ACTTCTGGCT TTGATGTGCT GTTCTCAGAC  300

CCTTACCAGA ATGTCAGCAT TCCAAGGGAG GCACACTTCA TAAAAACCAA AACCTGTAGG  360

TTTGGTACCA ACACCTGCAA GTACCTTCAA TCTTTTGGCT TTAATGTTTG TAGTGATGGG  420

GTGGATAAAG TTGTTGTAGG GTCGCCATTT GAACTGGAGG TTGAGGGGGT TCTCATTTGC  480

TTTGGAAAGG AGGCTGTAGA TCTAGCAGTT GCACACAATT CTGACTTCAA GTTGCCCTGC  540

GAGGTGCGGG GTTCAACATT TGACGTTGTA ACGTTATTGA AGTCCAGGGA TCCAACTTCA  600

GAAGATAAGC ATTGGTTCTA CGTTGCAGCC ACAAGGCATC GAAGTAAACT GATAATAATG  660

CAGTAA                                                             666
```

The first protein or polypeptide of the RSP47-4 triple gene block has a deduced amino acid sequence corresponding to SEQ. ID. No. 16 as follows:

```
Met Asn Asn Leu Val Lys Ala Leu Ser Ala Phe Glu Phe Val Gly Val
1               5                   10                  15

Phe Cys Val Leu Lys Phe Pro Val Val Val His Ser Val Pro Gly Ser
            20                  25                  30

Gly Lys Ser Ser Leu Ile Arg Glu Leu Ile Ser Glu Asp Glu Ala Phe
        35                  40                  45

Val Ala Phe Thr Ala Gly Val Pro Asp Ser Pro Asn Leu Thr Gly Arg
    50                  55                  60

Tyr Ile Lys Pro Tyr Ala Pro Gly Cys Ala Val Gln Gly Lys Ile Asn
65                  70                  75                  80

Ile Leu Asp Glu Tyr Leu Ser Val Ser Asp Thr Ser Gly Phe Asp Val
                85                  90                  95

Leu Phe Ser Asp Pro Tyr Gln Asn Val Ser Ile Pro Arg Glu Ala His
            100                 105                 110

Phe Ile Lys Thr Lys Thr Cys Arg Phe Gly Thr Asn Thr Cys Lys Tyr
        115                 120                 125

Leu Gln Ser Phe Gly Phe Asn Val Cys Ser Asp Gly Val Asp Lys Val
    130                 135                 140

Val Val Gly Ser Pro Phe Glu Leu Glu Val Glu Gly Val Leu Ile Cys
145                 150                 155                 160

Phe Gly Lys Glu Ala Val Asp Leu Ala Val Ala His Asn Ser Asp Phe
                165                 170                 175

Lys Leu Pro Cys Glu Val Arg Gly Ser Thr Phe Asp Val Val Thr Leu
            180                 185                 190

Leu Lys Ser Arg Asp Pro Thr Ser Glu Asp Lys His Trp Phe Tyr Val
        195                 200                 205

Ala Ala Thr Arg His Arg Ser Lys Leu Ile Ile Met Gln
    210                 215                 220
```

The first protein or polypeptide of the RSP47-4 triple gene block has a molecular weight of about 20 to 26 kDa., preferably 24.3 kDa.

Another DNA molecule of the present invention (RSP47-4 ORF3) includes nucleotides 1524–1877 of SEQ. ID. No. 12. This DNA molecule codes for a second protein or polypeptide of the RSP47-4 triple gene block and comprises a nucleotide sequence corresponding to SEQ. ID. No. 17 as follows:

```
ATGCCTTTTC AGCAACCTGC CAACTGGGCT AAGACCATAA CTCCATTAAC TATTGGTTTG   60

GGCATTGGGT TGGTTCTGCA CTTCTTAAGG AAATCAAATC TGCCATATTC AGGAGACAAT  120

ATTCACCAGT TCCCACACGG AGGGCATTAC AGGGACGGCA CGAAGAGTAT AACCTATTGT  180

GGCCCTAGGC AGTCATTCCC AAGCTCAGGA ATATTCGGTC AGTCTGAAAA TTTCGTACCT  240

CTAATATTGG TCGTGACTCT GGTCGCTTTT ATACATGCGT TATCTCTTTG GAATTCTGGT  300

CCTAGTAGGA GTTGCAATTG CCATCCAAAT CCTTGCACAT GTAGACAGCA GTAG        354
```

The second protein or polypeptide of the RSP47-4 triple gene block has a deduced amino acid sequence corresponding to SEQ. ID. No. 18 as follows:

```
Met Pro Phe Gln Gln Pro Ala Asn Trp Ala Lys Thr Ile Thr Pro Leu
1               5                   10                  15

Thr Ile Gly Leu Gly Ile Gly Leu Val Leu His Phe Leu Arg Lys Ser
            20                  25                  30

Asn Leu Pro Tyr Ser Gly Asp Asn Ile His Gln Phe Pro His Gly Gly
        35                  40                  45

His Tyr Arg Asp Gly Thr Lys Ser Ile Thr Tyr Cys Gly Pro Arg Gln
    50                  55                  60

Ser Phe Pro Ser Ser Gly Ile Phe Gly Gln Ser Glu Asn Phe Val Pro
65                  70                  75                  80

Leu Ile Leu Val Val Thr Leu Val Ala Phe Ile His Ala Leu Ser Leu
                85                  90                  95

Trp Asn Ser Gly Pro Ser Arg Ser Cys Asn Cys His Pro Asn Pro Cys
            100                 105                 110

Thr Cys Arg Gln Gln
        115
```

The second protein or polypeptide of the RSP47-4 triple gene block has a molecular weight of about 10 to 15 kDa., preferably 12.9 kDa.

Another DNA molecule of the present invention RSP47-4 ORF4) includes nucleotides 1798–2040 of SEQ. ID. No. 12. This DNA molecule codes for a third protein or polypeptide of the RSP47-4 triple gene block and comprises a nucleotide sequence corresponding to SEQ. ID. No. 19 as follows:

```
ATGCGTTATC TCTTTGGAAT TCTGGTCCTA GTAGGAGTTG CAATTGCCAT CCAAATCCTT    60

GCACATGTAG ACAGCAGTAG TGGCAACCAT CAAGGCTGTT TCATAAGAGC CACCGGGGAG   120

TCAATAGTAA TTGAGAATTG TGGGCCGAGC GAGGCCCTAG CTGCTACAGT CAAAGAGGTG   180

TTGGGCGGTC TAAAGGCTTT AGGGGTTAGC CAAAAGGTTG ATGAAATTAA TTACAGTTGT   240

TGA                                                                 243
```

The third protein or polypeptide of the RSP47-4 triple gene block has a deduced amino acid sequence corresponding to SEQ. ID. No. 20 as follows:

```
Met Arg Tyr Leu Phe Gly Ile Leu Val Leu Val Gly Val Ala Ile Ala
1               5                   10                  15

Ile Gln Ile Leu Ala His Val Asp Ser Ser Ser Gly Asn His Gln Gly
            20                  25                  30

Cys Phe Ile Arg Ala Thr Gly Glu Ser Ile Val Ile Glu Asn Cys Gly
        35                  40                  45

Pro Ser Glu Ala Leu Ala Ala Thr Val Lys Glu Val Leu Gly Gly Leu
    50                  55                  60

Lys Ala Leu Gly Val Ser Gln Lys Val Asp Glu Ile Asn Tyr Ser Cys
65                  70                  75                  80
```

The third protein or polypeptide of the RSP47-4 triple gene block has a molecular weight of about 5 to 10 kDa., preferably 8.3 kDa.

Yet another DNA molecule of the present invention (RSP47-4 ORF5) includes nucleotides 2050–2680 of SEQ. ID. No. 12. This DNA molecule codes for a partial RSP47-4 coat protein or polypeptide and comprises a nucleotide sequence corresponding to SEQ. ID. No. 21 as follows:

```
ATGGCAAGTC AAGTTGGAAA ATTGCCTGGC GAATCAAATG AAGCATATGA GGCTAGACTC   60
AAGGCTTTAG AGTTAGCAAG GGCCCAAAAA GCTCCAGAAG TCTCCAACCA ACCTCCCACA  120
CTTGGAGGCA TTCTAGCCAA AAGGAAAAGA GTGATTGAGA ATGCACTCTC AAAGACAGTG  180
GATATGCGTG AAGTCTTAAG GCATGAATCT GTTGTACTCT CCCCGAATGT AATGGACGAG  240
GGAGCAATAG ACGAGCTGAT TCGTGCCTTT GGGGAGTCGG GCATAGCTGA AAATGTGCAG  300
TTTGATGTTG CAATAGACAT TGCTCGCCAC TGTTCTGATG TGGGGAGCTC TCAGAGGTCA  360
ACCCTTATTG GTAAAAGCCC CTTCTGTGAG TTAAATAGGT CTGAAATTGC CGGAATAATA  420
AGGGAGGTGA CCACGCTGCG CAGATTTTGC ATGTACTACG CAAAGATTGT GTGGAACATC  480
CATTTGGAGA CGGGAATACC ACCAGCTAAT TGGGCCAAGA AAGGATTTAA TGAGAATGAA  540
AAGTTTGCAG CCTTTGACTT CTTCCTTGGk GTCACAGATG AAAGCGCGCT TGAGCCTAAG  600
GGTGGAGTCA AGAGAGCTCC AACAAAAGCA G                                 631
```

The polypeptide has a deduced amino acid sequence corresponding to SEQ. ID. No. 22 as follows:

```
Met Ala Ser Gln Val Gly Lys Leu Pro Gly Glu Ser Asn Glu Ala Tyr
1               5                   10                  15

Glu Ala Arg Leu Lys Ala Leu Glu Leu Ala Arg Ala Gln Lys Ala Pro
            20                  25                  30

Glu Val Ser Asn Gln Pro Pro Thr Leu Gly Gly Ile Leu Ala Lys Arg
        35                  40                  45

Lys Arg Val Ile Glu Asn Ala Leu Ser Lys Thr Val Asp Met Arg Glu
    50                  55                  60

Val Leu Arg His Glu Ser Val Val Leu Ser Pro Asn Val Met Asp Glu
65                  70                  75                  80

Gly Ala Ile Asp Glu Leu Ile Arg Ala Phe Gly Glu Ser Gly Ile Ala
                85                  90                  95

Glu Asn Val Gln Phe Asp Val Ala Ile Asp Ile Ala Arg His Cys Ser
            100                 105                 110

Asp Val Gly Ser Ser Gln Arg Ser Thr Leu Ile Gly Lys Ser Pro Phe
        115                 120                 125

Cys Glu Leu Asn Arg Ser Glu Ile Ala Gly Ile Ile Arg Glu Val Thr
    130                 135                 140

Thr Leu Arg Arg Phe Cys Met Tyr Tyr Ala Lys Ile Val Trp Asn Ile
145                 150                 155                 160

His Leu Glu Thr Gly Ile Pro Pro Ala Asn Trp Ala Lys Lys Gly Phe
                165                 170                 175

Asn Glu Asn Glu Lys Phe Ala Ala Phe Asp Phe Phe Leu Gly Val Thr
            180                 185                 190

Asp Glu Ser Ala Leu Glu Pro Lys Gly Gly Val Lys Arg Ala Pro Thr
        195                 200                 205

Lys Ala
    210
```

The DNA molecule which constitutes a substantial portion of the RSPaV strain RSP158 genome comprises the nucleotide sequence corresponding to SEQ. ID. No. 23 as follows:

```
GAAGCTAGCA CATTTCTGTT CAACACTATG GCTAACATGT TGTTCACTTT TCTGAGATAT    60
GAACTGACGG GTTCAGAGTC AATAGCATTT GCAGGGGATG ATATGTGTGC TAATAGAAGG   120
TTGCGGCTTA AAACGGAGCA TGAGGGTTTT CTGAACATGA TCTGCCTTAA GGCCAAGGTT   180
CAGTTTGTTT CCAACCCCAC ATTCTGTGGA TGGTGCTTAT TTAAGGAGGG AATCTTCAAG   240
AAACCTCAAC TAATTTGGGA GCGAATATGC ATAGCCAGAG AGATGGGCAA TCTGGAGAAC   300
TGTATTGACA ATTATGCGAT AGAAGTGTCC TATGCATATA GATTGGGTGA GCTATCAATT   360
GAAATGATGA CAGAAGAAGA AGTGGAGGCA CACTACAATT GTGTGAGGTT CCTGGTTAGG   420
AACAAGCATA AGATGAGGTG CTCAATTTCA GGCCTGTTTG AAGTGGTTGA TTAGGCCTTA   480
AGTATTTGGC GTTGTTCGAG TTATTATGAA TAATTTAGTT AAAGCATTAT CAGCCTTCGA   540
GTTTATAGGT GTTTTCAATG TGCTCAAATT TCCAGTTGTT ATACATAGTG TGCCTGGTAG   600
TGGTAAGAGT AGCTTAATAA GGGAATTAAT CTCAGAGGAC GAGAGTTTCG TGGCTTTCAC   660
AGCAGGTGTT CCAGACAGTC CTAACCTCAC AGGGAGGTAC ATCAAGCCTT ACTCACCAGG   720
ATGCGCAGTG CAAGGAAAAG TGAATATACT TGATGAGTAC TTGTCCGTTC AAGACATTTC   780
GGGTTTTGAT GTACTGTTTT CAGACCCGTA CCAGAATATC AGTATTCCCC AAGAGGCGCA   840
TTTCATTAAG TCCAAGACTT GTAGGTTTGG TGTGAACACT TGCAAATACC TTTCCTCTTT   900
CGGTTTCGAA GTTAGCAGCG ACGGGCTGGA CGACGTCATT GTGGGATCGC CCTTCACTCT   960
AGATGTTGAA GGGGTGCTGA TATGTTTTGG CAAGGAGGCG GTAGATCTCG CTGTTGCGCA  1020
CAACTCTGAA TTCAAGTTGC CGTGTGAGGT TCGAGGTTCA ACCTTCAATG TGGTAACCCT  1080
TTTGAAATCA AGAGACCCAA CCCCAGAGGA CAGGCACTGG TTTTACATCG CTGCCACAAG  1140
ACATAGGAAG AAATTGGTCA TTATGCAGTA AAATGCCTTT TCAGCAGCCT GCTAATTGGG  1200
CAAAAACCAT AACTCCATTG ACTATTGGCT TAGGAATTGG ACTTGTGCTG CATTTTCTGA  1260
GAAAGTCAAA TCTACCATAT TCAGGAGACA ACATCCATCA ATTTCCTCAC GGGGGGCGTT  1320
ACCGGGACGG CACAAAAAGT ATAACTTACT GTGGCCCTAA GCAGTCCTTC CCCAGTTCAG  1380
GAATATTTGG TCAGTCTGAG AATTTTGTGC CCTTAATGCT TGTCATAGGT CTAATTGCAT  1440
TCATACATGT ATTGTCTGTT TGGAATTCTG GTCTTGGTAG GAATTGCAAT TGCCATCCAA  1500
ATCCTTGCTC ATGTAGACAA CAGTAGTGGC AGTCACCAAG GTTGCTTTAT CAGGGCCACT  1560
GGAGAGTCTA TTTTGATTGA AAATTGTGGC CCAAGCGAGG CCCTTGCATC AACAGTGAGG  1620
GAGGTGTTGG GGGGTTTGAA GGCTTTAGGA ATTAGCCATA CTACTGAAGA AATTGATTAT  1680
CGTTGTTAAA TTGGTTAAAT GGCGAGTCAA GTTGGTAAGC TCCCCGGAGA ATCAAATGAG  1740
GCATTTGAAG CCCGGCTGAA ATCACTGGAG TTGGCTAGAG CTCAAAAGCA GCCAGAAGGT  1800
TCAAACACAC CGCCTACTCT CAGTGGTGTG CTTGCCAAAC GTAAGAGGGT TATTGAGAAT  1860
GCACTCTCAA AGACAGTGGA CATGAGGGAG GTGTTGAAAC ACGAAACGGT TGTAATTTCC  1920
CCAAATGTCA TGGATGAGGG TGCAATAGAT GAACTGATTC GTGCATTCGG AGAATCAGGC  1980
ATAGCTGAGA GCGCACAATT TGATGTGGC                                    2009
```

The RSP158 strain contains five open reading frames (i.e., ORF1–5). ORF1 and ORF5 are only partially sequenced. The nucleotide sequence of RSP158 is 87.6% identical to the corresponding region of RSPaV-1 (type strain). The numbers of amino acid residues of corresponding ORFs of RSP158 and RSPaV-1 (type strain) are exactly the same. In addition, the amino acid sequences of these ORFs have high identities to those of RSPaV-1: 99.3% for ORF1, 95% for ORF2, 99.1% for ORF3, 88.8% for ORF4, and 95.1% for ORF5. The nucleotide and amino acid sequence information of the RSP158 ORFs are described below.

Another DNA molecule of the present invention (RSP158 incomplete ORF1) includes nucleotides 1–447 of SEQ. ID. No. 23. This DNA molecule is believed to code for a polypeptide portion of a RSP158 replicase and comprises a nucleotide sequence corresponding to SEQ. ID. No. 24 as follows:

```
GAAGCTAGCA CATTTCTGTT CAACACTATG GCTAACATGT TGTTCACTTT TCTGAGATAT   60

GAACTGACGG GTTCAGAGTC AATAGCATTT GCAGGGGATG ATATGTGTGC TAATAGAAGG  120

TTGCGGCTTA AAACGGAGCA TGAGGGTTTT CTGAACATGA TCTGCCTTAA GGCCAAGGTT  180

CAGTTTGTTT CCAACCCCAC ATTCTGTGGA TGGTGCTTAT TTAAGGAGGG AATCTTCAAG  240

AAACCTCAAC TAATTTGGGA GCGAATATGC ATAGCCAGAG AGATGGGCAA TCTGGAGAAC  300

TGTATTGACA ATTATGCGAT AGAAGTGTCC TATGCATATA GATTGGGTGA GCTATCAATT  360

GAAATGATGA CAGAAGAAGA AGTGGAGGCA CACTACAATT GTGTGAGGTT CCTGGTTAGG  420

AACAAGCATA AGATGAGGTG CTCAATT                                      447
```

The polypeptide encoded by the nucleotide sequence of SEQ. ID. No. 24 has a deduced amino acid sequence corresponding to SEQ. ID. No. 25 as follows:

```
Glu Ala Ser Thr Phe Leu Phe Asn Thr Met Ala Asn Met Leu Phe Thr
1               5                   10                  15

Phe Leu Arg Tyr Glu Leu Thr Gly Ser Glu Ser Ile Ala Phe Ala Gly
            20                  25                  30

Asp Asp Met Cys Ala Asn Arg Arg Leu Arg Leu Lys Thr Glu His Glu
        35                  40                  45

Gly Phe Leu Asn Met Ile Cys Leu Lys Ala Lys Val Gln Phe Val Ser
    50                  55                  60

Asn Pro Thr Phe Cys Gly Trp Cys Leu Phe Lys Glu Gly Ile Phe Lys
65                  70                  75                  80

Lys Pro Gln Leu Ile Trp Glu Arg Ile Cys Ile Ala Arg Glu Met Gly
                85                  90                  95

Asn Leu Glu Asn Cys Ile Asp Asn Tyr Ala Ile Glu Val Ser Tyr Ala
            100                 105                 110

Tyr Arg Leu Gly Glu Leu Ser Ile Glu Met Met Thr Glu Glu Glu Val
        115                 120                 125

Glu Ala His Tyr Asn Cys Val Arg Phe Leu Val Arg Asn Lys His Lys
    130                 135                 140

Met Arg Cys Ser Ile
145
```

Another DNA molecule of the present invention (RSP158 ORF2) includes nucleotides 506–1171 of SEQ. ID. No. 23. This DNA molecule codes for a first protein or polypeptide of the RSP158 triple gene block and comprises a nucleotide sequence corresponding to SEQ. ID. No. 26 as follows:

```
ATGAATAATT TAGTTAAAGC ATTATCAGCC TTCGAGTTTA TAGGTGTTTT CAATGTGCTC   60

AAATTTCCAG TTGTTATACA TAGTGTGCCT GGTAGTGGTA AGAGTAGCTT AATAAGGGAA  120

TTAATCTCAG AGGACGAGAG TTTCGTGGCT TTCACAGCAG GTGTTCCAGA CAGTCCTAAC  180

CTCACAGGGA GGTACATCAA GCCTTACTCA CCAGGATGCG CAGTGCAAGG AAAAGTGAAT  240

ATACTTGATG AGTACTTGTC CGTTCAAGAC ATTTCGGGTT TTGATGTACT GTTTTCAGAC  300

CCGTACCAGA ATATCAGTAT TCCCCAAGAG GCGCATTTCA TTAAGTCCAA GACTTGTAGG  360

TTTGGTGTGA ACACTTGCAA ATACCTTTCC TCTTTCGGTT TCGAAGTTAG CAGCGACGGG  420

CTGGACGACG TCATTGTGGG ATCGCCCTTC ACTCTAGATG TTGAAGGGGT GCTGATATGT  480
```

-continued

```
TTTGGCAAGG AGGCGGTAGA TCTCGCTGTT GCGCACAACT CTGAATTCAA GTTGCCGTGT  540

GAGGTTCGAG GTTCAACCTT CAATGTGGTA ACCCTTTTGA AATCAAGAGA CCCAACCCCA  600

GAGGACAGGC ACTGGTTTTA CATCGCTGCC ACAAGACATA GGAAGAAATT GGTCATTATG  660

CAGTAA                                                             666
```

The first protein or polypeptide of the RSP158 triple gene block has a deduced amino acid sequence corresponding to SEQ. ID. No. 27 as follows:

```
Met Asn Asn Leu Val Lys Ala Leu Ser Ala Phe Glu Phe Ile Gly Val
1               5                   10                  15

Phe Asn Val Leu Lys Phe Pro Val Val Ile His Ser Val Pro Gly Ser
            20                  25                  30

Gly Lys Ser Ser Leu Ile Arg Glu Leu Ile Ser Glu Asp Glu Ser Phe
        35                  40                  45

Val Ala Phe Thr Ala Gly Val Pro Asp Ser Pro Asn Leu Thr Gly Arg
    50                  55                  60

Tyr Ile Lys Pro Tyr Ser Pro Gly Cys Ala Val Gln Gly Lys Val Asn
65                  70                  75                  80

Ile Leu Asp Glu Tyr Leu Ser Val Gln Asp Ile Ser Gly Phe Asp Val
                85                  90                  95

Leu Phe Ser Asp Pro Tyr Gln Asn Ile Ser Ile Pro Gln Glu Ala His
            100                 105                 110

Phe Ile Lys Ser Lys Thr Cys Arg Phe Gly Val Asn Thr Cys Lys Tyr
        115                 120                 125

Leu Ser Ser Phe Gly Phe Glu Val Ser Ser Asp Gly Leu Asp Asp Val
    130                 135                 140

Ile Val Gly Ser Pro Phe Thr Leu Asp Val Glu Gly Val Leu Ile Cys
145                 150                 155                 160

Phe Gly Lys Glu Ala Val Asp Leu Ala Val Ala His Asn Ser Glu Phe
                165                 170                 175

Lys Leu Pro Cys Glu Val Arg Gly Ser Thr Phe Asn Val Val Thr Leu
            180                 185                 190

Leu Lys Ser Arg Asp Pro Thr Pro Glu Asp Arg His Trp Phe Tyr Ile
        195                 200                 205

Ala Ala Thr Arg His Arg Lys Lys Leu Val Ile Met Gln
    210                 215                 220
```

The first protein or polypeptide of the RSP158 triple gene block has a molecular weight of about 20 to 26 kDa., preferably 24.4 kDa.

Another DNA molecule of the present invention (RSP158 ORF3) includes nucleotides 1173–1526 of SEQ. ID. No. 23. This DNA molecule codes for a second protein or polypeptide of the RSP158 triple gene block and comprises a nucleotide sequence corresponding to SEQ. ID. No. 28 as follows:

```
ATGCCTTTTC AGCAGCCTGC TAATTGGGCA AAAACCATAA CTCCATTGAC TATTGGCTTA   60

GGAATTGGAC TTGTGCTGCA TTTTCTGAGA AAGTCAAATC TACCATATTC AGGAGACAAC  120

ATCCATCAAT TTCCTCACGG GGGGCGTTAC CGGGACGGCA CAAAAAGTAT AACTTACTGT  180

GGCCCTAAGC AGTCCTTCCC CAGTTCAGGA ATATTTGGTC AGTCTGAGAA TTTTGTGCCC  240

TTAATGCTTG TCATAGGTCT AATTGCATTC ATACATGTAT TGTCTGTTTG GAATTCTGGT  300

CTTGGTAGGA ATTGCAATTG CCATCCAAAT CCTTGCTCAT GTAGACAACA GTAG         354
```

The second protein or polypeptide of the RSP158 triple gene block has a deduced amino acid sequence corresponding to SEQ. ID. No. 29 as follows:

```
Met Pro Phe Gln Gln Pro Ala Asn Trp Ala Lys Thr Ile Thr Pro Leu
1               5                   10                  15

Thr Ile Gly Leu Gly Ile Gly Leu Val Leu His Phe Leu Arg Lys Ser
            20                  25                  30

Asn Leu Pro Tyr Ser Gly Asp Asn Ile His Gln Phe Pro His Gly Gly
        35                  40                  45

Arg Tyr Arg Asp Gly Thr Lys Ile Thr Tyr Cys Gly Pro Lys Gln Ser
    50                  55                  60

Phe Pro Ser Ser Gly Ile Phe Gly Gln Ser Glu Asn Phe Val Pro Leu
65                  70                  75                  80

Met Leu Val Ile Gly Leu Ile Ala Phe Ile His Val Leu Ser Val Trp
                85                  90                  95

Asn Ser Gly Leu Gly Arg Asn Cys Asn Cys His Pro Asn Pro Cys Ser
            100                 105                 110

Cys Arg Gln Gln
        115
```

The second protein or polypeptide of the RSP158 triple gene block has a molecular weight of about 10 to 15 kDa., preferably 12.9 kDa.

Another DNA molecule of the present invention (RSP158 ORF4) includes nucleotides 1447–1689 of SEQ. ID. No. 23. This DNA molecule codes for a third protein or polypeptide of the RSP158 triple gene block and comprises a nucleotide sequence corresponding to SEQ. ID. No. 30 as follows:

```
ATGTATTGTC TGTTTGGAAT TCTGGTCTTG GTAGGAATTG CAATTGCCAT CCAAATCCTT   60

GCTCATGTAG ACAACAGTAG TGGCAGTCAC CAAGGTTGCT TTATCAGGGC CACTGGAGAG  120

TCTATTTTGA TTGAAAATTG TGGCCCAAGC GAGGCCCTTG CATCAACAGT GAGGGAGGTG  180

TTGGGGGGTT TGAAGGCTTT AGGAATTAGC CATACTACTG AAGAAATTGA TTATCGTTGT  240

TAA                                                                243
```

The third protein or polypeptide of the RSP158 triple gene block has a deduced amino acid sequence corresponding to SEQ. ID. No. 31 as follows:

```
Met Tyr Cys Leu Phe Gly Ile Leu Val Leu Val Gly Ile Ala Ile Ala
1               5                   10                  15

Ile Gln Ile Leu Ala His Val Asp Asn Ser Ser Gly Ser His Gln Gly
            20                  25                  30

Cys Phe Ile Arg Ala Thr Gly Glu Ser Ile Leu Ile Glu Asn Cys Gly
        35                  40                  45

Pro Ser Glu Ala Leu Ala Ser Thr Val Arg Glu Val Leu Gly Gly Leu
    50                  55                  60

Lys Ala Leu Gly Ile Ser His Thr Thr Glu Glu Ile Asp Tyr Arg Cys
65                  70                  75                  80
```

The third protein or polypeptide of the RSP158 triple gene block has a molecular weight of about 5 to 1 0 kDa., preferably 8.4 kDa.

Yet another DNA molecule of the present invention (RSP158 ORF5) includes nucleotides 1699–2009 of SEQ. ID. No. 23. This DNA molecule codes for a partial RSP158 coat protein or polypeptide and comprises a nucleotide sequence corresponding to SEQ. ID. No. 32 as follows:

```
ATGGCGAGTC AAGTTGGTAA GCTCCCCGGA GAATCAAATG AGGCATTTGA AGCCCGGCTG   60

AAATCACTGG AGTTGGCTAG AGCTCAAAAG CAGCCAGAAG GTTCAAACAC ACCGCCTACT  120

CTCAGTGGTG TGCTTGCCAA ACGTAAGAGG GTTATTGAGA ATGCACTCTC AAAGACAGTG  180

GACATGAGGG AGGTGTTGAA ACACGAAACG GTTGTAATTT CCCCAAATGT CATGGATGAG  240

GGTGCAATAG ATGAACTGAT TCGTGCATTC GGAGAATCAG GCATAGCTGA GAGCGCACAA  300

TTTGATGTGG C                                                       311
```

The polypeptide has a deduced amino acid sequence corresponding to SEQ. ID. No. 33 as follows:

```
Met Ala Ser Gln Val Gly Lys Leu Pro Gly Glu Ser Asn Glu Ala Phe
1               5                   10                  15

Glu Ala Arg Leu Lys Ser Leu Glu Leu Ala Arg Ala Gln Lys Gln Pro
            20                  25                  30

Glu Gly Ser Asn Thr Pro Pro Thr Leu Ser Gly Val Leu Ala Lys Arg
        35                  40                  45

Lys Arg Val Ile Glu Asn Ala Leu Ser Lys Thr Val Asp Met Arg Glu
    50                  55                  60

Val Leu Lys His Glu Thr Val Val Ile Ser Pro Asn Val Met Asp Glu
65                  70                  75                      80

Gly Ala Ile Asp Glu Leu Ile Arg Ala Phe Gly Glu Ser Gly Ile Ala
                85                  90                  95

Glu Ser Ala Gln Phe Asp Val
            100
```

The following seven cDNA clones are located at the central part of the ORF1 of RSPaV-1 and all have high identities (83.6–98.4%) in nucleotide sequence with the comparable regions of RSPaV-1. When their nucleotide sequences are aligned with MegAlign (DNAStar), a highly conserved region of ca. 600 nucleotides was found. The universal primers BM98-3F/BM98-3R (SEQ. ID. Nos. 51 and 52, infra) were designed based on the conserved nucleotide sequences of this region.

Portions of the genome from yet other strains of Rupestris stem pitting associated viruses have also been isolated and sequenced. These include strains designated 140/94-19 (T7+R1), 140/94-24 (T7+R1), 140/94-2 (T3+F1), 140/94+42 (T7+R1), 140/94-64 (T7+R1), 140-94-72 (T7+R1), and 140/94-6 (T3+BM98-3F+F2).

The nucleotide sequence of 140/94-19 (T7+R1) corresponds to SEQ. ID. No. 34 as follows:

```
GCAGGATTGA AGGCTGGCCA CTGTGTGATT TTTGATGAGG TCCAGTTGTT TCCTCCTGGA   60

TACATCGATC TATGCTTGCT TATTATACGT AGTGATGCTT TCATTTCACT TGCCGGTGAT  120

CCATGTCAAA GCACATATGA TTCGCAAAAG GATCGGGCAA TTTTGGGCGC TGAGCAGAGT  180

GACATACTTA GAATGCTTGA GGGCAAAACG TATAGGTATA ACATAGAAAG CAGGAGGTTT  240

GTGAACCCAA TGTTCGAATC AAGACTGCCA TGTCACTTCA AAAAGGGTTC GATGACTGCC  300

GCTTTCGCTG ATTATGCAAT CTTCCATAAT ATGCATGACT TTCTCCTGGC GAGGTCAAAA  360

GGTCCTTTGG ATGCCGTTTT GGTTTCCAGT TTTGAGGAGA AAAAGATAGT CCAGTCCTAC  420

TTTGGAATGA AACAGCTCAC ACTCACATTT GGTGAATCAA CTGGGTTGAA TTTCAAAAAT  480

GGGGGAATTC TCATATCACA TGATTCCTTT CACACAGATG ATCGGCCGGT GGCTTACTGC  540

TTTATCTCGC TTCAGCCACA ATTTGGATTT GGTGAACATT ACAGGTCTGA GGGTGGAAAG  600

TTTCCTCTCG CACTTTGCTG GCAAACCCCT CTACCATTTT TTAACAGCCA AAAGTGGGGA  660
```

-continued

```
GAATGTCATA CGAGATTTGC TCCCAGGTGA GCCTAACTTC TTCAGTGGCT TTAACGTTAG   720

CATTGGAAAG AATGAAGGTG TTAGGGAGGA GAAGTTATGT GGTGACCCAT GGTTAAAAGT   780

CATGCTTTTC CTGGGTCAAG ATGAGGATTG TGAAGTTGAA GAGATGGAGT CAGAGTGCTC   840

AAATGAAGAA TGGTTTAAAA CCCACATTCC CCTGAGTAAT CTGGAGTCAA CCAGGGCTAG   900

GTGGGTGGGT AAAATGGCTT TGAAAGAGTA TCGGGAGGTG CGTTGTGGTT ATGAAATGAC   960

TCAACAATTC TTTGATGAGC ATAGGGGTGG AACTGGTGAG CAACTGAGCA ATGCATGTGA  1020

GAGGTTTGAA AGCATTTACC CAAGGCATAA AGGAAATGAT TCAATAACCT TCCTTATGGC  1080

TGTCCGAAAG CGTCTCAAAT TTTCGAAGCC CCAGGTTGAA GCTGCCAAAC TGAGGCGGGC  1140

CAAACCATAT GGGAAATTCT TATTAGACTT TCCTATCCAA AATCCCATTG AAAGCCAGTC  1200

ATAATT                                                             1206
```

The nucleotide sequence of 140/94-24 (T7+R1) corresponds to SEQ. ID. No. 35 as follows:

```
ATTAACCCAA ATGGTAAGAT TTCCGCCTTG TTTGATATAA CCAATGAGCA CATAAGGCAT    60

GTTGAGAAGA TCGGCAATGG CCCTCAGAGC ATAAAAGTAG ATGAGTTGAG GAAGGTTAAG   120

CGATCCGCCC TTGATCTTCT TTCAATGAAT GGGTCCAAAA TAACCTATTT TCCAAACTTT   180

GAGCGGGCTG AAAAGTTGCA AGGGTGCTTG CTAGGGGGCC TAACTGGTGT CATAAGTGAT   240

GAAAAGTTCA GTGATGCAAA ACCCTGGCTT TCTGGTATAT CAACTGCGGA TATAAAGCCA   300

AGAGAGCTAA CTGTCGTGCT TGGCACTTTT GGGGCTGGAA AGAGTTTCTT GTATAAGAGT   360

TTCATGAAGA GATCTGAGGG AAAATTTGTA ACTTTTGTTT CCCCTAGACG AGCCTTGGCA   420

AATTCAATCA AAAATGATCT TGAAATGGAT GATGGCTGCA AAGTTGCCAA AGCAGGCAAA   480

TCAAAGAAGG AAGGGTGGGA TGTAGTGACC TTTGAAGTTT TCCTTAGAAA AGTTTCTGGT   540

TTGAAAGCTG GTCATTGTGT GATTTTTGAT GAGGTTCAGT TGTTTCCCCC TGGATACATC   600

GATCTGTGTT TACTTGTCAT ACGAAGTGAT GCTTTCATTT CACTTGCTGG TGATCCATGC   660

CAGAGCACAT ATGATTCACA GAAGGATCGA GCAATTTTGG GAGCTGAGCA GAGTGACATA   720

CTCAGACTGC TTGAAGGAAA GACATATAGG TACAACATAG AAAGCAGACG TTTTGTGAAC   780

CCAATGTTTG AATCTAGACT ACCATGTCAC TTCAAAAAGG GTTCAATGAC TGCAGCCTTT   840

GCTGATTATG CAATCTTCCA CAATATGCAT GACTTCCTCC TGGCGAGGTC AAAAGGCCCC   900

TTGGATGCTG TTCTAGTTTC CAGTTTTGAG GAGAAGAAAA TAGTCCAATC CTACTTTGGG   960

ATGAAGCAAC TCACTCTCAC ATTTGGTGAA TCAACTGGGT TGAACTTCAA AAATGGAGGA  1020

ATTCTCATAT CACATGACTC CTTTCATACT GACGATCGAC GGTGGCTTAC TGCTTTATCT  1080

CGATTCAGCC ATAATTTGGA TTTGGTGAAC ATCACAGGTC TTGAGGGTGG AAAGTTTTCT  1140

CTCACATTTT GCTGGTAAAC CCCTTTACCA CTTTTTGACG GCTTAAAAGT GGAGAGAATG  1200

TCATACGAGA CCTGCTTCAG GTGAGCCTAA CTTCTTTTAG GGGTTCAATG TCAGCATTGG  1260

AAAAAAATGG AAGGGGTTAG AGAA                                         1284
```

The nucleotide sequence of 140/94-2 (T3+F1) corresponds to SEQ. ID. No. 36 as follows:

```
CATTTTTAAA ATTTAATCCA GTCGACTCAC CAAATGTGAG CGTAAGCTGT TTCATCCCAA    60

AGTAGGACTG GACTATTTTC TTCTCCTCAA AACTAGAAAC CAGAATGGCA TCCAAAGGAC   120
```

-continued

```
CTTTTGACCT TGCCAGGAGG AAATCATGCA TATTGTGGAA AATGGCATAA TCAGCAAAGG   180
CAGCAGTCAT TGTACCCTTT TTGAAGTGAC ATGGCAGTCG AGATTCAAAC ATTGGGTTCA   240
CAAATCTTCT GCTTTCTATG TTGTACCTAT ACGTCTTGCC TTCAAGTATT TTGAGTATGT   300
CACTCTGCTC AGCGCCCAAA ATCGCCCGAT CTTTTTGTGA GTCATATGTG CTCTGACATG   360
GGTCACCAGC AAGTGAAATG AAAGCATCAC TACGTATAAT AAGCAAACAT AGATCGATGT   420
ATCCAGGGGG AAACAACTGG ACCTCATCGA AAATTACACA GTGACCAGCT TTTAGACCTG   480
CAACTTTTCT AAGGAAGACT TCAAAAGTCA CAACATCCCA TCCTTCCTTC TTTGACCTGC   540
CTGCTTTGGC AACTTTGCAG CTATCATCCA TTTCAAGATC ATTTTTGATT GAATTCGCTA   600
GAGCCCGTCT GGGGGAAACA AAAGTTACGA ATTTACCCTC AGATCTTTTC ATAAAGCTCT   660
TGTACAAAAA GCTTTTTCCG GCTCCAAATG TGCCAAGCAC AACAGTTAGC TCCCTCGGCT   720
TAATGTCAGT AGTTGATATA CCAGAAAGCC AGGGCTTTGC ATCACTGAAC TTCTCATCAC   780
TTATGACACC AGTTAGGCCT CCTAGCAGAC ACCCTTGCAA CTTTTCAGCC CGCTCAAAAC   840
TTGGGAAGTA GGTTACCTTG GACCCATTAA TTGAAAGAAG ATCAAGGGCG GATCGCTTGA   900
CCTTTCGCAA TTCATCTACT TTAATGCTCT GAGGGCCATT ACCTATCTTT TCAACATGCC   960
TTATGTGCTC ATTAGTTATG TCAAACAGAG CGGAAAACTT GCCATGTGGA TTAATCACCT  1020
CAATTTCCCC ATTTATGTCA CACTTAGCGC AAATGTCAAA AGCCTCAAAG GCTTCAGCTA  1080
AGTTACATCA TGTTGAGCCT CCCCCTTGGC AAAGCTCCTC AAAAATGTGG TTAGTGCTAG  1140
GCCTGCACAA TAATTAACAC ATCAACTTCA CCCTGCCAAT GCTGAACAAT ACTGTTATCA  1200
TGCAACCATC CATGGGGCAC ATGGTTGGAA TTGATTGATT TAAGGCAAAA ATCCCCACAG  1260
GGGGCATCCC CTTCCCCAAT TTCCACTGAT TCATACTCTG GCGTTATCAT ATCAACCCAA  1320
TGTGTCAAAT ACAAATAATG CAATCTCTCA TCTCCGATAA CATTTCCCCC ATTTTTTAAA  1380
AATGGTGGGG TGAAAATTGG AA                                            1402
```

The nucleotide sequence of 140/94-42 (T7+R1) corresponds to SEQ. ID. No. 37 as follows:

```
GTGGTTTTTG CAACAACAGG CCCAGGTCTA TCTAAGGTTT TGGAAATGCC TCGAAGCAAG    60
AAGCAATCTA TTCTGGTTCT TGAGGGAGCC CTATCCATAG AAACGGACTA TGGCCCAAAA   120
GTTCTGGGAT CTTTTGAAGT TTTCAAAGGG GATTTCAACA TTAAAAAAAT GGAAGAAAGT   180
TCCATCTTTG TAATAACATA CAAGGCCCCA GTTAGATCTA CTGGCAAGTT GAGGGTCCAC   240
CAATCAGAAT GCTCATTTTC TGGATCCAAG GAGGTATTGC TGGGTTGTCA GATTGAGGCA   300
TGTGCTGATT ATGATATTGA TGATTTCAAT ACTTTCTTTG TACCTGGTGA TGGTAATTGC   360
TTTTGGCATT CAGTTGGTTT CTTACTCAGT ACTGACGGAC TTGCTTTGAA GGCCGGCATT   420
CGTTCTTTCG TGGAGAGTGA ACGCCTGGTG AGTCCAGATC TTTCAGCCCC AACCATTTCT   480
AAACAACTGG GGGAAAATGC TTATGCCGAG AATGAGATGA TTGCATTATT TTGTATTCGA   540
CACCATGTGA GGCTGATAGT GATTACGCCA GAGTATGAAG TCAGTTGGAA ATTTGGGGAA   600
GGTGAATGGC CCCTGTGCGG AATTCTTTGC CTTAAATCAA ATCACTTCCA ACCATGTGCC   660
CCATTGAATG GTTGCATGAT TACAGCTATT GCTTCAGCAC TTGGTAGGCG TGAAGTTGAT   720
GTGCTTAATT ATCTGTGCAG GCCTAGCACT AACCACATTT TTGAGGAGCT TTGCCAAGGG   780
GGAGGCCTCA ACATGATGTA CTTAGCTGAA GCCTTTGAGG CTTTTGACAT TTGCGCTAAG   840
TGTGACATAA ATGGGGAAAT TGAGGTGATT AATCCACATG GCAAGTTTTC CGCTCTGTTT   900
```

-continued

```
GACATAACTA ATGAGCACAT AAGGCATGTT GAAAAGATAG GTAATGGCCC TCAGAGCATT   960

AAAGTAGATG AATTGCGAAA GGTCAAGCGA TCTGCCCTTG ATCTTCTTTC AATTAATGGG  1020

TCCAAGGTAA CCTACTTCCC AAGTTTTGAG CGGGCTGAAA AGTTGCAAGG GTGTCTGCTA  1080

GGAGGCCTAA CTGGTGTCAT AAGTGATGAG AAAGTCAGTG ATGCAAAGCC CTGCTTTTTG  1140

GTATATCAAC TACTGACATT AAGCCGAGGG AGCTAACTGT TGTGCTTTGG CACATTTGGA  1200

GCCCGGAAAA AGCCTTTTGT ACCAAGAGCT TTATTG                            1236
```

The nucleotide sequence of 140/94-6 (T3+BM98-3F+F2) corresponds to SEQ. ID. No. 38 as follows:

```
GTCTAACTGG CGTTATAAGT GATGAGAAAT TCAGTGATGC AAAACCTTGG CTTTCTGGTA    60

TATCTACTAC AGATATTAAG CCAAGGGAAT TAACTGTTGT GCTTGGTACA TTTGGGGCTG   120

GGAAGAGTTT CTTGTACAAG AGTTTCATGA AAAGGTCTGA GGGTAAATTC GTAACCTTTG   180

TTTCTCCCAG ACGTGCTTTA GCAAATTCAA TCAAAAATGA TCTTGAAATG GATGATAGCT   240

GCAAAGTTGC CAAAGCAGGT AGGTCAAAGA AGGAAGGGTG GGATGTAGTA ACTTTTGAGG   300

TCTTCCTCAG AAAAGTTGCA GGATTGAAGG CTGGCCACTG TGTGATTTTT GATGAGGTCC   360

AGTTGTTTCC TCCTGGATAC ATCGATCTAT GCTTGCTTAT TATACGTAGT GATGCTTTCA   420

TTTCACTTGC CGGTGATCCA TGTCAAAGCA CATATGATTC GCAAAAGGAT CGGGCAATTT   480

TGGGCGCTGA GCAGAGTGAC ATACTTAGAA TGCTTGAGGG CAAAACGTAT AGGTATAACA   540

TAGAAAGCAG GAGGTTTGTG AACCCAATGT TCGAATCAAG ACTGCCATGT CACTTCAAAA   600

AGGGTTCGAT GACTGCCGCT TTCGCTGATT ATGCAATCTT CCATAATATG CATGACTTTC   660

TCCTGGCGAG GTCAAAAGGT CCTTTGGATG CCGTTTTGGT TTCCAGTTTT GAGGAGAAAA   720

AGATAGTCCA GTCCTACTTT GGAATGAAAC AGCTCACACT CACATTTGGT GAATCAACTG   780

GGTTGAATTT CAAAAATGGG GGAATTCTCA TATCACATGA TTCCTTTCAC ACAGATGATC   840

GGCGGTGGCT TACTGCTTTA TCTCGCTTCA GCCACAATTT GGATTTGGTG AACATTACAG   900

GTCTGAGGTG GAAAGTTTCC TCTCGCACTT TGCTGGCAAA CCCCTCTACC ATTTTTTAAC   960

AGCCAAAAGT GGGGAGAATG TCATACGAGA TTTGCTCCCA GGTGAGCCTA ACTTCTTCAG  1020

TGGCTTTAAC GTTAGCATTG GAAAGAATGA AGGTGTTAGG GAGGAGAAGT TATGTGGTGA  1080

CCCATGGTTA AAAGTCATGC TTTTCCTGGG TCAAGATGAG GATTGTGAAG TTGAAGAGAT  1140

GGAGTCAGAG TGCTCAAATG AAGAATGGTT TAAAACCCAC ATTCCCCTGA GTAATCTGGA  1200

GTCAACCAGG GCTAGGTGGG TGGGTAAAAT GGCCTTGAAA GAGTATCGGG AGGTGCGTTG  1260

TGGTTATGAA ATGACTCAAC AATTCTTTGA TGACAT                            1296
```

The nucleotide sequence of 140/94-64 (T7+R1) corresponds to SEQ. ID. No. 39 as follows:

```
ATGTTCACCA AATCCAAATT ATGGCTGAAG CGAGATAAAG CAGTAAGCCA CCGCCGATCA   60

TCTGTGTGAA AGGAATCATG TGATATGAGA ATTCCCCCAT TTTTGAAATT CAACCCAGTT  120

GATTCACCAA ATGTGAGTGT GAGCTGTTTC ATTCCAAAGT AGGACTGGAC TATCTTTTTC  180

TCCTCAAAAC TGGAAACCAA AACGGCATCC AAAGGACCTT TTGACCTCGC CAGGAGAAAG  240

TCATGCATAT TATGGAAGAT TGCATAATCA GCGAAAGCGG CAGTCATTGA GCCCTTTTTG  300
```

-continued

```
AATTGACATG GCAGTCTTGA TTCGAACATT GGATTCACAA ACCTCCTGCT TTCAATGTTA  360

TACCTATACG TCTTGCCCTC AAGCAGTCTA AGTATGTCAC TCTGCTCAGC GCCCAAAATT  420

GCCCGATCCT TTTGCGAATC ATATGTGCTT TGACATGGAT CACCGGCAAG TGAAATGAAA  480

GCATCACTAC GTATAATAAG CAAGCATAGA TCGATGTATC CAGGAGGAAA CAACTGGACC  540

TCATCGAAAA TCACACAGTG GCCAGCCTTC AATCCTGCAA CTTTTCTGAG GAAAACCTCA  600

AAAGTTACTA CATCCCACCC TTCCTTCTTT GACCTACCTG CTTTAGCAAC TTTGCAGCTA  660

TCATCCATTT CAAGATCATT TTTGATTGAA TTTGCTAAAG CACGTCTGGG AGAAACAAAG  720

GTTACGAATT TACCCTCAGA CCTTTTCATG AAACTCTTGT ACAAGAAACT CTTCCCAGCC  780

CCAAATGTAC CAAGCACGAC AGTCAACTCC CTTGGCTTAA TATCAGTAGT AGATATACCA  840

GAAAGCCAAG GTTTTGCATC ACTGAACTTC TCATCACTTA TAACGCCAGT TAGGCCCCCT  900

AGCAAAC                                                            907
```

The nucleotide sequence of 140–94–72 (T7+R1) corresponds to SEQ. ID. No. 40 as follows:

```
AGAATGCTTA TGCTGAGAAT GAGATGATTG CATTATTTTG CATCCGGCAC CATGTAAGGC    60

TTATAGTAAT AACACCGGAA TATGAAGTTA GTTGGAAATT TGGGGAAAGT GAGTGGCCCC   120

TATGTGGAAT TCTTTGCCTG AGGTCCAATC ACTTCCAACC ATGCGCCCCG CTGAATGGTT   180

GCATGATCAC GGCTATTGCT TCAGCACTTG GGAGGCGTGA GGTTGATGTG TTAAATTATC   240

TGTGTAGGCC TAGCACTAAT CACATCTTTG AGGAGCTGTG CCAGGGCGGA GGGCTTAATA   300

TGATGTACTT GGCTGAAGCT TTTGAGGCCT TTGACATTTG TGCAAAGTGC GACATAAATG   366

GGGAAATTGA GGTCATTAAC CCAAATGGCA AGATTTCCGC CTTGTTTGAT ATAACTAATG   420

AGCACATAAG GCATGTTGAG AAGATCAGCA ATGGCCCTCA GAGCATAAAA ATAGATGAGT   480

TGAGGAAGGT TAAGCGATCC CGCCTTGACC TTCTTTCAAT GAATGGGTCC AAAATAACCT   540

ATTTTCCAAA CTTTGAGCGG GCTGAAAAGT TGCAAGGGTG CTTGCTAGAG GGCCTGACTG   600

GTGTCATAAG TGATGAAAAG TTCAGTGATG CAAAACCTTG GCTTTCTGGT ATATCAACTG   660

CGGATATTAA GCCAAGAGAG CTAACTGTCG TGCTTGGCAC ATTTGGTGCT GGAAAGAGTT   720

TCTTGTATAA GAGTTTCATG AAGAGATCTG AAGGAAAATT TGTAACTTTT GTTTCCCCTA   780

GGCGAGCTTT GGCCAATTCG ATCAAGAATG ATCTTGAAAT GGATGATGGC TGCAAAGTTG   840

CCAAAGCAGG CAAGTCAAAG AAGGAAGGGT GGGATGTGGT AACATTTGAG GTTTTCCTTA   900

GAAAAGTTTC TGGTTTGAAG GCTGGTCATT GTGTGATTTT CGATGAGGTT CAGTTGTTTC   960

CCCCTGGATA TATCGATCTA TGTTTACTTG TCATACGCAG TGATGCTTTT ATTTCACTTG  1020

CCGGTGATCC ATGCCAGAGC ACATATGATT CACAAAAGGA TCGGGCAATT TTGGGAGCTG  1080

AGCAGAGTGA CATACTCAGA TTGCTTGAAG GAAAGACGTA TAGGTACAAC ATAGAAAGCA  1140

GACGTTTTGT GAACCCAATG TTTGAATTTA GACTACCATG TCACTTCAAA AAAGGGTTCA  1200

ATGACTGCTG CCTTTGCTGA TTATGCAATC TT
```

Also encompassed by the present invention are fragments of the DNA molecules of the present invention. Suitable fragments capable of imparting RSP resistance to grape plants are constructed by using appropriate restriction sites, revealed by inspection of the DNA molecule's sequence, to: (i) insert an interposon (Felley et al., "Interposon Mutagenesis of Soil and Water Bacteria: A Family of DNA Fragments Designed for in vitro Insertion Mutagenesis of Gram-negative Bacteria," *Gene,* 52:147–15 (1987), which is hereby incorporated by reference) such that truncated forms of the RSP virus polypeptide or protein, that lack various amounts of the C-terminus, can be produced or (ii) delete various internal portions of the protein. Alternatively, the sequence can be used to amplify any portion of the coding region, such that it can be cloned into a vector supplying both transcription and translation start signals.

Suitable DNA molecules are those that hybridize to a DNA molecule comprising a nucleotide sequence of at least 15 continuous bases of SEQ. ID. No. 1 under stringent conditions characterized by a hybridization buffer comprising 0.9M sodium citrate ("SSC") buffer at a temperature of 37° C. and remaining bound when subject to washing with SSC buffer at 37° C.; and preferably in a hybridization buffer comprising 20% formamide in 0.9M saline/0.9M SSC buffer at a temperature of 42° C. and remaining bound when subject to washing at 42° C. with 0.2×SSC buffer at 42° C.

Variants may also (or alternatively) be modified by, for example, the deletion or addition of nucleotides that have minimal influence on the properties, secondary structure and hydropathic nature of the encoded protein or polypeptide. For example, the nucleotides encoding a protein or polypeptide may be conjugated to a signal (or leader) sequence at the N-terminal end of the protein which co-translationally or post-translationally directs transfer of the protein. The nucleotide sequence may also be altered so that the encoded protein or polypeptide is conjugated to a linker or other sequence for ease of synthesis, purification, or identification of the polypeptide.

The protein or polypeptide of the present invention is preferably produced in purified form (preferably, at least about 80%, more preferably 90%, pure) by conventional techniques. Typically, the protein or polypeptide of the present invention is isolated by lysing and sonication. After washing, the lysate pellet is re-suspended in buffer containing Tris-HCl. During dialysis, a precipitate forms from this protein solution. The solution is centrifuged, and the pellet is washed and re-suspended in the buffer containing Tris-HCl. Proteins are resolved by electrophoresis through an SDS 12% polyacrylamide gel.

The DNA molecule encoding the RSP virus protein or polypeptide of the present invention can be incorporated in cells using conventional recombinant DNA technology. Generally, this involves inserting the DNA molecule into an expression system to which the DNA molecule is heterologous (i.e., not normally present). The heterologous DNA molecule is inserted into the expression system or vector in proper sense orientation and correct reading frame. The vector contains the necessary elements for the transcription and translation of the inserted protein-coding sequences.

U.S. Pat. No. 4,237,224 to Cohen and Boyer, which is hereby incorporated by reference, describes the production of expression systems in the form of recombinant plasmids using restriction enzyme cleavage and ligation with DNA ligase. These recombinant plasmids are then introduced by means of transformation and replicated in unicellular cultures including procaryotic organisms and eukaryotic cells grown in tissue culture.

Recombinant genes may also be introduced into viruses, such as vaccinia virus. Recombinant viruses can be generated by transfection of plasmids into cells infected with virus.

Suitable vectors include, but are not limited to, the following viral vectors such as lambda vector system gt11, gt WES.tB, Charon 4, and plasmid vectors such as pBR322, pBR325, pACYC177, pACYC184, pUC8, pUC9, pUC18, pUC19, pLG339, pR290, pKC37, pKC101, SV 40, pBluescript II SK +/− or KS+/− (see "Stratagene Cloning Systems" Catalog (1993) from Stratagene, La Jolla, Calif., which is hereby incorporated by reference), pQE, pIH821, pGEX, pET series (see Studier et. al., "Use of T7 RNA Polymerase to Direct Expression of Cloned Genes," *Gene Expression Technology* vol. 185 (1990), which is hereby incorporated by reference), and any derivatives thereof Suitable vectors are continually being developed and identified. Recombinant molecules can be introduced into cells via transformation, transduction, conjugation, mobilization, or electroporation. The DNA sequences are cloned into the vector using standard cloning procedures in the art, as described by Maniatis et al., *Molecular Cloning: A Laboratory Manual*, Cold Springs Laboratory, Cold Springs Harbor, N.Y. (1982), which is hereby incorporated by reference.

A variety of host-vector systems may be utilized to express the protein-encoding sequence(s). Primarily, the vector system must be compatible with the host cell used. Host-vector systems include but are not limited to the following: bacteria transformed with bacteriophage DNA, plasmid DNA, or cosmid DNA; microorganisms such as yeast containing yeast vectors; mammalian cell systems infected with virus (e.g., vaccinia virus, adenovirus, etc.); insect cell systems infected with virus (e.g., baculovirus); and plant cells infected by bacteria or transformed via particle bombardment (i.e. biolistics). The expression elements of these vectors vary in their strength and specificities. Depending upon the host-vector system utilized, any one of a number of suitable transcription and translation elements can be used.

Different genetic signals and processing events control many levels of gene expression (e.g., DNA transcription and messenger RNA ("mRNA") translation).

Transcription of DNA is dependent upon the presence of a promoter which is a DNA sequence that directs the binding of RNA polymerase and thereby promotes mRNA synthesis. The DNA sequences of eukaryotic promoters differ from those of procaryotic promoters. Furthermore, eukaryotic promoters and accompanying genetic signals may not be recognized in or may not function in a procaryotic system, and, further, procaryotic promoters are not recognized and do not function in eukaryotic cells.

Similarly, translation of mRNA in procaryotes depends upon the presence of the proper procaryotic signals which differ from those of eukaryotes Efficient translation of mRNA in procaryotes requires a ribosome binding site called the Shine-Dalgarno ("SD") sequence on the mRNA. This sequence is a short nucleotide sequence of mRNA that is located before the start codon, usually AUG, which encodes the amino-terminal methionine of the protein. The SD sequences are complementary to the 3'-end of the 16S rRNA (ribosomal RNA) and probably promote binding of mRNA to ribosomes by duplexing with the rRNA to allow correct positioning of the ribosome. For a review on maximizing gene expression, see Roberts and Lauer, *Methods in Enzymology,* 68:473 (1979), which is hereby incorporated by reference.

Promoters vary in their "strength" (i.e., their ability to promote transcription). For the purposes of expressing a cloned gene, it is desirable to use strong promoters in order to obtain a high level of transcription and, hence, expression of the gene. Depending upon the host cell system utilized, any one of a number of suitable promoters may be used. For instance, when cloning in *E. coli,* its bacteriophages, or plasmids, promoters such as the T7 phage promoter, lac promoter, trp promoter, recA promoter, ribosomal RNA promoter, the $P_R$ and $P_L$ promoters of coliphage lambda and others, including but not limited, to lacUV5, ompF, bla, lpp, and the like, may be used to direct high levels of transcription of adjacent DNA segments. Additionally, a hybrid trp-lacUV5 (tac) promoter or other *E. coli* promoters produced by recombinant DNA or other synthetic DNA techniques may be used to provide for transcription of the inserted gene.

Bacterial host cell strains and expression vectors may be chosen which inhibit the action of the promoter unless specifically induced. In certain operons, the addition of specific inducers is necessary for efficient transcription of the inserted DNA. For example, the lac operon is induced by the addition of lactose or IPTG (isopropylthio-beta-D-galactoside). A variety of other operons, such as trp, pro, etc., are under different controls.

Specific initiation signals are also required for efficient gene transcription and translation in procaryotic cells. These transcription and translation initiation signals may vary in "strength" as measured by the quantity of gene specific messenger RNA and protein synthesized, respectively. The DNA expression vector, which contains a promoter, may also contain any combination of various "strong" transcription and/or translation initiation signals. For instance, efficient translation in *E. coli* requires a Shine-Dalgarno ("SD") sequence about 7–9 bases 5' to the initiation codon ("ATG") to provide a ribosome binding site. Thus, any SD-ATG combination that can be utilized by host cell ribosomes may be employed. Such combinations include but are not limited to the SD-ATG combination from the cro gene or the N gene of coliphage lambda, or from the *E. coli* tryptophan E, D, C, B or A genes. Additionally, any SD-ATG combination produced by recombinant DNA or other techniques involving incorporation of synthetic nucleotides may be used.

Once the isolated DNA molecules encoding the various Rupestris stem pitting associated virus proteins or polypeptides, as described above, have been cloned into an expression system, they are ready to be incorporated into a host cell. Such incorporation can be carried out by the various forms of transformation noted above, depending upon the vector/host cell system. Suitable host cells include, but are not limited to, bacteria, virus, yeast, mammalian cells, insect, plant, and the like.

The present invention also relates to RNA molecules which encode the various RSP virus proteins or polypeptides described above. The transcripts can be synthesized using the host cells of the present invention by any of the conventional techniques. The mRNA can be translated either in vitro or in vivo. Cell-free systems typically include wheat-germ or reticulocyte extracts. In vivo translation can be effected, for example, by microinjection into frog oocytes.

One aspect of the present invention involves using one or more of the above DNA molecules encoding the various proteins or polypeptides of a RSP virus to transform grape plants in order to impart RSP resistance to the plants. The mechanism by which resistance is imparted in not known. In one hypothetical mechanism, the transformed plant can express the coat protein or polypeptide, and, when the transformed plant is inoculated by a RSP virus, such as RSPaV-1, the expressed coat protein or polypeptide surrounds the virus, thereby preventing translation of the viral DNA.

In this aspect of the present invention, the subject DNA molecule incorporated in the plant can be constitutively expressed. Alternatively, expression can be regulated by a promoter which is activated by the presence of RSP virus. Suitable promoters for these purposes include those from genes expressed in response to RSP virus infiltration.

The isolated DNA molecules of the present invention can be utilized to impart RSP virus resistance for a wide variety of grapevine plants. The DNA molecules are particularly well suited to imparting resistance to Vitis scion or rootstock cultivars. Scion cultivars which can be protected include those commonly referred to as Table or Raisin Grapes, such as Alden, Almeria, Anab-E-Shahi, Autumn Black, Beauty Seedless, Black Corinth, Black Damascus, Black Malvoisie, Black Prince, Blackrose, Bronx Seedless, Burgrave, Calmeria, Campbell Early, Canner, Cardinal, Catawba, Christmas, Concord, Dattier, Delight, Diamond, Dizmar, Duchess, Early Muscat, Emerald Seedless, Emperor, Exotic, Ferdinand de Lesseps, Fiesta, Flame seedless, Flame Tokay, Gasconade, Gold, Himrod, Hunisa, Hussiene, Isabella, Italia, July Muscat, Khandahar, Katta, Kourgane, Kishmishi, Loose Perlette, Malaga, Monukka, Muscat of Alexandria, Muscat Flame, Muscat Hamburg, New York Muscat, Niabell, Niagara, Olivette blanche, Ontario, Pierce, Queen, Red Malaga, Ribier, Rish Baba, Romulus, Ruby Seedless, Schuyler, Seneca, Suavis (IP 365), Thompson seedless, and Thomuscat. They also include those used in wine production, such as Aleatico, Alicante Bouschet, Aligote, Alvarelhao, Aramon, Baco blanc (22A), Burger, Cabernet franc, Cabernet, Sauvignon, Calzin, Carignane, Charbono, Chardonnay, Chasselas dore, Chenin blanc, Clairette blanche, Early Burgundy, Emerald Riesling, Feher Szagos, Fernao Pires, Flora, French Colombard, Fresia, Furmint, Gamay, Gewurztraminer, Grand noir, Gray Riesling, Green Hungarian, Green Veltliner, Grenache, Grillo, Helena, Inzolia, Lagrein, Lambrusco de Salamino, Malbec, Malvasia bianca, Mataro, Melon, Merlot, Meunier, Mission, Montua de Pilas, Muscadelle du Bordelais, Muscat blanc, Muscat Ottonel, Muscat Saint-Vallier, Nebbiolo, Nebbiolo fino, Nebbiolo Lampia, Orange Muscat, Palomino, Pedro Ximenes, Petit Bouschet, Petite Sirah, Peverella, Pinot noir, Pinot Saint-George, Primitivo di Gioa, Red Veltliner, Refosco, Rkatsiteli, Royalty, Rubired, Ruby Cabernet, Saint-Emilion, Saint Macaire, Salvador, Sangiovese, Sauvignon blanc, Sauvignon gris, Sauvignon vert, Scarlet, Seibel 5279, Seibel 9110, Seibel 13053, Semillon, Servant, Shiraz, Souzao, Sultana Crimson, Sylvaner, Tannat, Teroldico, Tinta Madeira, Tinto cao, Touriga, Traminer, Trebbiano Toscano, Trousseau, Valdepenas, Viognier, Walschriesling, White Riesling, and Zinfandel. Rootstock cultivars which can be protected include Couderc 1202, Couderc 1613, Couderc 1616, Couderc 3309, Dog Ridge, Foex 33 EM, Freedom, Ganzin 1 (A×R #1), Harmony, Kober 5BB, LN33, Millardet & de Grasset 41B, Millardet & de Grasset 420A, Millardet & de Grasset 101–14, Oppenheim 4 (S04), Paulsen 775, Paulsen 1045, Paulsen 1103, Richter 99, Richter 110, Riparia Gloire, Ruggeri 225, Saint-George, Salt Creek, Teleki 5A, *Vitis rupestris* Constantia, *Vitis California*, and *Vitis girdiana*.

Plant tissue suitable for transformation include leaf tissue, root tissue, meristems, zygotic and somatic embryos, and anthers. It is particularly preferred to utilize embryos obtained from anther cultures.

The expression system of the present invention can be used to transform virtually any plant tissue under suitable conditions. Tissue cells transformed in accordance with the present invention can be grown in vitro in a suitable medium to impart RSPaV resistance. Transformed cells can be regenerated into whole plants such that the protein or polypeptide imparts resistance to RSPaV in the intact transgenic plants. In either case, the plant cells transformed with the recombinant DNA expression system of the present invention are grown and caused to express that DNA molecule to produce one of the above-described RSPaV proteins or polypeptides and, thus, to impart RSPaV resistance.

In producing transgenic plants, the DNA construct in a vector described above can be microinjected directly into plant cells by use of micropipettes to transfer mechanically the recombinant DNA. Crossway, *Mol. Gen. Genetics,* 202:179–85 (1985), which is hereby incorporated by reference. The genetic material may also be transferred into the plant cell using polyethylene glycol. Krens, et al., *Nature* 296:72–74 (1982), which is hereby incorporated by reference.

One technique of transforming plants with the DNA molecules in accordance with the present invention is by contacting the tissue of such plants with an inoculum of a bacteria transformed with a vector comprising a gene in accordance with the present invention which imparts RSPaV resistance. Generally, this procedure involves inoculating the plant tissue with a suspension of bacteria and incubating the tissue for 48 to 72 hours on regeneration medium without antibiotics at 25–28° C.

Bacteria from the genus Agrobacterium can be utilized to transform plant cells. Suitable species of such bacterium include *Agrobacterium tumefaciens* and *Agrobacterium rhizogenes. Agrobacterium tumefaciens* (e.g., strains C58, LBA4404, or EHA105) is particularly useful due to its well-known ability to transform plants.

Heterologous genetic sequences can be introduced into appropriate plant cells, by means of the Ti plasmid of *A. tumefaciens* or the Ri plasmid of *A. rhizogenes.* The Ti or Ri plasmid is transmitted to plant cells on infection by Agrobacterium and is stably integrated into the plant genome. J. Schell, *Science,* 237:1176–83 (1987), which is hereby incorporated by reference.

After transformation, the transformed plant cells must be regenerated.

Plant regeneration from cultured protoplasts is described in Evans et al., *Handbook of Plant Cell Cultures* Vol. 1: MacMillan Publishing Co., New York, 1983); and Vasil I.R. (ed.), *Cell Culture and Somatic Cell Genetics of Plants,* Acad. Press, Orlando, Vol. 1, 1984, and Vol. III (1986), which are hereby incorporated by reference.

It is known that practically all plants can be regenerated from cultured cells or tissues, including but not limited to, all major species of sugarcane, sugar beets, cotton, fruit trees, and legumes.

Means for regeneration vary from species to species of plants, but generally a suspension of transformed protoplasts or a petri plate containing explants is first provided. Callus tissue is formed and shoots may be induced from callus and subsequently rooted. Alternatively, embryo formation can be induced in the callus tissue. These embryos germinate as natural embryos to form plants. The culture media will generally contain various amino acids and hormones, such as auxin and cytokinins. It is also advantageous to add glutamic acid and proline to the medium. Efficient regeneration will depend on the medium, on the genotype, and on the history of the culture. If these three variables are controlled, then regeneration is usually reproducible and repeatable.

After the expression cassette is stably incorporated in transgenic plants, it can be transferred to other plants by sexual crossing. Any of a number of standard breeding techniques can be used, depending upon the species to be crossed.

Once transgenic plants of this type are produced, the plants themselves can be cultivated in accordance with conventional procedure so that the DNA construct is present in the resulting plants. Alternatively, transgenic seeds are recovered from the transgenic plants. These seeds can then be planted in the soil and cultivated using conventional procedures to produce transgenic plants.

Another approach to transforming plant cells with a gene which imparts resistance to pathogens is particle bombardment (also known as biolistic transformation) of the host cell. This can be accomplished in one of several ways. The first involves propelling inert or biologically active particles at cells. This technique is disclosed in U.S. Pat. Nos. 4,945,050, 5,036,006, and 5,100,792, all to Sanford et al., and in Emerschad et al., "Somatic Embryogenesis and Plant Development from Immature Zygotic Embryos of Seedless Grapes (*Vitis vinifera*)," *Plant Cell Reports,* 14:6–12 (1995) ("Emerschad (1995)"), which are hereby incorporated by reference. Generally, this procedure involves propelling inert or biologically active particles at the cells under conditions effective to penetrate the outer surface of the cell and to be incorporated within the interior thereof. When inert particles are utilized, the vector can be introduced into the cell by coating the particles with the vector containing the heterologous DNA. Alternatively, the target cell can be surrounded by the vector so that the vector is carried into the cell by the wake of the particle. Biologically active particles (e.g., dried bacterial cells containing the vector and heterologous DNA) can also be propelled into plant cells.

Once a grape plant tissue is transformed in-accordance with the present invention, it is regenerated to form a transgenic grape plant. Generally, regeneration is accomplished by culturing transformed tissue on medium containing the appropriate growth regulators and nutrients to allow for the initiation of shoot meristems. Appropriate antibiotics are added to the regeneration medium to inhibit the growth of Agrobacterium and to select for the development of transformed cells. Following shoot initiation, shoots are allowed to develop tissue culture and are screened for marker gene activity.

The DNA molecules of the present invention can be made capable of transcription to a messenger RNA that does not translate to the protein. This is known as RNA-mediated resistance. When a Vitis scion or rootstock cultivar is transformed with such a DNA molecule, the DNA molecule can be transcribed under conditions effective to maintain the messenger RNA in the plant cell at low level density readings. Density readings of between 15 and 50 using a Hewlet ScanJet and Image Analysis Program are preferred.

A portion of one or more DNA molecules of the present invention as well as other DNA molecules can be used in a transgenic grape plant in accordance with U.S. patent application Ser. No. 09/025,635, which is hereby incorporated herein by reference.

The RSPaV protein or polypeptide can also be used to raise antibodies or binding portions thereof or probes. The antibodies can be monoclonal or polyclonal.

Monoclonal antibody production may be effected by techniques which are well-known in the art. Basically, the process involves first obtaining immune cells (lymphocytes) from the spleen of a mammal (e.g., mouse) which has been previously immunized with the antigen of interest either in vivo or in vitro. The antibody-secreting lymphocytes are then fused with (mouse) myeloma cells or transformed cells, which are capable of replicating indefinitely in cell culture, thereby producing an immortal, immunoglobulin-secreting cell line. The resulting fused cells, or hybridomas, are cultured, and the resulting colonies screened for the production of the desired monoclonal antibodies. Colonies producing such antibodies are cloned, and grown either in vivo or in vitro to produce large quantities of antibody. A description of the theoretical basis and practical methodology of fusing such cells is set forth in Kohler and Milstein, *Nature,* 256:495 (1975), which is hereby incorporated by reference.

Mammalian lymphocytes are immunized by in vivo immunization of the animal (e.g., a mouse) with the protein or polypeptide of the present invention. Such immunizations are repeated as necessary at intervals of up to several weeks to obtain a sufficient titer of antibodies. Following the last antigen boost, the animals are sacrificed and spleen cells removed.

Fusion with mammalian myeloma cells or other fusion partners capable of replicating indefinitely in cell culture is effected by standard and well-known techniques, for example, by using polyethylene glycol ("PEG") or other fusing agents. (See Milstein and Kohler, *Eur. J. Immunol.,* 6:511 (1976), which is hereby incorporated by reference.) This immortal cell line, which is preferably murine, but may also be derived from cells of other mammalian species, including but not limited to rats and humans, is selected to be deficient in enzymes necessary for the utilization of certain nutrients, to be capable of rapid growth, and to have good fusion capability. Many such cell lines are known to those skilled in the art, and others are regularly described.

Procedures for raising polyclonal antibodies are also well known. Typically, such antibodies can be raised by administering the protein or polypeptide of the present invention subcutaneously to New Zealand white rabbits which have first been bled to obtain pre-immune serum. The antigens can be injected at a total volume of 100 $\mu$l per site at six different sites. Each injected material will contain synthetic surfactant adjuvant pluronic polyols, or pulverized acrylamide gel containing the protein or polypeptide after SDS-polyacrylamide gel electrophoresis. The rabbits are then bled two weeks after the first injection and periodically boosted with the same antigen three times every six weeks. A sample of serum is then collected 10 days after each boost. Polyclonal antibodies are then recovered from the serum by affinity chromatography using the corresponding antigen to capture the antibody. Ultimately, the rabbits are euthanized with pentobarbital 150 mg/Kg IV. This and other procedures for raising polyclonal antibodies are disclosed in Harlow et. al., editors, *Antibodies: A Laboratory Manual* (1988), which is hereby incorporated by reference.

In addition to utilizing whole antibodies, binding portions of such antibodies can be used. Such binding portions include Fab fragments, $F(ab')_2$ fragments, and Fv fragments. These antibody fragments can be made by conventional procedures, such as proteolytic fragmentation procedures, as described in Goding, *Monoclonal Antibodies: Principles and Practices*, New York: Academic Press, pp. 98–118 (1983), which is hereby incorporated by reference.

The present invention also relates to probes found either in nature or prepared synthetically by recombinant DNA procedures or other biological procedures. Suitable probes are molecules that bind to RSP viral antigens identified by the polyclonal antibodies of the present invention or bind to the nucleic acid of RSPaV. Such probes can be, for example, proteins, peptides, lectins, or nucleic acids.

The antibodies or binding portions thereof or probes can be administered to RSPaV infected scion cultivars or rootstock cultivars. Alternatively, at least the binding portions of these antibodies can be sequenced, and the encoding DNA synthesized. The encoding DNA molecule can be used to transform plants together with a promoter which causes expression of the encoded antibody when the plant is infected by an RSPaV. In either case, the antibody or binding portion thereof or probe will bind to the virus and help prevent the usual stem pitting response.

Antibodies raised against the proteins or polypeptides of the present invention or binding portions of these antibodies can be utilized in a method for detection of RSPaV in a sample of tissue, such as tissue from a grape scion or rootstock. Antibodies or binding portions thereof suitable for use in the detection method include those raised against a replicase, proteins or polypeptides of the triple gene block, or a coat protein or polypeptide in accordance with the present invention. Any reaction of the sample with the antibody is detected using an assay system which indicates the presence of RSPaV in the sample. A variety of assay systems can be employed, such as enzyme-linked immunosorbent assays, radioimmunoassays, gel diffusion precipitin reaction assays, immunodiffusion assays, agglutination assays, fluorescent immunoassays, protein A immunoassays, or immunoelectrophoresis assays.

Alternatively, the RSPaV can be detected in such a sample using the DNA molecules of the present, RNA molecules of the present invention, or DNA or RNA fragments thereof, as probes in nucleic acid hybridization assays for detecting the presence of complementary virus DNA or RNA in the various tissue samples described above. The nucleotide sequence is provided as a probe in a nucleic acid hybridization assay or a gene amplification detection procedure (e.g., using a polymerase chain reaction procedure). The nucleic acid probes of the present invention may be used in any nucleic acid hybridization assay system known in the art, including, but not limited to, Southern blots (Southern, E. M., "Detection of Specific Sequences Among DNA Fragments Separated by Gel Electrophoresis," *J. Mol. Biol.;* 98:503–17 (1975), which is hereby incorporated by reference), Northern blots (Thomas, P. S., "Hybridization of Denatured RNA and Small DNA Fragments Transferred to Nitrocellulose," *Proc. Nat'l Acad. Sci. USA,* 77:5201–05 (1980), which is hereby incorporated by reference), and Colony blots (Grunstein, M., et al., "Colony Hybridization: A Method for the Isolation of Cloned cDNAs that Contain a Specific Gene," *Proc. Nat'l Acad. Sci. USA,* 72:3961–65 (1975), which is hereby incorporated by reference). Alternatively, the isolated DNA molecules of the present invention or RNA transcripts thereof can be used in a gene amplification detection procedure (e.g., a polymerase chain reaction). Erlich, H. A., et. al., "Recent Advances in the Polymerase Chain Reaction," *Science* 252:1643–51 (1991), which is hereby incorporated by reference. Any reaction with the probe is detected so that the presence of RSP virus in the sample is indicated. Such detection is facilitated by providing the DNA molecule of the present invention with a label. Suitable labels include a radioactive compound, a fluorescent compound, a chemiluminescent compound, an enzymatic compound, or other equivalent nucleic acid labels.

Depending upon the desired scope of detection, it is possible to utilize probes having nucleotide sequences that correspond with conserved or variable regions of the ORF or UTR. For example, to distinguish RSPaV from other related viruses (as described herein), it is desirable to use probes which contain nucleotide sequences that correspond to sequences more highly conserved among all RSPaV strains. Also, to distinguish between different RSPaV strains (e.g., RSPaV-1, RSP47-4, RSP158), it is desirable to utilize probes containing nucleotide sequences that correspond to sequences less highly conserved among the RSP virus strains.

Nucleic acid (DNA or RNA) probes of the present invention will hybridize to complementary RSPaV-1 nucleic acid under stringent conditions. Less stringent conditions may also be selected. Generally, stringent conditions are selected to be about 50° C. lower than the thermal melting point ($T_m$) for the specific sequence at a defined ionic strength and pH. The $T_m$ is the temperature (under defined ionic strength and pH) at which 50% of the target sequence hybridizes to a perfectly matched probe. The $T_m$ is dependent upon the solution conditions and the base composition of the probe, and may be calculated using the following equation:

$$T_m = 79.8^\circ \text{ C.} + (18.5 \times \text{Log}[\text{Na}+]) + (58.4^\circ \text{ C.} \times \%[G + C]) - (820/\#bp \text{ in duplex}) - (0.5 \times \% \text{ formamide})$$

Nonspecific binding may also be controlled using any one of a number of known techniques such as, for example, blocking the membrane with protein-containing solutions, addition of heterologous RNA, DNA, and SDS to the hybridization buffer, and treatment with RNase. Generally, suitable stringent conditions for nucleic acid hybridization assays or gene amplification detection procedures are as set forth above. More or less stringent conditions may also be selected.

The development of a rapid detection method for RSP is a major breakthrough, because the only detection method now available is through inoculation of St. George grape indicators, which takes two to three years to develop symptoms. A serological or nucleic acid based detection tests developed for RSP will take only 1 to 2 days and it is less expensive. The woody indicator test on St. George costs $250 per sample, while a serological or nucleic acid based test would cost $30–50 per sample. Moreover, the rapid tests will speed up the introduction of grape imports into the US from the current three years to about six months. These applications will be valuable wherever grapes are grown. Since RSP is part of the rugose wood complex, development of rapid detection methods will be invaluable in determining the significance of RSP in the rugose wood complex. This will allow an investigator to determine whether RSP alone can cause the rugose wood complex or if other components are needed. In addition, these rapid detection methods are very useful to evaluate the resistance of transgenic plants to Rupestris stem pitting associated virus.

EXAMPLES

The following examples are provided to illustrate embodiments of the present invention but are by no means intended to limit its scope.

Example 1

Grapevine Materials for dsRNA Analysis

Samples from 15 accessions that induced pitting on graft-inoculated St. George were collected from the National Grapevine Germplasm Repository of the USDA Plant Genetic Resources Unit (PGRU) at Geneva and used for dsRNA analysis. Positive controls used included Thompson Seedless (RSP105) (Golino, "The Davis Grapevine Virus Collection," *Am. J. Enology Viticulture,* 43:200–05 (1992), which is hereby incorporated by reference) from the FPMS, University of California (Davis) and Pinot Noir (SVP186-09A2), which was kindly provided by Dr. R. Johnson of Center for Plant Health, Agriculture Canada, Sidney, British Columbia. Negative controls as judged by indexing on St. George included Freedom from the PGRU at Geneva, N.Y., and Verduzzo 233A. The latter was kindly provided by Dr. P. Silvano of the Sezione di Fitovirologia, ERSA Servizio Chimico-Agrario e della Certificazione, Pozzuolo del Friuh (UD), Italy.

Example 2

Grapevine Materials for RT-PCR

Dormant cuttings of 138 grapevine selections were collected from USA, Canada, Italy, and Portugal over three years. Samples included Vitis vinifera cultivars, hybrids, V. riparia, and rootstocks. 117 grapevine selections were indexed on St. George for RSP and other RW diseases. Pinot noir (1186-9A2) from Agriculture Canada, Center for Plant Health (Sidney, Canada) and Thompson seedless (RSP105) from University of California (Davis) were included as positive controls. Sauvignon blanc, generated from shoot tip tissue culture and tested free of viruses and viroids was provided by Dr. J. Semancik (University of California at Riverside) and used as a healthy control. In addition, six seedlings of five Vitis species were also included as negative controls.

Example 3 dsRNA Isolation and Analysis

Methods for isolating dsRNA were described by Hu et al., "Characterization of Closterovirus-like Particles Associated with Grapevine Leafroll Disease," *J. Phytopathology,* 128:1–14 (1990), which is hereby incorporated by reference, except that 1×STE with 15% ethanol (instead of 16.5%) was used to wash CF-11 cellulose columns prior to elution of dsRNAs. The dsRNAs were isolated from leaves, petioles, and the phloem tissue of dormant canes, electrophoresed on 1% agarose or low melting temperature agarose gels, and analyzed by staining with ethidium bromide (EtBr). Hind EII digested lambda DNA was used as markers to estimate the sizes of the dsRNA molecules.

Example 4 cDNA Synthesis and Cloning

The extremely low yield of dsRNA and the limited quantity of RSP-infected grape materials precluded the use of a single RSP-infected grapevine accession as the source of dsRNA for cloning purpose. Therefore, dsRNA preparations from Colobel 257, Ravat 34, Couderc 28-112, and Seyval were pooled and used as templates for cDNA synthesis. In order to get pure templates for cloning, dsRNA bands were excised from low melting temperature agarose gels after electrophoresis and recovered by extraction with phenol and chloroform (Sambrook et al., *Molecular Cloning: A Laboratory Manual,* 2nd ed., Cold Spring Harbor Laboratory Press, Cold Spring Harbor, N.Y. (1989), which is hereby incorporated by reference). The same recovery procedure was repeated once more. The purified dsRNA was denatured with 20 mM methyl mercuric hydroxide and cDNAs were synthesized using slightly modified methods of Jelkmann et al., "Cloning of Four Viruses from Small Quantities of Double-Stranded RNA," *Phytopathology*, 79:1250–53 (1989), which is incorporated herein be reference. The cDNA fragments were first blunt-ended with T4 DNA polymerase at 12° C. T4 DNA ligase was used to add EcoR I adapters to both ends of the cDNAs. Subsequently, the cDNA molecules with cohesive ends were ligated to EcoR I-prepared arms of lambda ZAP II. Finally, the resulting recombinant phages were packed into Gigapack II packaging extract following manufacturer's instructions (Stratagene, La Jolla, Calif.).

Example 5

Identification of cDNA Clones Specific to the dsRNA

Plaque hybridization was used to screen cDNA clones by transferring recombinant cDNA plaques to nylon membranes and hybridizing to $^{32}P$-labeled first-strand cDNA probes generated from the dsRNA according to manufacturer's recommendations (Du Pont, 1987). Clones with strong hybridization signals were converted into pBluescript SK through in vivo excision (Stratagene, 1991). After digestion of the resulting plasmids with EcoR I, 20 clones were selected and further analyzed in Southern hybridization with radio labeled first strand cDNA probes synthesized from the dsRNA. The specificity of two selected clones to the dsRNA was confirmed by Northern analysis using $^{32}P$ labeled inserts of the two clones.

Example 6

Bridging Gaps Between Clones

To bridge the gap between clones RSP3 and RSP94, a pair of specific primers were used in RT-PCR to generate cDNA fragments from the dsRNA. RSP3-RSP94 primer 1 (sense, nt 3629–3648) has a nucleotide sequence corresponding to SEQ. ID. No. 41 as follows:

GCTTCAGCAC TTGGAAGGCG 20

RSP3–RSP94 primer 2 (antisense, nt 4350–4366) has a nucleotide sequence corresponding to SEQ. ID. No. 42 as follows:

CACACAGTGG CCAGCCT 17

After gel electrophoresis, PCR amplified cDNA bands were excised from gels and recovered with the phenol/chloroform method (Sambrook et al., Molecular Cloning: *A Laboratory Manual,* 2nd ed., Cold Spring Harbor Laboratory Press, Cold Spring Harbor, N.Y. (1989), which is hereby incorporated by reference).

The same strategy was employed to bridge the gap between clones RSP94 and RSP95. RSP94–RSP95 primer 1 (sense, nt 5272–5291) has a nucleotide sequence corresponding to SEQ. ID. No. 43 as follows:

GGAGGTGCGT TGTGGTTATG 20

RSP94–RSP95 primer 2 (antisense, nt 6791–6808) has a nucleotide sequence corresponding to SEQ. ID. No. 44 as follows:

CCCTGGCACT GCACACCC 17

Example 7

Obtaining Nucleotide Sequences on Both Termini of RSPaV-1 Genome

To obtain the terminal 3' end sequences, a primer (sense, nt 8193–8210) having a nucleotide sequence corresponding to SEQ. ID. No. 45 as follows:

GGAGGTGACC ACATTACG 18 and a (dT)18 primer were used in RT-PCR to amplify cDNA from the dsRNA. Resulting PCR products were cloned into TA vector pCRII (Invitrogen) and sequenced. This approach was based on the assumption that the RSP associated dsRNA contained a poly (A) tail. For the terminal 5' end, the dsRNA was first tagged with poly (A) using yeast Poly (A) polymerase (USB) (Pappu et al., "Nucleotide Sequence and Organization of Eight 3' Open Reading Frames of the Citrus tristeza Closterovirus Genome," *Virology* 199:35–46 (1994), which is hereby incorporated by reference) and then used as templates to generate cDNA fragments by RT-PCR using (dT)18 primer and primer (antisense, nt 429–449) having a nucleotide sequence corresponding to SEQ. ID. NO. 46 as follows:

CATCACGACT TGTCACAAAC C 21

Example 8

Nucleotide Sequencing

CsCl or alkaline/PEG (polyethylene glycol) purified plasmids (Sambrook et al., *Molecular Cloning: A Laboratory Manual,* 2nd ed., Cold Spring Harbor Laboratory Press, Cold Spring Harbor, N.Y. (1989), which is hereby incorporated by reference; Applied Biosystems, Inc.) and RT-PCR amplified cDNA fragments were sequenced for completion on both strands. Nucleotide sequencing was done manually with Sequenase version 2.0 kit (USB) or automatically on ABI 373 automated sequencer with Taq DyeDeoxy™ terminator cycle sequencing kit (Applied Biosystems, Inc.). Vector primers (T3, T7, M13 Forward, and M13 Reverse) were used in initial sequencing and sequences were completed by primer walking strategy.

Example 9

Reverse Transcription-Polymerase Chain Reaction ST-PCR

Two pairs of primers were designed for RT-PCR: (1) RSP95F1 and RSP95R1; and (2) RSP149F1 and RSP149R1. Primer RSP95F1, an antisense strand primer, has a nucleotide sequence corresponding to SEQ. ID. NO. 47 as follows:

TGGGCCTCCA CTTCTTC 17

Primer RSP95R1, a sense strand primer, has a nucleotide sequence corresponding to SEQ. ID. No. 48 as follows:

GGGGTTGCCT GAAGAT 16

Primer RSP 1 49F 1, an antisense strand primer, has a nucleotide sequence corresponding to SEQ. ID. No. 49 as follows:

ACACCTGCTG TGA AGC 17

Primer RSP149R1, a sense strand primer, has a nucleotide sequence corresponding to SEQ. ID. No. 50 as follows:

GGCCAAGGTT CAGTTTG 17

RSP95F1/R1 were used in RT-PCR to test samples collected in 1994. RSP149RI/F1, alone or together with RSP95F1/R1, were used to test samples collected in 1995 and 1996. To avoid bias in the judgment of RT-PCR results, blind tests were conducted for samples from Canada in 1995 and 1996. The indexing results of these samples were kept untold until the RT-PCR tests were complete.

dsRNAs were denatured with methylmercuric hydroxide (CH4HgOH) and reverse transcribed into cDNAs with Moloney murine leukemia virus (MMV) or Avian Myeloblastosis Virus (AMV) reverse transcriptases (Promega) at 42° C. for 1 to 3 h. Five of 20 μL of the RT reactions were added to PCR mix and amplified in thermal cycler (FIYBAID OmniGene, National Labnet Company) with Taq DNA polymerase (buffer B, Promega) using the following parameters: initial denaturation at 94° C. for 5 min, 40 cycles of amplification at 94° C. for 45 s, 52° C. for 1 min, and 72° C. for 1 min, and a final extension at 72° C. for 10 min. PCR products were analyzed by electrophoresis on 1% agarose gels containing ethidium bromide. Hae III digested Phix 174 fragments were used as molecular weight markers.

Example 10

Southern Blot

DNA fragments amplified by PCR from cDNA clone RSP149 with primers RSP149F1/R1 were labeled with 32P by random priming and used as probes. Products of RT-PCR of randomly selected grapevines including 26 positives and 6 negatives by RT-PCR were electrophoresed on an 0.8% agarose gel, transferred to nylon membranes, and hybridized to the probes following manufacturer's instructions (Du Pont).

Example 11

Computer Assisted Analysis of Sequences and Genome Structure of RSPaV-1

Sequences were assembled with SeqMan program and potential open reading frames were generated with MapDraw program (DNASTAR, Madison, Wis.). BLAST program of the NCBI (the National Center for Biotechnology Information) was used to search for homologies in DNA and protein databases. Clustal analysis (with identity weight table) of MegAlign (DNASTAR) was employed to reveal sequence similarities between the putative proteins of RSPaV-1 and the analogous proteins of ASPV (Jelkmann, "Nucleotide Sequences of Apple Stem Pitting Virus and of the Coat Protein of a Similar Virus from Pear Associated with Vein Yellows Disease and Their Relationship with Potex- and Carlaviruses," *J. General Virology,* 75:1535–42 (1994), which is hereby incorporated by reference) and PVM (Zavriev et al., "Complete Nucleotide Sequence of Genomic RNA of the Potato M-Virus," *Molecular Biology* (*Mosk.*) 25:761–69 (1991), which is hereby incorporated by reference). In addition, nucleotide sequences of the untranslated regions (UTR) of these three viruses were also compared using MagAlign, as shown in FIGS. 6A and 6B.

Example 12

Consistent Association of a High Molecular Weight dsRNA with RSP

Figure 2A:
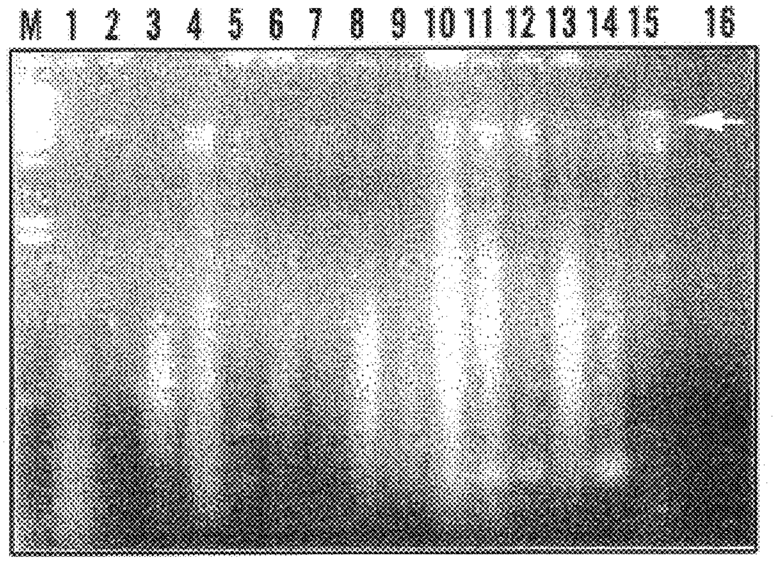
FIGS. 2A and 2B are photographs which respectively display the results of dsRNA analysis and Northern hybridization for dsRNA. Together the photographs may be used to correlate the dsRNA analysis of FIG. 2A with the Northern hybridization (for dsRNA isolated from grapevines indexed positive for Rupestris stem pitting (RSP)) of FIG. 2B. M. Hind III digested lambda DNA maker: lane 1, Aminia; lane 2, Bertille Seyve 5563; lane 3, Canandaigua; lane 4, Colobel 257; lane 5, Couderc 28-112; lane 6, Freedom; lane 7, Grande Glabre; lane 8, M 344-1; lane 9, Joffre; lane 10, Ravat 34; lane I11, Seyval; lane 12, Seyve Vinard 14-287; lane 13, Verdelet; lane 14, Pinot Noir (positive control); lane 15, Verduzzo 233A (negative control for RSP as judged by indexing on St. George); lane 16, insert of clone RSP149. Arrows indicate the position of the 8.7 kb dsRNA. With respect to lane 15 of FIG. 2A, the two dsRNA bands are larger or smaller than the 8.7 kb. dsRNA associated with RSP and they did not hybridize with the RSP specific probe in Northern analysis. Thus, they are not specific to RSP.
Figure 2B:
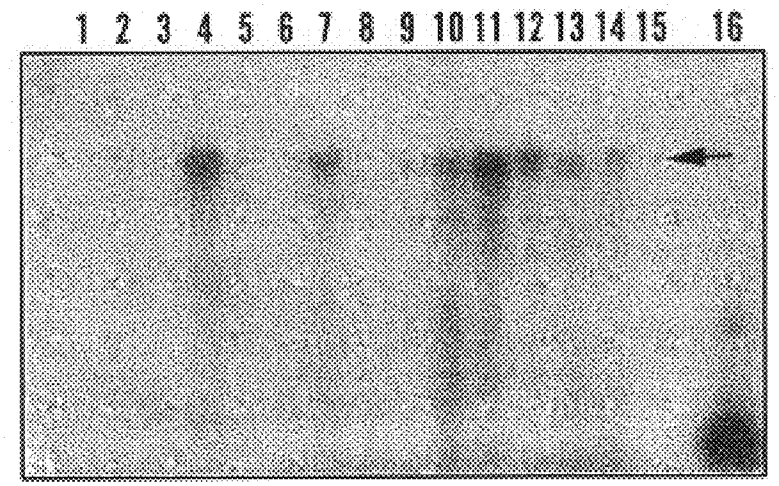

The 15 grapevine accessions used in this study were previously indexed on St. George where 12 accessions induced typical RSP symptoms (i.e., a narrow strip of small pits below the inoculum bud). FIG. 1A illustrates these typical RSP symptoms. A good correlation was found between the presence of the specific dsRNA and the indexing results on St. George. As shown in FIG. 2A and recorded in Table 1 below, twelve grapevine accessions with typical RSP symptoms revealed a dsRNA of ca. 8.7 kb with gel electrophoresis. In addition, a smaller dsRNA of about 6.6 kb was observed in Colobel 257 and Seyval. In contrast, although Aminia and Canandaigua elicited deep pits and grooves around the woody cylinder of St George, they did not reveal visible dsRNA of expected size in repeated experiments. Freedom, which indexed negative for RSP on St. George, did not reveal visible dsRNA. Although two dsRNA bands were observed in Verduzzo 233A (which was indexed free of RSP on St George), they were not specific to RSP based on the fact that they were larger or smaller than the 8.7 kb dsRNA associated with RSP (FIG. 2A) and that they did not hybridize to the RSP-specific probe in Northern analysis (FIG. 2B). In addition, the two dsRNA species isolated from Verduzzo 233A were not observed in other healthy grapevines such as Cabernet Franc and LN 33.

TABLE 1

| Accessions and Parentage | St. George Indicator | dsRNA | Northern |
|---|---|---|---|
| Aminia (Carter X Black Hamburg) | + | − | − |
| Bertille Seyve 3408 (BS 872 X Seibel 5410) | + | + | + |
| Bertille Seyve 5563 (Seibel 6905 X BS 3445) | + | + | + |
| Canandaigua (*V. labrusca* X *V. vinifera*) | + | − | − |
| Colobel 257 (Seibel 6150 X Seibel 5455) | + | + | + |
| Couderc 28-112 (Emily X *V. rupestris*) | + | + | + |
| Freedom (Couderc 1613 X Dog Ridge) | − | − | − |
| Grande Glabre (*V. riparia*) | + | + | + |
| III 344-1 (BS 2667 X Seibel 6905) | + | +† | −† |
| Joffre (*V. vinifera* X *V. riparia* X *V. rupestris*) | + | + | + |
| Ravat 34 (Berlandieri X Chardonnay) | + | + | + |
| Seyval (Seibel 4995 X Seibel 4986) | + | + | + |
| Seyve Villard 14-287 (*V. labrusca* X *V. rupestris* X *V. aestiv* X *V. cinerea* X *V. vinifera*) | + | + | + |
| Seyve Villard 3160 (Seibel 5163 X Seibel 2049) | + | + | + |
| Verdelet (Seibel 5455 X Seibel 4938) | + | + | + |
| Controls | | | |
| Pinot Noir (*V. vinifera*) | + | + | + |
| Thompson seedless (*V. vinifera*) | + | NT | + |
| Verduzzo 233A | − | −‡ | − |

Symbols:
*Probe used was insert from cDNA clone RSP149.
†A faint dsRNA band could be observed on the gel after electrophoresis but no hybridization signal could be seen in Northern analysis.
‡Although two dsRNA bands were observed in Verduzzo 233A, they were not specific to RSP, because they were either larger or smaller than the RSP-associated 8.7 kbp dsRNA and they did not hybridize to the probe in Northern analysis.

The yield of dsRNA was low and varied significantly among different accessions. When a comparable amount of phloem tissue (14 g for Bertille Seyve 5563 and Couderc 28-112; 18.5 g for the others) was used to isolate dsRNA, Colobel 257, Seyval, Ravat 34, Grande Glabre, and Seyve Villard 14-287 displayed strong dsRNA bands, while Bertille Seyve 5563, Couderc 28-112, Joffre, and Verdelet showed weak bands after staining with EtBr, as shown in FIG. 2A. Bertille Seyve 3408 and Seyve Villard 3160 were analyzed in separate experiments and dsRNA bands of the same size were observed.

Example 13

Selection and Specificity of cDNA Clones

A total of 182 clones were selected after plaque hybridization. Eighty clones with strong hybridization signals were subcloned into pbluescript SK through in vivo excision. Resulting plasmids were shown to have inserts ranging from 0.3 to 3.0 kb. A total of 20 clones with inserts of ca. 0.8 kb or larger were selected. Southern analysis of these 20 clones to radio labeled first strand cDNA probes derived from the dsRNA resulted in 15 clones with strong hybridization signals. Several of these clones were used to determine the genome sequence of the dsRNA: RSP3, RSP28, RSP94, RSP140, RSP95, and TA5. Another clone (RSP149), which was 97% similar in nucleotide sequence to RSP95, was used as one of the two probes in Northern hybridization.

Northern hybridization was employed to confirm the specific relationship of clones RSP95 and RSP149 to the isolated dsRNA. These two clones gave the strongest reaction in Southern analysis described above. Initial experiments showed that RSP95 insert hybridized with the dsRNA isolated from three accessions (Colobel 257, Seyval, and Ravat 34), from which the template dsRNAs used in cDNA synthesis were isolated. As shown in FIG. 2B and indicated in Table 1, use of RSP 149 insert as the probe showed that this clone hybridized with the dsRNA of ca. 8.7 kb isolated from RSP infected grapevines. Furthermore, the intensity of hybridization signals corresponded to that of the dsRNA bands observed on agarose gels stained with EtBr. Colobel 257, Seyval, Ravat 34, Grande Glabre, and Serve Villard 14-287 reacted strongly; Bertille Seyve 5563, Couderc 28-112, Joffre, and Verdelet had weak hybridization signals. The result for Ill 344-11 was not conclusive. Aminia and Canandaigua did not show visible dsRNAs or hybridization in Northern analysis. Bertille Seyve 3408, which was tested in a separate experiment, did show a ca. 8.7 kb dsRNA which hybridized to the probe from RSP149. Freedom and Verduzzo 233A, which had indexed negative for RSP on St. George, were also negative in Northern blot.

Example 14

Nucleotide Sequence and Genome Structure of RSPaV-1

Figures 3A, 3B:
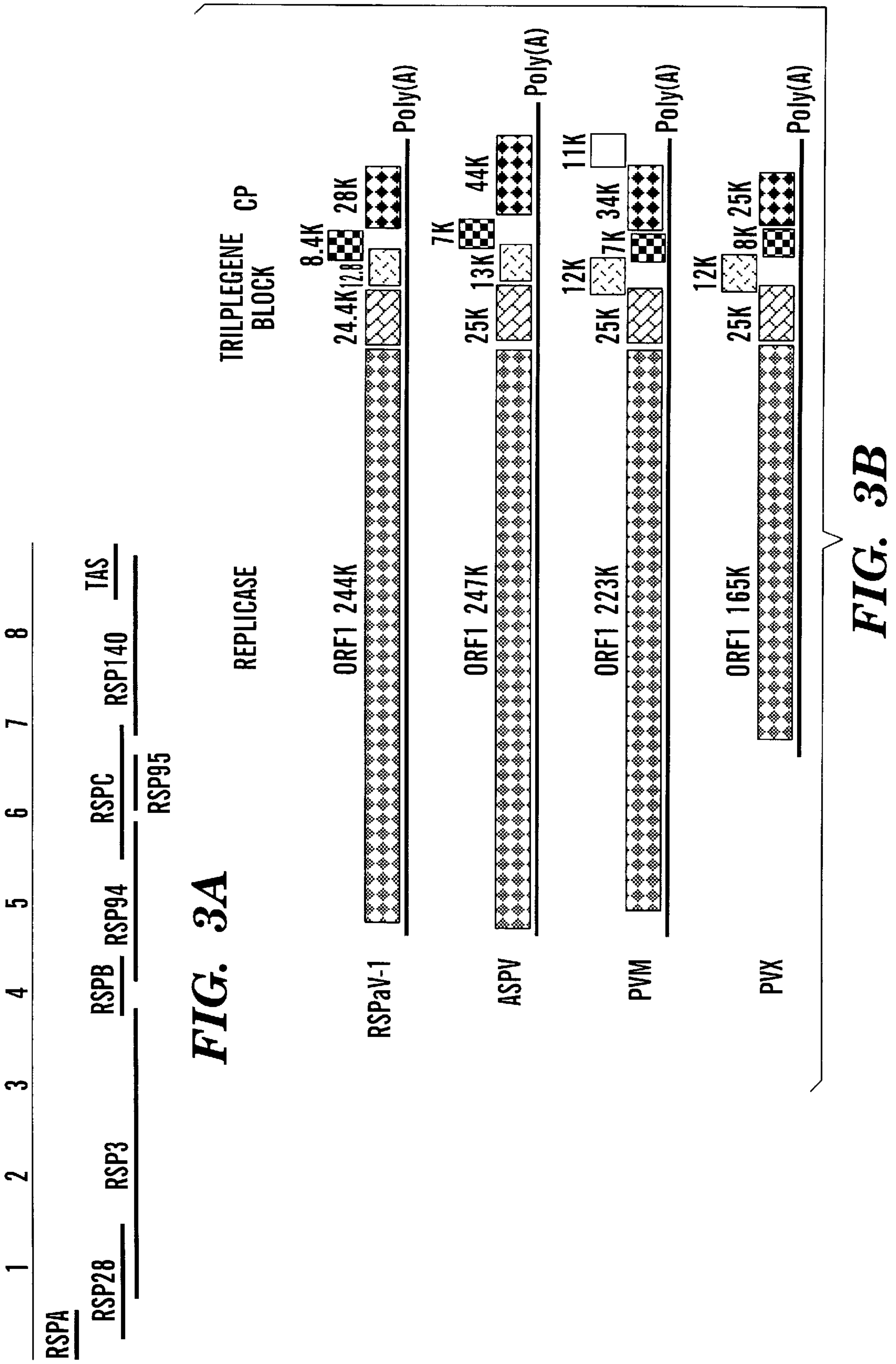
FIG. 3A is an illustration which depicts the strategy for obtaining the complete nucleotide sequence of RSPaV-1. The overlapping regions of the nucleotide sequences of the sequenced clones and RT-PCR-amplified cDNA fragments are as follows: 52–375 for RSPA/RSP28; 677–1474 for RSP28/RSP3; 3673–3766 for RSP3/RSPB; 4009–4320 for RSPB/RSP94; 5377–5750 for RSP94/RSPC; 5794–6537 for RSPC/RSP95; 6579–6771 for RSPC/RSP140; and 8193–8632 for RSP140/TA5.
FIG. 3B is an illustration which comparatively depicts the genome structures of RSPaV-1, ASPV, PVM, and PVX. Boxes with the same patterns represent the comparable ORFS.

Six cDNA clones and three RT-PCR amplified cDNA fragments (identified as RSPA, RSPB, and RSPC) were sequenced on both strands and used to obtain the complete nucleotide sequence of a viral agent, which is shown in FIG. 3A. The genome of RSPaV-1 consisted of 8726 nts excluding a poly (A) tail on the 3' end. The sequence of RSPA indicated that the 5' first base of the RSPaV-1 genome appeared to be a cytosine (C). Clone TA5, which represented the 3' end of the RSPaV-1 genome, contained a stretch of adenines (A) preceded by a cytosine.

MapDraw analysis, shown at FIG. 3B, indicated that the genome of RSPaV-1 had five potential ORFs on its positive strand, while no ORFs were observed on the negative strand (data not shown). ORF1 (nt 62 to 6547 of SEQ. ID. No. 1) has a nucleotide sequence corresponding to SEQ. ID. NO. 2. ORF1 believed to encode a protein or polypeptide having a molecular weight of about 244 kDa and an amino acid sequence corresponding to SEQ. ID. NO. 3. According to Lutcke et al., "Selection of AUG Initiation Codons Differs in Plants and Animals," *Eur. Mol. Biol. J*,. 6:43–48 (1987), which is hereby incorporated by reference, the start codon of ORF1 was in a favorable context: GCAAUGGC, where the "GC" after the start codon is important for initiating translation in a plant system. ORF2 (nt 6578 to 7243 of SEQ. ID. No. 1) has a nucleotide sequence corresponding to SEQ. ID. No. 4. ORF2 is believed to encode a protein or polypeptide having a molecular weight of about 24.4 kDa and an amino acid sequence corresponding to SEQ. ID. NO., 5. The first two ORFs were separated by an intergenic region of 30 nts. ORF3 (nt 7245 to 7598 of SEQ. ID. NO. 1) has a nucleotide sequence corresponding to SEQ. ID. No. 6. ORF3 is believed to encode a protein or polypeptide having a molecular weight of about 12.8 kDa and an amino acid sequence corresponding to SEQ. ID. NO. 7. ORF4 (nt 7519 to 7761 of SEQ. ID. NO. 1), which overlapped with ORF3 by 80 nts, has a nucleotide sequence corresponding to SEQ. ID. No. 8. ORF3 is believed to encode a protein or polypeptide having a molecular weight of about 8.4 kDa and an amino acid sequence corresponding to SEQ. ID. No. 9. Nine nucleotides downstream of ORF4 was the start of ORF5 (nt 7771 to 8550 of SEQ. ID. NO. 1), which has a nucleotide sequence corresponding to SEQ. ID. No. 10. ORF5 is believed to encode a protein or polypeptide having a molecular weight of about 28 kDa and an amino acid sequence corresponding to SEQ. ID. NO. 11. Downstream of ORF5 was the 3' end LJTR of 176 nts. Although computer assisted analysis indicated that two shorter ORFs may exist as alternatives to ORF1 and ORF5, neither of them were in good contexts for translation initiation.

Example 15

Comparison of the RSPaV-1 Genome with ASPV and PVM Carlavirus Genomes

The arrangement of the ORFs and the amino acid sequences of RSPaV-1 showed similarities to those of PVX (Skryabin et al., "The Nucleotide Sequence of Potato Virus X RNA," *Nucleic Acids Res.* 16: 10929–30 (1988), which is hereby incorporated by reference), PVM (Zavriev et al., "Complete Nucleotide Sequence of Genomic RNA of the Potato M-Virus," *Molecular Biology* (*Mosk.*) 25:761–69 (1991), which is hereby incorporated by reference), and ASPV (Jelkmann, "Nucleotide Sequences of Apple Stem Pitting Virus and of the Coat Protein of a Similar Virus from Pear Associated with Vein Yellows Disease and Their Relationship with Potex- and Carlaviruses," *J. General Virology* 75:1535–42 (1994), which is hereby incorporated by reference), with the latter two being the most similar to RSPaV-1. A representation of the sequence comparison is shown in FIG. 3B and the percent identities in amino acid sequences of the ORF of RSPaV-1 and the corresponding ORF of ASPV, PVM, and PVX are shown in Table 2 below. These analyses suggest that the ORFs of RSPaV-1 are compared with those of PVM and ASPV.

TABLE 2

| | Replicase ORF1 | | | | | | | Coat Protein |
|---|---|---|---|---|---|---|---|---|
| | Region I | Region II | | Triple Gene Block | | | | ORF5 |
| | aa 1–372 | aa1354–2161 | Total | ORF2 | ORF3 | ORF4 | Total | aa142–245 |
| ASPV | 49.2 | 57.5 | 39.6 | 38.0 | 39.3 | 27.1 | 31.3 | 49.5 |
| PVM | 47.2 | 53.2 | 37.6 | 34.8 | 31.2 | 19.0 | 21.2 | 33.3 |
| PVX | 18.9 | 20.4 | 15.7 | 23.5 | 31.3 | 22.9 | 27.4 | 42.9 |

When the total amino acid sequence of RSPaV-1 ORF1 was used for comparison, it showed 39.6% and 37.6% identities with the replicases of ASPV and PVM respectively (Table 2). These homologies were mainly found in regions I (aa 1 to 372) and II (aa 1354–2161), which are at the N and C terminal portions of the putative replicase, respectively, shown at FIGS. 4A and 4B. Within region I, the identities of RSPaV-1 with ASPV and PVM were 49.2% and 47.2%, respectively (Table 2). The methyltransferase domain, which is conserved in Sindbis-like superfamily of plant viruses Rozanov et al., "Conservation of the Putative Methyltransferase Domain: A Hallmark of the "Sindbis-like" Supergroup of Positive-Strand RNA Viruses," *J. General Virology* 73:2129–34 (1992), which is hereby incorporated by reference), was found in this region (FIG. 4A). Region II, on the other hand, showed even higher identities: 57.5% with ASPV and 53.2% with PVM (Table 2). A NTP binding motif "GXXXXGKS/T" (aa 1356 to 1363) ("X" stands for any amino acid residue), which is conserved in helicase proteins and helicase domains of eukaryotic positive strand RNA viruses (Gorbalenya et al., "A Novel Superfamily of Nucleotide Triphosphate-Binding Motif Containing Proteins which are Probably Involved in Duplex Unwinding in DNA and RNA Replication and Recombination," *FEBS Letters,* 235:16–24 (1988), which is hereby incorporated by reference), was found in the beginning of region II (FIG. 4B). The amino acid sequences of this motif in ASPV and PVM were identical to that of RSPaV-1 except for one position. Furthermore, amino acid sequence surrounding the GDD motif, which is conserved in all RNA dependent RNA polymerases of positive strand RNA viruses (Koonin, "The Phylogeny of RNA-Dependent RNA Polymerases of Positive-Stand RNA Viruses," *J. Gen. Virology* 72:2197–2206 (1991), which is hereby incorporated by reference), was located near the C terminus of the RSPaV-1 replicase protein and showed high identities to those of ASPV and PVM (FIG. 4B). Other conserved residues of positive strand RNA viruses as described by Koonin, "The Phylogeny of RNA-Dependent RNA Polymerases of Positive-Strand RNA Viruses," *J. Gen. Virology* 72:2197–2206 (1991), which is hereby incorporated by reference, were also found in this region. Based on these information, it was concluded that ORF1 of RSPaV-1 codes for the putative replicase protein.

The triple gene block is a common feature of several groups of plant viruses including carlaviruses, potexviruses, and ASPV. Comparison of RSPaV-1 ORF2 with those of PVM and ASPV showed evenly distributed homologies in amino acid sequence: 38.0% identity to ASPV and 34.8% to PVM (Table 2). The N terminal region of the 24.4K protein (ORF2) contained the consensus sequence "GXGKS S/T" (aa 31 to 36) (FIG. 5A), which is observed in its counterparts in carlaviruses (Zavriev et al., "Complete Nucleotide Sequence of Genomic RNA of the Potato M-Virus," *Molecular Biology* (*Mosk.*) 25:761–69 (1991), which is hereby incorporated by reference) and a number of ATP and GTP binding proteins (Zimmem, "Evolution of RNA Viruses," in *RNA Genetics*, Holland et al., eds., CRC Press, Boca Raton, Fla., USA (1987), which is hereby incorporated by reference). The 12.8K protein of RSPaV-1 encoded by ORF3 had 39.3% and 31.2% identities with its counterparts in ASPV and PVM respectively (Table 2). However, most of the matching occurred in a region from aa 29 to 62, among which 18 aa were fully conserved in all three viruses (FIG. 5B). These 12–13K proteins may function in membrane binding (Morozov et al., "Nucleotide Sequence of the Open Reading Frames Adjacent to the Coat Protein in Potato Virus X Genome," *FEBS Letters* 213:438–42 (1987), which is hereby incorporated by reference). The 8.4K protein encoded by RSPaV-1 ORF4, in contrast, showed much lower identities: 27.1% with that of ASPV and 19.0% with that of PVM (Table 2). However, four residues "TGES" (aa 38 to 41) were conserved in all three viruses (FIG. 5C). In vitro studies indicated that the analogous 7K protein of PVM may bind to single or double stranded nucleic acids (Gramstat et al., "The 12 kDa Protein of Potato Virus M Displays Properties of a Nucleic Acid-Binding Regulatory Protein," *FEBS Letters.* 276:34–38 (1990), which is hereby incorporated by reference) and to plasma membrane (Morozov et al., "In vitro Membrane Binding of the Translation Products of the Carlavirus 7-kDa Protein Genes," *Virology* 183:782–85 (1991), which is hereby incorporated by reference).

A sequence similarity search in a DNA database revealed identities between the putative protein encoded for by RSPaV-1 ORF5 to the coat proteins (CPs) of several groups of plant viruses, indicating that RSPaV-1 ORF5 may code for the coat protein. MegAlign analysis revealed that RSPaV-1 ORF5 had 31.3% and 21.2% identities with the CPs of ASPV and PVM, respectively (Table 2). Most of the identities were found in the C terminal portion of the coat proteins (aa 142 to 245 for RSPaV-1), while the N terminal portions were quite variable in the numbers and sequences of amino acid residues. When the C terminal portion of RSPaV-1 CP was compared to the corresponding regions of ASPV and PVM, it showed 49.5% and 33.3% identities with ASPV and PVM, respectively (Table 2). In addition, the "RR/QX-XFDF" motif was found in the central region of RSPaV-1 CP (FIG. 5D). This motif is conserved in the CPs of positive strand RNA viruses with filamentous morphology and were reported to be involved in salt bridge formation (Dolja et al., "Phylogeny of Capsid Proteins of Rod-Shaped and Filamentous RNA Plant Virus: Two Families with Distinct Patterns of Sequence and Probably Structure Conservation," *Virology* 184:79–86 (1991), which is hereby incorporated by reference). Therefore, it is believed that ORF5 encodes a putative coat protein.

MegAlign analysis, shown in FIGS. 6A and 6B, revealed that the 3' UTR of RSPaV-1 is more similar to that of PVM than to that of ASPV. For example, in a 75 nts stretch, RSPaV-1 had 68% identity with PVM. Within this region, 21 consecutive nucleotides were identical between these two viruses. The significance of this conservation in nucleotide sequence remains to be explored. In contrast, the 5' UTR of RSPaV-1 did not reveal significant similarities with those of PVM and ASPV.

It has been have shown that an 8.7 kbp dsRNA is consistently associated with grapevines that indexed positively on St. George for RSP. Sequence analyses of the dsRNA provide evidence that a virus is involved in RSP, which has now been named RSPaV-1. The complete nucleotide sequence of RSPaV-1 was determined from overlapping cDNA clones and RT-PCR-amplified cDNA fragments generated from the dsRNA. The RSPaV-1 genome has five ORFs coding for the putative replicase (ORF1), the triple gene block (ORF2–4), and the CP (ORF5). The existence of these ORFs and their potential to code for structural and non-structural viral proteins were further supported by the identification of conserved motifs which are the signatures of various viral proteins.

This work confirms and extends the findings of Walter and Cameron ("Double-stranded RNA Isolated from Grapevines Affected by Rupestris Stem Pitting Disease," *Am. J. Enology and Viticulture* 42:175–79 (1991), which is hereby incorporated by reference), and Azzam and Gonsalves ("Detection of dsRNA in Grapevines Showing Symptoms of Rupestris Stem Pitting Disease and the Variabilities Encountered," *Plant Disease* 75:960–64 (1991), which is hereby incorporated by reference), who observed a major dsRNA species of about 8.0–8.3 kbp in RSP-infected grapevines. In addition, such work also observed a smaller dsRNA of ca. 6.6 kbp. A dsRNA of similar size was also observed here, but it was consistently detected in only Colobel 257 and Seyval. The relationship, if any, of this smaller dsRNA to RSP remains to be determined. The small dsRNA of ca. 0.359 kbp, which Monette et al. ("Double-stranded RNA from Rupestris Stem Pitting-Affected Grapevines," *Vitis* 28:137–44 (1989), which is hereby incorporated by reference) isolated from RSP-infected grapevines growing in tissue culture, was not observed.

Electron microscopy evidence also suggests that RSP is caused by filamentous virus(es). Tzeng et al. ("Anatomical and Tissue Culture Studies of Rupestris Stem Pitting-Affected Grapevines," *Botan. Bulletin of Acad. Sinica* (*Taipei*) 34:73–82 (1993), which is hereby incorporated by reference) observed flexuous filamentous virus aggregates in the phloem parenchyma cells of young shoots of Sylvner grapevines that had indexed positively for RSP. Monette and Godkin ("Detection of Capillovirus-like Particles in a Grapevine Affected with Rugose Wood," *Vitis* 34:241–42 (i995), which is hereby. incorporated by reference) observed a filamentous virus in Sauvignon blanc infected by RSP and LNSG. The relationship of these virus particles to RSP disease remains to be studied.

Evidence suggests that the cDNA library generated from the isolated dsRNA templates is not homogeneous for only RSPaV-1. During the process of sequencing cDNA clones, several clones (e.g., RSP47-4 and RSP158) were identified with high, but not identical, sequence similarities to RSPaV-1.

RSPaV-1 has the most similarities to ASPV, which has not yet been grouped into a virus genus. Both viruses have the same genome organization and their ORFs code for putative proteins of similar sizes, except that the coat protein of ASPV is significantly larger (44 kDa) than that of RSPaV-1 (28 kDa). Comparisons of RSPaV-1 with PVM carlavirus show some similarities in genome organization except that RSPaV-1 lacks ORF6 which is located at the 3' end of PVM genome. Although the genome organization of RSPaV-1 is similar to PVX potexvirus, the latter has a much smaller putative replicase. RSPaV-1 has no relation to grape viruses whose genomes have been sequenced so far. The closest possibilities, GVA (Minafra et al., "Grapevine virus A: Nucleotide Sequence, Genome Organization, and Relationship in the Trichovirus Genus," *Arch. Virology* 142:417–23 (1997), which is hereby incorporated by reference) and GVB (Saldarelli et al., "The Nucleotide Sequence and Genomic Organization of Grapevine Virus B," *J. General Virology* 77:2645–52 (1996), which is hereby incorporated by reference), have different genome structures than RSPaV-1.

Example 16

Specific and Universal Primers and the Detection of Different Strains of RSPaV by Reverse Transcription-Polymerase Chain Reaction (RT-PCR)

Among the 138 grapevine entries collected, 25 indexed negatively and 93 indexed positively for RSP on St. George, while the others were not indexed (see Tables 3–7 below). Symptoms induced by RSP on the woody cylinder of St George after graft inoculation with chip-buds can be divided into two types. The first type is called "specific", that is, pits and/or grooves being restricted to the area on the woody cylinder below the inoculation sites. The other is called "nonspecific", that is, pits and/or grooves being present above, around, and below the inoculation sites.

TABLE 3

| Cultivar/Accession | ID | Index St. G | RT-PCR | Source |
|---|---|---|---|---|
| Almeria K3 P 661 | 1483-13D1 | – | – | C |
| Auxerrois CL 56 | 658-1A2 | – | –a | C |
| Auxerrois CL 56 | 658-1A1-1A2 | – | – | C |
| GM 32458 | 604-8A2-2A2 | – | – | C |
| GM 7117-10 | 1347-16A1 | – | –a | C |
| Italia | 1186-5B1 | – | – | C |
| Pslanka (H) | 23-10A2-2A2 | – | – | C |
| Ventura (V. 51061) (H) | 1166-2A1 | – | – | C |
| Verdelet (H) | 1170-3C2-2S1 | – | – | C |
| Verduzzo (V) | 233A | – | – | I |
| Vivant (V. 63331) (H) | 1166-3A1 | – | – | C |
| Control | | | | |
| Sauvignon Blanc (V) | AV-4 #2 | – | –a | U |

Symbols:
V., *Vitis vinefera*; R., *Vitis riparia*; H., hybrid; C., Canada; I., ItaIy; U., USA; P., Portugal;
a, tested by RSP149F1/R1 and 95F1/R1 and results agree to each other; b, tested by 95F1/R1 only

TABLE 4

| Cultivar/Accession | ID | Index St. G | RT-PCR | Source |
|---|---|---|---|---|
| Aragonez (Temperanillo) | 238 | – | + | P |
| Albalonga | 1058-4A2-2A1 | – | + | C |
| Cabernet Franc (V) | 147A | – | + | I |
| Chardonnay (V) | 80A | – | + | I |
| Ehrenfelser PM 1 (V) | 1169-1A1 | – | + | C |
| Freedom (H) | PI 588370 | – | +a | U |
| Harslevellu P 679 | 1483-2B1 | – | + | C |
| Heroldrebe | 1318-2A1 | – | + | C |
| Malvasia Fina | 340 | – | + | P |
| Perle of Zala | 1407-5A1 | – | + | C |
| Refosco (V) | 181A | – | + | I |
| San Giovese Brunello CL BBS 11 | 1497-2A1 | – | + | C |
| Touriga Francesa | 313 | – | + | P |

Symbols:
V., *Vitis vinefera*; R., *Vitis riparia*; H., hybrid; C., Canada; I., Italy; U., USA; P., Portugal;
a, tested by RSP149F1/R1 and 95F1/R1 and results agree to each other; b, tested by 95F1/R1 only

TABLE 5

| Cultivar/Accession | ID | Index St. G | RT-PCR | Source |
|---|---|---|---|---|
| Albalonga | 1058-4A2-1A2 | + | + | C |
| Aminia (H) | PI 588306 | + | + | U |
| Antao Vaz | CL 245 | + | + | P |
| Aragonez (Temperanillo) | 350 | + | + | P |
| Auxerrois CL 56 | 658-1A1 | + | + | C |
| Badacsony-10 | 1407-1A1 | + | + | C |
| Bertille Seyve 3408 (H) | GVIT 348 | + | +b | U |
| Bertille Seyve 5563 (H) | PI 181647 | + | +a | U |
| Blauer Spatburgunder | Q1378-1 | + | +b | C |
| Blauer Zwiegelt/5BB | 1240-1A1 | + | +a | C |
| Bonbino B 9 | 1586-17P3 | + | + | C |
| Brant (H) | 1078-1A1 | + | + | C |
| Cabernet Franc (V) | 151A | + | + | I |
| Cabernet Sauvignon (V) | 124A | + | + | I |
| Cardinal | Q390-13 | + | +b | C |
| Chardonnay (V) | Q661-4 | + | +b | C |
| Chardonnay CL 116 (V) | 1021-13A2 | + | +a | C |
| Chardonnay (V) | 128B | + | +b | I |
| Chardonnay (V) | 72A | + | +b | I |
| Chardonnay (V) | 73A | + | +b | I |

TABLE 5-continued

| Cultivar/Accession | ID | Index St. G | RT-PCR | Source |
|---|---|---|---|---|
| Chardonnay (V) | 83A | + | + | I |
| Chazan CL 538 | 1346-6A1 | + | +a | C |
| Chenin Blanc CL 220 | 1555-6A1 | + | + | C |
| Colobel 257 (Seibel 8357) (H) | PI 588062 | + | +a | U |
| Couderc 28-112 (H) | PI 588248 | + | +a | U |
| De Chaunac S9549 (H) | Q659-1 | + | +b | C |
| Durella 3 | 1586-13P1 | + | + | C |
| Esgana cao | 276 | + | + | P |
| Egri Csillagok-30 | 1407-3A1 | + | + | C |
| Gamay Precoce | 1500-2A1 | + | + | C |
| GM 31875 | 782-18A1 | + | +a | C |
| GM 32458 | 604-8A1 | + | + | C |
| GM 32458 | 782-21B1 | + | + | C |
| GM 6417-7 | 1347-7A1 | + | + | C |
| GM 6497-4 | 1347-14A1 | + | + | C |
| GM 7116-10 | 13624-4A1 | + | + | C |
| GM 7117-13 | 1347-17A2 | + | + | C |
| Grande Glabre (R) | 279897 | + | +a | U |
| Gyongyriziling | 1407-4A1 | + | + | C |
| ILL 344-1 (H) | GVIT 658 | + | +a | U |
| Joffre (Kuhlmann 187-1) (H) | GVIT 381 | + | +a | U |
| Koret (H) | Q1179-7 | + | +b | C |
| Malvasia (V) | 153A | + | + | I |
| Malvasia (V) | 161 A | + | + | I |
| Merlot CL 447 (V) | 1236-17A1 | + | + | C |
| Moureto | 87 | + | + | P |
| Moureto | 96 | + | + | P |
| Muscat De Hambourg CL 202 | 1346-5A1 | + | + | C |
| Perle of Csaba | Q806-1 | + | +b | C |
| Pinot Chardonnay CL 76 (V) | 949-3A2 | + | +a | C |
| Pinot Chardonny CL 277 (V) | 949-8B1 | + | + | C |
| Pinot Grigio (V) | 104A | + | +b | I |
| Pinot Grigio (V) | 108A | + | +b | I |
| Pinot Grigio (V) | 114A | + | + | I |
| Pollux B6-18 | 1357-4A1 | + | + | C |
| Pslanka (H) | 23-10A2 | + | + | C |
| Ravat 34 | PI 588247 | + | +a | U |
| Refosco (V) | 190A | + | +? | I |
| Refosco (V) | 195A | + | + | I |
| Riesling CL 49 (V) | 1555-2A1 | + | +a | C |
| San Giovese Brunello CL E BS 4 | 1497-3B1 | + | + | C |
| Schew-Rebe | 778-6A1 | + | +a | C |
| Semillon CL 299 (V) | 1555-7A1 | + | +a | C |
| Seyval Blanc (Seyve Villard 5-276) (H) | PI 588309 | + | +a | U |
| Seyve Villard 14-287 (H) | PI 588246 | + | +a | U |
| Seyve Villard 3160 (H) | PI 181630 | + | +a | U |
| Titan | Q1235-1 | + | +b | C |
| Verdelet (H) | PI 186260 | + | +a | U |
| Verdelho | 274 | + | + | P |
| Verduzzo (V) | 222A | + | +b | I |
| Verduzzo (V) | 226A | + | +b | I |
| Verduzzo (V) | 239A | + | + | I |
| Vidal Blanc | 1200-5A1 | + | +a | C |
| Weiser Burgunder | Q782-40 | + | +b | C |
| 3309 C | 330-4A1 | + | + | C |
| 420 A | 1483-4A1 | + | + | C |
| 7542 | Q1386-1 | + | +b | C |
| Pinot Noir (V) | 1186-9A2 | + | +a | C |
| Thompson Seedless (V) | RSP105 | + | +a | U |

Symbols:
V., *Vitis vinefera*; R., *Vitis riparia*; H., hybrid; C., Canada; I., Italy; U., USA; P., Portugal;
a, tested by RSP149F1/R1 and 95F1/R1 and results agree to each other; b, tested by 95F1/R1 only

TABLE 6

| Cultivar/Accession | ID | Index St. G | RT-PCR | Source |
|---|---|---|---|---|
| Aligote | Q637-2B2 | + | −b | C |
| Aragonez (Temperanillo) | 232 | + | − | P |

TABLE 6-continued

| Cultivar/Accession | ID | Index St. G | RT-PCR | Source |
|---|---|---|---|---|
| Canandaigua (H) | GVIT 566 | + | −a | U |
| Challenger (H) | Q1338-1 | + | −b | C |
| Fercal CL 242 | 1551-4A1 | + | −a | C |
| GM 7746-6 | 1362-6A1 | + | − | C |
| Gravesac CL 264 | 1551-3A1 | + | −a | C |
| Honey Red | 1339-6A1 | + | − | C |
| Kee-Wah-Din (H) | 1278-1A1 | + | − | C |
| Periquita | 72 | + | − | P |
| Tajoznyt Izumrud (H) | Q2-2 | + | −b | C |
| Thurling | 1047-4A2-1A2 | + | − | C |
| Verdelet | 1170-3D2-2A1 | + | − | C |
| 5BB CL 114 | 1236-2A1 | + | − | C |
| Alphonse Lavalle | | NI | + | I |
| Ancellotta | | NI | + | I |
| Chardonnay (V) | 127 | NI | + | I |
| Kober 5BB? | 100 | NI | + | I |
| Moscato d'Adda | 7 | NI | + | I |
| Periquita | 624 | NI | + | P |
| Periquita | 633 | NI | + | P |
| Riesling (V) | 3 | NI | + | I |
| Seyval (H) | Peterson | NI | + | U |
| Terrano | 1/1/3/K | NI | + | I |
| Thurling | 1047-4A2-2A1 | NI | − | C |
| Tocai Rosso 19 | 1586-21P4 | NI | + | C |
| Trebbiano Toscano | 67 | NI | − | I |
| Vidal | Peterson | NI | + | U |

Symbols:
V., *Vitis vinefera*; R., *Vitis riparia*; H., hybrid; NI, not indexed; C., Canada; I., Italy; U., USA; P., Portugal;
a, tested by RSP149F1/R1 and 95F1/R1 and results agree to each other; b, tested by 95F1/R1 only

TABLE 7

| Cultivar/Accession | ID | Index St. G | RT-PCR | Source |
|---|---|---|---|---|
| *V. acerifolia* | PI 588448 | NI | − | U |
| *V. acerifolia* | PI 588449 | NI | − | U |
| *V. cinerea* | PI 588446 | NI | − | U |
| *V. monticola* | PI 588454 | NI | − | U |
| *V. riparia* | PI 495622 | NI | − | U |
| *V.* sp. *yenshanesis* | PI 588421 | NI | − | U |

Symbols:
V., *Vitis vinefera*; R., *Vitis riparia*; H., hybrid; NI, not indexed; C., Canada; I., ItaIy; U., USA; P., Portugal;
a, tested by RSP149F1/R1 and 95F1/R1 and results agree to each other; b, tested by 95F1/R1 only Among the 93 RSP-infected grapevines, 79 (85%) produced cDNA fragments of expected sizes in repeated RT-PCR using RSP149F1/R1 primers (SEQ. ID. Nos. 49 and 50) and/or RSP95F1/R1 primers (SEQ. ID. Nos. 47 and 48), while the other 14 were negative (see Tables 5 and 6). Interestingly, 12 of 14 (85.7%) grapevine accessions which were not indexed for RSP also produced cDNA fragments of expected size in RT-PCR (see Table 6). Sauvignon blanc (healthy control) was negative in repeated RT-PCR (see Table 3).

Results of RT-PCR for grapevines indexed negatively for RSP were surprising (see Tables 3 and 4). While 11 were negative in RT-PCR tests (excluding Sauvignon blanc healthy control), the other 13 produced cDNA fragments of expected sizes.

Since RSPaV-1 was detected not only from grapevines which indexed positively for RSP but also from some of the grapevines indexed negatively for RSP, a search for more healthy materials for RT-PCR tests became necessary. As the majority of plant viruses do not pass on through seeds, grapevine seedlings are probably free of RSPaV-1. Based on this assumption, six seedlings from five Vitis species were included in RT-PCR (see Table 7). None of them produce cDNA of expected size in RT-PCR using RSP149R1/F1 primers (SEQ. ID. Nos. 49 and 50).

The data described above (and shown in Tables 3–7) indicate that RSPaV-1 is closely associated with RSP and that it is likely the causal agent of RSP. RT-PCR detected RSPaV-1 specific sequences from most of the RSP-infected grapevines collected from a wide range of viticultural regions of the world. Among the 93 grapevine accessions indexed positively for RSP on St. George, 85% were positive in RT-PCR (see Table 5). The data also suggests that RT-PCR has the potential to be used as a standard method for diagnosing RSP. This method is advantageous over the biological indexing on indicator St. George, because it is simpler, quicker, and more sensitive.

RT-PCR did not detect RSPaV-1 sequences from 14 of the grapevine accessions indexed positively for RSP (see Table 6). The discrepancy between RT-PCR and indicator indexing can be attributed to the existence in grapevines of different viruses or strains of the same virus which may all induce similar pitting and/or grooving symptoms on St. George upon graft-inoculation. It is believed these agents are only slightly different from RSPaV-1 at the level of their nucleotide sequences, but significant enough to hinder them from being detected by RT-PCR using RSPaV-1 specific primers.

It is likely that many RSPaV strains have genomes with nucleotide sequences that are highly similar to the nucleotide sequence of the RSPaV-1 genome. Evidence that supports this hypothesis includes the finding of a highly conserved region of ca. 600 bps among the nucleotide sequences of RSPaV-1 (type strain) and seven other cDNA clones, as shown in FIG. 9. The nucleotide sequence identities of these strains to RSPaV-1 (type strain) range from 83.6% to 98.4%. If oligonucleotides are chosen which are conserved among all these strains (i.e., with one or only a few mismatches), then the oligonucleotides should function as universal primers, allowing all of the strains to be detected by RT-PCR. Based on this theory, a primer pair (BM98-3F/BM98-3R) can be designed to amplify a DNA fragment of 320 bps from all these clones. BM98-3F has a nucleotide sequence corresponding to SEQ. ID. NO. 51 as follows:

GATGAGGTCCAGTTGTTTCC 20

BM98-3R has a nucleotide sequence corresponding to SEQ. ID. NO. 52 as follows:

ATCCAAAGGACCTTTTGACC 20

Primers BM98-3F/BM98-3R can be used in RT-PCR to test further some of the grapevine samples which were negative for RSPaV in RT-PCR using RSP95F1/RSP95R1 primers (SEQ. ID. Nos. 47 and 48, respectively) or RSP149F1/RSP149R1 primers (SEQ. ID. Nos. 49 and 50, respectively). Results show that 6 of the 9 samples included were positive for RSPaV in RT-PCR using BM98-3F/BM98-3R primers. This indicates that these universal primers can be used to achieve even higher detection rates.

Another pair of primers (BM98-1F/BM98-1R) can be designed in a way that they can amplify DNA of 760 bps from RSPaV-1, RSP47-4, and RSP158. BM98-1F has a nucleotide sequence corresponding to SEQ. ID. NO. 53 as follows:

CTTGATGAGTACTTGTC 17

BM98-1R has a nucleotide sequence corresponding to SEQ. ID. No. 54 as follows:

GCAAGGATTTGGATGGC 17

Other "universal primers" can be designed manually or with computer programs (such as PrimerSelect) in the same way so that they contain conserved regions of nucleotide sequences for different strains of RSPaV-1.

RT-PCR detected RSPaV-1 sequences from 54% of grapevines negative for RSP as judged by indexing on St. George (see Tables 3 and 4). Several possibilities may account for this discrepancy. First, RT-PCR is much more sensitive than indicator indexing. Virus(es) of extremely low concentration may not induce visible symptoms on St. George within the standard indexing period, while they can be detected by RT-PCR. Second, judging indexing results can, in some cases, be very subjective. For example, it is very difficult to reach a conclusion on whether a grapevine is infected with RSP when only one or a few small pits are present on the woody cylinder of St. George. Third, uneven distribution of virus(es) within grapevines and the relatively limited number of replicates of St George indicators may result in the failure to detect RSP-infection.

RSP seems to be widespread in different types of grapevines including *V, vinifera*, hybrids, *V. riparia*, and rootstocks. It occurs in a wide range of geographic regions including North America, Europe, Australia, and possibly many other countries as well. Testing grapevines from other areas of the world using RSPaV-1 specific primers will provide definitive information on the exact distribution of RSP throughout the world. It is also interesting to investigate whether RSP is transmitted by any vectors in nature.

RSP is a disease under quarantine in Washington and New York of the USA. Since this work and the work of others (Golino and Butler, "A Preliminary Analysis of Grapevine Indexing Records at Davis, Calif.," in *Proceedings of the* 10*th Meeting of the ICVG*, pp. 369–72, Rumbos et al., eds., Volos, Greece (1990); Azzam and Gonsalves, "Detection of dsRNA in Grapevines Showing Symptoms of Rupestris Stem Pitting Disease and the Variabilities Encountered," *Plant Disease,* 75:96–964 (1991); Garau, "Kober Stem Grooving and Grapevine Virus A: A Possible Relationship," in *Extended Abstracts of the* 11*th Meeting of the International Council for the Study of Viruses and Virus Diseases of the Grapevine*. p. 54, Montreux, Switzerland (1993); Credi, "Characterization of Grapevine Rugose Wood Sources from Italy," *Plant Disease,* 82:1288–92 (1997), all of which are hereby incorporated by reference) showed that RSP is so wide-spread, it is questionable whether or not RSP should be kept under plant quarantine any longer. The development and advance of rapid diagnostic methods will also allow us to investigate on the economic damage caused by RSP.

According to Goheen ("Rupestris Stem Pitting," in *Compendium of Grape Diseases*, p. 53, Pearson and Goheen, eds., American Phytopathological Society Press, St. Paul, Minn. , USA (1988), which is hereby incorporated by reference), RSP is a disease which induces, after graft-inoculation with a chip bud from an infected grapevine, a row of small pits on the woody cylinder of St. George below the point of inoculation. This definition may not be comprehensive. Indexing record indicated that two types of stem pitting (specific vs. nonspecific) were often observed on the woody cylinder of St. George upon graft inoculation with chip buds. For example, among 16 RSP-positive grapevines collected from Canada in 1995, eight developed specific type symptoms, while the others produced nonspecific symptoms. Credi ("Characterization of Grapevine Rugose Wood Sources from Italy," *Plant Disease,* 82:1288–92 (1997), which is hereby incorporated by reference) also observed these two types of stem pitting in his indexing work. However, from the primers used in RT-PCR, as described above, RSPaV-1 was detected in grapevines showing both types of symptoms on St. George.

Thus, RT-PCR detected RSPaV-1 sequences from a wide range of grapevines collected from a number of major grapevine growing countries. The data clearly suggest that RSPaV-1 is closely associated with Rupestris stem pitting of grapevines and that it is likely the causal virus of RSP. Use of "universal" primers which can detect multiple agents which are highly similar to RSPaV-1 in nucleotide sequences would improve the detection rate by RT-PCR. In addition, antibodies produced against bacteria-expressed coat proteins of RSPaV-1 will help in finding the viral particles from RSP infected grapevines and in rapid detection of RSP.

Example 17

Southern Hybridization

Figure 7A:
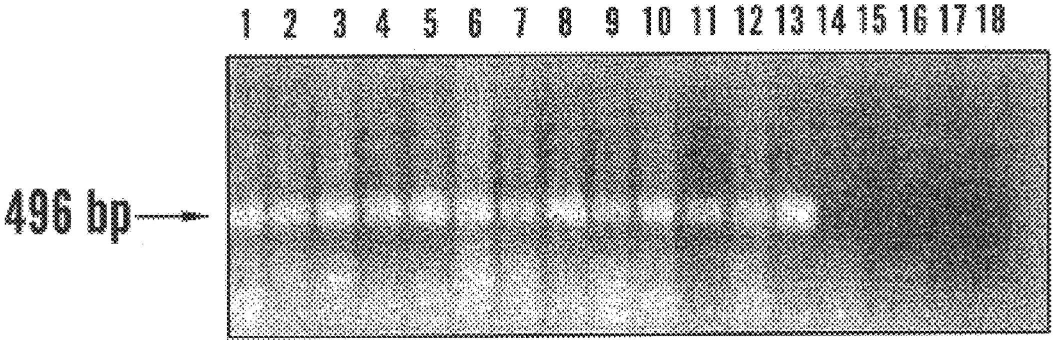
FIGS. 7A–B are photographs comparing the results of RT-PCR of grapevines using RSP149 primers (FIG. 7A) and Southern blot hybridization of RT-PCR amplified cDNA fragments to RSPaV-1 specific probe (FIG. 7B). MMLV-RT (Promega) was used in reverse transcription. Taq DNA polymerase (Promega) was used in PCR. For the RT-PCR and Southern blot hybridization: lane 1, Ehrenfelser PM1 (1169-1A1); lane 2, Cabernet franc 147A; lane 3, Chardonnay 80A; lane 4, Refosco 181A; lane 5, Touriga francesa 313; lane 6, 3309C (330–4A1); lane 7, 420A (1483–4A1); lane 8, Chardonnay 83A; lane 9, Malsavia 153A; lane 10, Aragnonex 350; lane 11, Aminia; lane 12, Chardonnay 127; lane 13, Kober 5BB 100; lane 14, Verduzzo 233A; lane 15, *V riparia*; lane 16, *V. monticola*; lane 17, $H_2O$.
Figure 7B:
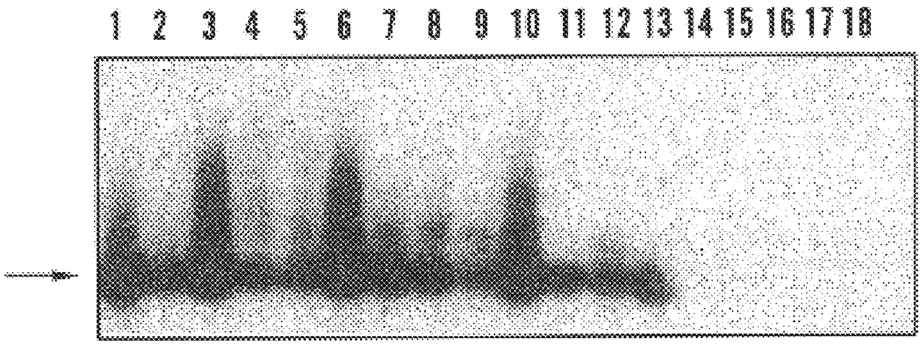
Figure 8:
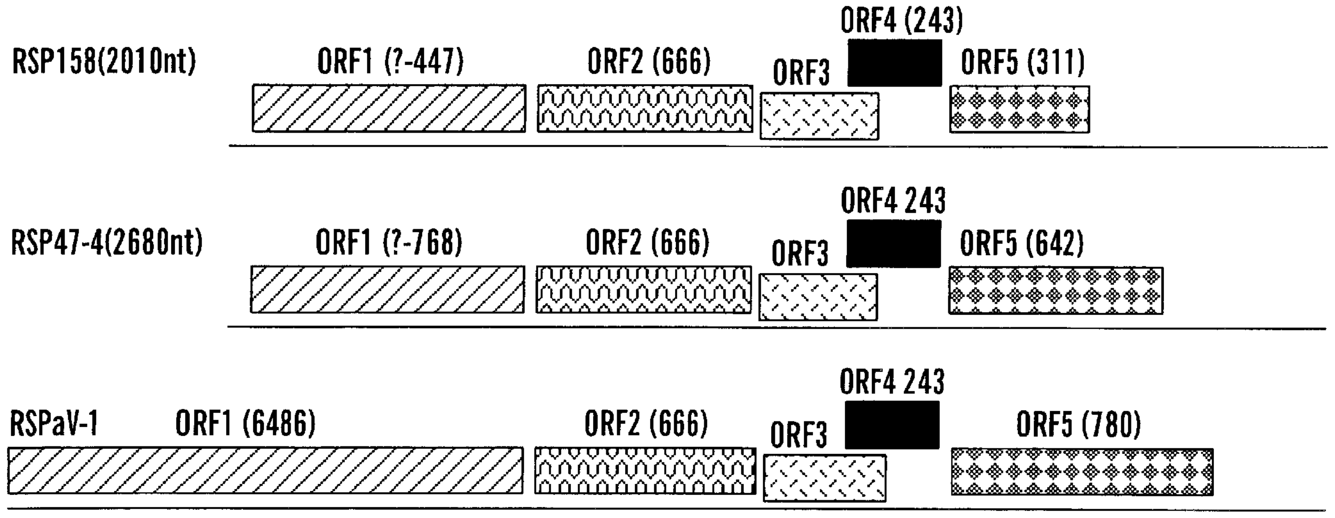
FIG. 8 is a schematic representation of the identical genome organization among RSPaV-1 (the type strain), RSP47-4, and RSP158. The number of amino acid residues of the comparable ORFs (boxes shaded with the same pattern) among these three strains are the same (note: ORF1 and ORF5 of RSP47-4 and RSP158 are incomplete). The comparable ORFs also have high nucleotide and amino acid sequence identities, which are indicated on the bottom. Only the C-terminal portion of the ORF1 of RSPaV-1 is shown in this diagram.
Figure 10:
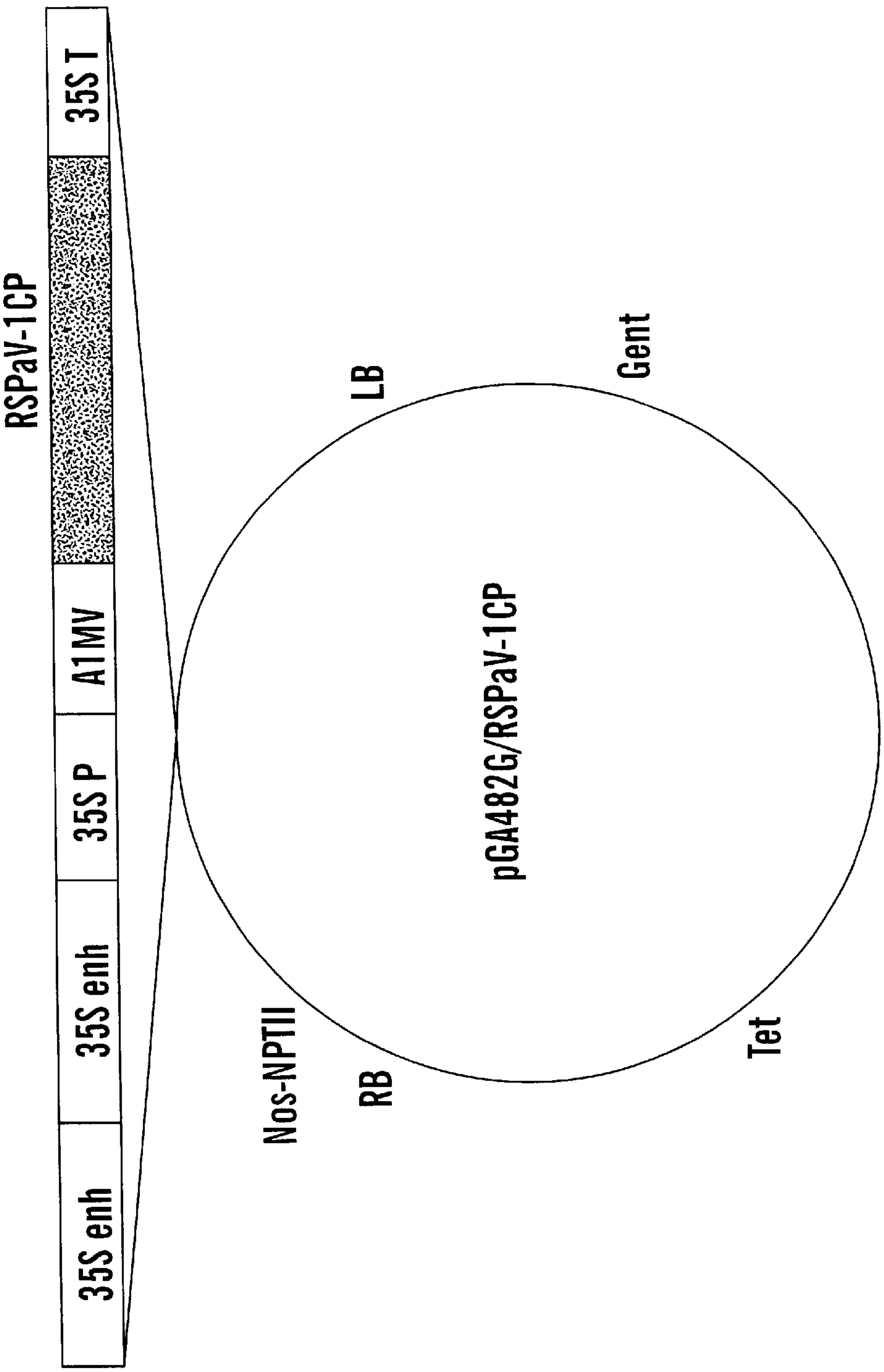
FIG. 10 is a schematic representation of a plant transformation vector containing the RSPaV-1 coat protein gene. This vector is designated pGA482G/RSPaV-1CP, which has the double CaMV 35S enhancers, the 35S promoter, the leader sequence of AlMV, and the 35S terminator sequence. RB, right border; LB, left border; Tet, tetracycline resistance gene; and Gent, gentamycin resistance gene.

To confirm the specificity of the RT-PCR products to RSPaV-1, Southern blot hybridization was conducted using 32P labeled probe specific to RSPaV-1. As shown in FIG. 7, the Southern blot hybridization confirmed the results of the RT-PCR in each of the tested samples. Specifically, cDNA fragments amplified by RT-PCR from 16 selected RT-PCR positive samples hybridized with the probe.

Example 18

Constructing Expression Systems, Expression of a Fusion Protein Containing the RSPaV-1 Coat Protein, Production of Antibodies against the Fusion Protein and Their Use in Detecting RSPaV-1 from Grapevines The coat protein gene (SEQ. ID. No. 10) of RSPaV-1 was cloned into the EcoRI and HindIII sites of the polylinker region of a protein expression vector pMAL-c2 which, upon induction by inducer IPTG, produces a fusion protein containing maltose binding protein (MBP) and the coat protein of RSPaV-1. The fusion protein of expected size (ca. 71 KDa) was produced in *E. coli* bacteria after induction with IPTG. This fusion protein was purified through affinity chromatography using an amylose column. Purified fusion protein was used as an antigen to immunize a rabbit (by subcutaneous injection along the back) with the following scheme:

first injection, 400 μg fusion protein in 0.5 ml column buffer with Freund's complete adjuvant;

second injection, 100 μg of protein in 0.5 ml column buffer with Freund's incomplete adjuvant; and third injection, 100 μg of protein in 0.5 ml buffer with Freund's incomplete adjuvant.

Blood containing the antibodies was collected 70 days after the first injection. The antibodies were recovered and successfully used in an enzyme linked immunoabsorbent assay to detect the presence of virus particles (i.e., coat protein) of RSPaV-1 from a variety of tissue types of grapevines infected with RSP.

The antibodies produced against the expressed RSPaV-1 coat protein, therefore, are useful in the identification of the particles associated with RSP disease of grapevines, in the purification of the particles of RSPaV-1, and in the development of a serological diagnosis for RSP in grapevine. The use of the antibodies is suitable for detecting different strains of RSPaV-1. Because the coat proteins for strains RSP47-4 and RSP158 have high amino acid identities with the coat protein of RSPaV-1, it is very likely that the antibodies raised against RSPaV-1 coat protein will also detect other strains. Antibodies can be used in an ELISA to assay rapidly a large number of samples, thus making commercial development and utilization of diagnostic kits possible.

Example—19

Transformation of Grapevines with a Vector Containing RSPaV-1 Coat Protein Gene and Analysis of Transgenic Grapevines for Resistance to RSP The DNA molecule coding for the RSPaV-1 coat protein (e.g., SEQ. ID. No. 10) was cloned into a pEPT8 plant expression vector that contains the double 35S enhancer at restriction sites SalI and BamHI. The resulting recombinant plasmid, designated pEPT8/RSPaV-1 coat protein, was then cloned into the plant transformation vector pGA482G, which has resistance genes to gentamycin and tetracycline as selection markers. The resultant pGA482G containing pEPT8/RSPaV-1CP was used to transform grapevines using the Agrobacterium method.

The rootstock *Vitis rupestris* Scheele St. George was used in genetic transformation. Anthers were excised aseptically from flower buds. The pollen was crushed on a microscope slide with acetocarmine to observe the cytological stage (Bouquet et al., "Influence du Gentype sur la Production de cals: Dembryoides et Plantes Entieres par Culture Danthers in vitro dans le Genre Vitis," *C.R. Acad. Sci. Paris III* 295:560–74 (1982), which is hereby incorporated by reference). This was done to determine which stage was most favorable for callus induction.

Anthers were plated under aseptic condition at a density of 40 to 50 per 9 cm diameter Petri dish containing MSE. Plates were cultured at 28° C. in the dark. After 60 days, embryos were induced and transferred to hormone-free medium (HMG) for differentiation. Torpedo stage embryos were transferred to MGC medium to promote embryo germination. Cultures were maintained in the dark at 26–28° C. and transferred to fresh medium at 3–4 week intervals. Elongated embryos were transferred to rooting medium (5–8 embryos per jar). The embryos were grown in a tissue culture room at 25° C. with a daily 16 h photoperiod (76 μmol. s) to induce shoot and root formation. After plants developed roots, they were transplanted to soil in the greenhouse.

The protocols used for transformation were modified from those described by Scorza et al., "Transformation of Grape (*Vitis vinifera* L.) Zygotic-Derived Somatic Embryos and Regeneration of Transgenic Plants," *Plant Cell Rpt.* 14:589–92 (1995), which is hereby incorporated by reference. Overnight cultures of Agrobacterium strain C58Z707 or LBA4404 were grown in LB medium at 28° C. in a shaking incubator. Bacteria were centrifuged for 5 minutes at 3000–5000 rpm and re-suspended in MS liquid medium (OD 1.0 at A600 nm). Calli with embryos were immersed in the bacterial suspension for 15–30 minutes, blotted dry, and transferred to HMG medium with or without acetosyringone (100 μM). Embryogenic calli were co-cultivated with the bacteria for 48 h in the dark at 28° C. The plant material was then washed in MS liquid plus cefotaxime (300 mg/ml) and carbenicillin (200 mg/ml) 2–3 times. To select transgenic embryos, the material was transferred to HMG medium containing either 20 or 40 mg/L kanamycin, 300 mg/L cefotaxime, and 200 mg/L carbenicillin. Alternatively, after co-cultivation, embryogenic calli were transferred to initiation MSE medium containing 25 mg/l kanamycin plus the same antibiotics listed above. All plant materials were incubated in continuous darkness at 28° C. After growth on selection medium for 3 months, embryos were transferred to HMG or MGC without kanamycin to promote elongation of embryos. They were then transferred to rooting medium without antibiotics. Non-transformed calli were grown on the same media with and without kanamycin to verify the efficiency of the kanamycin selection process.

The X-gluc (5-bromo4-chloro-3-indoyl-β-glucuronidase) histochemical assay was used to detect GUS (β-glucuronidase) activity in embryos and plants that were transformed with constructs containing the GUS gene that survived kanamycin selection. All propagated plants were screened using an enzyme linked immunoabsorbent assay (ELISA) system (5 Prime-3 Prime, Boulder, Colo.) to detect the NPTII (neomycin phosphotransferase II) protein in leaf extracts. ELISA tests with respective coat protein (CP)-specific antibodies were used to assay for CP. ELISA results were read on an SLT Spectra ELISA reader (pecan U.S. Inc., Research Triangle Park, N.C.) 15–60 minutes after the substrate was added.

PCR analysis was carried out to detect the presence of transgene sequences in grape plants. Genomic DNA was isolated from transformed and non-transformed grape plants according to the method of Lodhi et al., "A Simple and Efficient Method for DNA Extraction from Grapevine Cultivars and Vitis Species," *Plant Mol. Biol. Rpt.* 12:6–13 (1994), which is hereby incorporated by reference. Primer sets included those of specific primers to the transgene. DNA was initially denatured at 94° C. for 3 minutes, then amplified by 35 cycles of 1 minute at 94° C. (denaturing), 1 minute at 52° C. (annealing), and 2 minutes at 72° C. (polymerizing). Reaction samples were directly loaded and electrophoresed in 1.5% agarose gels.

Southern analysis of transformants was accomplished by extracting genomic DNA from young leaves of transformed and non-transformed plants (3309C) as described above. DNA (10 μg) was digested with the restriction enzyme Bgl II, electrophoresed on a 0.8% agarose gel in TAE buffer and transferred to a Genescreen Plus membrane by capillary in 10×SSC. A probe was prepared by random primer labeling of a PCR amplified gene coding sequence with radioisotope $^{32}$P-dATP (Dupont, NEN). Pre-hybridization and hybridization steps were carried out at 65° C. following the manufacturer's instruction. The autoradiograph was developed after overnight exposure.

Although the invention has been described in detail for the purposes of illustration, it is understood that such detail is solely for that purpose, and variations can be made therein by those skilled in the art without departing from the spirit and scope of the invention which is defined by the following claims.

What is claimed is:

1. A method for determining whether a sample includes a Rupestris stem pitting associated virus, said method comprising:

contacting the sample with a Rupestris stem pitting associated virus-specific nucleic acid probe under conditions that allow for hybridization of the probe to a Rupestris stem pitting associated virus nucleic acid molecule, wherein a detectable hybridization signal indicates that Rupestris stem pitting associated virus is present in the sample.

2. The method of claim 1, wherein hybridization is detected using a dot blot hybridization assay, tissue printing assay, southern hybridization assay, northern hybridization assay, or gene amplification detection procedure.

3. The method of claim 1, wherein said nucleic acid probe comprises a nucleic acid molecule that hybridizes with a nucleic acid molecule encoding an open reading frame of a Rupestris stem pitting associated virus protein or polypeptide.

4. The method of claim 1, wherein said sample comprises plant material.

5. The method of claim 4, wherein said plant material comprises a plant cell or tissue.

6. The method of claim 4, wherein said plant material comprises grape plant material.

7. The method of claim 6, wherein said grape plant material comprises a rootstock or scion.

8. The method of claim 4, wherein said plant material comprises propagated plant material.

9. The method of claim 1, wherein said method detects RSPaV-1, RSP47-4, or RSP158.

10. The method of claim 1, wherein said nucleic acid probe comprises SEQ. ID. No. 51, SEQ. ID. No. 52, SEQ. ID. No. 53, or SEQ. ID. No. 54.

11. A method for determining whether a Rupestris stem pitting associated virus is present in a sample, said method comprising:

contacting the sample with a Rupestris stem pitting associated virus-specific nucleic acid probe under conditions that allow for hybridization of the probe to a Rupestris stem pitting associated virus nucleic acid molecule, wherein an undetectable hybridization signal indicates that Rupestris stem pitting associated virus is not present in the sample.

12. The method of claim 11, wherein hybridization is detected using a dot blot hybridization assay, tissue printing assay, southern hybridization assay, northern hybridization assay, or gene amplification detection procedure.

13. The method of claim 11, wherein said nucleic acid probe comprises a nucleic acid molecule that hybridizes with a nucleic acid molecule encoding an open reading frame of a Rupestris stem pitting associated virus protein or polypeptide.

14. The method of claim 11, wherein said sample comprises plant material.

15. The method of claim 14, wherein said plant material comprises a plant cell or tissue.

16. The method of claim 14, wherein said plant material comprises grape plant material.

17. The method of claim 16, wherein said grape plant material comprises a rootstock or scion.

18. The method of claim 14, wherein said plant material comprises propagated plant material.

19. The method of claim 11, wherein said nucleic acid probe comprises SEQ. ID. No. 51, SEQ. ID. No. 52, SEQ. ID. No. 53, or SEQ. ID. No. 54.

20. A method of determining whether a plant is infected with a Rupestris stem pitting associated virus, said method comprising the steps of:

(a) providing a sample from said plant; and (b) contacting the sample with a nucleic acid probe comprising a Rupestris stem pitting virus nucleic acid molecule under conditions that allow for the hybridization of the probe to a Rupestris stem pitting associated virus nucleic acid molecule, wherein a detectable hybridization signal indicates that the plant is infected with Rupestris stem pitting associated virus.

21. The method of claim 20, further comprising selecting a plant that is infected with a Rupestris stem pitting associated virus.

22. The method of claim 20, wherein said hybridization is detected by using a dot blot hybridization assay, tissue printing assay, southern hybridization assay, northern hybridization assay, or gene amplification detection procedure.

23. The method of claim 20, wherein said nucleic acid probe comprises a nucleic acid molecule that hybridizes with a nucleic acid molecule encoding an open reading frame of a Rupestris stem pitting associated virus protein or polypeptide.

24. The method of claim 20, wherein said sample comprises plant material.

25. The method of claim 24, wherein said plant material comprises a plant cell or tissue.

26. The method of claim 24, wherein said plant material comprises grape plant material.

27. The method of claim 26, wherein said grape plant material comprises a rootstock or scion.

28. The method of claim 24, wherein said plant material comprises propagated plant material.

29. The method of claim 20, wherein said method detects RSPaV-1, RSP47-4,or RSP158.

30. The method of claim 20, wherein said nucleic acid probe comprises SEQ. ID. No. 51, SEQ. ID. No. 52, SEQ. ID. No. 53, or SEQ. ID. No. 54.

31. A method of determining whether a plant is infected with a Rupestris stem pitting associated virus, said method comprising the steps of:

(a) providing a sample from said plant; and (b) contacting the sample with a nucleic acid probe comprising a Rupestris stem pitting virus nucleic acid molecule under conditions that allow for the hybridization of the probe to a Rupestris stem pitting associated virus nucleic acid molecule, wherein an undetectable hybridization signal indicates that the plant is not infected with a Rupestris stem pitting associated virus.

32. The method of claim 31, further comprising selecting the plant that is not infected with a Rupestris stem pitting associated virus.

33. The method of claim 31, wherein said hybridization is detected by using a dot blot hybridization assay, tissue printing assay, southern hybridization assay, northern hybridization assay, or gene amplification detection procedure.

34. The method of claim 31, wherein said nucleic acid probe comprises a nucleic acid molecule that hybridizes with a nucleic acid molecule encoding an open reading frame of a Rupestris stem pitting associated virus protein or polypeptide.

35. The method of claim 31, wherein said sample comprises plant material.

36. The method of claim 35, wherein plant material comprises a plant cell or tissue.

37. The method of claim 35, wherein said plant material comprises grape plant material.

38. The method of claim 37, wherein said grape plant material comprises a rootstock or scion.

39. The method of claim 35, wherein said plant material comprises propagated plant material.

40. The method of claim 31, wherein said nucleic acid probe comprises SEQ. ID. No. 51, SEQ. ID. No. 52, SEQ. ID. No. 53, or SEQ. ID. No. 54.

* * * * *

UNITED STATES PATENT AND TRADEMARK OFFICE

CERTIFICATE OF CORRECTION

PATENT NO. : 6,395,490 B1 
DATED : May 28, 2002
INVENTOR(S) : Dennis Gonsalves and Baozhong Meng It is certified that error appears in the above-identified patent and that said Letters Patent is hereby corrected as shown below:

Title page,
Item [56], OTHER PUBLICATIONS,
"Meng et al.," replace "Necleotide" with -- Nucleotide --; "Azzam et al.," replace "rupestris" with -- Rupestris --; "Credi," replace ""Plant" with -- " Plant --; "Meng et al.," replace "DsRNA" with -- dsRNA --;

Column 1,
Line 32, replace "ate" with -- are --;

Column 2,
Line 25, replace "Diseases. p. 53" with -- Diseases, p. 53 --;
Lines 51-52, italicize "10th Meeting of the ICVG";

Column 3,
Line 28, insert the missing word "dsRNA" in between of and in;

Column 4,
Line 30, replace "specifics" with -- specific --;
Line 67, replace "kb." with -- kb --;

Column 5,
Line 29, replace "RSPaB-1" with -- RSPaV-1 --
Line 29, replace "Symbol#" with -- Symbol, #, --;

Column 45,
Line 26, replace "RSP47-4" with -- (RSP47-4 --;

Column 55,
Line 65, replace "1 0 kDa" with -- 10 kDA --;

Column 66,
Line 60, replace "52:147-15" with -- 52:147-54 --;

Column 68,
Line 38, replace "eukaryotes Efficient" with -- eukaryotes. Efficient --;

Column 70,
Line 45, replace "Vitis California" with -- Vitis california --;

UNITED STATES PATENT AND TRADEMARK OFFICE
CERTIFICATE OF CORRECTION

PATENT NO. : 6,395,490 B1

DATED : May 28, 2002
INVENTOR(S) : Dennis Gonsalves and Baozhong Meng

It is certified that error appears in the above-identified patent and that said Letters Patent is hereby corrected as shown below:

Column 72,
Line 20, replace "in-accordance" with -- in accordance --;
Lines 42-43, replace "patent application" with -- Patent Application --;

Column 73,
Line 35, replace "et." with -- et --;
Line 44, replace "Practices" with -- Practice --;
Line 60, replace "RSPaV.In" with -- RSPaV. In --;

Column 74,
Line 13, replace "present," with -- present invention, --;
Line 25, replace "Biol.;" with -- Biol., --;

Column 75,
Line 59, replace "SVP186-" with -- SVP1186- --;

Column 76,
Line 53, replace "be" with -- by --;

Column 78,
Line 32, replace "ST-PCTR" with -- (RT-PCR) --;
Line 47, replace "RSP 1 49F 1" with -- RSP149F1 --;

Column 79,
Line 1, replace "(MMV)" with -- MMLV --;
Line 5, replace "(FIYBAID" with -- (HYBAID --;

Column 80,
Line 61, replace "pbluescript" with -- pBluescript --;

Column 81,
Line 20, replace "344-11" with -- 344-1 --;

Column 83,
Line 38, replace "these" with -- this --;

UNITED STATES PATENT AND TRADEMARK OFFICE

CERTIFICATE OF CORRECTION

PATENT NO. : 6,395,490 B1
DATED : May 28, 2002
INVENTOR(S) : Dennis Gonsalves and Baozhong Meng It is certified that error appears in the above-identified patent and that said Letters Patent is hereby corrected as shown below:

Column 84,
Line 46, remove the word "have";

Column 85,
Line 23, replace "i995" with -- 1995 --;
Line 23, replace "hereby.incorporated" with -- hereby incorporated --;

Column 87,
Line 18, table 5, replace "13624-4A1" with -- 1362-4A1 --;

Column 90,
Line 28, replace "V," with -- V. --;

Column 93,
Line 16, replace "(5-bromo4-" with -- (5-bromo-4- --;
Line 26, replace "(pecan" with -- (Tecan --.

Signed and Sealed this

Twenty-ninth Day of April, 2003

JAMES E. ROGAN
*Director of the United States Patent and Trademark Office*

SEQUENCE LISTING

<160> NUMBER OF SEQ ID NOS: 97

<210> SEQ ID NO 1
<211> LENGTH: 8743
<212> TYPE: DNA
<213> ORGANISM: Rupestris stem pitting associated virus

<400> SEQUENCE: 1

```
cgataaacat aacaacagaa tctgcattgc agtaatattc cttgaatata attgcaacgc     60

aatggccctc tcttataggc ctgctgttga agaggtgctc gcaaaattca cctctgatga    120

acaatccagg gtttctgcta cagctctcaa ggcattagta gacttagagg aaagtcagca    180

caatttgttc tctttcgcat tgcctgatag aagcaaagaa aggctgatat cttctggcat    240

ttacttaagt ccttacagtt tcagacccca ctcacatcca gtttgtaaaa ctttagaaaa    300

tcacattttg tacaatgttt tacctagtta tgttaataat tcattttact ttgtaggaat    360

caaggatttt aagctgcagt tcttgaaaag gaggaataag gatctcagct tggtagcact    420

cataaatagg tttgtgacaa gtcgtgatgt tagtaggtat gggtctgagt tcgttataag    480

ttctagtgac aaatcaagtc aggttgtcag tagaaagggc attggtgatt ctaacacact    540

ccggagattg gtcccacgtg taatttccac aggtgccagg aatctttttc tgcatgatga    600

gattcactac tggtcaatta gtgatctgat caatttttg gacgttgcca agccaagcat    660

gctcttggca actgcagtaa tccctccaga agtgctggtt ggctctccag agagtcttaa    720

cccttgggcc taccagtata aaatcaatgg caaccaactg ctcttcgcac cagatggcaa    780

ctggaatgag atgtactcac aacctttgtc atgcagatac ctgctcaagg ccagatctgt    840
```

-continued

```
agttctgccc gatggctcac gctactcggt tgacatcatt cactcaaaat ttagtcacca    900
cttgcttagt ttcaccccta tgggtaatct tttgacttca aacatgcgat gtttttctgg    960
cttcgatgca ataggcataa aagatcttga acctctaagc cgcggcatgc acagttgctt   1020
cccagtacat catgatgttg taactaagat atatctttat ttgagaactc tcaagaagcc   1080
agataaggag tctgccgagg caaagcttcg acaactcata gaaaaaccca cagggaggga   1140
gataaagttt atcgaggatt tttcctcact agtaataaat tgtgggagga gtggctcttt   1200
gcttatgccc aacatttcta agttggtcat atcattcttt tgccggatga tgccaaatgc   1260
actcgccagg ctctcttcta gctttcgaga gtgttcgcta gattcatttg tgtactcact   1320
tgagcccttt aatttttccg ttaatttagt ggatataact cctgatttct ttgagcattt   1380
atttctcttc tcctgcctaa atgagttgat cgaggaggac gttgaagagg tcatggacaa   1440
ttcttggttt ggacttgggg acttacaatt caatcgccag agggccccgt tctttcttgg   1500
gtcttcatat tggctcaact ccaaattttc agttgagcac aagttttcag gcaccatcaa   1560
ttctcaaatc atgcaagtta ttttatcttt gatcccattt tctgatgatc ccacttttag   1620
gccatcttct acagaggtta accttgcact atcagaggtt aaggctgcgc tagaagctac   1680
tgggcagtca aaattgttca ggtttttggt ggacgactgt gctatgcgtg aggttagaag   1740
ttcctataag gtgggccttt ttaagcacat aaaagccctc actcattgct ttaattcttg   1800
tggcctccaa tggttcctcc ttaggcaaag gtccaacctc aaatttctga aggacagggc   1860
atcgtccttt gctgatcttg attgtgaggt tatcaaagtt tatcagcttg taacatcaca   1920
ggcaatactt cctgaggctc tgcttagctt gaccaaagtc tttgtcaggg attctgactc   1980
aaagggtgtt tccattccca gattggtctc gagaaatgag ctagaggaac tagctcaccc   2040
agctaattca gcccttgagg agcctcaatc agttgattgt aatgcaggca gggttcaagc   2100
aagcgtttca agttcccagc agcttgccga cacccactct cttggtagcg ttaagtcatc   2160
aattgagaca gctaacaagg cttttaactt ggaggagcta aggatcatga ttagagtctt   2220
gccggaggat tttaactggg tggcgaagaa cattggtttt aaagacaggc tgagaggcag   2280
gggtgcatca ttcttctcaa aaccaggaat ttcatgtcat agttacaatg gtgggagcca   2340
cacaagctta gggtggccaa agttcatgga tcagattcta agctccactg gtggacgtaa   2400
ttactacaat tcatgcctgg ctcagatcta tgaggaaaat tcaaaattgg ctcttcataa   2460
ggatgatgag agttgctatg aaattgggca caaagttttg actgttaatt taatcggctc   2520
agcaactttc actattagta agtcgcgaaa tttggttggg ggtaatcatt gcagcctgac   2580
aattgggcca aatgagtttt tcgaaatgcc taggggcatg caatgcaatt acttccatgg   2640
ggtttccaat tgtacgccag ggcgggtatc gctgaccttt aggcgccaaa agttggaaga   2700
tgatgatttg atcttcataa atccacaggt gcccattgag ctcaatcatg aaaagcttga   2760
ccgaagtatg tggcagatgg gccttcatgg aattaagaaa tctatttcta tgaatggcac   2820
gagttttacc tcagacctat gctcttgttt ctcttgccac aactttcata aattcaagga   2880
tctcatcaat aacttgagat tggccctagg agcacaaggg ctaggtcagt gtgacagggt   2940
tgtgtttgca acaacaggtc ctggtctatc taaggtttta gaaatgcctc ggagcaaaaa   3000
gcaatcaatt ttggttcttg aaggtgccct atccatagaa acagattatg gtccaaaagt   3060
cctggggtct tttgaagttt tcaaagggga ctttcacatt aagaagatgg aggaaggttc   3120
aatttttgta ataacgtaca aggccccaat tagatccact ggcaggttga gggttcacag   3180
ttcagaatgc tcattttccg gatccaaaga ggtattgcta ggctgccaga ttgaggcatg   3240
```

-continued

```
tgctgattat gatattgatg attttaacac tttctctgtg cctggtgatg gcaattgctt   3300
ttggcattct gttggttttt tacttagcac tgatggactt gccctaaagg ccggtattcg   3360
atctttcgtg gagagtgagc gcttggtaag tccagatctt tcagccccag caatttctaa   3420
acaattggaa gagaatgctt atgccgagaa tgagatgatc gcattattct gcattcggca   3480
ccacgtaagg cctatagtga tcacaccaga atatgaagtt agttggaaat tcggggaagg   3540
tgagtggccc ctatgtggaa ttctttgcct taaatcaaat cacttccaac catgcgcccc   3600
actgaatggt tgcatgatca cagccattgc ttcagcactt ggaaggcgtg aagttgatgt   3660
gttaaattat ctgtgtagac ccagcactaa tcatattttt gaggagcttt gtcagggagg   3720
gggccttaac atgatgtatt tagctgaagc ttttgaggcc tttgacattt gcgctaaatg   3780
tgatataaat ggagagattg aagtgattaa tccgtgtggt aaaatttctg cattgtttga   3840
cataactaat gagcacataa ggcatgttga gaaaataggt aatggccctc agagcataaa   3900
agtggatgaa ttgcggaagg tcaagcgatc cgccctcgat ttcctttcaa tgaatgggtc   3960
taaaataacc tacttcccaa gctttgagcg ggctgaaaag ttgcaaggat gtttgctagg   4020
gggcctaact ggcgttataa gtgatgagaa gttcagtgat gcaaaacctt ggctttctgg   4080
tatatctact actgatatta agccaaggga attgactgtc gtgcttggta catttggggc   4140
tgggaagagt ttcttgtaca agagtttcat gaaaaggtct gagggtaaat tcgtaacctt   4200
tgtttctccc agacgtgctt tagcaaattc aatcaaaaat gatcttgaaa tggatgatag   4260
ctgcaaagtt gctaaagcag gtaggtcaaa gaaggaaggg tgggatgtag taacttttga   4320
ggttttcctt agaaaagttg caggattgaa ggctggccac tgtgtgattt ttgatgaggt   4380
ccagttgttt cctcctggat acatcgatct atgcttgctt attatacgta gtgatgcttt   4440
catttcactt gctggtgatc catgtcaaag cacatatgac tcgcaaaagg atcgggcaat   4500
tttgggcgct gagcagagtg acatacttag actgcttgag ggcaaaacgt ataggtataa   4560
catagaaagc aggaggtttg tgaacccaat gttcgaatca agactgccat gtcacttcaa   4620
aaagggctcg atgactgccg ctttcgctga ttatgcaatc ttccataata tgcatgactt   4680
tctcctggcg aggtcaaaag gtcccttgga tgccgttttg gtttccagtt ttgaggagaa   4740
aaagatagtc cagtcctact ttggaatgaa acagctcaca ctcacatttg gtgaatcaac   4800
tgggttgaat ttcaaaaatg gggaattctt catatcacat gattcctttc acacagatga   4860
tcggcggtgg cttactgctt tatctcgctt cagccacaat ttggatttgg tgaacatcac   4920
aggtctgagg gtggaaagtt ttctctcgca ctttgctggc aaacccctct accatttttt   4980
aacagccaaa agtggggaga atgtcatacg agatttgctc ccaggtgagc ctaacttctt   5040
cagtggcttt aacgttagca ttggaaagaa tgaaggtgtt agggaggaga agttatgtgg   5100
tgacccatgg ttaaaagtta tgcttttcct gggtcaagat gaggattgtg aagttgaaga   5160
gatggagtca gaatgctcaa atgaagaatg gtttaaaacc cacatcccct tgagtaatct   5220
ggagtcaacc agggccaggt gggtgggtaa aatggccttg aaagagtatc gggaggtgcg   5280
ttgtggttat gaaatgactc aacaattctt tgatgagcat aggggtggaa ctggtgagca   5340
actgagcaat gcatgtgaga ggtttgaaag catttaccca aggcataaag gaaatgattc   5400
aataaccttc ctcatggctg tccgaaagcg tctcaaattt tcgaagcccc aggttgaagc   5460
tgccaaactg aggcgggcca aaccatatgg gaaattctta ttagattctt tcctatccaa   5520
aatcccattg aaagccagtc ataattccat catgtttcat gaagcggtac aggagtttga   5580
```

-continued

```
ggcgaagaag gctagtaaga gtgcagcaac tatagagaat catgcaggta ggtcatgcag   5640
ggattggtta ttagatgttg ctctgatttt tatgaagtca caacactgta ctaaatttga   5700
caacaggctt agagtagcta aagctgggca aacccttgct tgcttccaac atgctgttct   5760
ggttcgcttt gcaccctata tgagatacat tgagaaaaag ctaatgcaag ctctgaagcc   5820
taacttctac atccattcag ggaaaggtct gacgagctga acgagtgggt cagaactaga   5880
ggattcactg gaatttgcac agaatcagac tacgaagcct ttgatgcttc ccaagaccac   5940
ttcatcctag cattcgaatt gcagataatg aaatttttgg ggttacctga agatttaatt   6000
ttggactatg aattcataaa aattcatttg ggatcaaagc tcggatcatt ctctataatg   6060
aggtttactg ggaggccag cacatttctg tttaacacta tggctaacat gttgttcacc    6120
tttctgaggt acgaactaac aggctctgag tcaatagcat ttgcaggtga tgacatgtgt   6180
gctaatcgaa ggttgcggct taaaacagag catgagggtt ttctgaacat gatttgcctt   6240
aaggccaagg ttcagtttgt ttccaatccc acattctgcg gatggtgttt atttaaggaa   6300
gggatcttca agaagcctca attaatctgg gagcggatat gcattgctag ggagatgggc   6360
aacctggaga attgtattga caattatgcg atagaggtct cctatgcata ccgactggga   6420
gagctagcca ttgaaatgat gaccgaggaa gaagtggagg cccattataa ttgtgttaga   6480
ttcttggtca ggaacaagca taagatgaga tgctcaattt caggcctatt tgaagctatt   6540
gattaggcct taagtatttg gcattatttg agtattatga ataatttagt taaagcattg   6600
tcagcatttg agtttgtagg tgttttcagt gtgcttaaat ttccagtagt cattcatagt   6660
gtgcctggta gtggtaaaag tagtttaata agggagctaa tttccgagga tgagaatttc   6720
atagctttca cagcaggtgt tccagacagc cctaatctca caggaaggta cattaagcct   6780
tattctccag ggtgtgcagt gccagggaaa gttaatatac ttgatgagta cttgtccgtc   6840
caagattttt caggttttga tgtgctgttc tcggacccat accaaaacat cagcattcct   6900
aaagaggcac atttcatcaa gtcaaaaact tgtaggtttg gcgtgaatac ttgcaaatat   6960
ctttcctcct tcggttttaa ggttagcagt gacggtttgg acaaagtcat tgtggggtcg   7020
ccttttacac tagatgttga aggggtgcta atatgctttg gtaaggaggc agtggatctc   7080
gctgttgcgc acaactctga attcaaatta ccttgtgaag ttagaggttc aacttttaac   7140
gtcgtaactc ttttgaaatc aagagatcca accccagagg ataggcactg gttttacatt   7200
gctgctacaa gacacaggga gaaattgata atcatgcagt aagatgcctt ttcagcagcc   7260
tgcgaattgg gcaaaaacca taactccatt gacagttggc ttgggcattg ggcttgtgct   7320
gcattttctg aggaagtcaa atctacctta ttcaggggac aacatccatc aattccctca   7380
cggtgggcgt tacagggacg gtacaaaaag tataacttac tgtggtccaa agcaatcctt   7440
ccccagctct gggatattcg gccaatctga gaattttgtg cccttaatgc ttgtcatagg   7500
tctaatcgca ttcatacatg tattgtctgt ttggaattct ggtcttggta ggaattgtaa   7560
ttgccatcca aatccttgct catgtagaca gcagtagtgg caaccaccaa ggttgcttca   7620
ttagggccac tggagagtca attttgattg aaaactgcgg cccaagtgag gcccttgcat   7680
ccactgtgaa ggaggtgctg ggaggtttga aggctttagg ggttagccgt gctgttgaag   7740
aaattgatta tcattgttaa attggctgaa tggcaagtca aattgggaaa ctccccggtg   7800
aatcaaatga ggcttttgaa gcccggctaa aatcgctgga gttagctaga gctcaaaagc   7860
agccggaagg ttctaatgca ccacctactc tcagtggcat tcttgccaaa cgcaagagga   7920
ttatagagaa tgcactttca aagacggtgg acatgaggga ggttttgaaa cacgaaacgg   7980
```

-continued

```
tggtgatttc cccaaatgtc atggatgaag gtgcaataga cgagctgatt cgtgcatttg   8040
gtgaatctgg catagctgaa agcgtgcaat ttgatgtggc catagatata gcacgtcact   8100
gctctgatgt tggtagctcc cagaggtcaa ccctgattgg caagagtcca ttttgtgacc   8160
taaacagatc agaaatagct gggattataa gggaggtgac cacattacgt agattttgca   8220
tgtactatgc aaaaatcgtg tggaacatcc atctggagac ggggatacca ccagctaact   8280
gggccaagaa aggatttaat gagaatgaaa agtttgcagc ctttgatttt ttcttgggag   8340
tcacagatga gagtgcgctt gaaccaaagg gtggaattaa aagagctcca acgaaagctg   8400
agatggttgc taatatcgcc tcttttgagg ttcaagtgct cagacaagct atggctgaag   8460
gcaagcggag ttccaacctt ggagagatta gtggtggaac ggctggtgca ctcatcaaca   8520
accccttttc aaatgttaca catgaatgag gatgacgaag tcagcgacaa ttccgcagtc   8580
caataattcc ccgatttcaa ggctgggtta agcctgttcg ctggaatacc gtactaatag   8640
tattcccttt ccatgctaaa tcctatttaa tatataaggt gtggaaagta aaagaagatt   8700
tggtgtgttt ttatagtttt cattcaaaaa aaaaaaaaaa aaa                     8743
```

<210> SEQ ID NO 2
<211> LENGTH: 6485
<212> TYPE: DNA
<213> ORGANISM: Rupestris stem pitting associated virus

<400> SEQUENCE: 2

```
atggccctct cttataggcc tgctgttgaa gaggtgctcg caaaattcac ctctgatgaa     60
caatccaggg tttctgctac agctctcaag gcattagtag acttagagga aagtcagcac    120
aatttgttct ctttcgcatt gcctgataga agcaaagaaa ggctgatatc ttctggcatt    180
tacttaagtc cttacagttt cagaccccac tcacatccag tttgtaaaac tttagaaaat    240
cacattttgt acaatgtttt acctagttat gttaataatt cattttactt tgtaggaatc    300
aaggatttta agctgcagtt cttgaaaagg aggaataagg atctcagctt ggtagcactc    360
ataaataggt ttgtgacaag tcgtgatgtt agtaggtatg ggtctgagtt cgttataagt    420
tctagtgaca aatcaagtca ggttgtcagt agaaagggca ttggtgattc taacacactc    480
cggagattgg tcccacgtgt aatttccaca ggtgccagga atctttttct gcatgatgag    540
attcactact ggtcaattag tgatctgatc aatttttttgg acgttgccaa gccaagcatg    600
ctcttggcaa ctgcagtaat ccctccagaa gtgctggttg gctctccaga gagtcttaac    660
ccttgggcct accagtataa aatcaatggc aaccaactgc tcttcgcacc agatggcaac    720
tggaatgaga tgtactcaca acctttgtca tgcagatacc tgctcaaggc cagatctgta    780
gttctgcccg atggctcacg ctactcggtt gacatcattc actcaaaatt tagtcaccac    840
ttgcttagtt tcacccctat gggtaatctt ttgacttcaa acatgcgatg tttttctggc    900
ttcgatgcaa taggcataaa agatcttgaa cctctaagcc gcggcatgca cagttgcttc    960
ccagtacatc atgatgttgt aactaagata tatctttatt tgagaactct caagaagcca   1020
gataaggagt ctgccgaggc aaagcttcga caactcatag aaaaacccac agggagggag   1080
ataaagttta tcgaggattt ttcctcacta gtaataaatt gtgggaggag tggctctttg   1140
cttatgccca acatttctaa gttggtcata tcattctttt gccggatgat gccaaatgca   1200
ctcgccaggc tctcttctag ctttcgagag tgttcgctag attcatttgt gtactcactt   1260
gagcccttta atttttccgt taatttagtg gatataactc ctgatttctt tgagcattta   1320
```

-continued

```
tttctcttct cctgcctaaa tgagttgatc gaggaggacg ttgaagaggt catggacaat   1380
tcttggtttg gacttgggga cttacaattc aatcgccaga gggccccgtt ctttcttggg   1440
tcttcatatt ggctcaactc caaattttca gttgagcaca agttttcagg caccatcaat   1500
tctcaaatca tgcaagttat tttatctttg atcccatttt ctgatgatcc cacttttagg   1560
ccatcttcta cagaggttaa ccttgcacta tcagaggtta aggctgcgct agaagctact   1620
gggcagtcaa aattgttcag gtttttggtg gacgactgtg ctatgcgtga ggttagaagt   1680
tcctataagg tgggcctttt taagcacata aaagccctca ctcattgctt taattcttgt   1740
ggcctccaat ggttcctcct taggcaaagg tccaacctca aatttctgaa ggacagggca   1800
tcgtcctttg ctgatcttga ttgtgaggtt atcaaagttt atcagcttgt aacatcacag   1860
gcaatacttc ctgaggctct gcttagcttg accaaagtct ttgtcaggga ttctgactca   1920
aagggtgttt ccattcccag attggtctcg agaaatgagc tagaggaact agctcaccca   1980
gctaattcag cccttgagga gcctcaatca gttgattgta atgcaggcag ggttcaagca   2040
agcgtttcaa gttcccagca gcttgccgac acccactctc ttggtagcgt taagtcatca   2100
attgagacag ctaacaaggc ttttaacttg gaggagctaa ggatcatgat tagagtcttg   2160
ccggaggatt ttaactgggt ggcgaagaac attggtttta aagacaggct gagaggcagg   2220
ggtgcatcat tcttctcaaa accaggaatt tcatgtcata gttacaatgg tgggagccac   2280
acaagcttag ggtggccaaa gttcatggat cagattctaa gctccactgg tggacgtaat   2340
tactacaatt catgcctggc tcagatctat gaggaaaatt caaaattggc tcttcataag   2400
gatgatgaga gttgctatga aattgggcac aaagttttga ctgttaattt aatcggctca   2460
gcaactttca ctattagtaa gtcgcgaaat ttggttgggg gtaatcattg cagcctgaca   2520
attgggccaa atgagttttt cgaaatgcct aggggcatgc aatgcaatta cttccatggg   2580
gtttccaatt gtacgccagg gcgggtatcg ctgaccttta ggcgccaaaa gttggaagat   2640
gatgatttga tcttcataaa tccacaggtg cccattgagc tcaatcatga aaagcttgac   2700
cgaagtatgt ggcagatggg ccttcatgga attaagaaat ctatttctat gaatggcacg   2760
agttttacct cagacctatg ctcttgtttc tcttgccaca actttcataa attcaaggat   2820
ctcatcaata acttgagatt ggccctagga gcacaagggc taggtcagtg tgacagggtt   2880
gtgtttgcaa caacaggtcc tggtctatct aaggttttag aaatgcctcg gagcaaaaag   2940
caatcaattt tggttcttga aggtgcccta tccatagaaa cagattatgg tccaaaagtc   3000
ctggggtctt ttgaagtttt caaaggggac tttcacatta agaagatgga ggaaggttca   3060
atttttgtaa taacgtacaa ggccccaatt agatccactg gcaggttgag ggttcacagt   3120
tcagaatgct cattttccgg atccaaagag gtattgctag gctgccagat tgaggcatgt   3180
gctgattatg atattgatga ttttaacact ttctctgtgc ctggtgatgg caattgcttt   3240
tggcattctg ttggtttttt acttagcact gatggacttg ccctaaaggc cggtattcga   3300
tctttcgtgg agagtgagcg cttggtaagt ccagatcttt cagccccagc aatttctaaa   3360
caattggaag agaatgctta tgccgagaat gagatgatcg cattattctg cattcggcac   3420
cacgtaaggc ctatagtgat cacaccagaa tatgaagtta gttggaaatt cggggaaggt   3480
gagtggcccc tatgtggaat tctttgcctt aaatcaaatc acttccaacc atgcgcccca   3540
ctgaatggtt gcatgatcac agccattgct tcagcacttg gaaggcgtga agttgatgtg   3600
ttaaattatc tgtgtagacc cagcactaat catatttttg aggagctttg tcagggaggg   3660
ggccttaaca tgatgtattt agctgaagct tttgaggcct ttgacatttg cgctaaatgt   3720
```

-continued

```
gatataaatg gagagattga agtgattaat ccgtgtggta aaatttctgc attgtttgac   3780
ataactaatg agcacataag gcatgttgag aaaataggta atggccctca gagcataaaa   3840
gtggatgaat tgcggaaggt caagcgatcc gccctcgatt tcctttcaat gaatgggtct   3900
aaaataacct acttcccaag ctttgagcgg gctgaaaagt tgcaaggatg tttgctaggg   3960
ggcctaactg gcgttataag tgatgagaag ttcagtgatg caaaaccttg gctttctggt   4020
atatctacta ctgatattaa gccaagggaa ttgactgtcg tgcttggtac atttggggct   4080
gggaagagtt tcttgtacaa gagtttcatg aaaaggtctg agggtaaatt cgtaaccttt   4140
gtttctccca gacgtgcttt agcaaattca atcaaaaatg atcttgaaat ggatgatagc   4200
tgcaaagttg ctaaagcagg taggtcaaag aaggaagggt gggatgtagt aacttttgag   4260
gttttcctta gaaaagttgc aggattgaag gctggccact gtgtgatttt tgatgaggtc   4320
cagttgtttc ctcctggata catcgatcta tgcttgctta ttatacgtag tgatgctttc   4380
atttcacttg ctggtgatcc atgtcaaagc acatatgact cgcaaaagga tcgggcaatt   4440
ttgggcgctg agcagagtga catacttaga ctgcttgagg gcaaaacgta taggtataac   4500
atagaaagca ggaggtttgt gaacccaatg ttcgaatcaa gactgccatg tcacttcaaa   4560
aagggctcga tgactgccgc tttcgctgat tatgcaatct tccataatat gcatgacttt   4620
ctcctggcga ggtcaaaagg tcccttggat gccgttttgg tttccagttt tgaggagaaa   4680
aagatagtcc agtcctactt tggaatgaaa cagctcacac tcacatttgg tgaatcaact   4740
gggttgaatt tcaaaaatgg gggaattctc atatcacatg attcctttca cacagatgat   4800
cggcggtggc ttactgcttt atctcgcttc agccacaatt tggatttggt gaacatcaca   4860
ggtctgaggg tggaaagttt tctctcgcac tttgctggca aacccctcta ccattttta    4920
acagccaaaa gtggggagaa tgtcatacga gatttgctcc caggtgagcc taacttcttc   4980
agtggcttta acgttagcat tggaaagaat gaaggtgtta gggaggagaa gttatgtggt   5040
gacccatggt taaaagttat gcttttcctg ggtcaagatg aggattgtga agttgaagag   5100
atggagtcag aatgctcaaa tgaagaatgg tttaaaaccc acatcccctt gagtaatctg   5160
gagtcaacca gggccaggtg ggtgggtaaa atggccttga aagagtatcg ggaggtgcgt   5220
tgtggttatg aaatgactca acaattcttt gatgagcata ggggtggaac tggtgagcaa   5280
ctgagcaatg catgtgagag gtttgaaagc atttacccaa ggcataaagg aaatgattca   5340
ataaccttcc tcatggctgt ccgaaagcgt ctcaaatttt cgaagcccca ggttgaagct   5400
gccaaactga ggcgggccaa accatatggg aaattcttat tagattcttt cctatccaaa   5460
atcccattga aagccagtca taattccatc atgtttcatg aagcggtaca ggagtttgag   5520
gcgaagaagg ctagtaagag tgcagcaact atagagaatc atgcaggtag gtcatgcagg   5580
gattggttat tagatgttgc tctgattttt atgaagtcac aacactgtac taaatttgac   5640
aacaggctta gagtagctaa agctgggcaa acccttgctt gcttccaaca tgctgttctg   5700
gttcgctttg caccctatat gagatacatt gagaaaaagc taatgcaagc tctgaagcct   5760
aacttctaca tccattcagg gaaaggtctg acgagctgaa cgagtgggtc agaactagag   5820
gattcactgg aatttgcaca gaatcagact acgaagcctt tgatgcttcc caagaccact   5880
tcatcctagc attcgaattg cagataatga aattttgggg gttacctgaa gatttaattt   5940
tggactatga attcataaaa attcatttgg gatcaaagct cggatcattc tctataatga   6000
ggtttactgg ggaggccagc acatttctgt ttaacactat ggctaacatg ttgttcacct   6060
```

-continued

```
ttctgaggta cgaactaaca ggctctgagt caatagcatt tgcaggtgat gacatgtgtg   6120

ctaatcgaag gttgcggctt aaaacagagc atgagggttt tctgaacatg atttgcctta   6180

aggccaaggt tcagtttgtt tccaatccca cattctgcgg atggtgttta tttaaggaag   6240

ggatcttcaa gaagcctcaa ttaatctggg agcggatatg cattgctagg gagatgggca   6300

acctggagaa ttgtattgac aattatgcga tagaggtctc ctatgcatac cgactgggag   6360

agctagccat tgaaatgatg accgaggaag aagtggaggc ccattataat tgtgttagat   6420

tcttggtcag gaacaagcat aagatgagat gctcaatttc aggcctattt gaagctattg   6480

attag                                                               6485
```

<210> SEQ ID NO 3
<211> LENGTH: 2161
<212> TYPE: PRT
<213> ORGANISM: Rupestris stem pitting associated virus

<400> SEQUENCE: 3

```
Met Ala Leu Ser Tyr Arg Pro Ala Val Glu Glu Val Leu Ala Lys Phe
 1               5                  10                  15

Thr Ser Asp Glu Gln Ser Arg Val Ser Ala Thr Ala Leu Lys Ala Leu
            20                  25                  30

Val Asp Leu Glu Glu Ser Gln His Asn Leu Phe Ser Phe Ala Leu Pro
        35                  40                  45

Asp Arg Ser Lys Glu Arg Leu Ile Ser Ser Gly Ile Tyr Leu Ser Pro
    50                  55                  60

Tyr Ser Phe Arg Pro His Ser His Pro Val Cys Lys Thr Leu Glu Asn
65                  70                  75                  80

His Ile Leu Tyr Asn Val Leu Pro Ser Tyr Val Asn Asn Ser Phe Tyr
                85                  90                  95

Phe Val Gly Ile Lys Asp Phe Lys Leu Gln Phe Leu Lys Arg Arg Asn
            100                 105                 110

Lys Asp Leu Ser Leu Val Ala Leu Ile Asn Arg Phe Val Thr Ser Arg
        115                 120                 125

Asp Val Ser Arg Tyr Gly Ser Glu Phe Val Ile Ser Ser Ser Asp Lys
    130                 135                 140

Ser Ser Gln Val Val Ser Arg Lys Gly Ile Gly Asp Ser Asn Thr Leu
145                 150                 155                 160

Arg Arg Leu Val Pro Arg Val Ile Ser Thr Gly Ala Arg Asn Leu Phe
                165                 170                 175

Leu His Asp Glu Ile His Tyr Trp Ser Ile Ser Asp Leu Ile Asn Phe
            180                 185                 190

Leu Asp Val Ala Lys Pro Ser Met Leu Leu Ala Thr Ala Val Ile Pro
        195                 200                 205

Pro Glu Val Leu Val Gly Ser Pro Glu Ser Leu Asn Pro Trp Ala Tyr
    210                 215                 220

Gln Tyr Lys Ile Asn Gly Asn Gln Leu Leu Phe Ala Pro Asp Gly Asn
225                 230                 235                 240

Trp Asn Glu Met Tyr Ser Gln Pro Leu Ser Cys Arg Tyr Leu Leu Lys
                245                 250                 255

Ala Arg Ser Val Val Leu Pro Asp Gly Ser Arg Tyr Ser Val Asp Ile
            260                 265                 270

Ile His Ser Lys Phe Ser His His Leu Leu Ser Phe Thr Pro Met Gly
        275                 280                 285

Asn Leu Leu Thr Ser Asn Met Arg Cys Phe Ser Gly Phe Asp Ala Ile
```

-continued

```
    290                 295                 300

Gly Ile Lys Asp Leu Glu Pro Leu Ser Arg Gly Met His Ser Cys Phe
305                 310                 315                 320

Pro Val His His Asp Val Val Thr Lys Ile Tyr Leu Tyr Leu Arg Thr
                325                 330                 335

Leu Lys Lys Pro Asp Lys Glu Ser Ala Glu Ala Lys Leu Arg Gln Leu
            340                 345                 350

Ile Glu Lys Pro Thr Gly Arg Glu Ile Lys Phe Ile Glu Asp Phe Ser
        355                 360                 365

Ser Leu Val Ile Asn Cys Gly Arg Ser Gly Ser Leu Leu Met Pro Asn
    370                 375                 380

Ile Ser Lys Leu Val Ile Ser Phe Phe Cys Arg Met Met Pro Asn Ala
385                 390                 395                 400

Leu Ala Arg Leu Ser Ser Ser Phe Arg Glu Cys Ser Leu Asp Ser Phe
                405                 410                 415

Val Tyr Ser Leu Glu Pro Phe Asn Phe Ser Val Asn Leu Val Asp Ile
            420                 425                 430

Thr Pro Asp Phe Phe Glu His Leu Phe Leu Phe Ser Cys Leu Asn Glu
        435                 440                 445

Leu Ile Glu Glu Asp Val Glu Glu Val Met Asp Asn Ser Trp Phe Gly
    450                 455                 460

Leu Gly Asp Leu Gln Phe Asn Arg Gln Arg Ala Pro Phe Phe Leu Gly
465                 470                 475                 480

Ser Ser Tyr Trp Leu Asn Ser Lys Phe Ser Val Glu His Lys Phe Ser
                485                 490                 495

Gly Thr Ile Asn Ser Gln Ile Met Gln Val Ile Leu Ser Leu Ile Pro
            500                 505                 510

Phe Ser Asp Asp Pro Thr Phe Arg Pro Ser Ser Thr Glu Val Asn Leu
        515                 520                 525

Ala Leu Ser Glu Val Lys Ala Ala Leu Glu Ala Thr Gly Gln Ser Lys
    530                 535                 540

Leu Phe Arg Phe Leu Val Asp Asp Cys Ala Met Arg Glu Val Arg Ser
545                 550                 555                 560

Ser Tyr Lys Val Gly Leu Phe Lys His Ile Lys Ala Leu Thr His Cys
                565                 570                 575

Phe Asn Ser Cys Gly Leu Gln Trp Phe Leu Leu Arg Gln Arg Ser Asn
            580                 585                 590

Leu Lys Phe Leu Lys Asp Arg Ala Ser Ser Phe Ala Asp Leu Asp Cys
        595                 600                 605

Glu Val Ile Lys Val Tyr Gln Leu Val Thr Ser Gln Ala Ile Leu Pro
    610                 615                 620

Glu Ala Leu Leu Ser Leu Thr Lys Val Phe Val Arg Asp Ser Asp Ser
625                 630                 635                 640

Lys Gly Val Ser Ile Pro Arg Leu Val Ser Arg Asn Glu Leu Glu Glu
                645                 650                 655

Leu Ala His Pro Ala Asn Ser Ala Leu Glu Glu Pro Gln Ser Val Asp
            660                 665                 670

Cys Asn Ala Gly Arg Val Gln Ala Ser Val Ser Ser Ser Gln Gln Leu
        675                 680                 685

Ala Asp Thr His Ser Leu Gly Ser Val Lys Ser Ser Ile Glu Thr Ala
    690                 695                 700

Asn Lys Ala Phe Asn Leu Glu Glu Leu Arg Ile Met Ile Arg Val Leu
705                 710                 715                 720
```

-continued

```
Pro Glu Asp Phe Asn Trp Val Ala Lys Asn Ile Gly Phe Lys Asp Arg
                725                 730                 735

Leu Arg Gly Arg Gly Ala Ser Phe Phe Ser Lys Pro Gly Ile Ser Cys
            740                 745                 750

His Ser Tyr Asn Gly Gly Ser His Thr Ser Leu Gly Trp Pro Lys Phe
        755                 760                 765

Met Asp Gln Ile Leu Ser Ser Thr Gly Gly Arg Asn Tyr Tyr Asn Ser
    770                 775                 780

Cys Leu Ala Gln Ile Tyr Glu Glu Asn Ser Lys Leu Ala Leu His Lys
785                 790                 795                 800

Asp Asp Glu Ser Cys Tyr Glu Ile Gly His Lys Val Leu Thr Val Asn
                805                 810                 815

Leu Ile Gly Ser Ala Thr Phe Thr Ile Ser Lys Ser Arg Asn Leu Val
            820                 825                 830

Gly Gly Asn His Cys Ser Leu Thr Ile Gly Pro Asn Glu Phe Phe Glu
        835                 840                 845

Met Pro Arg Gly Met Gln Cys Asn Tyr Phe His Gly Val Ser Asn Cys
    850                 855                 860

Thr Pro Gly Arg Val Ser Leu Thr Phe Arg Arg Gln Lys Leu Glu Asp
865                 870                 875                 880

Asp Asp Leu Ile Phe Ile Asn Pro Gln Val Pro Ile Glu Leu Asn His
                885                 890                 895

Glu Lys Leu Asp Arg Ser Met Trp Gln Met Gly Leu His Gly Ile Lys
            900                 905                 910

Lys Ser Ile Ser Met Asn Gly Thr Ser Phe Thr Ser Asp Leu Cys Ser
        915                 920                 925

Cys Phe Ser Cys His Asn Phe His Lys Phe Lys Asp Leu Ile Asn Asn
    930                 935                 940

Leu Arg Leu Ala Leu Gly Ala Gln Gly Leu Gly Gln Cys Asp Arg Val
945                 950                 955                 960

Val Phe Ala Thr Thr Gly Pro Gly Leu Ser Lys Val Leu Glu Met Pro
                965                 970                 975

Arg Ser Lys Lys Gln Ser Ile Leu Val Leu Glu Gly Ala Leu Ser Ile
            980                 985                 990

Glu Thr Asp Tyr Gly Pro Lys Val Leu Gly Ser Phe Glu Val Phe Lys
        995                 1000                1005

Gly Asp Phe His Ile Lys Lys Met Glu Glu Gly Ser Ile Phe Val Ile
    1010                1015                1020

Thr Tyr Lys Ala Pro Ile Arg Ser Thr Gly Arg Leu Arg Val His Ser
1025                1030                1035                1040

Ser Glu Cys Ser Phe Ser Gly Ser Lys Glu Val Leu Leu Gly Cys Gln
                1045                1050                1055

Ile Glu Ala Cys Ala Asp Tyr Asp Ile Asp Asp Phe Asn Thr Phe Ser
            1060                1065                1070

Val Pro Gly Asp Gly Asn Cys Phe Trp His Ser Val Gly Phe Leu Leu
        1075                1080                1085

Ser Thr Asp Gly Leu Ala Leu Lys Ala Gly Ile Arg Ser Phe Val Glu
    1090                1095                1100

Ser Glu Arg Leu Val Ser Pro Asp Leu Ser Ala Pro Ala Ile Ser Lys
1105                1110                1115                1120

Gln Leu Glu Glu Asn Ala Tyr Ala Glu Asn Glu Met Ile Ala Leu Phe
                1125                1130                1135
```

-continued

```
Cys Ile Arg His His Val Arg Pro Ile Val Ile Thr Pro Glu Tyr Glu
            1140                1145                1150

Val Ser Trp Lys Phe Gly Glu Gly Glu Trp Pro Leu Cys Gly Ile Leu
        1155                1160                1165

Cys Leu Lys Ser Asn His Phe Gln Pro Cys Ala Pro Leu Asn Gly Cys
    1170                1175                1180

Met Ile Thr Ala Ile Ala Ser Ala Leu Gly Arg Arg Glu Val Asp Val
1185                1190                1195                1200

Leu Asn Tyr Leu Cys Arg Pro Ser Thr Asn His Ile Phe Glu Glu Leu
                1205                1210                1215

Cys Gln Gly Gly Gly Leu Asn Met Met Tyr Leu Ala Glu Ala Phe Glu
            1220                1225                1230

Ala Phe Asp Ile Cys Ala Lys Cys Asp Ile Asn Gly Glu Ile Glu Val
        1235                1240                1245

Ile Asn Pro Cys Gly Lys Ile Ser Ala Leu Phe Asp Ile Thr Asn Glu
    1250                1255                1260

His Ile Arg His Val Glu Lys Ile Gly Asn Gly Pro Gln Ser Ile Lys
1265                1270                1275                1280

Val Asp Glu Leu Arg Lys Val Lys Arg Ser Ala Leu Asp Phe Leu Ser
                1285                1290                1295

Met Asn Gly Ser Lys Ile Thr Tyr Phe Pro Ser Phe Glu Arg Ala Glu
            1300                1305                1310

Lys Leu Gln Gly Cys Leu Leu Gly Gly Leu Thr Gly Val Ile Ser Asp
        1315                1320                1325

Glu Lys Phe Ser Asp Ala Lys Pro Trp Leu Ser Gly Ile Ser Thr Thr
    1330                1335                1340

Asp Ile Lys Pro Arg Glu Leu Thr Val Val Leu Gly Thr Phe Gly Ala
1345                1350                1355                1360

Gly Lys Ser Phe Leu Tyr Lys Ser Phe Met Lys Arg Ser Glu Gly Lys
                1365                1370                1375

Phe Val Thr Phe Val Ser Pro Arg Arg Ala Leu Ala Asn Ser Ile Lys
            1380                1385                1390

Asn Asp Leu Glu Met Asp Asp Ser Cys Lys Val Ala Lys Ala Gly Arg
        1395                1400                1405

Ser Lys Lys Glu Gly Trp Asp Val Val Thr Phe Glu Val Phe Leu Arg
    1410                1415                1420

Lys Val Ala Gly Leu Lys Ala Gly His Cys Val Ile Phe Asp Glu Val
1425                1430                1435                1440

Gln Leu Phe Pro Pro Gly Tyr Ile Asp Leu Cys Leu Leu Ile Ile Arg
                1445                1450                1455

Ser Asp Ala Phe Ile Ser Leu Ala Gly Asp Pro Cys Gln Ser Thr Tyr
            1460                1465                1470

Asp Ser Gln Lys Asp Arg Ala Ile Leu Gly Ala Glu Gln Ser Asp Ile
        1475                1480                1485

Leu Arg Leu Leu Glu Gly Lys Thr Tyr Arg Tyr Asn Ile Glu Ser Arg
    1490                1495                1500

Arg Phe Val Asn Pro Met Phe Glu Ser Arg Leu Pro Cys His Phe Lys
1505                1510                1515                1520

Lys Gly Ser Met Thr Ala Ala Phe Ala Asp Tyr Ala Ile Phe His Asn
                1525                1530                1535

Met His Asp Phe Leu Leu Ala Arg Ser Lys Gly Pro Leu Asp Ala Val
            1540                1545                1550

Leu Val Ser Ser Phe Glu Glu Lys Lys Ile Val Gln Ser Tyr Phe Gly
```

-continued

```
        1555                1560                1565

Met Lys Gln Leu Thr Leu Thr Phe Gly Glu Ser Thr Gly Leu Asn Phe
    1570                1575                1580

Lys Asn Gly Gly Ile Leu Ile Ser His Asp Ser Phe His Thr Asp Asp
1585                1590                1595                1600

Arg Arg Trp Leu Thr Ala Leu Ser Arg Phe Ser His Asn Leu Asp Leu
                1605                1610                1615

Val Asn Ile Thr Gly Leu Arg Val Glu Ser Phe Leu Ser His Phe Ala
            1620                1625                1630

Gly Lys Pro Leu Tyr His Phe Leu Thr Ala Lys Ser Gly Glu Asn Val
        1635                1640                1645

Ile Arg Asp Leu Leu Pro Gly Glu Pro Asn Phe Phe Ser Gly Phe Asn
    1650                1655                1660

Val Ser Ile Gly Lys Asn Glu Gly Val Arg Glu Glu Lys Leu Cys Gly
1665                1670                1675                1680

Asp Pro Trp Leu Lys Val Met Leu Phe Leu Gly Gln Asp Glu Asp Cys
                1685                1690                1695

Glu Val Glu Glu Met Glu Ser Glu Cys Ser Asn Glu Glu Trp Phe Lys
            1700                1705                1710

Thr His Ile Pro Leu Ser Asn Leu Glu Ser Thr Arg Ala Arg Trp Val
        1715                1720                1725

Gly Lys Met Ala Leu Lys Glu Tyr Arg Glu Val Arg Cys Gly Tyr Glu
    1730                1735                1740

Met Thr Gln Gln Phe Phe Asp Glu His Arg Gly Gly Thr Gly Glu Gln
1745                1750                1755                1760

Leu Ser Asn Ala Cys Glu Arg Phe Glu Ser Ile Tyr Pro Arg His Lys
                1765                1770                1775

Gly Asn Asp Ser Ile Thr Phe Leu Met Ala Val Arg Lys Arg Leu Lys
            1780                1785                1790

Phe Ser Lys Pro Gln Val Glu Ala Ala Lys Leu Arg Arg Ala Lys Pro
        1795                1800                1805

Tyr Gly Lys Phe Leu Leu Asp Ser Phe Leu Ser Lys Ile Pro Leu Lys
    1810                1815                1820

Ala Ser His Asn Ser Ile Met Phe His Glu Ala Val Gln Glu Phe Glu
1825                1830                1835                1840

Ala Lys Lys Ala Ser Lys Ser Ala Ala Thr Ile Glu Asn His Ala Gly
                1845                1850                1855

Arg Ser Cys Arg Asp Trp Leu Leu Asp Val Ala Leu Ile Phe Met Lys
            1860                1865                1870

Ser Gln His Cys Thr Lys Phe Asp Asn Arg Leu Arg Val Ala Lys Ala
        1875                1880                1885

Gly Gln Thr Leu Ala Cys Phe Gln His Ala Val Leu Val Arg Phe Ala
    1890                1895                1900

Pro Tyr Met Arg Tyr Ile Glu Lys Lys Leu Met Gln Ala Leu Lys Pro
1905                1910                1915                1920

Asn Phe Tyr Ile His Ser Gly Lys Gly Leu Asp Glu Leu Asn Glu Trp
                1925                1930                1935

Val Arg Thr Arg Gly Phe Thr Gly Ile Cys Thr Glu Ser Asp Tyr Glu
            1940                1945                1950

Ala Phe Asp Ala Ser Gln Asp His Phe Ile Leu Ala Phe Glu Leu Gln
        1955                1960                1965

Ile Met Lys Phe Leu Gly Leu Pro Glu Asp Leu Ile Leu Asp Tyr Glu
    1970                1975                1980
```

-continued

```
Phe Ile Lys Ile His Leu Gly Ser Lys Leu Gly Ser Phe Ser Ile Met
1985                1990                1995                2000

Arg Phe Thr Gly Glu Ala Ser Thr Phe Leu Phe Asn Thr Met Ala Asn
                2005                2010                2015

Met Leu Phe Thr Phe Leu Arg Tyr Glu Leu Thr Gly Ser Glu Ser Ile
            2020                2025                2030

Ala Phe Ala Gly Asp Asp Met Cys Ala Asn Arg Arg Leu Arg Leu Lys
        2035                2040                2045

Thr Glu His Glu Gly Phe Leu Asn Met Ile Cys Leu Lys Ala Lys Val
    2050                2055                2060

Gln Phe Val Ser Asn Pro Thr Phe Cys Gly Trp Cys Leu Phe Lys Glu
2065                2070                2075                2080

Gly Ile Phe Lys Lys Pro Gln Leu Ile Trp Glu Arg Ile Cys Ile Ala
                2085                2090                2095

Arg Glu Met Gly Asn Leu Glu Asn Cys Ile Asp Asn Tyr Ala Ile Glu
            2100                2105                2110

Val Ser Tyr Ala Tyr Arg Leu Gly Glu Leu Ala Ile Glu Met Met Thr
        2115                2120                2125

Glu Glu Glu Val Glu Ala His Tyr Asn Cys Val Arg Phe Leu Val Arg
    2130                2135                2140

Asn Lys His Lys Met Arg Cys Ser Ile Ser Gly Leu Phe Glu Ala Ile
2145                2150                2155                2160

Asp


<210> SEQ ID NO 4
<211> LENGTH: 663
<212> TYPE: DNA
<213> ORGANISM: Rupestris stem pitting associated virus

<400> SEQUENCE: 4

atgaataatt tagttaaagc attgtcagca tttgagtttg taggtgtttt cagtgtgctt      60

aaatttccag tagtcattca tagtgtgcct ggtagtggta aaagtagttt aataagggag     120

ctaatttccg aggatgagaa tttcatagct ttcacagcag gtgttccaga cagccctaat     180

ctcacaggaa ggtacattaa gccttattct ccagggtgtg cagtgccagg gaaagttaat     240

atacttgatg agtacttgtc cgtccaagat ttttcaggtt ttgatgtgct gttctcggac     300

ccataccaaa acatcagcat tcctaaagag gcacatttca tcaagtcaaa aacttgtagg     360

tttggcgtga atacttgcaa atatctttcc tccttcggtt ttaaggttag cagtgacggt     420

ttggacaaag tcattgtggg gtcgcctttt acactagatg ttgaaggggt gctaatatgc     480

tttggtaagg aggcagtgga tctcgctgtt gcgcacaact ctgaattcaa attaccttgt     540

gaagttagag gttcaacttt taacgtcgta actcttttga aatcaagaga tccaacccca     600

gaggataggc actggtttta cattgctgct acaagacaca gggagaaatt gataatcatg     660

cag                                                                   663


<210> SEQ ID NO 5
<211> LENGTH: 221
<212> TYPE: PRT
<213> ORGANISM: Rupestris stem pitting associated virus

<400> SEQUENCE: 5

Met Asn Asn Leu Val Lys Ala Leu Ser Ala Phe Glu Phe Val Gly Val
 1               5                  10                  15
```

-continued

```
Phe Ser Val Leu Lys Phe Pro Val Val Ile His Ser Val Pro Gly Ser
            20                  25                  30

Gly Lys Ser Ser Leu Ile Arg Glu Leu Ile Ser Glu Asp Glu Asn Phe
        35                  40                  45

Ile Ala Phe Thr Ala Gly Val Pro Asp Ser Pro Asn Leu Thr Gly Arg
    50                  55                  60

Tyr Ile Lys Pro Tyr Ser Pro Gly Cys Ala Val Pro Gly Lys Val Asn
65                  70                  75                  80

Ile Leu Asp Glu Tyr Leu Ser Val Gln Asp Phe Ser Gly Phe Asp Val
                85                  90                  95

Leu Phe Ser Asp Pro Tyr Gln Asn Ile Ser Ile Pro Lys Glu Ala His
            100                 105                 110

Phe Ile Lys Ser Lys Thr Cys Arg Phe Gly Val Asn Thr Cys Lys Tyr
        115                 120                 125

Leu Ser Ser Phe Gly Phe Lys Val Ser Ser Asp Gly Leu Asp Lys Val
    130                 135                 140

Ile Val Gly Ser Pro Phe Thr Leu Asp Val Glu Gly Val Leu Ile Cys
145                 150                 155                 160

Phe Gly Lys Glu Ala Val Asp Leu Ala Val Ala His Asn Ser Glu Phe
                165                 170                 175

Lys Leu Pro Cys Glu Val Arg Gly Ser Thr Phe Asn Val Val Thr Leu
            180                 185                 190

Leu Lys Ser Arg Asp Pro Thr Pro Glu Asp Arg His Trp Phe Tyr Ile
        195                 200                 205

Ala Ala Thr Arg His Arg Glu Lys Leu Ile Ile Met Gln
    210                 215                 220
```

<210> SEQ ID NO 6
<211> LENGTH: 351
<212> TYPE: DNA
<213> ORGANISM: Rupestris stem pitting associated virus

<400> SEQUENCE: 6

```
atgccttttc agcagcctgc gaattgggca aaaaccataa ctccattgac agttggcttg     60

ggcattgggc ttgtgctgca ttttctgagg aagtcaaatc taccttattc aggggacaac    120

atccatcaat tccctcacgg tgggcgttac agggacggta caaaaagtat aacttactgt    180

ggtccaaagc aatccttccc cagctctggg atattcggcc aatctgagaa ttttgtgccc    240

ttaatgcttg tcataggtct aatcgcattc atacatgtat tgtctgtttg gaattctggt    300

cttggtagga attgtaattg ccatccaaat ccttgctcat gtagacagca g             351
```

<210> SEQ ID NO 7
<211> LENGTH: 117
<212> TYPE: PRT
<213> ORGANISM: Rupestris stem pitting associated virus

<400> SEQUENCE: 7

```
Met Pro Phe Gln Gln Pro Ala Asn Trp Ala Lys Thr Ile Thr Pro Leu
 1               5                  10                  15

Thr Val Gly Leu Gly Ile Gly Leu Val Leu His Phe Leu Arg Lys Ser
            20                  25                  30

Asn Leu Pro Tyr Ser Gly Asp Asn Ile His Gln Phe Pro His Gly Gly
        35                  40                  45

Arg Tyr Arg Asp Gly Thr Lys Ser Ile Thr Tyr Cys Gly Pro Lys Gln
    50                  55                  60
```

-continued

```
Ser Phe Pro Ser Ser Gly Ile Phe Gly Gln Ser Glu Asn Phe Val Pro
65                  70                  75                  80

Leu Met Leu Val Ile Gly Leu Ile Ala Phe Ile His Val Leu Ser Val
                85                  90                  95

Trp Asn Ser Gly Leu Gly Arg Asn Cys Asn Cys His Pro Asn Pro Cys
            100                 105                 110

Ser Cys Arg Gln Gln
        115


<210> SEQ ID NO 8
<211> LENGTH: 240
<212> TYPE: DNA
<213> ORGANISM: Rupestris stem pitting associated virus

<400> SEQUENCE: 8

atgtattgtc tgtttggaat tctggtcttg gtaggaattg taattgccat ccaaatcctt      60

gctcatgtag acagcagtag tggcaaccac caaggttgct tcattagggc cactggagag     120

tcaattttga ttgaaaactg cggcccaagt gaggcccttg catccactgt gaaggaggtg     180

ctgggaggtt tgaaggcttt aggggttagc cgtgctgttg aagaaattga ttatcattgt     240


<210> SEQ ID NO 9
<211> LENGTH: 80
<212> TYPE: PRT
<213> ORGANISM: Rupestris stem pitting associated virus

<400> SEQUENCE: 9

Met Tyr Cys Leu Phe Gly Ile Leu Val Leu Val Gly Ile Val Ile Ala
 1               5                  10                  15

Ile Gln Ile Leu Ala His Val Asp Ser Ser Ser Gly Asn His Gln Gly
            20                  25                  30

Cys Phe Ile Arg Ala Thr Gly Glu Ser Ile Leu Ile Glu Asn Cys Gly
        35                  40                  45

Pro Ser Glu Ala Leu Ala Ser Thr Val Lys Glu Val Leu Gly Gly Leu
    50                  55                  60

Lys Ala Leu Gly Val Ser Arg Ala Val Glu Glu Ile Asp Tyr His Cys
65                  70                  75                  80


<210> SEQ ID NO 10
<211> LENGTH: 777
<212> TYPE: DNA
<213> ORGANISM: Rupestris stem pitting associated virus

<400> SEQUENCE: 10

atggcaagtc aaattgggaa actccccggt gaatcaaatg aggcttttga agcccggcta      60

aaatcgctgg agttagctag agctcaaaag cagccggaag gttctaatgc accacctact     120

ctcagtggca ttcttgccaa acgcaagagg attatagaga atgcactttc aaagacggtg     180

gacatgaggg aggttttgaa acacgaaacg gtggtgattt ccccaaatgt catggatgaa     240

ggtgcaatag acgagctgat tcgtgcattt ggtgaatctg gcatagctga aagcgtgcaa     300

tttgatgtgg ccatagatat agcacgtcac tgctctgatg ttggtagctc ccagagttca     360

accctgattg gcaagagtcc attttgtgac ctaaacagat cagaaatagc tgggattata     420

agggaggtga ccacattacg tagattttgc atgtactatg caaaaatcgt gtggaacatc     480

catctggaga cggggatacc accagctaac tgggccaaga aaggatttaa tgagaatgaa     540

aagtttgcag cctttgattt tttcttggga gtcacagatg agagtgcgct tgaaccaaag     600
```

-continued

```
ggtggaatta aaagagctcc aacgaaagct gagatggttg ctaatatcgc ctcttttgag    660

gttcaagtgc tcagacaagc tatggctgaa ggcaagcgga gttccaacct tggagagatt    720

agtggtggaa cggctggtgc actcatcaac aacccctttt caaatgttac acatgaa       777
```

<210> SEQ ID NO 11
<211> LENGTH: 259
<212> TYPE: PRT
<213> ORGANISM: Rupestris stem pitting associated virus

<400> SEQUENCE: 11

```
Met Ala Ser Gln Ile Gly Lys Leu Pro Gly Glu Ser Asn Glu Ala Phe
 1               5                  10                  15

Glu Ala Arg Leu Lys Ser Leu Glu Leu Ala Arg Ala Gln Lys Gln Pro
            20                  25                  30

Glu Gly Ser Asn Ala Pro Pro Thr Leu Ser Gly Ile Leu Ala Lys Arg
        35                  40                  45

Lys Arg Ile Ile Glu Asn Ala Leu Ser Lys Thr Val Asp Met Arg Glu
    50                  55                  60

Val Leu Lys His Glu Thr Val Val Ile Ser Pro Asn Val Met Asp Glu
65                  70                  75                  80

Gly Ala Ile Asp Glu Leu Ile Arg Ala Phe Gly Glu Ser Gly Ile Ala
                85                  90                  95

Glu Ser Val Gln Phe Asp Val Ala Ile Asp Ile Ala Arg His Cys Ser
            100                 105                 110

Asp Val Gly Ser Ser Gln Ser Ser Thr Leu Ile Gly Lys Ser Pro Phe
        115                 120                 125

Cys Asp Leu Asn Arg Ser Glu Ile Ala Gly Ile Ile Arg Glu Val Thr
    130                 135                 140

Thr Leu Arg Arg Phe Cys Met Tyr Tyr Ala Lys Ile Val Trp Asn Ile
145                 150                 155                 160

His Leu Glu Thr Gly Ile Pro Pro Ala Asn Trp Ala Lys Lys Gly Phe
                165                 170                 175

Asn Glu Asn Glu Lys Phe Ala Ala Phe Asp Phe Phe Leu Gly Val Thr
            180                 185                 190

Asp Glu Ser Ala Leu Glu Pro Lys Gly Gly Ile Lys Arg Ala Pro Thr
        195                 200                 205

Lys Ala Glu Met Val Ala Asn Ile Ala Ser Phe Glu Val Gln Val Leu
    210                 215                 220

Arg Gln Ala Met Ala Glu Gly Lys Arg Ser Ser Asn Leu Gly Glu Ile
225                 230                 235                 240

Ser Gly Gly Thr Ala Gly Ala Leu Ile Asn Asn Pro Phe Ser Asn Val
                245                 250                 255

Thr His Glu
```

<210> SEQ ID NO 12
<211> LENGTH: 2680
<212> TYPE: DNA
<213> ORGANISM: Rupestris stem pitting associated virus

<400> SEQUENCE: 12

```
ggctgggcaa actttggcct gctttcaaca cgccgtcttg gttcgctttg caccctacat     60

gcgatacatt gaaaagaagc ttgtgcaggc attgaaacca aatttctaca ttcattctgg    120

caaaggtctt gatgagctaa gtgaatgggt tagagccaga ggtttcacag gtgtgtgtac    180

tgagtcagac tatgaagctt ttgatgcatc ccaagatcat ttcatcctgg catttgaact    240
```

-continued

```
gcaaatcatg agatttttag gactgccaga agatctgatt ttagattatg agttcatcaa    300
aattcatctt gggtcaaagc ttggctcttt tgcaattatg agattcacag gtgaggcaag    360
caccttccta ttcaatacta tggccaacat gctattcact ttcctgaggt atgagttgac    420
aggttctgaa tcaattgcat ttgctggaga tgatatgtgt gctaatcgca ggttaagact    480
caagactgag cacgccggct ttctaaacat gatctgtctc aaagctaagg tgcagtttgt    540
cacaaatccc accttctgtg gatggtgttt gtttaaagag ggaatcttta aaaaacccca    600
gctcatttgg gaaaggatct gcattgctag ggaaatgggt aacttggaca attgcattga    660
caattacgca attgaggtgt cttatgctta cagacttggg gaattgtcca taggcgtgat    720
gactgaggag gaagttgaag cacattctaa ctgcgtgcgt ttcctggttc gcaataagca    780
caagatgagg tgctcaattt ctggtttgtt tgaagtaatt gtttaggcct taagtgtttg    840
gcatggtgtg agtattatga ataacttagt caaagctttg tctgcttttg aatttgttgg    900
tgtgttttgt gtacttaaat ttccagttgt tgttcacagt gttccaggta gcggtaaaag    960
tagcctaata agggagctca tttctgaaga cgaggctttt gtggccttta cagcaggtgt   1020
gccagacagt ccaaatctga cagggaggta catcaagccc tacgctccag ggtgtgcagt   1080
gcaagggaaa ataaacatac ttgatgagta cttgtctgtc tctgatactt ctggctttga   1140
tgtgctgttc tcagaccctt accagaatgt cagcattcca agggaggcac acttcataaa   1200
aaccaaaacc tgtaggtttg gtaccaacac ctgcaagtac cttcaatctt ttggctttaa   1260
tgtttgtagt gatggggtgg ataaagttgt tgtagggtcg ccatttgaac tggaggttga   1320
gggggttctc atttgctttg gaaaggaggc tgtagatcta gcagttgcac acaattctga   1380
cttcaagttg ccctgcgagg tgcggggttc aacatttgac gttgtaacgt tattgaagtc   1440
cagggatcca acttcagaag ataagcattg gttctacgtt gcagccacaa ggcatcgaag   1500
taaactgata ataatgcagt aaaatgcctt ttcagcaacc tgccaactgg gctaagacca   1560
taactccatt aactattggt ttgggcattg ggttggttct gcacttctta aggaaatcaa   1620
atctgccata ttcaggagac aatattcacc agttcccaca cggagggcat tacagggacg   1680
gcacgaagag tataacctat tgtggcccta ggcagtcatt cccaagctca ggaatattcg   1740
gtcagtctga aaatttcgta cctctaatat tggtcgtgac tctggtcgct tttatacatg   1800
cgttatctct ttggaattct ggtcctagta ggagttgcaa ttgccatcca aatccttgca   1860
catgtagaca gcagtagtgg caaccatcaa ggctgtttca taagagccac cggggagtca   1920
atagtaattg agaattgtgg gccgagcgag gccctagctg ctacagtcaa agaggtgttg   1980
ggcggtctaa aggctttagg ggttagccaa aaggttgatg aaattaatta cagttgttga   2040
gacagttgaa tggcaagtca agttggaaaa ttgcctggcg aatcaaatga agcatatgag   2100
gctagactca aggctttaga gttagcaagg gcccaaaaag ctccagaagt ctccaaccaa   2160
cctcccacac ttggaggcat tctagccaaa aggaaaagag tgattgagaa tgcactctca   2220
aagacagtgg atatgcgtga agtcttaagg catgaatctg ttgtactctc cccgaatgta   2280
atggacgagg gagcaataga cgagctgatt cgtgcctttg gggagtcggg catagctgaa   2340
aatgtgcagt ttgatgttgc aatagacatt gctcgccact gttctgatgt ggggagctct   2400
cagaggtcaa cccttattgg taaaagcccc ttctgtgagt taaataggtc tgaaattgcc   2460
ggaataataa gggaggtgac cacgctgcgc agattttgca tgtactacgc aaagattgtg   2520
tggaacatcc atttggagac gggaatacca ccagctaatt gggccaagaa aggatttaat   2580
```

-continued

```
gagaatgaaa agtttgcagc ctttgacttc ttccttggag tcacagatga aagcgcgctt   2640

gagcctaagg gtggagtcaa gagagctcca acaaaagcag                         2680


<210> SEQ ID NO 13
<211> LENGTH: 767
<212> TYPE: DNA
<213> ORGANISM: Rupestris stem pitting associated virus

<400> SEQUENCE: 13

atgcgataca ttgaaaagaa gcttgtgcag gcattgaaac caaatttcta cattcattct     60

ggcaaaggtc ttgatgagct aagtgaatgg gttagagcca gaggtttcac aggtgtgtgt    120

actgagtcag actatgaagc ttttgatgca tcccaagatc atttcatcct ggcatttgaa    180

ctgcaaatca tgagattttt aggactgcca gaagatctga ttttagatta tgagttcatc    240

aaaattcatc ttgggtcaaa gcttggctct tttgcaatta tgagattcac aggtgaggca    300

agcaccttcc tattcaatac tatggccaac atgctattca ctttcctgag gtatgagttg    360

acaggttctg aatcaattgc atttgctgga gatgatatgt gtgctaatcg caggttaaga    420

ctcaagactg agcacgccgg ctttctaaac atgatctgtc tcaaagctaa ggtgcagttt    480

gtcacaaatc ccaccttctg tggatggtgt ttgtttaaag agggaatctt taaaaaaccc    540

cagctcattt gggaaaggat ctgcattgct agggaaatgg gtaacttgga caattgcatt    600

gacaattacg caattgaggt gtcttatgct tacagacttg gggaattgtc cataggcgtg    660

atgactgagg aggaagttga agcacattct aactgcgtgc gtttcctggt tcgcaataag    720

cacaagatga ggtgctcaat ttctggtttg tttgaagtaa ttgttta                  767


<210> SEQ ID NO 14
<211> LENGTH: 255
<212> TYPE: PRT
<213> ORGANISM: Rupestris stem pitting associated virus

<400> SEQUENCE: 14

Met Arg Tyr Ile Glu Lys Lys Leu Val Gln Ala Leu Lys Pro Asn Phe
 1               5                  10                  15

Tyr Ile His Ser Gly Lys Gly Leu Asp Glu Leu Ser Glu Trp Val Arg
            20                  25                  30

Ala Arg Gly Phe Thr Gly Val Cys Thr Glu Ser Asp Tyr Glu Ala Phe
        35                  40                  45

Asp Ala Ser Gln Asp His Phe Ile Leu Ala Phe Glu Leu Gln Ile Met
    50                  55                  60

Arg Phe Leu Gly Leu Pro Glu Asp Leu Ile Leu Asp Tyr Glu Phe Ile
65                  70                  75                  80

Lys Ile His Leu Gly Ser Lys Leu Gly Ser Phe Ala Ile Met Arg Phe
                85                  90                  95

Thr Gly Glu Ala Ser Thr Phe Leu Phe Asn Thr Met Ala Asn Met Leu
            100                 105                 110

Phe Thr Phe Leu Arg Tyr Glu Leu Thr Gly Ser Glu Ser Ile Ala Phe
        115                 120                 125

Ala Gly Asp Asp Met Cys Ala Asn Arg Arg Leu Arg Leu Lys Thr Glu
    130                 135                 140

His Ala Gly Phe Leu Asn Met Ile Cys Leu Lys Ala Lys Val Gln Phe
145                 150                 155                 160

Val Thr Asn Pro Thr Phe Cys Gly Trp Cys Leu Phe Lys Glu Gly Ile
                165                 170                 175
```

-continued

```
Phe Lys Lys Pro Gln Leu Ile Trp Glu Arg Ile Cys Ile Ala Arg Glu
            180                 185                 190

Met Gly Asn Leu Asp Asn Cys Ile Asp Asn Tyr Ala Ile Glu Val Ser
        195                 200                 205

Tyr Ala Tyr Arg Leu Gly Glu Leu Ser Ile Gly Val Met Thr Glu Glu
    210                 215                 220

Glu Val Glu Ala His Ser Asn Cys Val Arg Phe Leu Val Arg Asn Lys
225                 230                 235                 240

His Lys Met Arg Cys Ser Ile Ser Gly Leu Phe Glu Val Ile Val
                245                 250                 255


<210> SEQ ID NO 15
<211> LENGTH: 666
<212> TYPE: DNA
<213> ORGANISM: Rupestris stem pitting associated virus

<400> SEQUENCE: 15

atgaataact tagtcaaagc tttgtctgct tttgaatttg ttggtgtgtt ttgtgtactt      60

aaatttccag ttgttgttca cagtgttcca ggtagcggta aaagtagcct aataagggag     120

ctcatttctg aagacgaggc ttttgtggcc tttacagcag gtgtgccaga cagtccaaat     180

ctgacaggga ggtacatcaa gccctacgct ccagggtgtg cagtgcaagg gaaaataaac     240

atacttgatg agtacttgtc tgtctctgat acttctggct ttgatgtgct gttctcagac     300

ccttaccaga atgtcagcat tccaagggag gcacacttca taaaaaccaa aacctgtagg     360

tttggtacca acacctgcaa gtaccttcaa tcttttggct ttaatgtttg tagtgatggg     420

gtggataaag ttgttgtagg gtcgccattt gaactggagg ttgaggggt tctcatttgc     480

tttggaaagg aggctgtaga tctagcagtt gcacacaatt ctgacttcaa gttgccctgc     540

gaggtgcggg gttcaacatt tgacgttgta acgttattga agtccaggga tccaacttca     600

gaagataagc attggttcta cgttgcagcc acaaggcatc gaagtaaact gataataatg     660

cagtaa                                                                666


<210> SEQ ID NO 16
<211> LENGTH: 221
<212> TYPE: PRT
<213> ORGANISM: Rupestris stem pitting associated virus

<400> SEQUENCE: 16

Met Asn Asn Leu Val Lys Ala Leu Ser Ala Phe Glu Phe Val Gly Val
 1               5                  10                  15

Phe Cys Val Leu Lys Phe Pro Val Val Val His Ser Val Pro Gly Ser
            20                  25                  30

Gly Lys Ser Ser Leu Ile Arg Glu Leu Ile Ser Glu Asp Glu Ala Phe
        35                  40                  45

Val Ala Phe Thr Ala Gly Val Pro Asp Ser Pro Asn Leu Thr Gly Arg
    50                  55                  60

Tyr Ile Lys Pro Tyr Ala Pro Gly Cys Ala Val Gln Gly Lys Ile Asn
65                  70                  75                  80

Ile Leu Asp Glu Tyr Leu Ser Val Ser Asp Thr Ser Gly Phe Asp Val
                85                  90                  95

Leu Phe Ser Asp Pro Tyr Gln Asn Val Ser Ile Pro Arg Glu Ala His
            100                 105                 110

Phe Ile Lys Thr Lys Thr Cys Arg Phe Gly Thr Asn Thr Cys Lys Tyr
        115                 120                 125
```

-continued

```
Leu Gln Ser Phe Gly Phe Asn Val Cys Ser Asp Gly Val Asp Lys Val
    130                 135                 140

Val Val Gly Ser Pro Phe Glu Leu Glu Val Glu Gly Val Leu Ile Cys
145                 150                 155                 160

Phe Gly Lys Glu Ala Val Asp Leu Ala Val Ala His Asn Ser Asp Phe
                165                 170                 175

Lys Leu Pro Cys Glu Val Arg Gly Ser Thr Phe Asp Val Val Thr Leu
            180                 185                 190

Leu Lys Ser Arg Asp Pro Thr Ser Glu Asp Lys His Trp Phe Tyr Val
        195                 200                 205

Ala Ala Thr Arg His Arg Ser Lys Leu Ile Ile Met Gln
    210                 215                 220


<210> SEQ ID NO 17
<211> LENGTH: 354
<212> TYPE: DNA
<213> ORGANISM: Rupestris stem pitting associated virus

<400> SEQUENCE: 17

atgccttttc agcaacctgc caactgggct aagaccataa ctccattaac tattggtttg     60

ggcattgggt tggttctgca cttcttaagg aaatcaaatc tgccatattc aggagacaat    120

attcaccagt tcccacacgg agggcattac agggacggca cgaagagtat aacctattgt    180

ggccctaggc agtcattccc aagctcagga atattcggtc agtctgaaaa tttcgtacct    240

ctaatattgg tcgtgactct ggtcgctttt atacatgcgt tatctctttg gaattctggt    300

cctagtagga gttgcaattg ccatccaaat ccttgcacat gtagacagca gtag          354


<210> SEQ ID NO 18
<211> LENGTH: 117
<212> TYPE: PRT
<213> ORGANISM: Rupestris stem pitting associated virus

<400> SEQUENCE: 18

Met Pro Phe Gln Gln Pro Ala Asn Trp Ala Lys Thr Ile Thr Pro Leu
 1               5                  10                  15

Thr Ile Gly Leu Gly Ile Gly Leu Val Leu His Phe Leu Arg Lys Ser
            20                  25                  30

Asn Leu Pro Tyr Ser Gly Asp Asn Ile His Gln Phe Pro His Gly Gly
        35                  40                  45

His Tyr Arg Asp Gly Thr Lys Ser Ile Thr Tyr Cys Gly Pro Arg Gln
    50                  55                  60

Ser Phe Pro Ser Ser Gly Ile Phe Gly Gln Ser Glu Asn Phe Val Pro
65                  70                  75                  80

Leu Ile Leu Val Val Thr Leu Val Ala Phe Ile His Ala Leu Ser Leu
                85                  90                  95

Trp Asn Ser Gly Pro Ser Arg Ser Cys Asn Cys His Pro Asn Pro Cys
            100                 105                 110

Thr Cys Arg Gln Gln
        115


<210> SEQ ID NO 19
<211> LENGTH: 243
<212> TYPE: DNA
<213> ORGANISM: Rupestris stem pitting associated virus

<400> SEQUENCE: 19

atgcgttatc tctttggaat tctggtccta gtaggagttg caattgccat ccaaatcctt     60
```

-continued

```
gcacatgtag acagcagtag tggcaaccat caaggctgtt tcataagagc caccggggag    120

tcaatagtaa ttgagaattg tgggccgagc gaggccctag ctgctacagt caaagaggtg    180

ttgggcggtc taaaggcttt aggggttagc caaaaggttg atgaaattaa ttacagttgt    240

tga                                                                  243
```

<210> SEQ ID NO 20
<211> LENGTH: 80
<212> TYPE: PRT
<213> ORGANISM: Rupestris stem pitting associated virus

<400> SEQUENCE: 20

```
Met Arg Tyr Leu Phe Gly Ile Leu Val Leu Val Gly Val Ala Ile Ala
 1               5                  10                  15

Ile Gln Ile Leu Ala His Val Asp Ser Ser Ser Gly Asn His Gln Gly
            20                  25                  30

Cys Phe Ile Arg Ala Thr Gly Glu Ser Ile Val Ile Glu Asn Cys Gly
        35                  40                  45

Pro Ser Glu Ala Leu Ala Ala Thr Val Lys Glu Val Leu Gly Gly Leu
    50                  55                  60

Lys Ala Leu Gly Val Ser Gln Lys Val Asp Glu Ile Asn Tyr Ser Cys
65                  70                  75                  80
```

<210> SEQ ID NO 21
<211> LENGTH: 631
<212> TYPE: DNA
<213> ORGANISM: Rupestris stem pitting associated virus

<400> SEQUENCE: 21

```
atggcaagtc aagttggaaa attgcctggc gaatcaaatg aagcatatga ggctagactc     60

aaggctttag agttagcaag ggcccaaaaa gctccagaag tctccaacca acctccccaca   120

cttggaggca ttctagccaa aaggaaaaga gtgattgaga atgcactctc aaagacagtg    180

gatatgcgtg aagtcttaag gcatgaatct gttgtactct ccccgaatgt aatggacgag    240

ggagcaatag acgagctgat tcgtgccttt ggggagtcgg gcatagctga aaatgtgcag    300

tttgatgttg caatagacat tgctcgccac tgttctgatg tggggagctc tcagaggtca    360

acccttattg gtaaaagccc cttctgtgag ttaaataggt ctgaaattgc cggaataata    420

agggaggtga ccacgctgcg cagattttgc atgtactacg caaagattgt gtggaacatc    480

catttggaga cgggaatacc accagctaat tgggccaaga aaggatttaa tgagaatgaa    540

aagtttgcag cctttgactt cttccttgga gtcacagatg aaagcgcgct tgagcctaag    600

ggtggagtca agagagctcc aacaaaagca g                                   631
```

<210> SEQ ID NO 22
<211> LENGTH: 210
<212> TYPE: PRT
<213> ORGANISM: Rupestris stem pitting associated virus

<400> SEQUENCE: 22

```
Met Ala Ser Gln Val Gly Lys Leu Pro Gly Glu Ser Asn Glu Ala Tyr
 1               5                  10                  15

Glu Ala Arg Leu Lys Ala Leu Glu Leu Ala Arg Ala Gln Lys Ala Pro
            20                  25                  30

Glu Val Ser Asn Gln Pro Pro Thr Leu Gly Gly Ile Leu Ala Lys Arg
        35                  40                  45
```

-continued

```
Lys Arg Val Ile Glu Asn Ala Leu Ser Lys Thr Val Asp Met Arg Glu
    50                  55                  60

Val Leu Arg His Glu Ser Val Val Leu Ser Pro Asn Val Met Asp Glu
65                  70                  75                  80

Gly Ala Ile Asp Glu Leu Ile Arg Ala Phe Gly Glu Ser Gly Ile Ala
                85                  90                  95

Glu Asn Val Gln Phe Asp Val Ala Ile Asp Ile Ala Arg His Cys Ser
            100                 105                 110

Asp Val Gly Ser Ser Gln Arg Ser Thr Leu Ile Gly Lys Ser Pro Phe
        115                 120                 125

Cys Glu Leu Asn Arg Ser Glu Ile Ala Gly Ile Ile Arg Glu Val Thr
    130                 135                 140

Thr Leu Arg Arg Phe Cys Met Tyr Tyr Ala Lys Ile Val Trp Asn Ile
145                 150                 155                 160

His Leu Glu Thr Gly Ile Pro Pro Ala Asn Trp Ala Lys Lys Gly Phe
                165                 170                 175

Asn Glu Asn Glu Lys Phe Ala Ala Phe Asp Phe Phe Leu Gly Val Thr
            180                 185                 190

Asp Glu Ser Ala Leu Glu Pro Lys Gly Gly Val Lys Arg Ala Pro Thr
        195                 200                 205

Lys Ala
    210

<210> SEQ ID NO 23
<211> LENGTH: 2009
<212> TYPE: DNA
<213> ORGANISM: Rupestris stem pitting associated virus

<400> SEQUENCE: 23

gaagctagca catttctgtt caacactatg gctaacatgt tgttcacttt tctgagatat     60

gaactgacgg gttcagagtc aatagcattt gcaggggatg atatgtgtgc taatagaagg    120

ttgcggctta aaacggagca tgagggtttt ctgaacatga tctgccttaa ggccaaggtt    180

cagtttgttt ccaaccccac attctgtgga tggtgcttat ttaaggaggg aatcttcaag    240

aaacctcaac taatttggga gcgaatatgc atagccagag agatgggcaa tctggagaac    300

tgtattgaca attatgcgat agaagtgtcc tatgcatata gattgggtga gctatcaatt    360

gaaatgatga cagaagaaga agtggaggca cactacaatt gtgtgaggtt cctggttagg    420

aacaagcata agatgaggtg ctcaatttca ggcctgtttg aagtggttga ttaggcctta    480

agtatttggc gttgttcgag ttattatgaa taatttagtt aaagcattat cagccttcga    540

gtttataggt gttttcaatg tgctcaaatt tccagttgtt atacatagtg tgcctggtag    600

tggtaagagt agcttaataa gggaattaat ctcagaggac gagagtttcg tggctttcac    660

agcaggtgtt ccagacagtc ctaacctcac agggaggtac atcaagcctt actcaccagg    720

atgcgcagtg caaggaaaag tgaatatact tgatgagtac ttgtccgttc aagacatttc    780

gggttttgat gtactgtttt cagacccgta ccagaatatc agtattcccc aagaggcgca    840

tttcattaag tccaagactt gtaggtttgg tgtgaacact tgcaaatacc tttcctcttt    900

cggtttcgaa gttagcagcg acgggctgga cgacgtcatt gtgggatcgc ccttcactct    960

agatgttgaa ggggtgctga tatgttttgg caaggaggcg gtagatctcg ctgttgcgca   1020

caactctgaa ttcaagttgc cgtgtgaggt tcgaggttca accttcaatg tggtaaccct   1080

tttgaaatca agagacccaa ccccagagga caggcactgg ttttacatcg ctgccacaag   1140
```

-continued

```
acataggaag aaattggtca ttatgcagta aaatgccttt tcagcagcct gctaattggg   1200

caaaaaccat aactccattg actattggct taggaattgg acttgtgctg cattttctga   1260

gaaagtcaaa tctaccatat tcaggagaca acatccatca atttcctcac ggggggcgtt   1320

accgggacgg cacaaaaagt ataacttact gtggccctaa gcagtccttc cccagttcag   1380

gaatatttgg tcagtctgag aattttgtgc ccttaatgct tgtcataggt ctaattgcat   1440

tcatacatgt attgtctgtt tggaattctg gtcttggtag gaattgcaat tgccatccaa   1500

atccttgctc atgtagacaa cagtagtggc agtcaccaag gttgctttat cagggccact   1560

ggagagtcta ttttgattga aaattgtggc ccaagcgagg cccttgcatc aacagtgagg   1620

gaggtgttgg ggggtttgaa ggctttagga attagccata ctactgaaga aattgattat   1680

cgttgttaaa ttggttaaat ggcgagtcaa gttggtaagc tccccggaga atcaaatgag   1740

gcatttgaag cccggctgaa atcactggag ttggctagag ctcaaaagca gccagaaggt   1800

tcaaacacac cgcctactct cagtggtgtg cttgccaaac gtaagagggt tattgagaat   1860

gcactctcaa agacagtgga catgagggag gtgttgaaac acgaaacggt tgtaatttcc   1920

ccaaatgtca tggatgaggg tgcaatagat gaactgattc gtgcattcgg agaatcaggc   1980

atagctgaga gcgcacaatt tgatgtggc                                    2009
```

<210> SEQ ID NO 24
<211> LENGTH: 447
<212> TYPE: DNA
<213> ORGANISM: Rupestris stem pitting associated virus

<400> SEQUENCE: 24

```
gaagctagca catttctgtt caacactatg gctaacatgt tgttcacttt tctgagatat     60

gaactgacgg gttcagagtc aatagcattt gcaggggatg atatgtgtgc taatagaagg    120

ttgcggctta aaacggagca tgagggtttt ctgaacatga tctgccttaa ggccaaggtt    180

cagtttgttt ccaaccccac attctgtgga tggtgcttat ttaaggaggg aatcttcaag    240

aaacctcaac taatttggga gcgaatatgc atagccagag agatgggcaa tctggagaac    300

tgtattgaca attatgcgat agaagtgtcc tatgcatata gattgggtga gctatcaatt    360

gaaatgatga cagaagaaga agtggaggca cactacaatt gtgtgaggtt cctggttagg    420

aacaagcata agatgaggtg ctcaatt                                        447
```

<210> SEQ ID NO 25
<211> LENGTH: 149
<212> TYPE: PRT
<213> ORGANISM: Rupestris stem pitting associated virus

<400> SEQUENCE: 25

```
Glu Ala Ser Thr Phe Leu Phe Asn Thr Met Ala Asn Met Leu Phe Thr
 1               5                  10                  15

Phe Leu Arg Tyr Glu Leu Thr Gly Ser Glu Ser Ile Ala Phe Ala Gly
            20                  25                  30

Asp Asp Met Cys Ala Asn Arg Arg Leu Arg Leu Lys Thr Glu His Glu
        35                  40                  45

Gly Phe Leu Asn Met Ile Cys Leu Lys Ala Lys Val Gln Phe Val Ser
    50                  55                  60

Asn Pro Thr Phe Cys Gly Trp Cys Leu Phe Lys Glu Gly Ile Phe Lys
65                  70                  75                  80

Lys Pro Gln Leu Ile Trp Glu Arg Ile Cys Ile Ala Arg Glu Met Gly
                85                  90                  95
```

-continued

```
Asn Leu Glu Asn Cys Ile Asp Asn Tyr Ala Ile Glu Val Ser Tyr Ala
            100                 105                 110

Tyr Arg Leu Gly Glu Leu Ser Ile Glu Met Met Thr Glu Glu Glu Val
        115                 120                 125

Glu Ala His Tyr Asn Cys Val Arg Phe Leu Val Arg Asn Lys His Lys
    130                 135                 140

Met Arg Cys Ser Ile
145


<210> SEQ ID NO 26
<211> LENGTH: 666
<212> TYPE: DNA
<213> ORGANISM: Rupestris stem pitting associated virus

<400> SEQUENCE: 26

atgaataatt tagttaaagc attatcagcc ttcgagttta taggtgtttt caatgtgctc      60

aaatttccag ttgttataca tagtgtgcct ggtagtggta agagtagctt aataagggaa     120

ttaatctcag aggacgagag tttcgtggct ttcacagcag gtgttccaga cagtcctaac     180

ctcacaggga ggtacatcaa gccttactca ccaggatgcg cagtgcaagg aaaagtgaat     240

atacttgatg agtacttgtc cgttcaagac atttcgggtt ttgatgtact gttttcagac     300

ccgtaccaga atatcagtat tccccaagag gcgcatttca ttaagtccaa gacttgtagg     360

tttggtgtga acacttgcaa atacctttcc tctttcggtt tcgaagttag cagcgacggg     420

ctggacgacg tcattgtggg atcgcccttc actctagatg ttgaaggggt gctgatatgt     480

tttggcaagg aggcggtaga tctcgctgtt gcgcacaact ctgaattcaa gttgccgtgt     540

gaggttcgag gttcaacctt caatgtggta accctttttga aatcaagaga cccaacccca     600

gaggacaggc actggtttta catcgctgcc acaagacata ggaagaaatt ggtcattatg     660

cagtaa                                                                666


<210> SEQ ID NO 27
<211> LENGTH: 221
<212> TYPE: PRT
<213> ORGANISM: Rupestris stem pitting associated virus

<400> SEQUENCE: 27

Met Asn Asn Leu Val Lys Ala Leu Ser Ala Phe Glu Phe Ile Gly Val
 1               5                  10                  15

Phe Asn Val Leu Lys Phe Pro Val Val Ile His Ser Val Pro Gly Ser
            20                  25                  30

Gly Lys Ser Ser Leu Ile Arg Glu Leu Ile Ser Glu Asp Glu Ser Phe
        35                  40                  45

Val Ala Phe Thr Ala Gly Val Pro Asp Ser Pro Asn Leu Thr Gly Arg
    50                  55                  60

Tyr Ile Lys Pro Tyr Ser Pro Gly Cys Ala Val Gln Gly Lys Val Asn
65                  70                  75                  80

Ile Leu Asp Glu Tyr Leu Ser Val Gln Asp Ile Ser Gly Phe Asp Val
                85                  90                  95

Leu Phe Ser Asp Pro Tyr Gln Asn Ile Ser Ile Pro Gln Glu Ala His
            100                 105                 110

Phe Ile Lys Ser Lys Thr Cys Arg Phe Gly Val Asn Thr Cys Lys Tyr
        115                 120                 125

Leu Ser Ser Phe Gly Phe Glu Val Ser Ser Asp Gly Leu Asp Asp Val
    130                 135                 140
```

-continued

```
Ile Val Gly Ser Pro Phe Thr Leu Asp Val Glu Gly Val Leu Ile Cys
145                 150                 155                 160

Phe Gly Lys Glu Ala Val Asp Leu Ala Val Ala His Asn Ser Glu Phe
                165                 170                 175

Lys Leu Pro Cys Glu Val Arg Gly Ser Thr Phe Asn Val Val Thr Leu
            180                 185                 190

Leu Lys Ser Arg Asp Pro Thr Pro Glu Asp Arg His Trp Phe Tyr Ile
        195                 200                 205

Ala Ala Thr Arg His Arg Lys Lys Leu Val Ile Met Gln
    210                 215                 220
```

<210> SEQ ID NO 28
<211> LENGTH: 354
<212> TYPE: DNA
<213> ORGANISM: Rupestris stem pitting associated virus

<400> SEQUENCE: 28

```
atgccttttc agcagcctgc taattgggca aaaaccataa ctccattgac tattggctta     60

ggaattggac ttgtgctgca ttttctgaga aagtcaaatc taccatattc aggagacaac    120

atccatcaat ttcctcacgg ggggcgttac cgggacggca caaaaagtat aacttactgt    180

ggccctaagc agtccttccc cagttcagga atatttggtc agtctgagaa ttttgtgccc    240

ttaatgcttg tcataggtct aattgcattc atacatgtat tgtctgtttg gaattctggt    300

cttggtagga attgcaattg ccatccaaat ccttgctcat gtagacaaca gtag          354
```

<210> SEQ ID NO 29
<211> LENGTH: 116
<212> TYPE: PRT
<213> ORGANISM: Rupestris stem pitting associated virus

<400> SEQUENCE: 29

```
Met Pro Phe Gln Gln Pro Ala Asn Trp Ala Lys Thr Ile Thr Pro Leu
 1               5                  10                  15

Thr Ile Gly Leu Gly Ile Gly Leu Val Leu His Phe Leu Arg Lys Ser
            20                  25                  30

Asn Leu Pro Tyr Ser Gly Asp Asn Ile His Gln Phe Pro His Gly Gly
        35                  40                  45

Arg Tyr Arg Asp Gly Thr Lys Ile Thr Tyr Cys Gly Pro Lys Gln Ser
    50                  55                  60

Phe Pro Ser Ser Gly Ile Phe Gly Gln Ser Glu Asn Phe Val Pro Leu
65                  70                  75                  80

Met Leu Val Ile Gly Leu Ile Ala Phe Ile His Val Leu Ser Val Trp
                85                  90                  95

Asn Ser Gly Leu Gly Arg Asn Cys Asn Cys His Pro Asn Pro Cys Ser
            100                 105                 110

Cys Arg Gln Gln
        115
```

<210> SEQ ID NO 30
<211> LENGTH: 243
<212> TYPE: DNA
<213> ORGANISM: Rupestris stem pitting associated virus

<400> SEQUENCE: 30

```
atgtattgtc tgtttggaat tctggtcttg gtaggaattg caattgccat ccaaatcctt     60

gctcatgtag acaacagtag tggcagtcac caaggttgct ttatcagggc cactggagag    120
```

-continued

```
tctattttga ttgaaaattg tggcccaagc gaggcccttg catcaacagt gagggaggtg    180

ttggggggtt tgaaggcttt aggaattagc catactactg aagaaattga ttatcgttgt    240

taa                                                                  243


<210> SEQ ID NO 31
<211> LENGTH: 80
<212> TYPE: PRT
<213> ORGANISM: Rupestris stem pitting associated virus

<400> SEQUENCE: 31

Met Tyr Cys Leu Phe Gly Ile Leu Val Leu Val Gly Ile Ala Ile Ala
 1              5                   10                  15

Ile Gln Ile Leu Ala His Val Asp Asn Ser Ser Gly Ser His Gln Gly
            20                  25                  30

Cys Phe Ile Arg Ala Thr Gly Glu Ser Ile Leu Ile Glu Asn Cys Gly
        35                  40                  45

Pro Ser Glu Ala Leu Ala Ser Thr Val Arg Glu Val Leu Gly Gly Leu
    50                  55                  60

Lys Ala Leu Gly Ile Ser His Thr Thr Glu Glu Ile Asp Tyr Arg Cys
65                  70                  75                  80


<210> SEQ ID NO 32
<211> LENGTH: 311
<212> TYPE: DNA
<213> ORGANISM: Rupestris stem pitting associated virus

<400> SEQUENCE: 32

atggcgagtc aagttggtaa gctccccgga gaatcaaatg aggcatttga agcccggctg     60

aaatcactgg agttggctag agctcaaaag cagccagaag gttcaaacac accgcctact    120

ctcagtggtg tgcttgccaa acgtaagagg gttattgaga atgcactctc aaagacagtg    180

gacatgaggg aggtgttgaa acacgaaacg gttgtaattt ccccaaatgt catggatgag    240

ggtgcaatag atgaactgat tcgtgcattc ggagaatcag gcatagctga gagcgcacaa    300

tttgatgtgg c                                                         311


<210> SEQ ID NO 33
<211> LENGTH: 103
<212> TYPE: PRT
<213> ORGANISM: Rupestris stem pitting associated virus

<400> SEQUENCE: 33

Met Ala Ser Gln Val Gly Lys Leu Pro Gly Glu Ser Asn Glu Ala Phe
 1              5                   10                  15

Glu Ala Arg Leu Lys Ser Leu Glu Leu Ala Arg Ala Gln Lys Gln Pro
            20                  25                  30

Glu Gly Ser Asn Thr Pro Pro Thr Leu Ser Gly Val Leu Ala Lys Arg
        35                  40                  45

Lys Arg Val Ile Glu Asn Ala Leu Ser Lys Thr Val Asp Met Arg Glu
    50                  55                  60

Val Leu Lys His Glu Thr Val Val Ile Ser Pro Asn Val Met Asp Glu
65                  70                  75                  80

Gly Ala Ile Asp Glu Leu Ile Arg Ala Phe Gly Glu Ser Gly Ile Ala
                85                  90                  95

Glu Ser Ala Gln Phe Asp Val
            100
```

-continued

<210> SEQ ID NO 34
<211> LENGTH: 1206
<212> TYPE: DNA
<213> ORGANISM: Rupestris stem pitting associated virus

<400> SEQUENCE: 34

```
gcaggattga aggctggcca ctgtgtgatt tttgatgagg tccagttgtt tcctcctgga      60
tacatcgatc tatgcttgct tattatacgt agtgatgctt tcatttcact tgccggtgat     120
ccatgtcaaa gcacatatga ttcgcaaaag gatcgggcaa ttttgggcgc tgagcagagt     180
gacatactta gaatgcttga gggcaaaacg tataggtata acatagaaag caggaggttt     240
gtgaacccaa tgttcgaatc aagactgcca tgtcacttca aaaagggttc gatgactgcc     300
gctttcgctg attatgcaat cttccataat atgcatgact ttctcctggc gaggtcaaaa     360
ggtcctttgg atgccgtttt ggtttccagt tttgaggaga aaaagatagt ccagtcctac     420
tttggaatga aacagctcac actcacattt ggtgaatcaa ctgggttgaa tttcaaaaat     480
gggggaattc tcatatcaca tgattccttt cacacagatg atcggccggt ggcttactgc     540
tttatctcgc ttcagccaca atttggattt ggtgaacatt acaggtctga gggtggaaag     600
tttcctctcg cactttgctg gcaaacccct ctaccatttt ttaacagcca aaagtgggga     660
gaatgtcata cgagatttgc tcccaggtga gcctaacttc ttcagtggct ttaacgttag     720
cattggaaag aatgaaggtg ttagggagga gaagttatgt ggtgacccat ggttaaaagt     780
catgcttttc ctgggtcaag atgaggattg tgaagttgaa gagatggagt cagagtgctc     840
aaatgaagaa tggtttaaaa cccacattcc cctgagtaat ctggagtcaa ccagggctag     900
gtgggtgggt aaaatggctt tgaaagagta tcgggaggtg cgttgtggtt atgaaatgac     960
tcaacaattc tttgatgagc atagggggtgg aactggtgag caactgagca atgcatgtga    1020
gaggtttgaa agcatttacc caaggcataa aggaaatgat tcaataacct tccttatggc    1080
tgtccgaaag cgtctcaaat tttcgaagcc ccaggttgaa gctgccaaac tgaggcgggc    1140
caaaccatat gggaaattct tattagactt tcctatccaa aatcccattg aaagccagtc    1200
ataatt                                                                1206
```

<210> SEQ ID NO 35
<211> LENGTH: 1284
<212> TYPE: DNA
<213> ORGANISM: Rupestris stem pitting associated virus

<400> SEQUENCE: 35

```
attaacccaa atggtaagat ttccgccttg tttgatataa ccaatgagca cataaggcat      60
gttgagaaga tcggcaatgg ccctcagagc ataaaaagtag atgagttgag gaaggttaag     120
cgatccgccc ttgatcttct ttcaatgaat gggtccaaaa taacctattt tccaaacttt     180
gagcgggctg aaaagttgca agggtgcttg ctagggggcc taactggtgt cataagtgat     240
gaaaagttca gtgatgcaaa accctggctt tctggtatat caactgcgga tataaagcca     300
agagagctaa ctgtcgtgct tggcactttt ggggctggaa agagtttctt gtataagagt     360
ttcatgaaga gatctgaggg aaaatttgta acttttgttt cccctagacg agccttggca     420
aattcaatca aaaatgatct tgaaatggat gatggctgca aagttgccaa agcaggcaaa     480
tcaaagaagg aagggtggga tgtagtgacc tttgaagttt tccttagaaa agtttctggt     540
ttgaaagctg gtcattgtgt gatttttgat gaggttcagt tgtttccccc tggatacatc     600
gatctgtgtt tacttgtcat acgaagtgat gctttcattt cacttgctgg tgatccatgc     660
```

-continued

```
cagagcacat atgattcaca gaaggatcga gcaattttgg gagctgagca gagtgacata    720

ctcagactgc ttgaaggaaa gacatatagg tacaacatag aaagcagacg ttttgtgaac    780

ccaatgtttg aatctagact accatgtcac ttcaaaaagg gttcaatgac tgcagccttt    840

gctgattatg caatcttcca caatatgcat gacttcctcc tggcgaggtc aaaaggcccc    900

ttggatgctg ttctagtttc cagttttgag gagaagaaaa tagtccaatc ctactttggg    960

atgaagcaac tcactctcac atttggtgaa tcaactgggt tgaacttcaa aaatggagga   1020

attctcatat cacatgactc ctttcatact gacgatcgac ggtggcttac tgctttatct   1080

cgattcagcc ataatttgga tttggtgaac atcacaggtc ttgagggtgg aaagttttct   1140

ctcacatttt gctggtaaac ccctttacca ctttttgacg gcttaaaagt ggagagaatg   1200

tcatacgaga cctgcttcag gtgagcctaa cttcttttag gggttcaatg tcagcattgg   1260

aaaaaaatgg aaggggttag agaa                                          1284
```

<210> SEQ ID NO 36
<211> LENGTH: 1402
<212> TYPE: DNA
<213> ORGANISM: Rupestris stem pitting associated virus

<400> SEQUENCE: 36

```
catttttaaa atttaatcca gtcgactcac caaatgtgag cgtaagctgt ttcatcccaa     60

agtaggactg gactattttc ttctcctcaa aactagaaac cagaatggca tccaaaggac    120

cttttgacct tgccaggagg aaatcatgca tattgtggaa aatggcataa tcagcaaagg    180

cagcagtcat tgtacccttt ttgaagtgac atggcagtcg agattcaaac attgggttca    240

caaatcttct gctttctatg ttgtacctat acgtcttgcc ttcaagtatt ttgagtatgt    300

cactctgctc agcgcccaaa atcgcccgat ctttttgtga gtcatatgtg ctctgacatg    360

ggtcaccagc aagtgaaatg aaagcatcac tacgtataat aagcaaacat agatcgatgt    420

atccaggggg aaacaactgg acctcatcga aaattacaca gtgaccagct tttagacctg    480

caacttttct aaggaagact tcaaaagtca caacatccca tccttccttc tttgacctgc    540

ctgctttggc aactttgcag ctatcatcca tttcaagatc atttttgatt gaattcgcta    600

gagcccgtct gggggaaaca aaagttacga atttaccctc agatcttttc ataaagctct    660

tgtacaaaaa gctttttccg gctccaaatg tgccaagcac aacagttagc tccctcggct    720

taatgtcagt agttgatata ccagaaagcc agggctttgc atcactgaac ttctcatcac    780

ttatgacacc agttaggcct cctagcagac acccttgcaa cttttcagcc cgctcaaaac    840

ttgggaagta ggttaccttg gacccattaa ttgaaagaag atcaagggcg gatcgcttga    900

cctttcgcaa ttcatctact ttaatgctct gagggccatt acctatcttt tcaacatgcc    960

ttatgtgctc attagttatg tcaaacagag cggaaaactt gccatgtgga ttaatcacct   1020

caatttcccc atttatgtca cacttagcgc aaatgtcaaa agcctcaaag gcttcagcta   1080

agttacatca tgttgagcct ccccccttggc aaagctcctc aaaaatgtgg ttagtgctag   1140

gcctgcacaa taattaacac atcaacttca ccctgccaat gctgaacaat actgttatca   1200

tgcaaccatc catggggcac atggttggaa ttgattgatt taaggcaaaa atccccacag   1260

ggggcatccc cttccccaat ttccactgat tcatactctg gcgttatcat atcaacccaa   1320

tgtgtcaaat acaaataatg caatctctca tctccgataa catttccccc attttttaaa   1380

aatggtgggg tgaaaattgg aa                                            1402
```

-continued

<210> SEQ ID NO 37
<211> LENGTH: 1236
<212> TYPE: DNA
<213> ORGANISM: Rupestris stem pitting associated virus

<400> SEQUENCE: 37
gtggtttttg caacaacagg cccaggtcta tctaaggttt tggaaatgcc tcgaagcaag 60
aagcaatcta ttctggttct tgagggagcc ctatccatag aaacggacta tggcccaaaa 120
gttctgggat cttttgaagt tttcaaaggg gatttcaaca ttaaaaaaat ggaagaaagt 180
tccatctttg taataacata caaggcccca gttagatcta ctggcaagtt gagggtccac 240
caatcagaat gctcattttc tggatccaag gaggtattgc tgggttgtca gattgaggca 300
tgtgctgatt atgatattga tgatttcaat actttctttg tacctggtga tggtaattgc 360
ttttggcatt cagttggttt cttactcagt actgacggac ttgctttgaa ggccggcatt 420
cgttctttcg tggagagtga acgcctggtg agtccagatc tttcagcccc aaccatttct 480
aaacaactgg gggaaaatgc ttatgccgag aatgagatga ttgcattatt ttgtattcga 540
caccatgtga ggctgatagt gattacgcca gagtatgaag tcagttggaa atttggggaa 600
ggtgaatggc ccctgtgcgg aattctttgc cttaaatcaa atcacttcca accatgtgcc 660
ccattgaatg gttgcatgat tacagctatt gcttcagcac ttggtaggcg tgaagttgat 720
gtgcttaatt atctgtgcag gcctagcact aaccacattt ttgaggagct ttgccaaggg 780
ggaggcctca acatgatgta cttagctgaa gcctttgagg cttttgacat ttgcgctaag 840
tgtgacataa atggggaaat tgaggtgatt aatccacatg gcaagttttc cgctctgttt 900
gacataacta atgagcacat aaggcatgtt gaaaagatag gtaatggccc tcagagcatt 960
aaagtagatg aattgcgaaa ggtcaagcga tctgcccttg atcttctttc aattaatggg 1020
tccaaggtaa cctacttccc aagttttgag cgggctgaaa agttgcaagg gtgtctgcta 1080
ggaggcctaa ctggtgtcat aagtgatgag aaagtcagtg atgcaaagcc ctgctttttg 1140
gtatatcaac tactgacatt aagccgaggg agctaactgt tgtgctttgg cacatttgga 1200
gcccggaaaa agccttttgt accaagagct ttattg 1236

<210> SEQ ID NO 38
<211> LENGTH: 1296
<212> TYPE: DNA
<213> ORGANISM: Rupestris stem pitting associated virus

<400> SEQUENCE: 38
gtctaactgg cgttataagt gatgagaaat tcagtgatgc aaaaccttgg ctttctggta 60
tatctactac agatattaag ccaagggaat taactgttgt gcttggtaca tttggggctg 120
ggaagagttt cttgtacaag agtttcatga aaaggtctga gggtaaattc gtaacctttg 180
tttctcccag acgtgcttta gcaaattcaa tcaaaaatga tcttgaaatg gatgatagct 240
gcaaagttgc caaagcaggt aggtcaaaga aggaagggtg ggatgtagta acttttgagg 300
tcttcctcag aaaagttgca ggattgaagg ctggccactg tgtgattttt gatgaggtcc 360
agttgtttcc tcctggatac atcgatctat gcttgcttat tatacgtagt gatgctttca 420
tttcacttgc cggtgatcca tgtcaaagca catatgattc gcaaaaggat cgggcaattt 480
tgggcgctga gcagagtgac atacttagaa tgcttgaggg caaaacgtat aggtataaca 540
tagaaagcag gaggtttgtg aacccaatgt tcgaatcaag actgccatgt cacttcaaaa 600
agggttcgat gactgccgct ttcgctgatt atgcaatctt ccataatatg catgactttc 660

-continued

```
tcctggcgag gtcaaaaggt cctttggatg ccgttttggt ttccagtttt gaggagaaaa    720

agatagtcca gtcctacttt ggaatgaaac agctcacact cacatttggt gaatcaactg    780

ggttgaattt caaaaatggg ggaattctca tatcacatga ttcctttcac acagatgatc    840

ggcggtggct tactgcttta tctcgcttca gccacaattt ggatttggtg aacattacag    900

gtctgaggtg gaaagtttcc tctcgcactt tgctggcaaa cccctctacc atttttttaac    960

agccaaaagt ggggagaatg tcatacgaga tttgctccca ggtgagccta acttcttcag   1020

tggctttaac gttagcattg gaaagaatga aggtgttagg gaggagaagt tatgtggtga   1080

cccatggtta aaagtcatgc ttttcctggg tcaagatgag gattgtgaag ttgaagagat   1140

ggagtcagag tgctcaaatg aagaatggtt taaaacccac attcccctga gtaatctgga   1200

gtcaaccagg gctaggtggg tgggtaaaat ggccttgaaa gagtatcggg aggtgcgttg   1260

tggttatgaa atgactcaac aattctttga tgacat                             1296
```

<210> SEQ ID NO 39
<211> LENGTH: 907
<212> TYPE: DNA
<213> ORGANISM: Rupestris stem pitting associated virus

<400> SEQUENCE: 39

```
atgttcacca aatccaaatt atggctgaag cgagataaag cagtaagcca ccgccgatca     60

tctgtgtgaa aggaatcatg tgatatgaga attcccccat tttgaaatt caacccagtt    120

gattcaccaa atgtgagtgt gagctgtttc attccaaagt aggactggac tatctttttc    180

tcctcaaaac tggaaaccaa aacggcatcc aaaggacctt ttgacctcgc caggagaaag    240

tcatgcatat tatggaagat tgcataatca gcgaaagcgg cagtcattga gcccttttttg    300

aattgacatg gcagtcttga ttcgaacatt ggattcacaa acctcctgct ttcaatgtta    360

tacctatacg tcttgccctc aagcagtcta agtatgtcac tctgctcagc gcccaaaatt    420

gcccgatcct tttgcgaatc atatgtgctt tgacatggat caccggcaag tgaaatgaaa    480

gcatcactac gtataataag caagcataga tcgatgtatc caggaggaaa caactggacc    540

tcatcgaaaa tcacacagtg gccagccttc aatcctgcaa cttttctgag gaaaacctca    600

aaagttacta catcccaccc ttccttcttt gacctacctg ctttagcaac tttgcagcta    660

tcatccattt caagatcatt tttgattgaa tttgctaaag cacgtctggg agaaacaaag    720

gttacgaatt taccctcaga ccttttcatg aaactcttgt acaagaaact cttcccagcc    780

ccaaatgtac caagcacgac agtcaactcc cttggcttaa tatcagtagt agatatacca    840

gaaagccaag gttttgcatc actgaacttc tcatcactta taacgccagt taggccccct    900

agcaaac                                                              907
```

<210> SEQ ID NO 40
<211> LENGTH: 1232
<212> TYPE: DNA
<213> ORGANISM: Rupestris stem pitting associated virus

<400> SEQUENCE: 40

```
agaatgctta tgctgagaat gagatgattg cattattttg catccggcac catgtaaggc     60

ttatagtaat aacaccggaa tatgaagtta gttggaaatt tggggaaagt gagtggcccc    120

tatgtggaat tctttgcctg aggtccaatc acttccaacc atgcgccccg ctgaatggtt    180

gcatgatcac ggctattgct tcagcacttg ggaggcgtga ggttgatgtg ttaaattatc    240
```

-continued

```
tgtgtaggcc tagcactaat cacatctttg aggagctgtg ccagggcgga gggcttaata    300

tgatgtactt ggctgaagct tttgaggcct ttgacatttg tgcaaagtgc gacataaatg    360

gggaaattga ggtcattaac ccaaatggca agatttccgc cttgtttgat ataactaatg    420

agcacataag gcatgttgag aagatcagca atggccctca gagcataaaa atagatgagt    480

tgaggaaggt taagcgatcc cgccttgacc ttctttcaat gaatgggtcc aaaataacct    540

attttccaaa ctttgagcgg gctgaaaagt tgcaagggtg cttgctagag ggcctgactg    600

gtgtcataag tgatgaaaag ttcagtgatg caaaaccttg gctttctggt atatcaactg    660

cggatattaa gccaagagag ctaactgtcg tgcttggcac atttggtgct ggaaagagtt    720

tcttgtataa gagtttcatg aagagatctg aaggaaaatt tgtaactttt gtttccccta    780

ggcgagcttt ggccaattcg atcaagaatg atcttgaaat ggatgatggc tgcaaagttg    840

ccaaagcagg caagtcaaag aaggaagggt gggatgtggt aacatttgag gttttcctta    900

gaaaagtttc tggtttgaag gctggtcatt gtgtgatttt cgatgaggtt cagttgtttc    960

cccctggata tatcgatcta tgtttacttg tcatacgcag tgatgctttt atttcacttg   1020

ccggtgatcc atgccagagc acatatgatt cacaaaagga tcgggcaatt ttgggagctg   1080

agcagagtga catactcaga ttgcttgaag gaaagacgta taggtacaac atagaaagca   1140

gacgttttgt gaacccaatg tttgaattta gactaccatg tcacttcaaa aaagggttca   1200

atgactgctg cctttgctga ttatgcaatc tt                                 1232
```

<210> SEQ ID NO 41
<211> LENGTH: 20
<212> TYPE: DNA
<213> ORGANISM: Artificial Sequence
<220> FEATURE:
<223> OTHER INFORMATION: Synthetic based on Rupestris stem pitting associated virus

<400> SEQUENCE: 41

```
gcttcagcac ttggaaggcg                                                 20
```

<210> SEQ ID NO 42
<211> LENGTH: 17
<212> TYPE: DNA
<213> ORGANISM: Artificial Sequence
<220> FEATURE:
<223> OTHER INFORMATION: Synthetic based on Rupestris stem pitting associated virus

<400> SEQUENCE: 42

```
cacacagtgg ccagcct                                                    17
```

<210> SEQ ID NO 43
<211> LENGTH: 20
<212> TYPE: DNA
<213> ORGANISM: Artificial Sequence
<220> FEATURE:
<223> OTHER INFORMATION: Synthetic based on Rupestris stem pitting associated virus

<400> SEQUENCE: 43

```
ggaggtgcgt tgtggttatg                                                 20
```

<210> SEQ ID NO 44
<211> LENGTH: 18
<212> TYPE: DNA
<213> ORGANISM: Artificial Sequence
<220> FEATURE:

-continued

<223> OTHER INFORMATION: Synthetic based on Rupestris stem pitting
      associated virus

<400> SEQUENCE: 44
ccctggcact gcacaccc 18

<210> SEQ ID NO 45
<211> LENGTH: 18
<212> TYPE: DNA
<213> ORGANISM: Artificial Sequence
<220> FEATURE:
<223> OTHER INFORMATION: Synthetic based on Rupestris stem pitting
      associated virus

<400> SEQUENCE: 45
ggaggtgacc acattacg 18

<210> SEQ ID NO 46
<211> LENGTH: 21
<212> TYPE: DNA
<213> ORGANISM: Artificial Sequence
<220> FEATURE:
<223> OTHER INFORMATION: Synthetic based on Rupestris stem pitting
      associated virus

<400> SEQUENCE: 46
catcacgact tgtcacaaac c 21

<210> SEQ ID NO 47
<211> LENGTH: 17
<212> TYPE: DNA
<213> ORGANISM: Artificial Sequence
<220> FEATURE:
<223> OTHER INFORMATION: Synthetic based on Rupestris stem pitting
      associated virus

<400> SEQUENCE: 47
tgggcctcca cttcttc 17

<210> SEQ ID NO 48
<211> LENGTH: 16
<212> TYPE: DNA
<213> ORGANISM: Artificial Sequence
<220> FEATURE:
<223> OTHER INFORMATION: Synthetic based on Rupestris stem pitting
      associated virus

<400> SEQUENCE: 48
ggggttgcct gaagat 16

<210> SEQ ID NO 49
<211> LENGTH: 17
<212> TYPE: DNA
<213> ORGANISM: Artificial Sequence
<220> FEATURE:
<223> OTHER INFORMATION: Synthetic based on Rupestris stem pitting
      associated virus

<400> SEQUENCE: 49
acacctgctg tgaaagc 17

<210> SEQ ID NO 50
<211> LENGTH: 17
<212> TYPE: DNA
<213> ORGANISM: Artificial Sequence
<220> FEATURE:
<223> OTHER INFORMATION: Synthetic based on Rupestris stem pitting -continued associated virus

<400> SEQUENCE: 50
ggccaaggtt cagtttg 17

<210> SEQ ID NO 51
<211> LENGTH: 20
<212> TYPE: DNA
<213> ORGANISM: Artificial Sequence
<220> FEATURE:
<223> OTHER INFORMATION: Synthetic based on Rupestris stem pitting associated virus

<400> SEQUENCE: 51
gatgaggtcc agttgtttcc 20

<210> SEQ ID NO 52
<211> LENGTH: 20
<212> TYPE: DNA
<213> ORGANISM: Artificial Sequence
<220> FEATURE:
<223> OTHER INFORMATION: Synthetic based on Rupestris stem pitting associated virus

<400> SEQUENCE: 52
atccaaagga ccttttgacc 20

<210> SEQ ID NO 53
<211> LENGTH: 17
<212> TYPE: DNA
<213> ORGANISM: Artificial Sequence
<220> FEATURE:
<223> OTHER INFORMATION: Synthetic based on Rupestris stem pitting associated virus

<400> SEQUENCE: 53
cttgatgagt acttgtc 17

<210> SEQ ID NO 54
<211> LENGTH: 17
<212> TYPE: DNA
<213> ORGANISM: Artificial Sequence
<220> FEATURE:
<223> OTHER INFORMATION: Synthetic based on Rupestris stem pitting associated virus

<400> SEQUENCE: 54
gcaaggattt ggatggc 17

<210> SEQ ID NO 55
<211> LENGTH: 379
<212> TYPE: PRT
<213> ORGANISM: Rupestris stem pitting associated virus
<220> FEATURE:
<221> NAME/KEY: VARIANT
<222> LOCATION: (1)...(379)
<223> OTHER INFORMATION: Xaa = Any Amino Acid

<400> SEQUENCE: 55

```
Met Ala Xaa Xaa Xaa Arg Xaa Xaa Xaa Glu Xaa Xaa Xaa Xaa Xaa Phe
 1               5                  10                  15

Xaa Xaa Xaa Xaa Xaa Gln Xaa Xaa Xaa Xaa Xaa Xaa Ala Xaa Xaa Xaa
            20                  25                  30

Xaa Xaa Xaa Xaa Glu Xaa Xaa Xaa Xaa Xaa Phe Xaa Xaa Xaa Leu Xaa
        35                  40                  45
```

-continued

```
Xaa Xaa Xaa Lys Xaa Xaa Leu Xaa Xaa Xaa Gly Ile Tyr Leu Ser Pro
    50                  55                  60

Xaa Ser Xaa Xaa Xaa His Ser His Pro Val Cys Lys Thr Leu Glu Asn
65                  70                  75                  80

Xaa Ile Leu Xaa Asn Xaa Leu Pro Ser Tyr Xaa Xaa Xaa Xaa Ser Phe
                85                  90                  95

Tyr Xaa Val Xaa Ile Lys Xaa Xaa Lys Xaa Xaa Xaa Leu Lys Xaa Xaa
            100                 105                 110

Xaa Xaa Xaa Leu Xaa Xaa Val Xaa Xaa Xaa Asn Arg Xaa Xaa Xaa Ser
        115                 120                 125

Xaa Asp Xaa Xaa Arg Tyr Xaa Xaa Xaa Phe Xaa Xaa Xaa Xaa Ser Xaa
    130                 135                 140

Xaa Xaa Xaa Xaa Xaa Xaa Xaa Xaa Xaa Xaa Xaa Xaa Gly Xaa Xaa Xaa
145                 150                 155                 160

Asp Xaa Xaa Xaa Leu Xaa Xaa Leu Xaa Xaa Xaa Xaa Xaa Xaa Xaa Xaa
                165                 170                 175

Xaa Xaa Xaa Xaa Phe Xaa His Asp Glu Xaa His Tyr Trp Xaa Xaa Xaa
            180                 185                 190

Xaa Leu Ile Xaa Xaa Phe Leu Asp Xaa Xaa Xaa Pro Xaa Xaa Xaa Leu
        195                 200                 205

Xaa Xaa Xaa Val Xaa Pro Pro Glu Xaa Leu Xaa Gly Xaa Xaa Glu Ser
    210                 215                 220

Leu Asn Pro Trp Xaa Tyr Xaa Tyr Xaa Ile Xaa Gly Xaa Xaa Leu Xaa
225                 230                 235                 240

Phe Xaa Pro Asp Gly Xaa Xaa Xaa Glu Xaa Tyr Xaa Gln Pro Leu Xaa
                245                 250                 255

Xaa Xaa Tyr Leu Leu Xaa Ala Arg Ser Xaa Xaa Leu Pro Asp Gly Xaa
            260                 265                 270

Xaa Tyr Xaa Val Asp Xaa Xaa Xaa Ser Xaa Phe Xaa His His Leu Xaa
        275                 280                 285

Ser Xaa Thr Xaa Xaa Gly Xaa Xaa Xaa Xaa Xaa Xaa Xaa Arg Xaa Phe
    290                 295                 300

Xaa Xaa Phe Xaa Ala Xaa Xaa Xaa Xaa Xaa Leu Xaa Xaa Xaa Leu Xaa
305                 310                 315                 320

Xaa Xaa Xaa Xaa Xaa Xaa Xaa Pro Xaa Xaa Xaa Xaa Xaa Xaa Xaa Lys
                325                 330                 335

Ile Tyr Xaa Tyr Leu Arg Thr Leu Lys Lys Pro Asp Xaa Xaa Ser Ala
            340                 345                 350

Xaa Ala Lys Leu Xaa Gln Xaa Xaa Xaa Xaa Pro Xaa Gly Xaa Glu Ile
        355                 360                 365

Xaa Phe Xaa Glu Xaa Phe Xaa Xaa Leu Xaa Xaa
    370                 375
```

<210> SEQ ID NO 56
<211> LENGTH: 371
<212> TYPE: PRT
<213> ORGANISM: Rupestris stem pitting associated virus

<400> SEQUENCE: 56

```
Met Ala Val Thr Tyr Arg Thr Pro Met Glu Asp Ile Val Asn Cys Phe
 1               5                  10                  15

Glu Pro Ala Thr Gln Ala Val Ile Ala Asn Ser Ala Ala Thr Leu Tyr
            20                  25                  30

Lys Asn Phe Glu Glu Asn His Cys Gln Tyr Phe Asn Tyr Leu Ser Pro
        35                  40                  45
```

-continued

```
Leu Ala Lys Arg Lys Leu Ser Met Ala Gly Ile Tyr Leu Ser Pro Tyr
    50                  55                  60

Ser Ala Val Val His Ser His Pro Val Cys Lys Thr Leu Glu Asn Tyr
65                  70                  75                  80

Ile Leu Tyr Ser Val Leu Pro Ser Tyr Ile Asn Ser Ser Phe Tyr Phe
                85                  90                  95

Val Gly Ile Lys Glu Arg Lys Leu Gln Leu Leu Lys Ser Lys Cys Lys
            100                 105                 110

Asn Leu Asp Ser Val Gln Val Val Asn Arg Tyr Val Thr Ser Ala Asp
        115                 120                 125

Arg Met Arg Tyr Thr Asn Asp Phe Val Pro Tyr Gly Ser Tyr Glu His
    130                 135                 140

Glu Cys Leu Val His Lys Gly Val Gly Leu Asp Asn Glu Ala Leu Arg
145                 150                 155                 160

Gly Leu Val Gly Pro Leu Arg Arg His Lys Ala Lys Asn Leu Phe Phe
                165                 170                 175

His Asp Glu Leu His Tyr Trp Ser Ser Lys Val Leu Ile Asp Phe Leu
            180                 185                 190

Asp Val Met Arg Pro Asp Lys Leu Leu Gly Thr Val Val Tyr Pro Pro
        195                 200                 205

Glu Leu Leu Phe Lys Pro Thr Arg Ser Leu Asn Glu Trp Cys Tyr Thr
    210                 215                 220

Tyr Asp Ile Val Gly Asp Thr Leu Met Phe Phe Pro Asp Gly Val Gln
225                 230                 235                 240

Ser Glu Gly Tyr Gln Gln Pro Leu Lys Gly Gly Tyr Leu Leu Gly Ala
                245                 250                 255

Arg Ser Leu Lys Leu Pro Asp Gly Thr Val Tyr Met Val Asp Val Leu
            260                 265                 270

Cys Ser Lys Phe Pro His His Leu Ile Ser Ile Thr Lys Gly Glu Ala
        275                 280                 285

Ala Ala Pro Thr His Arg Ala Phe Gly Pro Phe Glu Ala Val Ala Ser
    290                 295                 300

Glu Ala Leu Lys Ala Thr Leu Ser Pro Asp Tyr Pro Cys Ala Phe Pro
305                 310                 315                 320

Val Ser Tyr Glu Val Val Asn Lys Ile Tyr Arg Tyr Leu Arg Thr Leu
                325                 330                 335

Lys Lys Pro Asp Glu Gln Ser Ala Ile Ala Lys Leu Ser Gln Ile Ile
            340                 345                 350

Ala Glu Pro Ser Gly Arg Glu Ile Asp Phe Val Glu Cys Phe Ala Arg
        355                 360                 365

Leu Val Ile
    370


<210> SEQ ID NO 57
<211> LENGTH: 373
<212> TYPE: PRT
<213> ORGANISM: Rupestris stem pitting associated virus

<400> SEQUENCE: 57

Met Ala Leu Leu Ser Arg Thr Ala Ala Glu Glu Val Ile Ala Ser Phe
 1               5                  10                  15

Thr Ser Glu Glu Gln Ser Arg Ile Ser Thr Gln Ala Val Leu Ala Leu
            20                  25                  30

Thr Asn Val Glu Lys Asp Lys His Asp Leu Phe Asn Tyr Ala Leu Pro
```

-continued

```
        35                  40                  45

Glu Leu Ala Lys Met Arg Leu Phe Asn Ser Gly Ile Tyr Leu Ser Pro
    50                  55                  60

His Ser Tyr Arg Pro His Ser His Pro Val Cys Lys Thr Leu Glu Asn
65                  70                  75                  80

Asn Ile Leu Phe Asn Ile Leu Pro Ser Tyr Leu Asp Asn Ser Phe Tyr
                85                  90                  95

Leu Val Ser Ile Lys Lys Asn Lys Val Asp Phe Leu Lys Arg Arg His
            100                 105                 110

Pro Asp Leu Gln Met Val Glu Thr Ile Asn Arg Tyr Ile Ser Ser Ile
        115                 120                 125

Asp Lys Thr Arg Tyr Gly Gly Phe Phe His Val Ser Pro Ser Lys Ile
    130                 135                 140

Ser Ala Lys Phe Lys Cys Asp Arg Arg Thr Gly Phe Glu Asp Asp Ala
145                 150                 155                 160

Ser Leu Ile Asp Leu Ile Pro Gly Cys Met Glu Gly Ala Arg Lys Arg
                165                 170                 175

Phe Phe Phe His Asp Glu Leu His Tyr Trp Thr Lys Glu Ala Leu Ile
            180                 185                 190

Thr Phe Leu Asp His Val Lys Pro Glu Val Met Leu Ala Ser Ile Val
        195                 200                 205

Phe Pro Pro Glu Ile Leu Ala Gly Ala Lys Glu Ser Leu Asn Pro Trp
    210                 215                 220

Cys Tyr Thr Phe Arg Ile Val Gly Lys Asp Leu Val Phe Phe Pro Asp
225                 230                 235                 240

Gly Glu Gln Ser Glu Ala Tyr Ile Gln Pro Val Ala Gly Ser Tyr Leu
                245                 250                 255

Leu Arg Thr Gly Lys Ile Thr Thr Pro Ser Gly Asp Ile Phe Gln Leu
            260                 265                 270

Asp Leu Leu Lys Ser Ser Phe Ser His His Leu Ile Ser Ile Thr Lys
        275                 280                 285

Gly Glu Ala Ile Gly Gln Lys Met Arg Phe Phe Asn Gly Phe Glu Ala
    290                 295                 300

Val Ala Met Lys Gly Leu Asn Pro Leu Arg Arg Lys Val Glu Ser Cys
305                 310                 315                 320

Leu Pro Ile Ser Lys Asn Thr Ile Leu Lys Ile Tyr Arg Tyr Leu Arg
                325                 330                 335

Thr Leu Lys Lys Pro Asp Leu Gln Ser Ala Met Ala Lys Leu Ser Gln
            340                 345                 350

Val Cys Lys Asp Pro Asn Gly Tyr Glu Ile Lys Phe Phe Glu Glu Phe
        355                 360                 365

Ser Lys Leu Cys Leu
    370


<210> SEQ ID NO 58
<211> LENGTH: 372
<212> TYPE: PRT
<213> ORGANISM: Rupestris stem pitting associated virus

<400> SEQUENCE: 58

Met Ala Leu Ser Tyr Arg Pro Ala Val Glu Glu Val Leu Ala Lys Phe
 1               5                  10                  15

Thr Ser Asp Glu Gln Ser Arg Val Ser Ala Thr Ala Leu Lys Ala Leu
            20                  25                  30
```

-continued

```
Val Asp Leu Glu Glu Ser Gln His Asn Leu Phe Ser Phe Ala Leu Pro
        35                  40                  45

Asp Arg Ser Lys Glu Arg Leu Ile Ser Ser Gly Ile Tyr Leu Ser Pro
    50                  55                  60

Tyr Ser Phe Arg Pro His Ser His Pro Val Cys Lys Thr Leu Glu Asn
65                  70                  75                  80

His Ile Leu Tyr Asn Val Leu Pro Ser Tyr Val Asn Asn Ser Phe Tyr
                85                  90                  95

Phe Val Gly Ile Lys Asp Phe Lys Leu Gln Phe Leu Lys Arg Arg Asn
            100                 105                 110

Lys Asp Leu Ser Leu Val Ala Leu Ile Asn Arg Phe Val Thr Ser Arg
        115                 120                 125

Asp Val Ser Arg Tyr Gly Ser Glu Phe Val Ile Ser Ser Ser Asp Lys
    130                 135                 140

Ser Ser Gln Val Val Ser Arg Lys Gly Ile Gly Asp Ser Asn Thr Leu
145                 150                 155                 160

Arg Arg Leu Val Pro Arg Val Ile Ser Thr Gly Ala Arg Asn Leu Phe
                165                 170                 175

Leu His Asp Glu Ile His Tyr Trp Ser Ile Ser Asp Leu Ile Asn Phe
            180                 185                 190

Leu Asp Val Ala Lys Pro Ser Met Leu Leu Ala Thr Ala Val Ile Pro
        195                 200                 205

Pro Glu Val Leu Val Gly Ser Pro Glu Ser Leu Asn Pro Trp Ala Tyr
    210                 215                 220

Gln Tyr Lys Ile Asn Gly Asn Gln Leu Leu Phe Ala Pro Asp Gly Asn
225                 230                 235                 240

Trp Asn Glu Met Tyr Ser Gln Pro Leu Ser Cys Arg Tyr Leu Leu Lys
                245                 250                 255

Ala Arg Ser Val Val Leu Pro Asp Gly Ser Arg Tyr Ser Val Asp Ile
            260                 265                 270

Ile His Ser Lys Phe Ser His His Leu Leu Ser Phe Thr Pro Met Gly
        275                 280                 285

Asn Leu Leu Thr Ser Asn Met Arg Cys Phe Ser Gly Phe Asp Ala Ile
    290                 295                 300

Gly Ile Lys Asp Leu Glu Pro Leu Ser Arg Gly Met His Ser Cys Phe
305                 310                 315                 320

Pro Val His His Asp Val Val Thr Lys Ile Tyr Leu Tyr Leu Arg Thr
                325                 330                 335

Leu Lys Lys Pro Asp Lys Glu Ser Ala Glu Ala Lys Leu Arg Gln Leu
            340                 345                 350

Ile Glu Lys Pro Thr Gly Arg Glu Ile Lys Phe Ile Glu Asp Phe Ser
        355                 360                 365

Ser Leu Val Ile
    370


<210> SEQ ID NO 59
<211> LENGTH: 420
<212> TYPE: PRT
<213> ORGANISM: Rupestris stem pitting associated virus
<220> FEATURE:
<221> NAME/KEY: VARIANT
<222> LOCATION: (1)...(420)
<223> OTHER INFORMATION: Xaa = Any Amino Acid

<400> SEQUENCE: 59

Xaa Xaa Gly Thr Phe Gly Xaa Gly Lys Ser Xaa Leu Xaa Xaa Lys Xaa
```

-continued

```
1               5                   10                  15

Xaa Xaa Xaa Xaa Xaa Xaa Gly Lys Xaa Xaa Xaa Phe Val Ser Pro Arg
            20                  25                  30

Arg Xaa Leu Ala Xaa Xaa Xaa Xaa Xaa Xaa Xaa Xaa Xaa Xaa Xaa Xaa
        35                  40                  45

Xaa Xaa Xaa Xaa Lys Xaa Gly Xaa Xaa Xaa Xaa Xaa Xaa Xaa Xaa Xaa
    50                  55                  60

Val Xaa Thr Xaa Glu Xaa Phe Xaa Xaa Xaa Xaa Xaa Xaa Xaa Xaa Xaa
65                  70                  75                  80

Gly Xaa Xaa Val Xaa Xaa Asp Glu Xaa Gln Leu Xaa Pro Pro Gly Tyr
                85                  90                  95

Xaa Asp Leu Xaa Xaa Xaa Xaa Xaa Xaa Xaa Xaa Xaa Xaa Xaa Xaa Xaa
            100                 105                 110

Xaa Gly Asp Pro Xaa Gln Ser Xaa Tyr Asp Xaa Xaa Xaa Asp Arg Xaa
        115                 120                 125

Xaa Xaa Xaa Xaa Xaa Xaa Xaa Xaa Xaa Xaa Xaa Xaa Leu Xaa Xaa Xaa
    130                 135                 140

Xaa Tyr Xaa Xaa Xaa Xaa Xaa Ser Xaa Arg Phe Xaa Asn Xaa Xaa Phe
145                 150                 155                 160

Xaa Xaa Arg Leu Pro Cys Xaa Xaa Xaa Lys Xaa Xaa Xaa Thr Xaa Xaa
                165                 170                 175

Xaa Xaa Xaa Xaa Xaa Xaa Xaa Xaa Xaa Xaa Xaa Xaa Xaa Xaa Xaa Xaa
            180                 185                 190

Xaa Xaa Xaa Xaa Xaa Xaa Xaa Xaa Val Leu Val Ser Ser Phe Xaa Glu
        195                 200                 205

Lys Xaa Xaa Val Xaa Xaa Xaa Xaa Xaa Xaa Xaa Xaa Xaa Xaa Xaa Thr
    210                 215                 220

Xaa Gly Glu Ser Thr Gly Leu Xaa Phe Xaa Xaa Gly Xaa Ile Xaa Xaa
225                 230                 235                 240

Xaa Xaa Xaa Ser Xaa Xaa Thr Xaa Xaa Arg Arg Trp Xaa Thr Ala Leu
                245                 250                 255

Xaa Arg Phe Xaa Xaa Xaa Xaa Xaa Xaa Xaa Asn Xaa Xaa Gly Xaa Xaa
            260                 265                 270

Xaa Xaa Xaa Xaa Xaa Xaa Xaa Xaa Xaa Gly Xaa Xaa Xaa Xaa Xaa Phe
        275                 280                 285

Xaa Xaa Xaa Xaa Xaa Xaa Xaa Xaa Xaa Xaa Xaa Xaa Xaa Leu Pro Gly
    290                 295                 300

Xaa Xaa Xaa Xaa Xaa Xaa Xaa Xaa Xaa Xaa Xaa Xaa Gly Xaa Xaa Glu
305                 310                 315                 320

Gly Val Arg Glu Xaa Lys Leu Xaa Gly Asp Pro Trp Leu Lys Xaa Met
                325                 330                 335

Xaa Xaa Leu Xaa Gln Xaa Xaa Xaa Xaa Glu Xaa Xaa Xaa Xaa Xaa Xaa
            340                 345                 350

Xaa Xaa Xaa Xaa Glu Xaa Trp Phe Xaa Thr His Xaa Pro Xaa Xaa Xaa
        355                 360                 365

Leu Glu Xaa Xaa Arg Ala Xaa Trp Val Xaa Lys Xaa Xaa Xaa Xaa Glu
    370                 375                 380

Xaa Arg Glu Xaa Arg Xaa Gly Xaa Xaa Xaa Xaa Xaa Gln Phe Xaa Xaa
385                 390                 395                 400

Xaa His Xaa Xaa Xaa Xaa Gly Xaa Xaa Xaa Leu Xaa Asn Ala Xaa Glu
                405                 410                 415

Arg Xaa Glu Xaa
            420
```

-continued

<210> SEQ ID NO 60
<211> LENGTH: 412
<212> TYPE: PRT
<213> ORGANISM: Rupestris stem pitting associated virus

<400> SEQUENCE: 60

```
Ile Val Gly Thr Phe Gly Ser Gly Lys Ser Thr Leu Phe Lys Asn Leu
 1               5                  10                  15

Leu Lys Tyr Gly Ala Gly Lys Ser Leu Asp Phe Val Ser Pro Arg Arg
            20                  25                  30

Ala Leu Ala Glu Asp Phe Lys Arg Thr Val Gly Met Asn Glu Arg Gly
        35                  40                  45

Gly Arg Ala Lys Ala Gly Gln Glu Asn Trp Arg Val Thr Thr Leu Glu
    50                  55                  60

Thr Phe Leu Ala Arg Val Glu Phe Leu Thr Glu Gly Gln Val Val Ile
65                  70                  75                  80

Leu Asp Glu Met Gln Leu Tyr Pro Pro Gly Tyr Phe Asp Leu Val Val
                85                  90                  95

Ser Met Leu Lys Val Asp Val Arg Leu Phe Leu Val Gly Asp Pro Ala
            100                 105                 110

Gln Ser Asp Tyr Asp Ser Glu Lys Asp Arg Leu Val Leu Gly Ala Met
        115                 120                 125

Glu Glu Asn Met Ser Val Val Leu Gly Ala Arg Glu Tyr Asn Tyr Lys
    130                 135                 140

Val Arg Ser His Arg Phe Leu Asn Cys Asn Phe Ile Gly Arg Leu Pro
145                 150                 155                 160

Cys Glu Ile Asn Lys Asp Asp Cys Thr Ile Asp Glu Pro His Ile Met
                165                 170                 175

Arg Met His Leu Glu Asn Leu Leu Asp Val Ala Glu Glu Tyr Lys Ser
            180                 185                 190

Val Val Leu Val Ser Ser Phe Asp Glu Lys Met Val Val Cys Ala His
        195                 200                 205

Leu Pro Glu Ala Lys Val Leu Thr Phe Gly Glu Ser Thr Gly Leu Thr
    210                 215                 220

Phe Met His Gly Thr Ile Tyr Ile Ser Ala Val Ser Glu Arg Thr Asn
225                 230                 235                 240

Glu Arg Arg Trp Ile Thr Ala Leu Arg Arg Phe Arg Phe Asn Leu Cys
                245                 250                 255

Phe Val Asn Cys Ser Gly Met Asp Tyr Gln Gln Leu Ala Gly Arg Tyr
            260                 265                 270

Lys Gly Arg Val Arg Ser Lys Phe Leu Cys Lys Thr Ala Ile Pro Asp
        275                 280                 285

Asp Leu Asn Ser Met Leu Pro Gly Gln Ala Leu Phe Lys Ser Glu Tyr
    290                 295                 300

Pro Arg Leu Ile Gly Lys Asp Glu Gly Val Arg Glu Glu Lys Leu Ala
305                 310                 315                 320

Gly Asp Pro Trp Leu Lys Thr Met Ile Asn Leu Tyr Gln Ala Pro Glu
                325                 330                 335

Val Glu Ile Ala Glu Glu Pro Glu Val Val Met Gln Glu Glu Trp Phe
            340                 345                 350

Arg Thr His Leu Pro Arg Asp Glu Leu Glu Ser Val Arg Ala Gln Trp
        355                 360                 365

Val His Lys Ile Leu Ala Lys Glu Tyr Arg Glu Val Arg Met Gly Asp
```

```
    370                 375                 380

Met Val Ser Glu Gln Phe Thr His Asp His Thr Lys Gln Leu Gly Ala
385                 390                 395                 400

Lys Gln Leu Thr Asn Ala Ala Glu Arg Phe Glu Thr
                405                 410


<210> SEQ ID NO 61
<211> LENGTH: 416
<212> TYPE: PRT
<213> ORGANISM: Rupestris stem pitting associated virus

<400> SEQUENCE: 61

Ile Leu Gly Thr Phe Gly Cys Gly Lys Ser Ser Leu Phe Lys Lys Phe
 1               5                  10                  15

Ile Glu Lys Ser Pro Gly Lys Ala Ile Thr Phe Val Ser Pro Arg Arg
            20                  25                  30

Ser Leu Ala Glu Ser Ile Asn His Asp Leu Gly Leu Ala Arg Val Gly
        35                  40                  45

Gly Lys Lys Thr Gly Lys Ser Lys Asp Leu Lys Asn Val Arg Val Lys
    50                  55                  60

Thr Phe Glu Leu Phe Ile Leu His Leu Asp Ser Ile Lys Glu Gly His
65                  70                  75                  80

Thr Val Val Ile Asp Glu Ile Gln Leu Phe Pro Pro Gly Tyr Ile Asp
                85                  90                  95

Leu Ile Ile Leu Gly Leu Lys Pro Asn Val Asn Ile Ile Ile Ala Gly
            100                 105                 110

Asp Pro Cys Gln Ser Asp Tyr Asp Cys Ser Ser Asp Arg His Ile Phe
        115                 120                 125

Ala Gly Ser Glu Ser Asp Ile Met Arg Ile Leu Ser Gly Arg Ser Tyr
    130                 135                 140

Lys Phe Asn Ile Leu Ser Gln Arg Phe Arg Asn Pro Val Phe Tyr Gly
145                 150                 155                 160

Arg Leu Pro Cys Asn Leu Asn Lys Thr Arg Leu Thr Leu Asp Glu Glu
                165                 170                 175

Glu Tyr Thr Leu Trp Asp Ser Ile Gln Glu Phe Ser Met Met Gly Arg
            180                 185                 190

Lys Asp Cys Pro Val Val Leu Val Ser Ser Phe Glu Glu Lys Lys Ile
        195                 200                 205

Val Ala Ala His Leu Gly Leu Lys Met Lys Cys Ile Thr Tyr Gly Glu
    210                 215                 220

Ser Thr Gly Leu Asn Phe Gln Lys Gly Ala Ile Leu Val Thr Tyr Glu
225                 230                 235                 240

Ser Ala Leu Thr Ser Asp Arg Arg Trp Trp Thr Ala Leu Ser Arg Phe
                245                 250                 255

Ser His Asp Ile His Phe Ile Asn Gly Met Gly Val Thr Trp Asp Asn
            260                 265                 270

Ala Ile Thr His Phe Val Gly Lys Pro Leu His Lys Phe Phe Thr Lys
        275                 280                 285

Arg Ala Cys Asn Asp Asp Ile Ile Asp Leu Leu Pro Gly Arg Pro Glu
    290                 295                 300

Leu Ile Glu Gly Phe Gln Ser Gln Val Gly Ala Asp Glu Gly Val Arg
305                 310                 315                 320

Glu Ala Lys Leu Val Gly Asp Pro Trp Leu Lys Thr Lys Ile Phe Leu
                325                 330                 335
```

-continued

```
Gly Gln Asn Pro Asp Phe Glu Ile Glu Ile Ala Asp Glu Val Glu Ala
            340                 345                 350

Ala Glu Asp Trp Phe Lys Thr His Ile Pro Ile Met Ser Leu Glu Ala
        355                 360                 365

Val Arg Ala Gln Trp Val His Lys Leu Ile Ser Arg Glu Asp Arg Glu
    370                 375                 380

Phe Arg Ile Gly Asp Ile Thr Thr Glu Gln Phe Thr Asp Asp His Ser
385                 390                 395                 400

Lys Asn Arg Gly Gln Glu Leu Thr Asn Ala Ala Glu Arg Tyr Glu Ala
                405                 410                 415


<210> SEQ ID NO 62
<211> LENGTH: 417
<212> TYPE: PRT
<213> ORGANISM: Rupestris stem pitting associated virus

<400> SEQUENCE: 62

Val Leu Gly Thr Phe Gly Ala Gly Lys Ser Phe Leu Tyr Lys Ser Phe
 1               5                  10                  15

Met Lys Arg Ser Glu Gly Lys Phe Val Thr Phe Val Ser Pro Arg Arg
            20                  25                  30

Ala Leu Ala Asn Ser Ile Lys Asn Asp Leu Glu Met Asp Asp Ser Cys
        35                  40                  45

Lys Val Ala Lys Ala Gly Arg Ser Lys Lys Glu Gly Trp Asp Val Val
    50                  55                  60

Thr Phe Glu Val Phe Leu Arg Lys Val Ala Gly Leu Lys Ala Gly His
65                  70                  75                  80

Cys Val Ile Phe Asp Glu Val Gln Leu Phe Pro Pro Gly Tyr Ile Asp
                85                  90                  95

Leu Cys Leu Leu Ile Ile Arg Ser Asp Ala Phe Ile Ser Leu Ala Gly
            100                 105                 110

Asp Pro Cys Gln Ser Thr Tyr Asp Ser Gln Lys Asp Arg Ala Ile Leu
        115                 120                 125

Gly Ala Glu Gln Ser Asp Ile Leu Arg Leu Leu Glu Gly Lys Thr Tyr
    130                 135                 140

Arg Tyr Asn Ile Glu Ser Arg Arg Phe Val Asn Pro Met Phe Glu Ser
145                 150                 155                 160

Arg Leu Pro Cys His Phe Lys Lys Gly Ser Met Thr Ala Ala Phe Ala
                165                 170                 175

Asp Tyr Ala Ile Phe His Asn Met His Asp Phe Leu Leu Ala Arg Ser
            180                 185                 190

Lys Gly Pro Leu Asp Ala Val Leu Val Ser Ser Phe Glu Glu Lys Lys
        195                 200                 205

Ile Val Gln Ser Tyr Phe Gly Met Lys Gln Leu Thr Leu Thr Phe Gly
    210                 215                 220

Glu Ser Thr Gly Leu Asn Phe Lys Asn Gly Gly Ile Leu Ile Ser His
225                 230                 235                 240

Asp Ser Phe His Thr Asp Asp Arg Arg Trp Leu Thr Ala Leu Ser Arg
                245                 250                 255

Phe Ser His Asn Leu Asp Leu Val Asn Ile Thr Gly Leu Arg Val Glu
            260                 265                 270

Ser Phe Leu Ser His Phe Ala Gly Lys Pro Leu Tyr His Phe Leu Thr
        275                 280                 285

Ala Lys Ser Gly Glu Asn Val Ile Arg Asp Leu Leu Pro Gly Glu Pro
    290                 295                 300
```

-continued

```
Asn Phe Phe Ser Gly Phe Asn Val Ser Ile Gly Lys Asn Glu Gly Val
305                 310                 315                 320

Arg Glu Glu Lys Leu Cys Gly Asp Pro Trp Leu Lys Val Met Leu Phe
                325                 330                 335

Leu Gly Gln Asp Glu Asp Cys Glu Val Glu Glu Met Glu Ser Glu Cys
            340                 345                 350

Ser Asn Glu Glu Trp Phe Lys Thr His Ile Pro Leu Ser Asn Leu Glu
        355                 360                 365

Ser Thr Arg Ala Arg Trp Val Gly Lys Met Ala Leu Lys Glu Tyr Arg
    370                 375                 380

Glu Val Arg Cys Gly Tyr Glu Met Thr Gln Gln Phe Phe Asp Glu His
385                 390                 395                 400

Arg Gly Gly Thr Gly Glu Gln Leu Ser Asn Ala Cys Glu Arg Phe Glu
                405                 410                 415

Ser
```

```
<210> SEQ ID NO 63
<211> LENGTH: 385
<212> TYPE: PRT
<213> ORGANISM: Rupestris stem pitting associated virus
<220> FEATURE:
<221> NAME/KEY: VARIANT
<222> LOCATION: (1)...(385)
<223> OTHER INFORMATION: Xaa = Any Amino Acid

<400> SEQUENCE: 63

Ile Tyr Pro Arg His Xaa Xaa Xaa Asp Xaa Xaa Thr Phe Leu Met Ala
 1               5                  10                  15

Val Xaa Lys Arg Leu Xaa Phe Ser Xaa Pro Xaa Xaa Glu Xaa Xaa Xaa
            20                  25                  30

Leu Xaa Xaa Ala Xaa Xaa Xaa Gly Lys Xaa Leu Leu Xaa Xaa Phe Leu
        35                  40                  45

Xaa Xaa Xaa Pro Leu Xaa Xaa Xaa His Xaa Xaa Xaa Xaa Xaa Xaa Glu
    50                  55                  60

Ala Xaa Xaa Xaa Xaa Phe Glu Xaa Lys Lys Xaa Ser Lys Ser Xaa Ala
65                  70                  75                  80

Thr Ile Glu Asn His Xaa Gly Arg Ser Cys Xaa Asp Trp Xaa Xaa Asp
                85                  90                  95

Xaa Ala Xaa Ile Phe Xaa Lys Ser Gln Xaa Cys Thr Lys Phe Asp Asn
            100                 105                 110

Arg Xaa Xaa Arg Xaa Ala Lys Ala Xaa Gln Xaa Xaa Xaa Cys Phe Gln
        115                 120                 125

His Xaa Val Leu Xaa Arg Phe Ala Pro Tyr Met Arg Tyr Ile Glu Xaa
    130                 135                 140

Lys Xaa Xaa Xaa Xaa Leu Xaa Xaa Asn Xaa Tyr Ile His Ser Gly Lys
145                 150                 155                 160

Xaa Xaa Xaa Xaa Leu Xaa Xaa Trp Val Xaa Xaa Xaa Xaa Xaa Phe Xaa
                165                 170                 175

Xaa Xaa Cys Thr Glu Ser Asp Tyr Glu Ala Phe Asp Ala Ser Gln Asp
            180                 185                 190

Xaa Phe Ile Xaa Ala Phe Glu Leu Xaa Xaa Met Lys Xaa Leu Xaa Leu
        195                 200                 205

Pro Xaa Asp Leu Ile Xaa Asp Tyr Xaa Phe Ile Lys Xaa Xaa Leu Gly
    210                 215                 220

Ser Lys Leu Gly Xaa Phe Xaa Ile Met Arg Phe Xaa Gly Glu Ala Ser
```

-continued

```
225                 230                 235                 240

Thr Phe Leu Phe Asn Thr Xaa Ala Asn Met Leu Phe Thr Phe Xaa Arg
                245                 250                 255

Tyr Xaa Xaa Xaa Gly Xaa Glu Xaa Ile Xaa Phe Ala Gly Asp Asp Met
            260                 265                 270

Cys Ala Xaa Xaa Arg Leu Xaa Xaa Xaa Xaa Xaa Xaa Xaa Xaa Phe Leu
        275                 280                 285

Xaa Xaa Ile Xaa Leu Lys Ala Lys Val Gln Phe Xaa Xaa Xaa Xaa Xaa
    290                 295                 300

Xaa Xaa Xaa Pro Thr Phe Cys Gly Trp Xaa Leu Xaa Xaa Xaa Gly Xaa
305                 310                 315                 320

Xaa Lys Lys Pro Xaa Leu Xaa Xaa Glu Arg Xaa Xaa Ile Ala Xaa Glu
                325                 330                 335

Xaa Xaa Asn Leu Xaa Asn Cys Ile Asp Asn Tyr Ala Ile Glu Val Xaa
            340                 345                 350

Xaa Ala Tyr Xaa Xaa Gly Glu Xaa Xaa Xaa Xaa Xaa Xaa Xaa Xaa Xaa
        355                 360                 365

Glu Val Xaa Ala Xaa Tyr Asn Cys Val Arg Xaa Xaa Val Xaa Xaa Xaa
    370                 375                 380

His
385


<210> SEQ ID NO 64
<211> LENGTH: 379
<212> TYPE: PRT
<213> ORGANISM: Rupestris stem pitting associated virus

<400> SEQUENCE: 64

Ile Tyr Pro Arg His Arg Ala Ser Asp Thr Val Thr Phe Leu Met Ala
 1               5                  10                  15

Val Lys Lys Arg Leu Ser Phe Ser Asn Pro Gly Lys Glu Lys Gly Asn
            20                  25                  30

Leu Phe His Ala Ala Ser Tyr Gly Lys Ala Leu Leu Ser Glu Phe Leu
        35                  40                  45

Lys Arg Val Pro Leu Lys Pro Asn His Asn Val Arg Phe Met Glu Glu
    50                  55                  60

Ala Leu Trp Asn Phe Glu Glu Lys Lys Leu Ser Lys Ser Ala Ala Thr
65                  70                  75                  80

Ile Glu Asn His Ser Gly Arg Ser Cys Arg Asp Trp Pro Thr Asp Val
                85                  90                  95

Ala Gln Ile Phe Ser Lys Ser Gln Leu Cys Thr Lys Phe Asp Asn Arg
            100                 105                 110

Phe Arg Val Ala Lys Ala Ala Gln Ser Ile Val Cys Phe Gln His Ala
        115                 120                 125

Val Leu Cys Arg Phe Ala Pro Tyr Met Arg Tyr Ile Glu Met Lys Val
    130                 135                 140

His Glu Val Leu Pro Lys Asn Tyr Tyr Ile His Ser Gly Lys Gly Leu
145                 150                 155                 160

Glu Glu Leu Asp Ala Trp Val Lys Lys Gly Lys Phe Asp Arg Ile Cys
                165                 170                 175

Thr Glu Ser Asp Tyr Glu Ala Phe Asp Ala Ser Gln Asp Glu Phe Ile
            180                 185                 190

Met Ala Phe Glu Leu Glu Leu Met Lys Tyr Leu Arg Leu Pro Ser Asp
        195                 200                 205
```

-continued

```
Leu Ile Glu Asp Tyr Lys Phe Ile Lys Thr Ser Leu Gly Ser Lys Leu
    210                 215                 220

Gly Asn Phe Ala Ile Met Arg Phe Ser Gly Glu Ala Ser Thr Phe Leu
225                 230                 235                 240

Asn Thr Leu Ala Asn Met Leu Phe Thr Phe Met Arg Tyr Asn Ile Arg
                245                 250                 255

Gly Asp Glu Phe Ile Cys Phe Ala Gly Asp Asp Met Cys Ala Ser Arg
            260                 265                 270

Arg Leu Gln Pro Thr Lys Lys Phe Ala His Phe Leu Asp Lys Leu Lys
        275                 280                 285

Leu Lys Ala Lys Val Gln Phe Val Gln Phe Val Asn Lys Pro Thr Phe
    290                 295                 300

Cys Gly Trp His Leu Cys Pro Asp Gly Ile Tyr Lys Lys Pro Gln Leu
305                 310                 315                 320

Val Leu Glu Arg Met Cys Ile Ala Lys Glu Met Asn Asn Leu Ser Asn
                325                 330                 335

Cys Ile Asp Asn Tyr Ala Ile Glu Val Ala Tyr Ala Tyr Lys Leu Gly
            340                 345                 350

Glu Lys Ala Val Asn Arg Met Asp Glu Glu Glu Val Ala Ala Phe Tyr
        355                 360                 365

Asn Cys Val Arg Ile Ile Val Arg Asn Lys His
    370                 375


<210> SEQ ID NO 65
<211> LENGTH: 377
<212> TYPE: PRT
<213> ORGANISM: Rupestris stem pitting associated virus

<400> SEQUENCE: 65

Ile Tyr Pro Arg His Lys Gly Thr Asp Thr Ala Thr Phe Leu Met Ala
 1               5                  10                  15

Val Lys Lys Arg Leu Ser Phe Ser Ser Pro Ala Ala Glu His Ala Lys
            20                  25                  30

Leu Arg Arg Ala Lys Pro Phe Gly Lys Phe Leu Leu Asp Thr Phe Leu
        35                  40                  45

Lys Arg Val Pro Leu Asn Ser Ser His Asp Glu Lys Met Met Gln Glu
    50                  55                  60

Ala Val His Ala Phe Glu Glu Lys Lys Leu Ser Lys Ser Met Ala Thr
65                  70                  75                  80

Ile Glu Asn His Ser Gly Arg Ser Cys Glu Asp Trp Pro Val Asp Lys
                85                  90                  95

Ala Leu Ile Phe Met Lys Ser Gln Leu Cys Thr Lys Phe Asp Asn Arg
            100                 105                 110

Phe Arg Ser Ala Lys Ala Gly Gln Thr Leu Ala Cys Phe Gln His Ser
        115                 120                 125

Val Leu Cys Arg Phe Ala Pro Tyr Met Arg Tyr Ile Glu Ser Lys Val
    130                 135                 140

Thr Glu Val Leu Pro Lys Asn Leu Tyr Ile His Ser Gly Lys Asn Ile
145                 150                 155                 160

Asp Asp Leu Ala Ala Trp Val Thr Thr Ser Lys Phe Asn Gly Val Cys
                165                 170                 175

Thr Glu Ser Asp Tyr Glu Ala Phe Asp Ala Ser Gln Asp His Phe Ile
            180                 185                 190

Leu Ala Phe Glu Leu Glu Val Met Lys Phe Leu Gly Leu Pro Ser Asp
        195                 200                 205
```

-continued

```
Leu Ile Ala Asp Tyr Thr Phe Ile Lys Thr His Leu Gly Ser Lys Leu
    210                 215                 220

Gly Ser Phe Ala Ile Met Arg Phe Thr Gly Glu Ala Ser Thr Phe Leu
225                 230                 235                 240

Phe Asn Thr Met Ala Asn Met Leu Phe Thr Phe Leu Arg Tyr Asp Leu
                245                 250                 255

Asn Gly Arg Glu Ala Ile Cys Phe Ala Gly Asp Asp Met Cys Ala Asn
            260                 265                 270

Ser Arg Leu Lys Val Thr Asn Arg Phe Ser Asn Phe Leu Asp Lys Ile
        275                 280                 285

Lys Leu Lys Ala Lys Val Gln Phe Thr Ala Thr Pro Thr Phe Cys Gly
    290                 295                 300

Trp Gly Leu Cys Glu His Gly Val Phe Lys Lys Pro Asp Leu Val Leu
305                 310                 315                 320

Glu Arg Leu Gln Ile Ala Arg Glu Thr Arg Asn Leu Glu Asn Cys Ile
                325                 330                 335

Asp Asn Tyr Ala Ile Glu Val Ser Cys Ala Tyr Lys Met Gly Glu Asn
            340                 345                 350

Leu Asn Leu Tyr Leu Thr Pro Gln Glu Val Asp Ala His Tyr Asn Cys
        355                 360                 365

Val Arg Phe Ile Val Gln His Asn His
    370                 375


<210> SEQ ID NO 66
<211> LENGTH: 377
<212> TYPE: PRT
<213> ORGANISM: Rupestris stem pitting associated virus

<400> SEQUENCE: 66

Ile Tyr Pro Arg His Lys Gly Asn Asp Ser Ile Thr Phe Leu Met Ala
 1               5                  10                  15

Val Arg Lys Arg Leu Lys Phe Ser Lys Pro Gln Val Glu Ala Ala Lys
            20                  25                  30

Leu Arg Arg Ala Lys Pro Tyr Gly Lys Phe Leu Leu Asp Ser Phe Leu
        35                  40                  45

Ser Lys Ile Pro Leu Lys Ala Ser His Asn Ser Ile Met Phe His Glu
    50                  55                  60

Ala Val Gln Glu Phe Glu Ala Lys Lys Ala Ser Lys Ser Ala Ala Thr
65                  70                  75                  80

Ile Glu Asn His Ala Gly Arg Ser Cys Arg Asp Trp Leu Leu Asp Val
                85                  90                  95

Ala Leu Ile Phe Met Lys Ser Gln His Cys Thr Lys Phe Asp Asn Arg
            100                 105                 110

Leu Arg Val Ala Lys Ala Gly Gln Thr Leu Ala Cys Phe Gln His Ala
        115                 120                 125

Val Leu Val Arg Phe Ala Pro Tyr Met Arg Tyr Ile Glu Lys Lys Leu
    130                 135                 140

Met Gln Ala Leu Lys Pro Asn Phe Tyr Ile His Ser Gly Lys Gly Leu
145                 150                 155                 160

Asp Glu Leu Asn Glu Trp Val Arg Thr Arg Gly Phe Thr Gly Ile Cys
                165                 170                 175

Thr Glu Ser Asp Tyr Glu Ala Phe Asp Ala Ser Gln Asp His Phe Ile
            180                 185                 190

Leu Ala Phe Glu Leu Gln Ile Met Lys Phe Leu Gly Leu Pro Glu Asp
```

-continued

```
        195                 200                 205

Leu Ile Leu Asp Tyr Glu Phe Ile Lys Ile His Leu Gly Ser Lys Leu
    210                 215                 220

Gly Ser Phe Ser Ile Met Arg Phe Thr Gly Glu Ala Ser Thr Phe Leu
225                 230                 235                 240

Phe Asn Thr Met Ala Asn Met Leu Phe Thr Phe Leu Arg Tyr Glu Leu
                245                 250                 255

Thr Gly Ser Glu Ser Ile Ala Phe Ala Gly Asp Asp Met Cys Ala Asn
            260                 265                 270

Arg Arg Leu Arg Leu Lys Thr Glu His Glu Gly Phe Leu Asn Met Ile
        275                 280                 285

Cys Leu Lys Ala Lys Val Gln Phe Val Ser Asn Pro Thr Phe Cys Gly
    290                 295                 300

Trp Cys Leu Phe Lys Glu Gly Ile Phe Lys Lys Pro Gln Leu Ile Trp
305                 310                 315                 320

Glu Arg Ile Cys Ile Ala Arg Glu Met Gly Asn Leu Glu Asn Cys Ile
                325                 330                 335

Asp Asn Tyr Ala Ile Glu Val Ser Tyr Ala Tyr Arg Leu Gly Glu Leu
            340                 345                 350

Ala Ile Glu Met Met Thr Glu Glu Glu Val Glu Ala His Tyr Asn Cys
        355                 360                 365

Val Arg Phe Leu Val Arg Asn Lys His
    370                 375


<210> SEQ ID NO 67
<211> LENGTH: 227
<212> TYPE: PRT
<213> ORGANISM: Rupestris stem pitting associated virus
<220> FEATURE:
<221> NAME/KEY: VARIANT
<222> LOCATION: (1)...(227)
<223> OTHER INFORMATION: Xaa = Any Amino Acid

<400> SEQUENCE: 67

Met Xaa Xaa Xaa Xaa Xaa Xaa Leu Xaa Xaa Xaa Xaa Phe Xaa Xaa Xaa
 1               5                  10                  15

Xaa Xaa Xaa Leu Xaa Xaa Xaa Pro Xaa Val Xaa His Xaa Val Pro Gly
            20                  25                  30

Xaa Gly Lys Xaa Xaa Leu Ile Xaa Xaa Xaa Xaa Xaa Xaa Xaa Xaa Xaa
        35                  40                  45

Xaa Xaa Ala Xaa Thr Xaa Gly Val Xaa Xaa Xaa Xaa Xaa Xaa Xaa Gly
    50                  55                  60

Xaa Xaa Ile Xaa Xaa Xaa Xaa Xaa Gly Xaa Xaa Xaa Xaa Gly Xaa Xaa
65                  70                  75                  80

Xaa Xaa Leu Asp Glu Tyr Xaa Xaa Xaa Xaa Xaa Xaa Xaa Xaa Xaa Xaa
                85                  90                  95

Xaa Leu Phe Xaa Asp Pro Xaa Gln Xaa Asn Xaa Xaa Xaa Xaa Xaa Xaa
            100                 105                 110

Ala Xaa Phe Xaa Xaa Xaa Xaa Xaa Xaa Arg Phe Gly Xaa Xaa Thr Xaa
        115                 120                 125

Xaa Xaa Leu Xaa Xaa Xaa Gly Xaa Xaa Xaa Xaa Xaa Xaa Ser Xaa Xaa
    130                 135                 140

Xaa Asp Xaa Val Xaa Xaa Xaa Xaa Xaa Xaa Xaa Xaa Xaa Xaa Xaa Gly
145                 150                 155                 160

Xaa Xaa Xaa Xaa Xaa Xaa Xaa Xaa Xaa Xaa Xaa Xaa Xaa Xaa Xaa His
                165                 170                 175
```

-continued

```
Xaa Xaa Glu Xaa Xaa Xaa Xaa Xaa Xaa Xaa Xaa Gly Xaa Thr Phe Xaa
            180                 185                 190

Xaa Val Thr Xaa Xaa Xaa Xaa Xaa Xaa Xaa Xaa Xaa Xaa Xaa Xaa Xaa
        195                 200                 205

Xaa Xaa Xaa Xaa Xaa Xaa Xaa Thr Arg His Arg Xaa Xaa Xaa Xaa Xaa
    210                 215                 220

Xaa Xaa Xaa
225


<210> SEQ ID NO 68
<211> LENGTH: 221
<212> TYPE: PRT
<213> ORGANISM: Rupestris stem pitting associated virus

<400> SEQUENCE: 68

Met Asp Val Ile Val Asp Leu Leu Tyr Lys Tyr Lys Phe Glu Arg Leu
 1               5                  10                  15

Ser Asn Lys Leu Val Cys Pro Ile Val Val His Cys Val Pro Gly Ala
            20                  25                  30

Gly Lys Ser Ser Leu Ile Arg Glu Leu Leu Glu Leu Asp Ser Arg Phe
        35                  40                  45

Cys Ala Tyr Thr Ala Gly Val Glu Asp Gln Pro Arg Leu Ser Gly Asn
    50                  55                  60

Trp Ile Arg Lys Trp Ser Gly Gln Gln Pro Glu Gly Lys Phe Val Val
65                  70                  75                  80

Leu Asp Glu Tyr Thr Leu Leu Thr Glu Val Pro Pro Val Phe Ala Leu
                85                  90                  95

Phe Gly Asp Pro Ile Gln Ser Asn Thr Ser Ala Val Gln Arg Ala Asp
            100                 105                 110

Phe Val Cys Ser Val Ser Arg Arg Phe Gly Ser Ala Thr Cys Gly Leu
        115                 120                 125

Leu Arg Glu Leu Gly Trp Asn Val Arg Ser Glu Lys Ala Asp Leu Val
    130                 135                 140

Gln Val Ser Asp Ile Tyr Thr Lys Asp Pro Leu Gly Lys Val Val Phe
145                 150                 155                 160

Ser Glu Glu Glu Val Gly Cys Leu Leu Arg Ser His Gly Val Glu Ala
                165                 170                 175

Leu Ser Leu Gln Glu Ile Thr Gly Gln Thr Phe Glu Val Val Thr Phe
            180                 185                 190

Val Thr Ser Glu Asn Ser Pro Val Ile Asn Arg Ala Ala Ala Tyr Gln
        195                 200                 205

Cys Met Thr Arg His Arg Arg Leu Cys Thr Ser Val Ser
    210                 215                 220


<210> SEQ ID NO 69
<211> LENGTH: 223
<212> TYPE: PRT
<213> ORGANISM: Rupestris stem pitting associated virus

<400> SEQUENCE: 69

Met Glu Thr Val Leu Ser Leu Leu Asn Glu Phe Gly Phe Glu Arg Thr
 1               5                  10                  15

Val Glu Pro Leu Ser Asp Pro Ile Val Val His Ala Val Pro Gly Ser
            20                  25                  30

Gly Lys Thr Thr Leu Ile Lys Gln Ala Leu Ile Arg Asn Asn Asn Ile
        35                  40                  45
```

-continued

```
Glu Ala Val Thr Phe Gly Val Pro Glu Lys Ala Asn Ile His Gly Thr
    50                  55                  60

Tyr Ile Lys Lys Ala Arg Gln Gly Gln Arg Gly Arg Gly Asn Tyr Ser
65                  70                  75                  80

Ile Leu Asp Glu Tyr Leu Ser Gly Glu Tyr Ser Thr Gly Phe Asn Cys
                85                  90                  95

Leu Phe Ser Asp Pro Tyr Gln Asn His Gly Asp Cys Leu Arg Ala His
            100                 105                 110

Phe Ile Gly Arg Cys Ser His Arg Phe Gly Arg Gln Thr Val Gln Ile
        115                 120                 125

Leu Arg Asp Leu Gly Tyr Asn Ile Ala Ser Ser Lys Glu Asp Ile Val
    130                 135                 140

Glu Lys Lys Asn Ile Phe Gln Leu Ile Glu Pro Glu Gly Val Ile Ile
145                 150                 155                 160

Cys Leu Glu Lys Gly Val Glu Asp Phe Leu Lys Trp His Ser Val Glu
                165                 170                 175

Tyr Lys Phe Pro Cys Gln Val Arg Gly Ala Thr Phe Asp Ile Val Thr
            180                 185                 190

Phe Ile His Glu Lys Pro Leu Glu Glu Leu Val Gly Pro Asp Leu Phe
        195                 200                 205

Val Ala Leu Thr Arg His Arg Ser Lys Leu Val Leu Val Ser Asn
    210                 215                 220


<210> SEQ ID NO 70
<211> LENGTH: 220
<212> TYPE: PRT
<213> ORGANISM: Rupestris stem pitting associated virus

<400> SEQUENCE: 70

Met Asn Asn Leu Val Lys Ala Leu Ser Ala Phe Glu Phe Val Gly Val
 1               5                  10                  15

Phe Ser Val Leu Lys Phe Pro Val Val Ile His Ser Val Pro Gly Ser
            20                  25                  30

Gly Lys Ser Ser Leu Ile Arg Glu Leu Ile Ser Glu Asp Glu Asn Phe
        35                  40                  45

Ile Ala Phe Thr Ala Gly Val Pro Asp Ser Pro Asn Leu Thr Gly Arg
    50                  55                  60

Tyr Ile Lys Pro Tyr Ser Pro Gly Cys Ala Val Pro Gly Lys Val Asn
65                  70                  75                  80

Ile Leu Asp Glu Tyr Leu Ser Val Gln Asp Phe Ser Gly Phe Asp Val
                85                  90                  95

Leu Phe Ser Asp Pro Tyr Gln Asn Ile Ser Ile Pro Lys Glu Ala His
            100                 105                 110

Phe Ile Lys Ser Lys Thr Cys Arg Phe Gly Val Asn Thr Cys Lys Tyr
        115                 120                 125

Leu Ser Ser Phe Gly Lys Val Ser Ser Asp Gly Leu Asp Lys Val Ile
    130                 135                 140

Val Gly Ser Pro Phe Thr Leu Asp Val Glu Gly Val Leu Ile Cys Phe
145                 150                 155                 160

Gly Lys Glu Ala Val Asp Leu Ala Val Ala His Asn Ser Glu Phe Lys
                165                 170                 175

Leu Pro Cys Glu Val Arg Gly Ser Thr Phe Asn Val Val Thr Leu Leu
            180                 185                 190

Lys Ser Arg Asp Pro Thr Pro Glu Asp Arg His Trp Phe Tyr Ile Ala
```

-continued

```
        195                 200                 205

Ala Thr Arg His Arg Glu Lys Leu Ile Ile Met Gln
    210                 215                 220


<210> SEQ ID NO 71
<211> LENGTH: 124
<212> TYPE: PRT
<213> ORGANISM: Rupestris stem pitting associated virus
<220> FEATURE:
<221> NAME/KEY: VARIANT
<222> LOCATION: (1)...(124)
<223> OTHER INFORMATION: Xaa = Any Amino Acid

<400> SEQUENCE: 71

Met Pro Xaa Xaa Xaa Xaa Xaa Xaa Xaa Xaa Pro Xaa Xaa Xaa Xaa Lys
 1               5                  10                  15

Xaa Xaa Xaa Xaa Xaa Xaa Xaa Gly Xaa Xaa Xaa Xaa Xaa Val Xaa Xaa
            20                  25                  30

Xaa Leu Xaa Xaa Ser Xaa Leu Pro Xaa Xaa Gly Asp Xaa Xaa His Xaa
        35                  40                  45

Xaa Pro His Gly Gly Xaa Tyr Xaa Asp Gly Thr Lys Xaa Xaa Xaa Tyr
    50                  55                  60

Xaa Xaa Pro Xaa Xaa Xaa Xaa Xaa Xaa Ser Xaa Xaa Xaa Xaa Xaa Xaa
65                  70                  75                  80

Xaa Xaa Xaa Xaa Xaa Xaa Xaa Xaa Xaa Leu Xaa Xaa Xaa Xaa Xaa Xaa
                85                  90                  95

Xaa Xaa Xaa Xaa Xaa Xaa Xaa Xaa Xaa Xaa Xaa Xaa Xaa Xaa Xaa Xaa
            100                 105                 110

Xaa Xaa Xaa Xaa Xaa Xaa Xaa Xaa Xaa Xaa Xaa Xaa
        115                 120


<210> SEQ ID NO 72
<211> LENGTH: 109
<212> TYPE: PRT
<213> ORGANISM: Rupestris stem pitting associated virus

<400> SEQUENCE: 72

Met Pro Leu Thr Pro Pro Pro Asp Phe Thr Lys Val Tyr Leu Ser Ala
 1               5                  10                  15

Ala Leu Gly Val Ser Leu Ala Leu Val Val Trp Leu Leu Ile Arg Ser
            20                  25                  30

Thr Leu Pro Val Val Gly Asp Arg Asp His Asn Leu Pro His Gly Gly
        35                  40                  45

Trp Tyr Arg Asp Gly Thr Lys Ser Val Phe Tyr Asn Ser Pro Gly Arg
    50                  55                  60

Leu Asn Ser Ile Glu Ala Arg Lys Ala Pro Leu Leu Gly Gln Pro Trp
65                  70                  75                  80

Ala Ile Val Val Leu Leu Val Leu Leu Ile Trp Ala Ser His Lys Leu
                85                  90                  95

Gly Arg Pro Asn Cys Arg Ala Cys Ala Gly Ser His Thr
            100                 105


<210> SEQ ID NO 73
<211> LENGTH: 120
<212> TYPE: PRT
<213> ORGANISM: Rupestris stem pitting associated virus

<400> SEQUENCE: 73

Met Pro Phe Ala Gln Pro Pro Asp Tyr Ser Lys Ser Val Phe Pro Ile
```

-continued

```
 1               5                   10                  15

Ala Val Gly Ile Ala Val Ala Val Val Leu Phe Thr Leu Thr Arg Ser
            20                  25                  30

Thr Leu Pro Gln Val Gly Asp Asn Ile His Asn Leu Pro His Gly Gly
        35                  40                  45

Asn Tyr Gln Asp Gly Thr Lys Arg Ile Ser Tyr Cys Gly Pro Arg Asp
    50                  55                  60

Ser Phe Pro Ser Ser Ser Leu Ile Ser Ser Gly Thr Pro Met Ile Ile
65                  70                  75                  80

Gly Ile Ile Ile Phe Leu Ile Phe Ala Ile Tyr Val Ser Glu Lys Trp
                85                  90                  95

Ser Arg Ser Gly Ser Arg Arg Cys Ser Cys Cys Val Pro Gly Ala Pro
            100                 105                 110

Ala Cys Thr Ala Thr Val His Glu
        115                 120


<210> SEQ ID NO 74
<211> LENGTH: 117
<212> TYPE: PRT
<213> ORGANISM: Rupestris stem pitting associated virus

<400> SEQUENCE: 74

Met Pro Phe Gln Gln Pro Ala Asn Trp Ala Lys Thr Ile Thr Pro Leu
 1               5                   10                  15

Thr Val Gly Leu Gly Ile Gly Leu Val Leu His Phe Leu Arg Lys Ser
            20                  25                  30

Asn Leu Pro Tyr Ser Gly Asp Asn Ile His Gln Phe Pro His Gly Gly
        35                  40                  45

Arg Tyr Arg Asp Gly Thr Lys Ser Ile Thr Tyr Cys Gly Pro Lys Gln
    50                  55                  60

Ser Phe Pro Ser Ser Gly Ile Phe Gly Gln Ser Glu Asn Phe Val Pro
65                  70                  75                  80

Leu Met Leu Val Ile Gly Leu Ile Ala Phe Ile His Val Leu Ser Val
                85                  90                  95

Trp Asn Ser Gly Leu Gly Arg Asn Cys Asn Cys His Pro Asn Pro Cys
            100                 105                 110

Ser Cys Arg Gln Gln
        115


<210> SEQ ID NO 75
<211> LENGTH: 49
<212> TYPE: PRT
<213> ORGANISM: Rupestris stem pitting associated virus
<220> FEATURE:
<221> NAME/KEY: VARIANT
<222> LOCATION: (1)...(49)
<223> OTHER INFORMATION: Xaa = Any Amino Acid

<400> SEQUENCE: 75

Met Xaa Xaa Xaa Xaa Leu Xaa Xaa Val Xaa Xaa Leu Xaa Xaa Xaa Xaa
 1               5                   10                  15

Cys Xaa Xaa Xaa Xaa Thr Gly Glu Ser Xaa Xaa Cys Xaa Xaa Xaa Xaa
            20                  25                  30

Xaa Xaa Xaa Xaa Xaa Xaa Xaa Xaa Xaa Xaa Xaa Xaa Xaa Xaa Xaa Xaa
        35                  40                  45

Gly
```

-continued

<210> SEQ ID NO 76
<211> LENGTH: 63
<212> TYPE: PRT
<213> ORGANISM: Rupestris stem pitting associated virus

<400> SEQUENCE: 76

```
Met Ile Val Tyr Val Leu Val Gly Leu Ser Ala Phe Cys Ile Val Leu
 1               5                  10                  15

Tyr Leu Ile Ser Gln Gly Gln Ser Asp Cys Val Val Leu Ile Thr Gly
            20                  25                  30

Glu Ser Val Arg Val Gln Gly Cys Arg Ile Asp Gly Glu Phe Gly Ser
        35                  40                  45

Val Leu Ser Lys Leu Lys Pro Phe Gly Cys Gly Ser Phe Arg Ser
    50                  55                  60
```

<210> SEQ ID NO 77
<211> LENGTH: 70
<212> TYPE: PRT
<213> ORGANISM: Rupestris stem pitting associated virus

<400> SEQUENCE: 77

```
Met Phe Pro Arg Ser Gly Leu Gly Leu Ala Val Ala Ala Ala Val Val
 1               5                  10                  15

Ala Tyr Leu Val Leu Leu Leu Ala Gln Gln Leu Tyr Met Ser Asn Ser
            20                  25                  30

Ser Gln Cys Thr Ile Val Ile Thr Gly Glu Ser Val Ser Val Val Gly
        35                  40                  45

Cys Val Tyr Ser Glu Ala Phe Ile Glu Leu Val Lys Gly Leu Lys Pro
    50                  55                  60

Tyr Tyr His Pro Leu Gly
65                  70
```

<210> SEQ ID NO 78
<211> LENGTH: 80
<212> TYPE: PRT
<213> ORGANISM: Rupestris stem pitting associated virus

<400> SEQUENCE: 78

```
Met Tyr Cys Leu Phe Gly Ile Leu Val Leu Val Gly Ile Val Ile Ala
 1               5                  10                  15

Ile Gln Ile Leu Ala His Val Asp Ser Ser Ser Gly Asn His Gln Gly
            20                  25                  30

Cys Phe Ile Arg Ala Thr Gly Glu Ser Ile Leu Ile Glu Asn Cys Gly
        35                  40                  45

Pro Ser Glu Ala Leu Ala Ser Thr Val Lys Glu Val Leu Gly Gly Leu
    50                  55                  60

Lys Ala Leu Gly Val Ser Arg Ala Val Glu Glu Ile Asp Tyr His Cys
65                  70                  75                  80
```

<210> SEQ ID NO 79
<211> LENGTH: 105
<212> TYPE: PRT
<213> ORGANISM: Rupestris stem pitting associated virus
<220> FEATURE:
<221> NAME/KEY: VARIANT
<222> LOCATION: (1)...(105)
<223> OTHER INFORMATION: Xaa = Any Amino Acid

<400> SEQUENCE: 79

```
Xaa Xaa Xaa Thr Leu Arg Xaa Xaa Cys Xaa Xaa Tyr Ala Xaa Xaa Xaa
 1               5                  10                  15
```

-continued

```
Trp Asn Xaa Xaa Leu Xaa Xaa Xaa Xaa Pro Pro Ala Xaa Trp Xaa Xaa
            20                  25                  30

Xaa Xaa Phe Xaa Xaa Xaa Ala Xaa Phe Asp Xaa Phe Xaa Xaa Val Xaa
        35                  40                  45

Xaa Xaa Xaa Pro Xaa Xaa Gly Xaa Xaa Arg Xaa Pro Thr Xaa Xaa Glu
    50                  55                  60

Xaa Val Ala Xaa Xaa Xaa Xaa Xaa Xaa Xaa Xaa Xaa Xaa Xaa Xaa Arg
65                  70                  75                  80

Xaa Xaa Xaa Xaa Xaa Xaa Xaa Xaa Xaa Xaa Xaa Xaa Xaa Glu Xaa Xaa
                85                  90                  95

Gly Gly Xaa Xaa Gly Xaa Xaa Xaa Xaa
            100                 105


<210> SEQ ID NO 80
<211> LENGTH: 117
<212> TYPE: PRT
<213> ORGANISM: Rupestris stem pitting associated virus

<400> SEQUENCE: 80

Asp Ala Glu Thr Leu Arg Arg Val Cys Arg Leu Tyr Ala Pro Val Thr
 1               5                  10                  15

Trp Asn His Met Leu Thr His Asn Ala Pro Pro Ala Glu Trp Ala Ala
            20                  25                  30

Met Gly Phe Gln Tyr Glu Asp Arg Phe Ala Pro Phe Asp Cys Phe Asp
        35                  40                  45

Tyr Val Glu Asn Thr Ala Ala Val Gln Pro Leu Glu Gly Leu Ile Arg
    50                  55                  60

Arg Pro Thr Pro Arg Glu Lys Val Ala His Asn Thr His Lys Asp Ile
65                  70                  75                  80

Ala Leu Arg Gly Ala Asn Arg Asn Gln Val Phe Ser Ser Leu Asn Ala
                85                  90                  95

Glu Val Thr Gly Gly Met Asn Gly Pro Glu Leu Thr Arg Asp Tyr Val
            100                 105                 110

Lys Ser Asn Arg Lys
        115


<210> SEQ ID NO 81
<211> LENGTH: 114
<212> TYPE: PRT
<213> ORGANISM: Rupestris stem pitting associated virus

<400> SEQUENCE: 81

Glu Gly Cys Thr Leu Arg Gln Tyr Cys Ala Phe Tyr Ala Lys His Val
 1               5                  10                  15

Trp Asn Leu Met Leu Gln Thr Gln Ser Pro Pro Ala Asn Trp Val Gly
            20                  25                  30

Lys Glu Phe Lys Phe Glu Thr Arg Tyr Ala Ala Phe Asp Phe Phe Phe
        35                  40                  45

Gly Val Glu Ser Thr Ala Ser Leu Glu Pro Ala Asp Gly Leu Ile Arg
    50                  55                  60

Leu Pro Thr Gln Ala Glu Arg Val Ala Asn Ala Thr Ser Lys Glu Ile
65                  70                  75                  80

Gln Met Tyr Arg Ile Arg Ser Met Glu Gly Thr Gln Ala Val Asn Phe
                85                  90                  95

Gly Glu Val Thr Gly Gly Lys Ile Gly Pro Lys Pro Val Leu Ser Ile
            100                 105                 110
```

Arg Lys

<210> SEQ ID NO 82
<211> LENGTH: 118
<212> TYPE: PRT
<213> ORGANISM: Rupestris stem pitting associated virus

<400> SEQUENCE: 82

```
Glu Val Thr Thr Leu Arg Arg Phe Cys Met Tyr Tyr Ala Lys Ile Val
 1               5                  10                  15

Trp Asn Ile His Leu Glu Thr Gly Ile Pro Pro Ala Asn Trp Ala Lys
            20                  25                  30

Lys Gly Phe Asn Glu Asn Glu Lys Phe Ala Ala Phe Asp Phe Phe Leu
        35                  40                  45

Gly Val Thr Asp Glu Ser Ala Leu Glu Pro Lys Gly Gly Ile Lys Arg
    50                  55                  60

Ala Pro Thr Lys Ala Glu Met Val Ala Asn Ile Ala Ser Phe Glu Val
65                  70                  75                  80

Gln Val Leu Arg Gln Ala Met Ala Glu Gly Lys Arg Ser Ser Asn Leu
                85                  90                  95

Gly Glu Ile Ser Gly Gly Thr Ala Gly Ala Leu Ile Asn Asn Pro Phe
            100                 105                 110

Ser Asn Val Thr His Glu
        115
```

<210> SEQ ID NO 83
<211> LENGTH: 180
<212> TYPE: DNA
<213> ORGANISM: Rupestris stem pitting associated virus
<220> FEATURE:
<221> NAME/KEY: misc_feature
<222> LOCATION: (1)...(180)
<223> OTHER INFORMATION: n=A,T,C, or G

<400> SEQUENCE: 83

```
nnngntnann aantcnncnn canttcnnnn ntncantant tnnncnnttt nnnaangntg     60

nnnnnancct nnncgnnggn nnncnntnnn nnnngtntnn nnnttncatg ctnnancnta    120

tttnnnnnnn nnnntgtnnn nnnnnnnnnn nnntttnnnn nnnnnnnnta gntttnnntc    180
```

<210> SEQ ID NO 84
<211> LENGTH: 132
<212> TYPE: DNA
<213> ORGANISM: Rupestris stem pitting associated virus

<400> SEQUENCE: 84

```
ttagttaatt aattctcctg cattcaattt cagtacttat gctttttagt aaagttgatc     60

ccaacctaac cggggcggct atgtgtgtgt ttctttcatg ctttagctta tttttgtttt    120

aactagattt tc                                                        132
```

<210> SEQ ID NO 85
<211> LENGTH: 174
<212> TYPE: DNA
<213> ORGANISM: Rupestris stem pitting associated virus

<400> SEQUENCE: 85

```
ggatgacgaa gtagcacaat tccgcagtcc aataattccc cgatttcaag gctgggttaa     60

gcctgttcgc tggaataccg tactaatagt attccctttc catgctaaat cctatttaat    120
```

-continued

```
atataaggtg tggaaagtaa aagaagattt ggtgtgtttt tatagttttc attc         174


<210> SEQ ID NO 86
<211> LENGTH: 212
<212> TYPE: DNA
<213> ORGANISM: Rupestris stem pitting associated virus
<220> FEATURE:
<221> NAME/KEY: misc_feature
<222> LOCATION: (1)...(212)
<223> OTHER INFORMATION: n=A,T,C or G

<400> SEQUENCE: 86

nnnnnnnnnn nnnnnnnnnn nnnnnnnnnn nnnnnnnnnn nnnnnnnnnn nnnnnnnnnn    60

nnnnnnnnnn nnnnnnnnnn nnnnnnnnnn nnnnnnnnnn nnnnnnnnnn nnnnnnnnnn   120

nnnnnnnnnn nnnnnnncca tnntaaatcc tatttaatat ataangtgtg nnannnnaaa   180

naananttgg tntntnnnta tnnttttnnn nn                                 212


<210> SEQ ID NO 87
<211> LENGTH: 71
<212> TYPE: DNA
<213> ORGANISM: Rupestris stem pitting associated virus

<400> SEQUENCE: 87

ccattaaatc ctatttaata tataacgtgt gctactataa ataaaacttg gtttttaact    60

atttttagcc a                                                         71


<210> SEQ ID NO 88
<211> LENGTH: 176
<212> TYPE: DNA
<213> ORGANISM: Rupestris stem pitting associated virus

<400> SEQUENCE: 88

ggatgacgaa gtcagcgaca attccgcagt ccaataattc cccgatttca aggctgggtt    60

aagcctgttc gctggaatac cgtactaata gtattccctt tccatgctaa atcctattta   120

atatataagg tgtggaaagt aaaagaagat ttggtgtgtt tttatagttt tcattc       176


<210> SEQ ID NO 89
<211> LENGTH: 398
<212> TYPE: DNA
<213> ORGANISM: Rupestris stem pitting associated virus
<220> FEATURE:
<221> NAME/KEY: misc_feature
<222> LOCATION: (1)...(398)
<223> OTHER INFORMATION: n = A,T,C or G

<400> SEQUENCE: 89

ncnggnntna angntggnca ntgtgtnatt ttngangagg tncagttgtt tccnccngga    60

nanatcgatn tnngntnnct tntnanacgn agngangctt tnatttnact ngcnggtgan   120

ccatgncnna gcacatatga ntcncanaan gatcgngcna ttttgggngc tgagcagagt   180

gacatactna nantncttga nggnaanacn tataggtana acatngaaag cagnngnttt   240

gtgaanccaa tgttngaatn nngactncca tgtcanttca aaaangggnn cnatgactgc   300

ngcnttngct gattatgcna tnttnnnnnn nnnnnnnnnn nnnnnnnnnn nnnnnnnnnn   360

nnnnnnnnnn nnnnnnnnnn nnnnnnnnnn nnnnnnnn                           398


<210> SEQ ID NO 90
<211> LENGTH: 399
<212> TYPE: DNA
<213> ORGANISM: Rupestris stem pitting associated virus
```

-continued

<400> SEQUENCE: 90
gcaggattga aggctggcca ctgtgtgatt tttgatgagg tccagttgtt tcctcctgga 60
tacatcgatc tatgcttgct tattatacgt agtgatgctt tcatttcact tgccggtgat 120
ccatgtcaaa gcacatatga ttcgcaaaag gatcgggcaa ttttgggcgc tgagcagagt 180
gacatactta gaatgcttga gggcaaaacg tataggtata acatagaaag caggaggttt 240
gtgaacccaa tgttcgaatc aagactgcca tgtcacttca aaaagggttc gatgactgcc 300
gctttcgctg attatgcaat cttccataat atgcatgact ttctcctggc gaggtcaaaa 360
ggtcctttgg atgccgtttt ggtttccagt tttgaggag 399

<210> SEQ ID NO 91
<211> LENGTH: 399
<212> TYPE: DNA
<213> ORGANISM: Rupestris stem pitting associated virus

<400> SEQUENCE: 91
tctggtttga aagctggtca ttgtgtgatt tttgatgagg ttcagttgtt tccccctgga 60
tacatcgatc tgtgtttact tgtcatacga agtgatgctt tcatttcact tgctggtgat 120
ccatgccaga gcacatatga ttcacagaag gatcgagcaa ttttgggagc tgagcagagt 180
gacatactca gactgcttga aggaaagaca tataggtaca acatagaaag cagacgtttt 240
gtgaacccaa tgtttgaatc tagactacca tgtcacttca aaaagggttc aatgactgca 300
gcctttgctg attatgcaat cttccacaat atgcatgact tcctcctggc gaggtcaaaa 360
ggccccttgg atgctgttct agtttccagt tttgaggag 399

<210> SEQ ID NO 92
<211> LENGTH: 400
<212> TYPE: DNA
<213> ORGANISM: Rupestris stem pitting associated virus

<400> SEQUENCE: 92
gcaggtctaa aagctggtca ctgtgtaatt ttcgatgagg tccagttgtt tccccctgga 60
tacatcgatc tatgtttcgc ttattatacg tagtgatgct ttcatttcac ttgctggtga 120
cccatgtcag agcacatatg actcacaaaa agatcgggcg attttgggcg ctgagcagag 180
tgacatactc aaaatacttg aaggcaagac gtataggtac aacatagaaa gcagaagatt 240
tgtgaaccca atgtttgaat ctcgactgcc atgtcacttc aaaaagggta caatgactgc 300
tgcctttgct gattatgcca ttttccacaa tatgcatgat ttcctcctgg caaggtcaaa 360
aggtcctttg gatgccattc tggtttctag ttttgaggag 400

<210> SEQ ID NO 93
<211> LENGTH: 397
<212> TYPE: DNA
<213> ORGANISM: Rupestris stem pitting associated virus
<220> FEATURE:
<221> NAME/KEY: misc_feature
<222> LOCATION: (1)...(397)
<223> OTHER INFORMATION: n = A,T,C or G

<400> SEQUENCE: 93
gcaggtntaa aagttggtca ctgtgtaatt ttggangagg tccagttgtt tcccccngga 60
acatcgatnt angttngtta tnanacgtag ngangctttc atttnactng ctggtgaccc 120
atgtcngagc acatatgant cacaaaaaga tcgggcgatt ttggggcgtg agcagagtga 180

-continued

```
catactcaaa atacttgaag gcaagacgta taggtacaac atagaaagca gaagatttgt    240

gaacccaatg tttgaatctc gactgccatg tcacttcaaa aagggtacaa tgactgctgc    300

ctttgctgat tatgccattt tccacaatat gcatgatttc ctcctggcaa ggtcaaaagg    360

tcctttggat gccattctgg tttcaagttt tgaggag                             397
```

<210> SEQ ID NO 94
<211> LENGTH: 399
<212> TYPE: DNA
<213> ORGANISM: Rupestris stem pitting associated virus

<400> SEQUENCE: 94

```
gcaggattga aggctggcca ctgtgtgatt ttcgatgagg tccagttgtt tcctcctgga     60

tacatcgatc tatgcttgct tattatacgt agtgatgctt tcatttcact tgccggtgat    120

ccatgtcaaa gcacatatga ttcgcaaaag gatcgggcaa ttttgggcgc tgagcagagt    180

gacatactta gactgcttga gggcaagacg tataggtata acattgaaag caggaggttt    240

gtgaatccaa tgttcgaatc aagactgcca tgtcaattca aaaagggctc aatgactgcc    300

gctttcgctg attatgcaat cttccataat atgcatgact ttctcctggc gaggtcaaaa    360

ggtcctttgg atgccgtttt ggtttccagt tttgaggag                           399
```

<210> SEQ ID NO 95
<211> LENGTH: 399
<212> TYPE: DNA
<213> ORGANISM: Rupestris stem pitting associated virus

<400> SEQUENCE: 95

```
gcaggattga aggctggcca ctgtgtgatt tttgatgagg tccagttgtt tcctcctgga     60

tacatcgatc tatgcttgct tattatacgt agtgatgctt tcatttcact tgccggtgat    120

ccatgtcaaa gcacatatga ttcgcaaaag gatcgggcaa ttttgggcgc tgagcagagt    180

gacatactta gaatgcttga gggcaaaacg tataggtata acatagaaag caggaggttt    240

gtgaacccaa tgttcgaatc aagactgcca tgtcacttca aaaagggttc gatgactgcc    300

gctttcgctg attatgcaat cttccataat atgcatgact ttctcctggc gaggtcaaaa    360

ggtcctttgg atgccgtttt ggtttccagt tttgaggag                           399
```

<210> SEQ ID NO 96
<211> LENGTH: 324
<212> TYPE: DNA
<213> ORGANISM: Rupestris stem pitting associated virus

<400> SEQUENCE: 96

```
tctggtttga aggctggtca ttgtgtgatt ttcgatgagg ttcagttgtt tccccctgga     60

tatatcgatc tatgtttact tgtcatacgc agtgatgctt ttatttcact tgccggtgat    120

ccatgccaga gcacatatga ttcacaaaag gatcgggcaa ttttgggagc tgagcagagt    180

gacatactca gattgcttga aggaaagacg tataggtaca acatagaaag cagacgtttt    240

gtgaacccaa tgtttgaatt tagactacca tgtcacttca aaaaagggtt caatgactgc    300

tgcctttgct gattatgcaa tctt                                           324
```

<210> SEQ ID NO 97
<211> LENGTH: 393
<212> TYPE: DNA
<213> ORGANISM: Rupestris stem pitting associated virus

<400> SEQUENCE: 97

-continued

```
gcaggattga aggctggcca ctgtgtgatt tttgatgagg tccagttgtt tcctggatac     60

atcgatctat gcttgcttat tatacgtagt gatgctttca tttcacttgc tggtgatcca    120

tgtcaaagca catatgactc gcaaaaggat cgggcaattt tgggcgctga gcagagtgac    180

atacttagac tgcttgaggg caaaacgtat aggtataaca tagaaagcag gaggtttgtg    240

aacccaatgt tcgaatcaag actgccatgt cacttcaaaa agggctcgat gactgccgct    300

ttcgctgatt atgcaatctt ccataatatg catgactttc tggcgaggtc aaaaggtccc    360

ttggatgccg ttttggtttc cagttttgag gag                                 393
```